(12) United States Patent
Auricchio et al.

(10) Patent No.: US 12,285,495 B2
(45) Date of Patent: Apr. 29, 2025

(54) GENOME EDITING METHODS AND CONSTRUCTS

(71) Applicant: FONDAZIONE TELETHON, Rome (IT)

(72) Inventors: Alberto Auricchio, Pozzuoli (IT); Manel Llado Santaeularia, Pozzuoli (IT)

(73) Assignee: FONDAZIONE TELETHON ETS, Rome (IT)

( * ) Notice: Subject to any disclaimer, the term of this patent is extended or adjusted under 35 U.S.C. 154(b) by 933 days.

(21) Appl. No.: 17/285,755

(22) PCT Filed: Oct. 15, 2019

(86) PCT No.: PCT/EP2019/078019
§ 371 (c)(1),
(2) Date: Apr. 15, 2021

(87) PCT Pub. No.: WO2020/079033
PCT Pub. Date: Apr. 23, 2020

(65) Prior Publication Data
US 2022/0001030 A1    Jan. 6, 2022

Related U.S. Application Data

(60) Provisional application No. 62/745,540, filed on Oct. 15, 2018.

(51) Int. Cl.
| | | |
|---|---|---|
| *C12N 9/00* | (2006.01) |
| *A61K 48/00* | (2006.01) |
| *A61P 27/02* | (2006.01) |
| *C12N 9/22* | (2006.01) |
| *C12N 15/11* | (2006.01) |
| *C12N 15/90* | (2006.01) |

(52) U.S. Cl.
CPC .......... *A61K 48/0058* (2013.01); *A61P 27/02* (2018.01); *C12N 9/22* (2013.01); *C12N 15/11* (2013.01); *C12N 15/907* (2013.01); *C12N 2310/20* (2017.05); *C12N 2750/14143* (2013.01)

(58) Field of Classification Search
CPC ............ A61K 48/0058; C07K 2317/73; C07K 2319/02; C07K 14/4702; C07K 2319/00; C12N 15/1138; C12N 15/113; C12N 15/86; C12N 9/22
USPC .................................................... 424/93.21
See application file for complete search history.

(56) References Cited

U.S. PATENT DOCUMENTS

2015/0065376 A1    3/2015   Knaut et al.

FOREIGN PATENT DOCUMENTS

| JP | 2007-238629 A | 9/2007 |
| JP | 2016-533769 A | 11/2016 |
| WO | 2002/070710 A1 | 9/2002 |
| WO | 2016/176690 A2 | 11/2016 |
| WO | 2018/013932 A1 | 1/2018 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Keiichiro Suzuki et al, "In vivo genome editing via CRISPR/Cas9 mediated homology-independent targeted integration", Nature, vol. 540, No. 7631, Nov. 16, 2016 (Nov. 16, 2016), p. 144-149.
Keiichiro Suzuki and Juan Carlos Izpisua Belmonte, "In vivo genome editing via the HITI method as a tool for gene therapy", Nov. 13, 2017 (Nov. 13, 2017), vol. 63, No. 2, p. 157-164.
A. Ahier and S. Jarriault, "Simultaneous expression of multiple proteins under a single promoter in Caenorhabditis elegans via a versatile 2A-based toolkit", Genetics, vol. 196, No. 3, Dec. 20, 2013 (Dec. 20, 2013), p. 605-613.
Sasaki Y. et al., "Multi-gene gateway clone design for expression of multiple heterologous genes in living cells: Eukaryotic clones containing two and three ORF multi-gene cassettes expressed from a single promoter", Sep. 10, 2008 (Sep. 10, 2008), vol. 136, No. 3-4, p. 103-112.
Alekseeva Ekaterina et al., "Enhancement of the expression of HCV core gene does not enhance core-specific Immune response in DNA immunization: advantages of the heterologous DNA prime, protein boost immunization regimen", Genetic Vaccines and Therapy, Biomed Central, London, GB, vol. 7, No. 1, Jun. 8, 2009 (Jun. 8, 2009), p. 7.

(Continued)

*Primary Examiner* — Robert B Mondesi
*Assistant Examiner* — Mohammad Y Meah
(74) *Attorney, Agent, or Firm* — Silvia Salvadori, P.C.; Silvia Salvadori

(57) ABSTRACT

The present invention relates to a method of integrating an exogenous DNA sequence into a genome of a cell comprising contacting the cell with: a) a donor nucleic acid comprising: —at least one STOP codon and a translation initiation sequence (TIS) or—a ribosomal skipping sequence, and—said exogenous DNA sequence wherein said donor nucleic acid is flanked at 5' and 3' by inverted targeting sequences; b) a complementary strand oligonucleotide homologous to the targeting sequence and c) a nuclease that recognizes the targeting sequence.

10 Claims, 21 Drawing Sheets

Specification includes a Sequence Listing.

(56) References Cited

OTHER PUBLICATIONS

Michael Bröker and Egon Amann, "pUC12-STOP: an expression vector with portable translation stop signals", Applied Microbiology and Biotechnology, Springer, Berlin, DE, vol. 23, No. 3-4, Jan. 1, 1986 (Jan. 1, 1986), p. 294-296.
Joanna M. Feehan et al., "Modeling dominant and recessive forms of Retinitis Pigmentosa by editing three Rhodopsin-encoding genes in Xenopus laevis using Crispr/Cas9", Scientific Reports, vol. 7, No. 1, Jul. 31, 2017 (Jul. 31, 2017), p. 1-14.
Jin Peng et al., "Production of human Albumin in pigs through CRISPR/Cas9-mediated knockin of human cDNA into swine Albumin locus in the zygotes", Scientific Reports, vol. 5, No. 1, Nov. 12, 2015 (Nov. 12, 2015), p. 1-6.
Pfarr D. S. et al., "Differential effects of polyadenylation regions on gene expression in mammalian cells", DNA, Mary Ann Liebert, New York, NY, US, vol. 5, No. 2, Jan. 1, 1986 (Jan. 1, 1986), p. 115-122.
European Patent Office, "PCT International Search Report and Written Opinion" which were issued in connection with PCT International Application No. PCT/EP2019/078019 and mailed Mar. 27, 2020 (17 pages).

\* cited by examiner

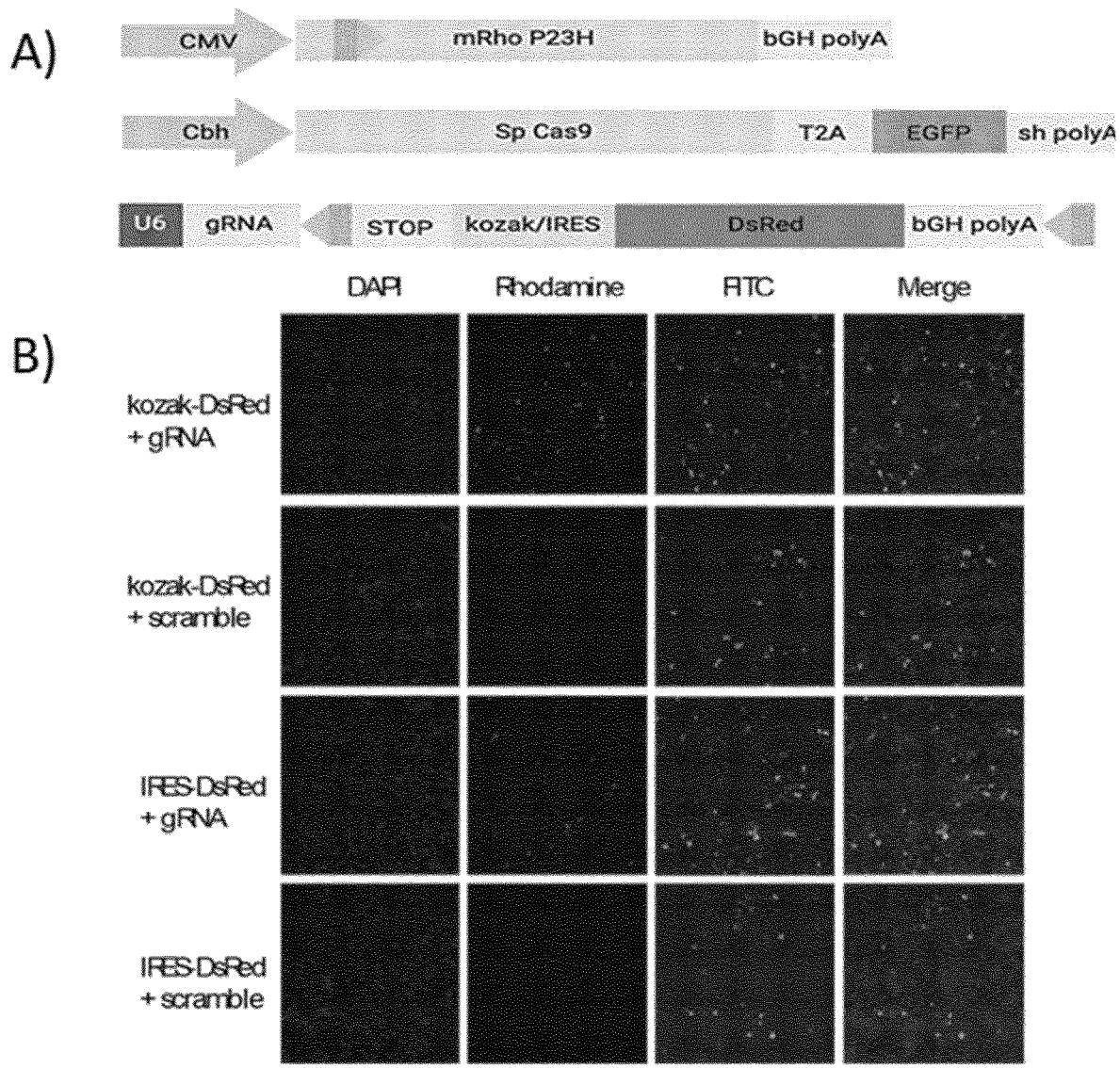
Fig. 2 (1/3)

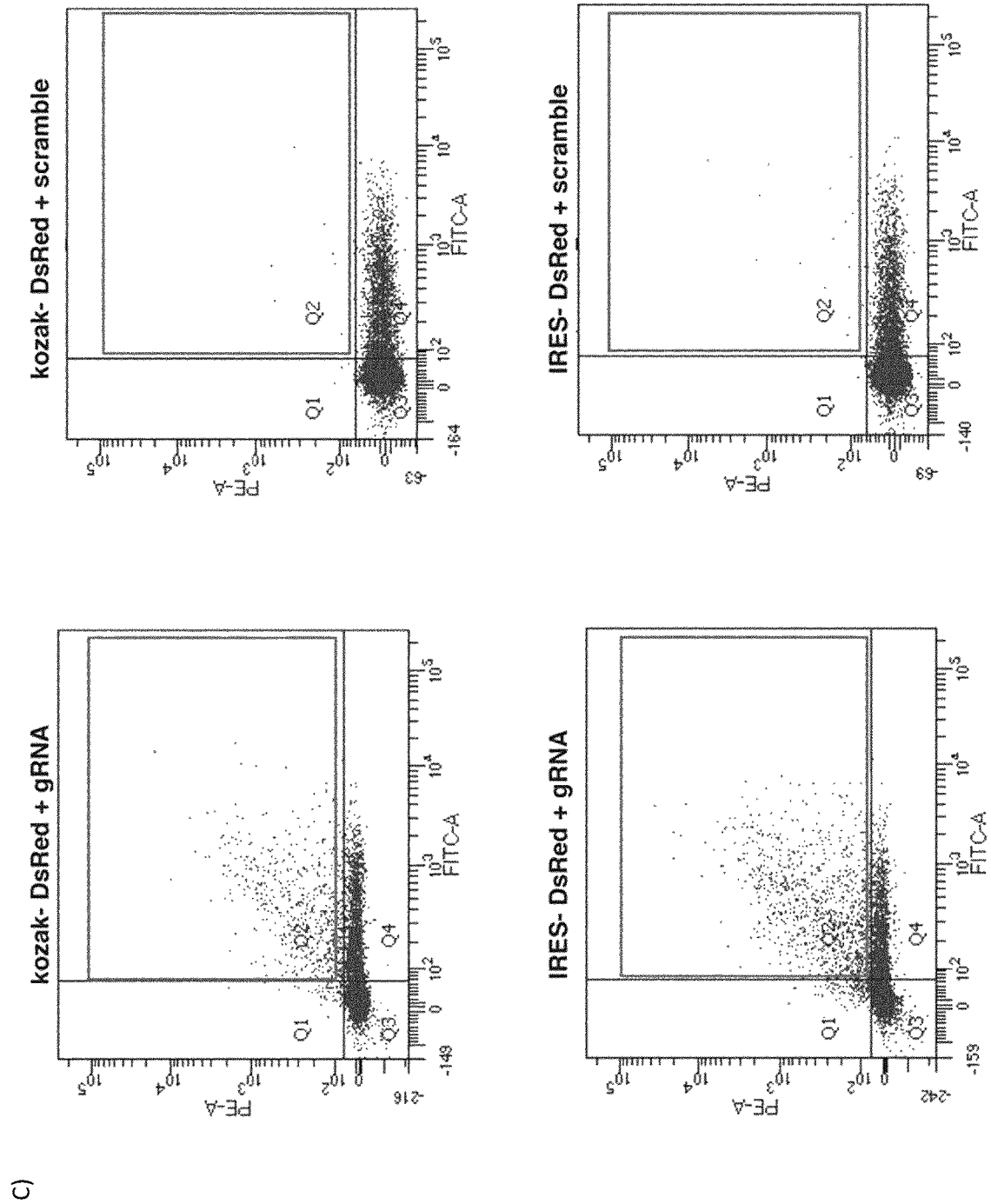
Fig. 2 (2/3)

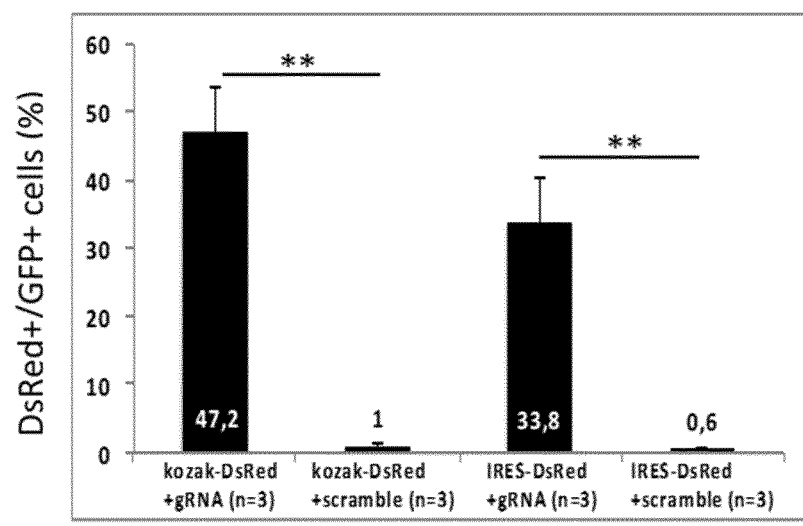
Fig. 2(3/3)

A)
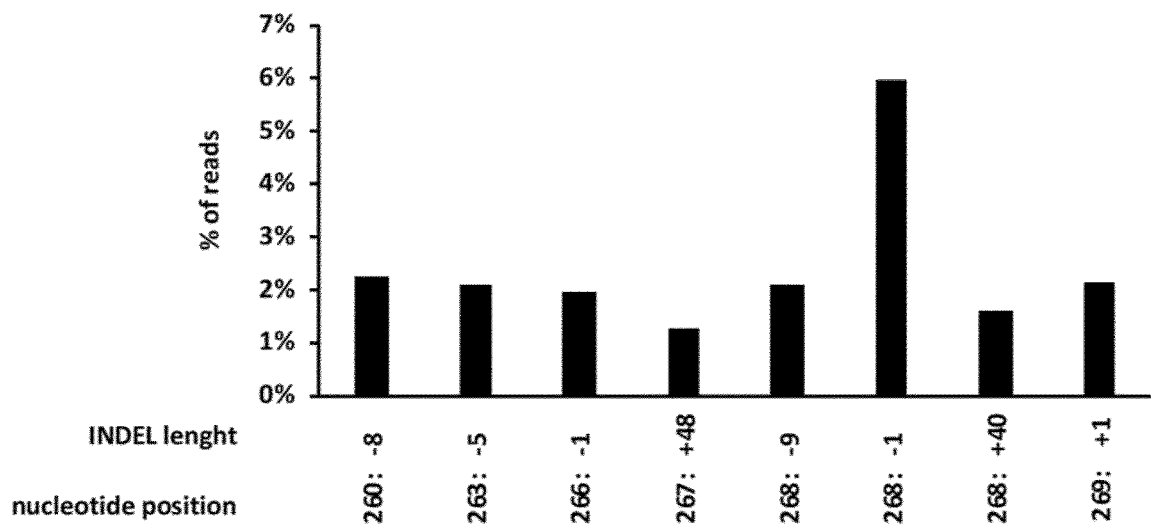
B)
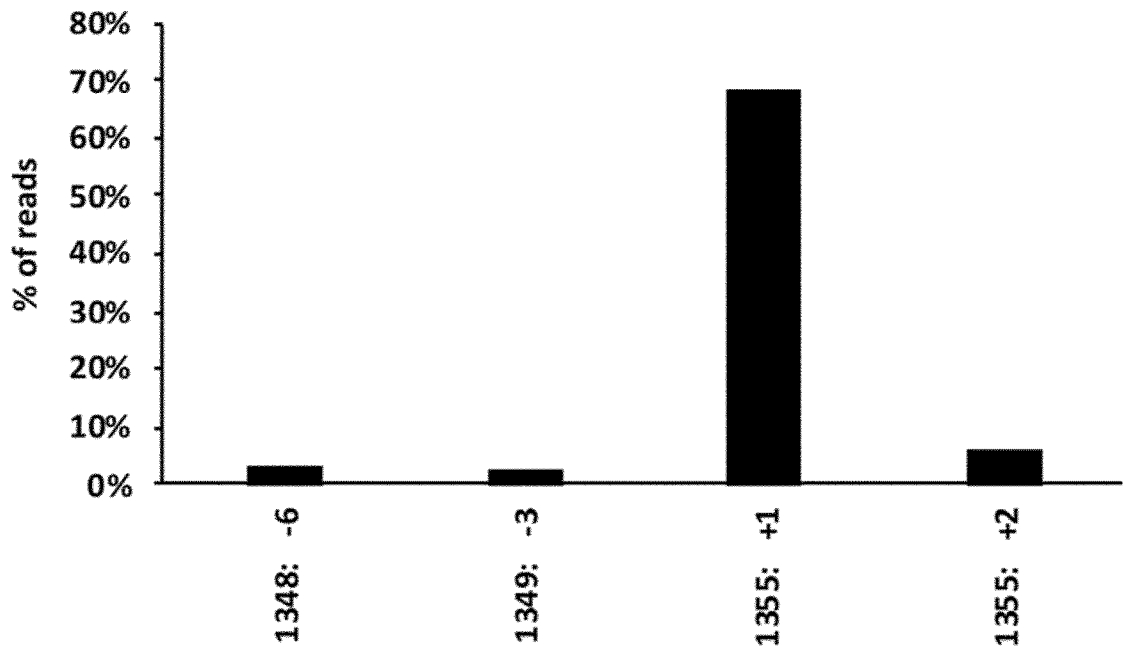
Fig. 6

A)
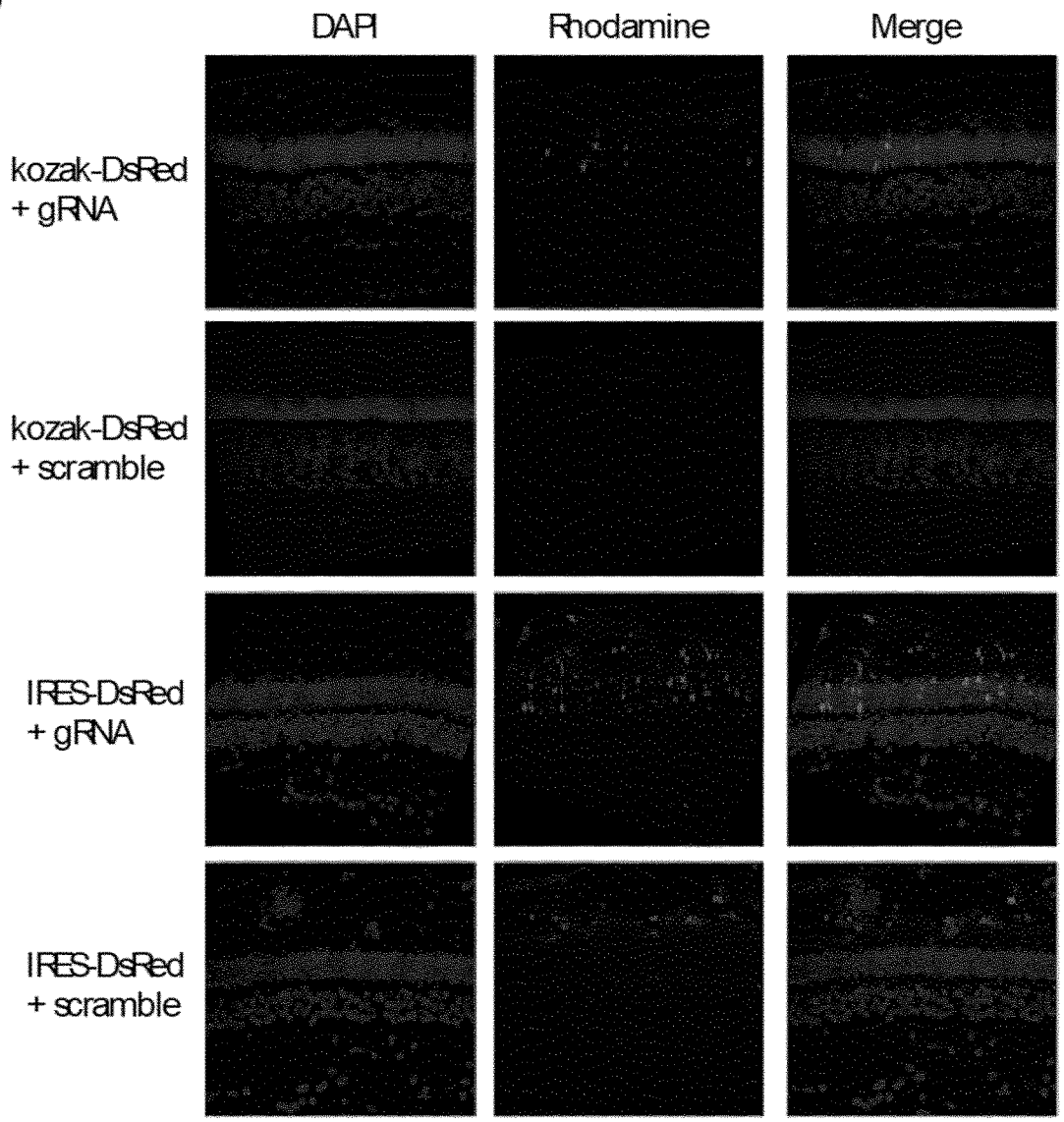
B)
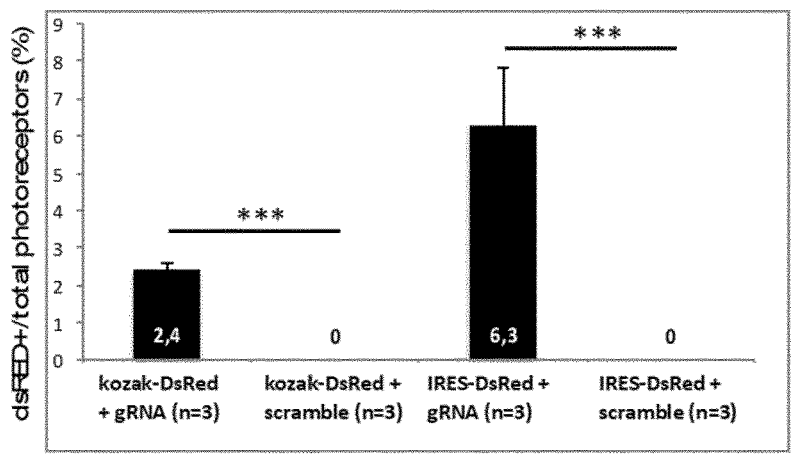
Fig. 7

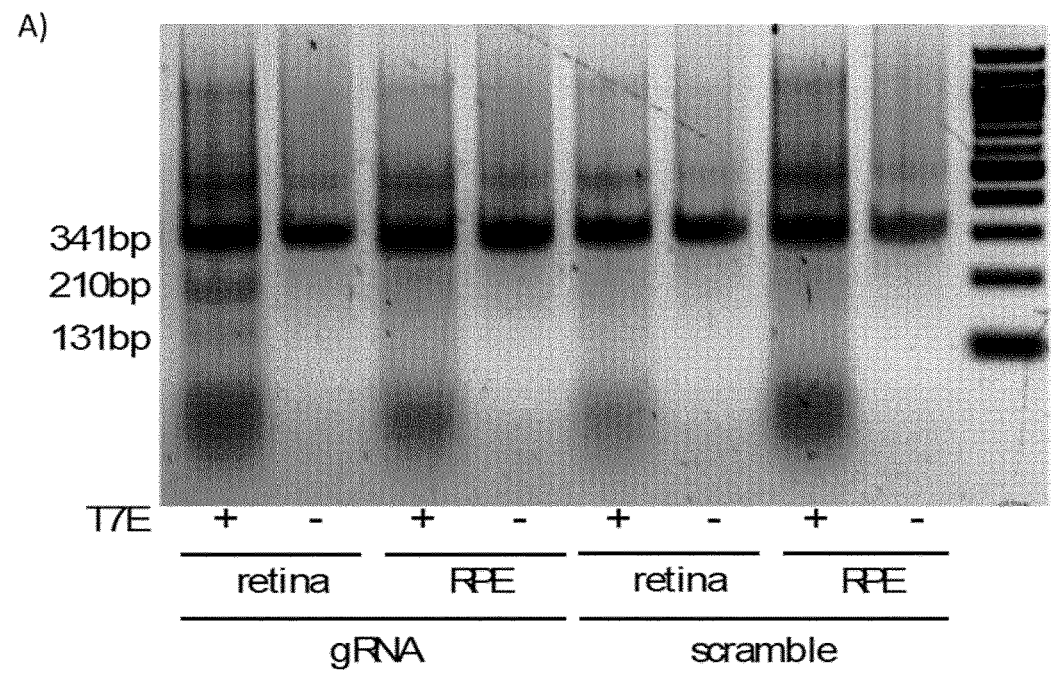
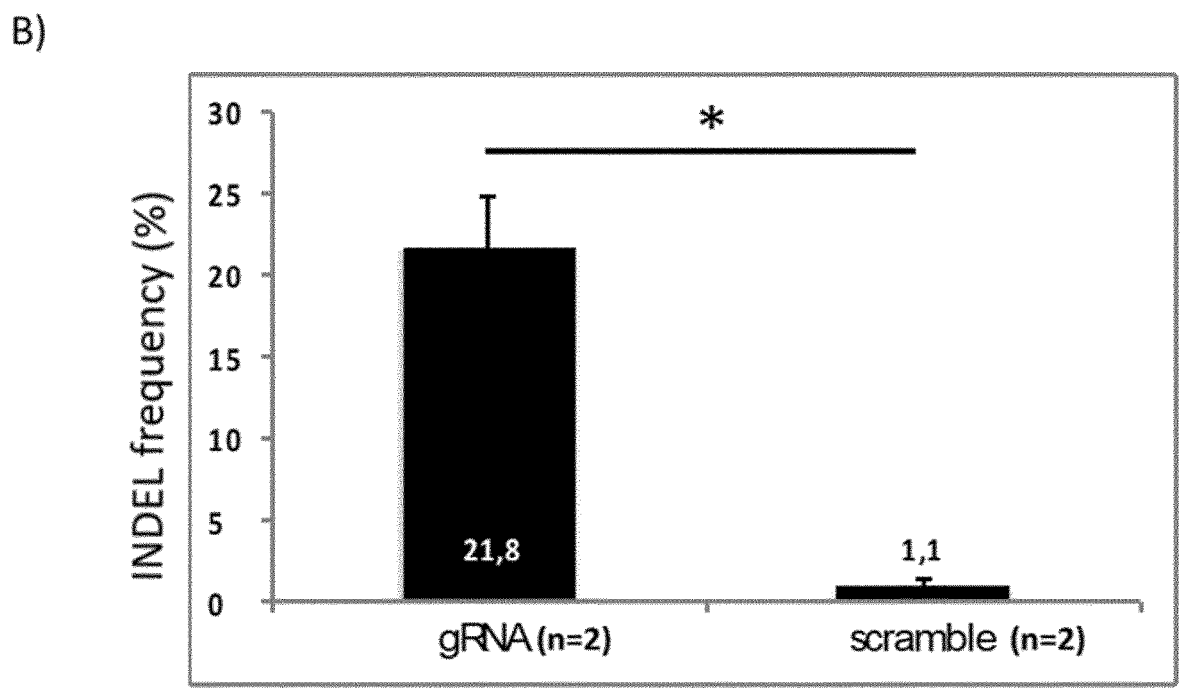
Fig. 8

A)
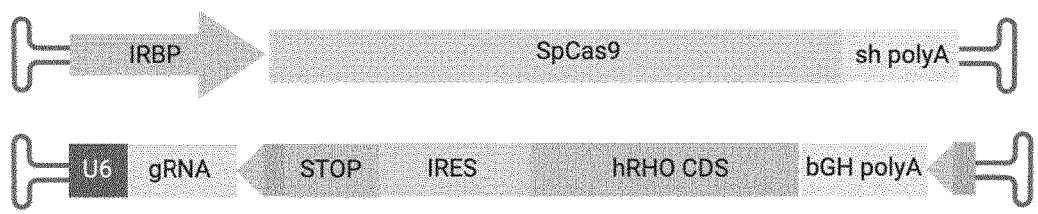
B)
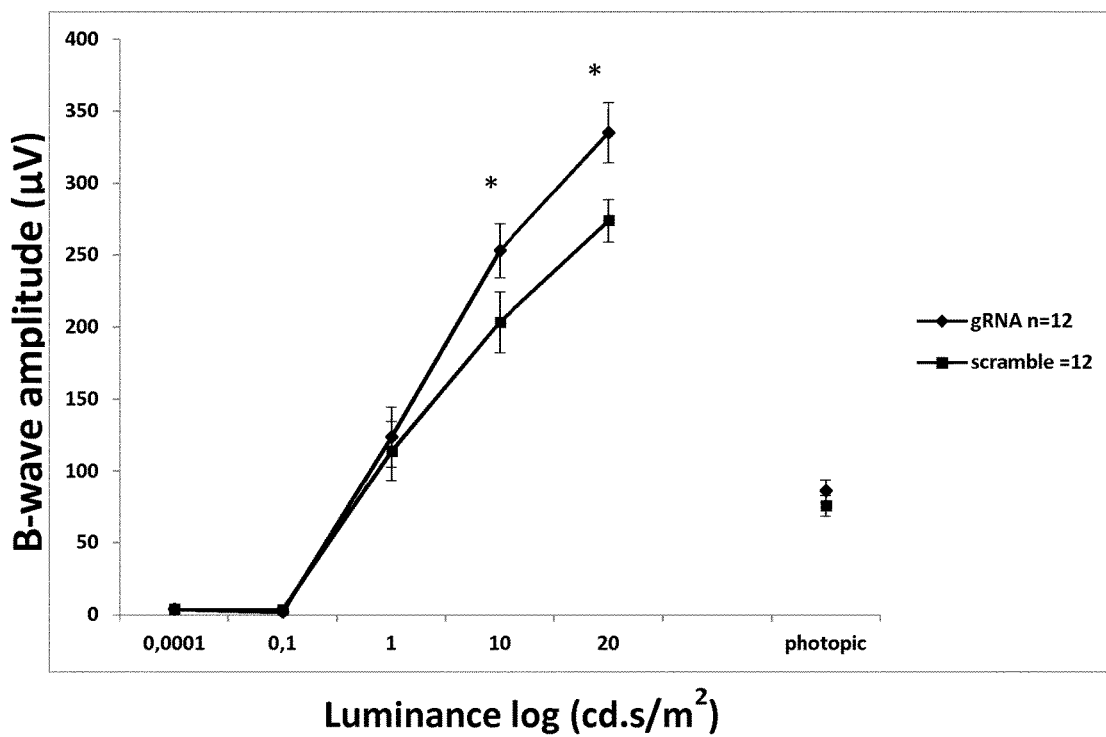
Fig. 9

A)
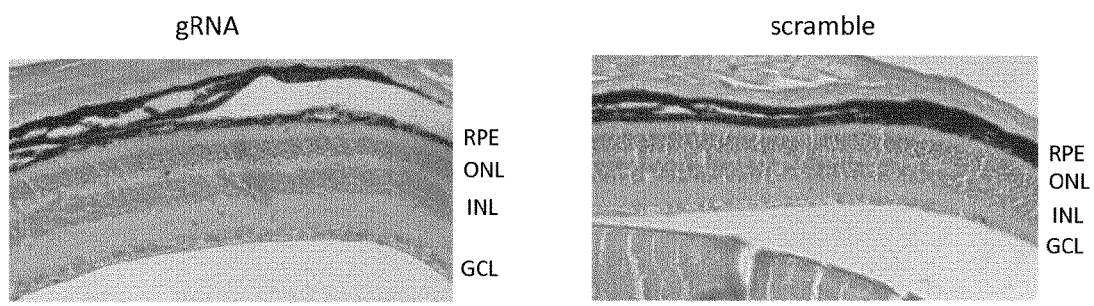
B)
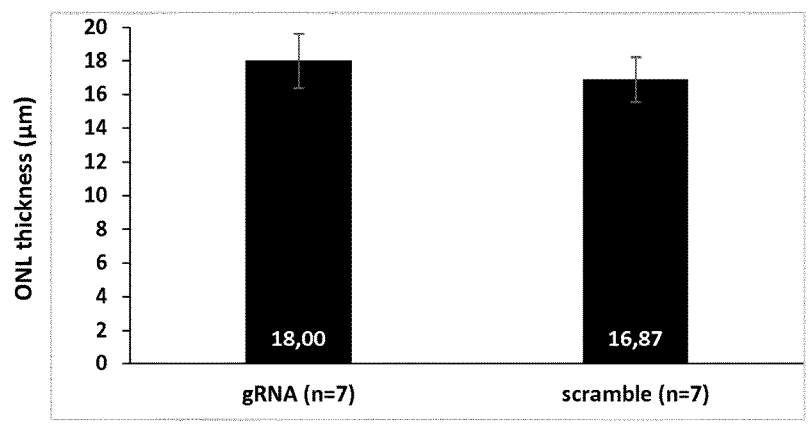
Fig. 10

A)
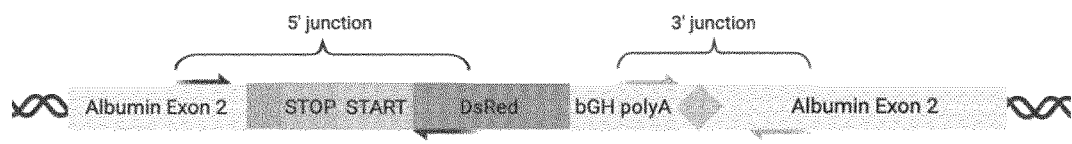
B)
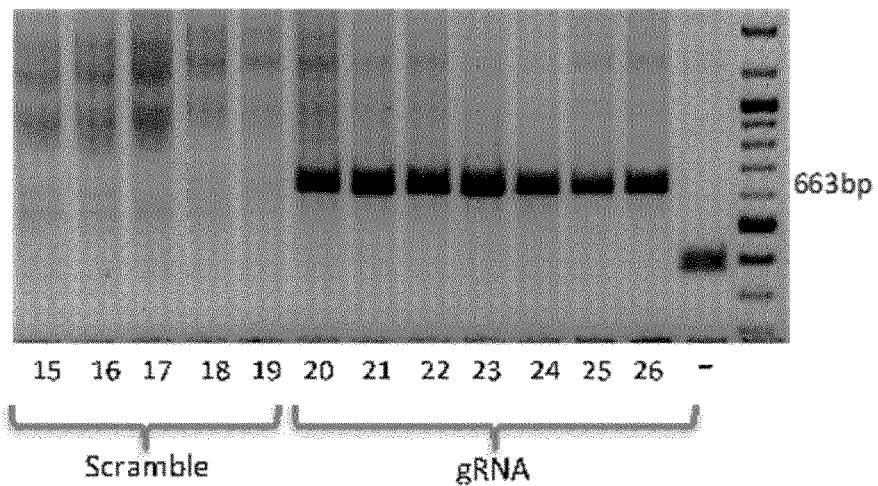
C)
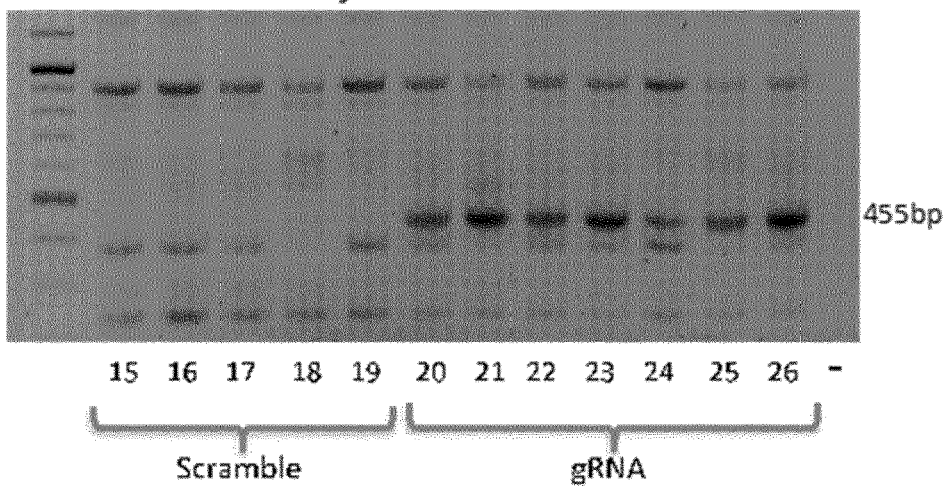
Fig. 15

A)
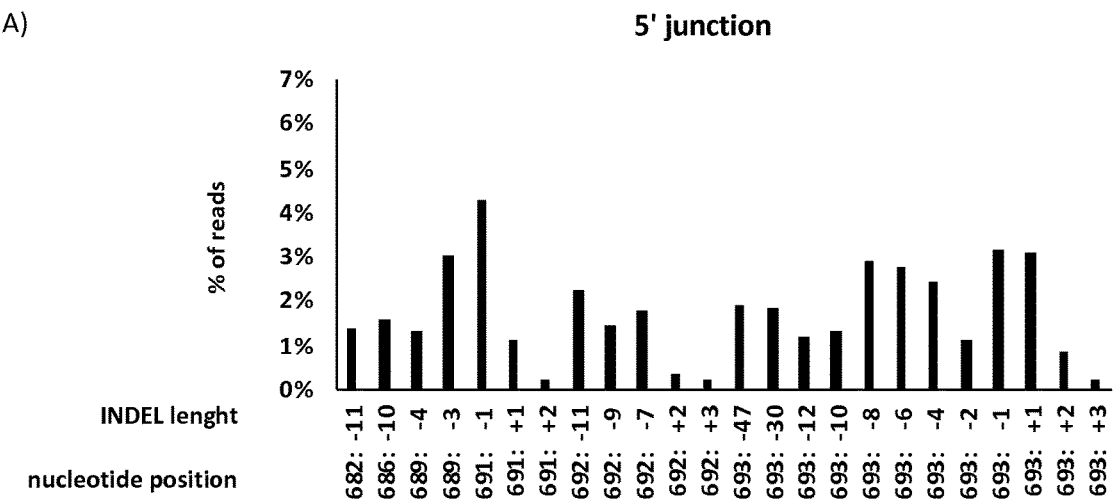
B)
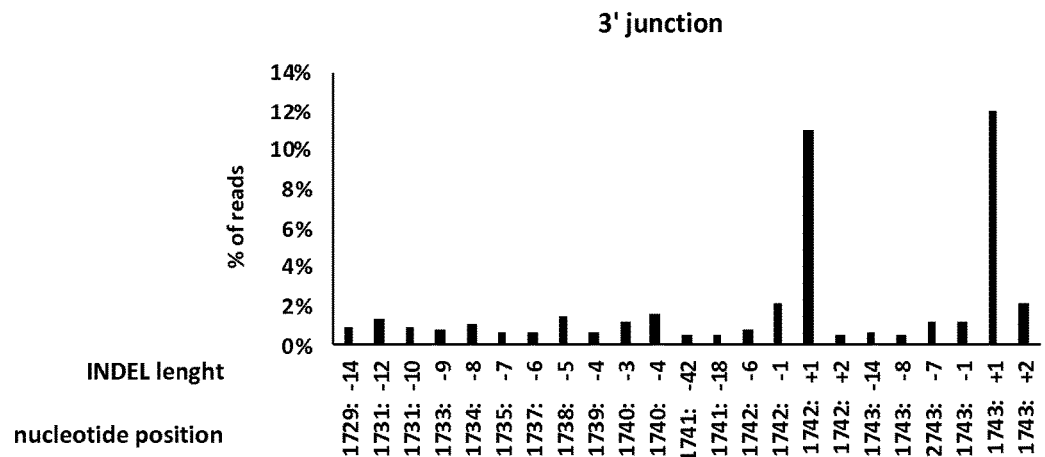
Fig. 16

GENOME EDITING METHODS AND CONSTRUCTS

CROSS-REFERENCE TO RELATED APPLICATIONS

This application is a 371 of PCT/EP2019/078019, filed Oct. 15, 2019, which claims the benefit of U.S. Provisional Patent Application No. 62/745,540, filed Oct. 15, 2018.

TECHNICAL FIELD

The present invention relates to a method of integrating an exogenous DNA sequence into a genome of a cell comprising contacting the cell with a donor nucleic acid, a complementary strand oligonucleotide homologous to the targeting sequence and a nuclease that recognizes the targeting sequence. The invention also relates to vectors comprising said donor nucleic acid and/or complementary strand oligonucleotide homologous to the targeting sequence and/or nuclease and to medical uses thereof.

BACKGROUND

Mendelian diseases inherited as dominant pose a problem for therapy, since conventional gene therapy can only replace gene function and is not able to avoid the degenerative effects of gain-of-function (GOF) mutations. Genome Editing has emerged in the last years as a viable option for the treatment of dominantly inherited diseases. Genome editing uses an endonuclease, usually CRISPR/Cas9 [1, 2]. CRISPR-Cas9 is a ribonucleoprotein that binds a sequence called guide RNA (gRNA) and uses it to recognize the target DNA sequence by Watson-Crick base complementarity. This target DNA sequence must be adjacent to a protospacer-adjacent motif (PAM) sequence, which allows Cas9 to bind to the DNA and cleave the target sequence [3]. The RNA-based targeting of Cas9 facilitates its design for targeting different loci and even allows the targeting of 2 different sequences by delivering Cas9 and 2 different gRNAs to the same cell. After Cas9 is targeted to a particular location in the genome, it generates a double-strand brake (DSB), which will be repaired by one of two repair mechanisms:

Non homologous end joining (NHEJ) is the most dominant mechanism in most cell types, since it is active in all phases of the cell cycle, and consists of the insertion or deletion of random bases in the site of the DSB in order to repair it. This random insertion or deletion (INDEL) often causes a change in the reading frame, thus knocking out the expression of the targeted gene [3]. Allele-specific knockout of a GOF mutation should leave the wildtype copy unaffected, thus maintaining the normal function of the gene while avoiding the effect of the GOF allele [4]. While this approach uses the widely active NHEJ repair pathway, its application is limited by both the availability of gRNA/PAM combinations at the GOF allele, and by a use that is restricted to that specific mutation, i.e. each mutation should have its own set of therapeutic AAV vectors; Homology-Directed Repair (HDR) is a process that occurs mainly in the G and S2 phases of the cell cycle, and uses a homologous template, which can be provided by an external donor DNA or by the other allele, for precise correction of the DSB. [3]. Gene correction by HDR has been successfully used in vitro [5] and in vivo [6-9], even in the absence of Cas9 [7]. However its efficiency in vivo is limited by the low activity of the homologous recombination pathway in differentiated cells [10]. Thus, there is a need in the field for alternative therapeutic gene replacement strategies which enable gene correction in tissues not undergoing active regeneration and in differentiated cells. There is a further need for mutation independent gene replacement strategies wherein both the mutant and wildtype alleles are exchanged with a correct copy of the gene allowing simultaneously silencing of the mutant allele and replacement of the wild type sequence. Homology-Independent Targeted Integration (HITI) has recently been developed [11, 12] to overcome the limitations of both allele-specific knock-out and gene correction by HDR. HITI uses a donor DNA that is flanked by the same gRNA target sequences within the gene of interest (FIG. 2). After Cas9 cleaves both the gene and the donor DNA, the NHEJ machinery of the cell can include the donor DNA in the repairing of the cleavage, with a surprisingly high (60-80%) rate of integration in the absence of INDELS. The possible inverted integration of the donor DNA is avoided by inverting its gRNA target sequences, so that Cas9 can recognize and cut again the target sequence if inverted integration occurs. Because HITI uses NHEJ, it is effective in terminally differentiated cells like neurons or tissues like liver independently of its regeneration potential (for instance both in adult and children tissues) [12]. In addition, HITI-mediated insertion of a wild-type copy of the therapeutic gene has the potential of being therapeutic independently of the specific disease-causing mutation and of the potential proliferative status of the target cells [12]. The present inventors have surprisingly found that HITI can be used for treatment of dominantly inherited diseases by replacing both the mutant and wildtype alleles with a correct copy of the gene provided by the donor DNA. This would avoid the target sequence restrictions imposed by allele-specificity of knockout and would broaden the applicability of the therapy to all mutations in the same gene as well as enabling targeting of non-dividing cells and tissues such as the nervous system or the retina. Furthermore, the inventors have used HITI to convert the liver in a factory for systemic release of high levels of a therapeutic protein, which is desirable for therapy of many inherited and common conditions caused by loss-of-function or conditions where the factor to be replaced is secreted from the liver and/or has to reach other target organs through the blood to perform its function, like in hemophilia, LSDs, or diabetes, overcoming limitations of current available therapies as the low efficient enzyme replacement therapy, traditional gene therapy and gene editing. Vectors based on adeno-associated viruses (AAVs) are the most frequently used for in vivo applications of gene therapy, because of their safety profile, wide tropism and ability to provide long-term transgene expression [13]. However, given the episomal status of AAV genomes, hepatic transgene expression from AAV can be lost over time in a developing liver or if there is hepatic damage [14]. Hence there is a need for more stable and efficient hepatic transgene expression. The AAV-mediated HITI overcomes said limitations by inserting the coding sequence of a secreted protein of interest, i.e. ARSB, in the highly-transcribed Albumin locus [6-9], providing long-term expression of high levels of proteins secreted systemically. Retinitis pigmentosa (RP) is a heterogeneous group of inherited retinal diseases (IRDs) affecting 1/3.000-5.000 people worldwide. 30-40% of all cases of RP have an autosomal dominant inheritance. Mutations in the rhodopsin (RHO) gene are responsible for about 25% of dominant RP cases in the United States and about 20% of cases elsewhere in the world. P23H is the most common mutation in North America, representing 9% of all cases of RP in the United States, and is almost absent in other continents. The P23H mutation impairs the correct folding of rhodopsin, and thus it accumulates in the endoplasmic reticulum (ER). This activates the Unfolded Protein Response (UPR) and the proteasome, in order to eliminate the mutant rhodopsin. Both mechanisms are constitutively activated by its presence, which leads to cytotoxicity in the photoreceptor. Several animal models carrying the P23H are widely used for research, especially the mRho-P23H knock-in and the hRHO-P23H transgenic mice. On the other side, mutations at the P347 (S and L) position are frequent in Europe and Asia. In Spain and Italy [18], P347L represents 4,5% of dominant RP. Mutations at the P347 position have a dominant negative effect, altering the trafficking of both mutant and wildtype rhodopsin to the outer segment of the rod. This causes impairment in the function of the rod in phototransduction and also the membrane trafficking, leading to the eventual death of the photoreceptor [19]. A transgenic mouse model expressing hRHO-P347S was generated by T.Dryja et al. and is herein used. In both cases, the disease phenotype is caused by a mutation with a gain-of-function/dominant negative effect, and thus reducing the levels of the toxic product, rather than or in addition to adding a correct copy of the gene (conventional gene therapy) is required to provide significant benefits. Thus, a desirable approach for treating dominant retinitis pigmentosa would be to specifically knockout the mutant allele without altering the wildtype allele. Recent efforts include knockdown of the P347S RHO mRNA using an engineered Zinc-Finger Nuclease and the allele-specific knockout of the GOF allele using endonucleases to cleave it. This depends on very specific recognition of the mutant allele, which most times is caused by a point mutation. Lately, different publications have shown the feasibility of allele-specific knockout in the retina for treatment of different kinds of Retinitis Pigmentosa. Bakondi et al showed that the mouse S334Ter-3 allele was discriminated from the WT rat allele in a transgenic rat model [22]. However, these approaches are tailored to one single mutation, and dominant retinitis pigmentosa can be caused by several different mutations. A need still exists for a therapeutic strategy that allows mutation independent silencing of the mutated allele and replacement with the functional gene, which will be applicable to more patients. Muccopolysaccharidosis type VI (MPS VI) is a rare lysosomal storage disorder (LSD) that is caused by arylsulfatase B (ARSB) deficiency, which results in widespread accumulation and urinary excretion of toxic glycosaminoglycans (GAGs). Clinically, the MPS VI phenotype is characterized by growth retardation, coarse facial features, skeletal deformities, joint stiffness, corneal clouding, cardiac valve thickening, and organomegaly, with absence of primary cognitive impairment [24]. Therapies for MPS rely on normal lysosomal hydrolases being secreted and then up taken by most cells via the mannose-6-phosphate receptor pathway. The present inventors demonstrated that a single systemic administration of a recombinant AAV vector serotype 8 (AAV2/8), which encodes ARSB under the transcriptional control of the liver-specific thyroxine-binding globulin (TBG) promoter (AAV2/8.TBG.hARSB), results in sustained liver transduction and phenotypic improvement in MPS VI animal models [25-31]. The present inventors also showed that this is at least as effective in MPS VI mice as weekly administrations of enzyme replacement therapy (ERT), which is the current standard of care for this condition [32-34]. The present inventors have recently initiated a phase I/II clinical trial (ClinicalTrials.gov Identifier: NCT03173521) to test both the safety and efficacy of this approach in MPS VI patients. HITI at the highly transcribed Albumin locus has the potential to overcome several limitations of the otherwise safe and effective liver gene therapy with AAV, including: i. levels of transgene expression, which are particularly high from the Albumin locus; ii. Stability of transgene expression guaranteed by the insertion of the therapeutic coding sequence at a genomic locus, which would be replicated should hepatocyte cell loss occur. The inventors' successful proof of efficacy of this approach in a model of lysosomal storage disease, MPS VI, lays the bases for a novel gene therapy strategy for other LSDs or other chronic debilitating conditions that require the stable expression of systemic therapeutic proteins such as hemophilia, alfa-1-antitrypsin deficiency, diabetes, chronic inflammatory bowel disease among others. Therefore, there is still the need for gene therapy strategies for diseases requiring stable systemic expression of therapeutic proteins.

SUMMARY OF THE INVENTION

The present invention relates to non homologous end joining (NHEJ)-based gene editing strategies to integrate exogenous constructs into target genes. Said strategies allow efficient targeting of non dividing cells, resulting in better targeting yields and expression of therapeutic levels of genes of interest. Favorably, the methods of the invention allow insertion of the corrected gene directly in the locus of the mutated allele, with the advantage of expressing the correct gene under the endogenous promoter, resulting in physiological levels of expression which is particularly advantageous for diseases where supraphysiological expression of the gene may result in toxic effects. A further advantage resulting from use of NHEJ in case of AAV mediated delivery of the therapeutic compositions of the invention is the ability of carrying larger exogenous constructs, and targeting diseases caused by mutations in large genes. In fact, compared to HDR-based gene editing strategies, the homologous regions needed for targeted integration are minimal. For dominant negative mutants like the Rho P347S, an additional advantage is the concomitant silencing of the toxic allele. The present invention is also amenable to gene specific targeting, depending on the guide RNA design, eg the guide RNA (gRNA or sgRNA) may recognize specifically the mutated allele versus the wild type allele. Advantageously, methods of the present invention may be directed to targeting a safe locus gene, eg a genomic locus known for being a neutral "safe" genomic region wherein insertion of exogenous gene sequences does not result in toxic events, for instance the AAVS1 site, and/or a gene expressed in a tissue of interest, for instance the Albumin gene locus. The present invention relies on insertion of the sequence of interest within the locus of a gene expressed at high levels in the liver, for instance albumin. Advantageously, as a consequence of the NHEJ mediated gene targeting, the albumin gene is not expressed and the gene of interest is expressed under the Albumin promoter. This results in high levels of expression of the gene of interest, albeit from a relatively small number of cells within the liver parenchima, therefore, albumin expression as a whole is not undermined, and expression of the gene of interest is sufficiently high to achieve a therapeutic effect. Furthermore, since the gene of interest is stably integrated in the liver genome, upon tissue regeneration (in children or upon liver damage), expression of the gene of interest is not lost.

DETAILED DESCRIPTION OF THE INVENTION

Therefore it is an object of the invention a method of integrating an exogenous DNA sequence into a genome of a cell comprising contacting the cell with:
 a) a donor nucleic acid comprising:
  at least one STOP codon and a translation initiation sequence (TIS) or
  a ribosomal skipping sequence, and
  said exogenous DNA sequence
  wherein said donor nucleic acid is flanked at 5' and 3' by inverted targeting sequences;
 b) a complementary strand oligonucleotide homologous to the targeting sequence and
 c) a nuclease that recognizes the targeting sequence.

Preferably the translation initiation sequence (TIS) is a kozak consensus sequence or an IRES sequence. Preferably, the ribosomal-skipping sequence is a T2A, P2A, E2A, F2A, preferably T2A sequence. Preferably said IRES sequence being a synthetic sequence of 60-70 bp, preferably of about 50 bp, more preferably of 50 bp.

In a preferred embodiment the donor nucleic acid comprises:
 at least one STOP codon and
 a translation initiation sequence (TIS), wherein said TIS is
  a kozak sequence or an IRES sequence being a synthetic sequence of 60-70 bp, preferably of about 50 bp, more preferably of 50 bp and
 said exogenous DNA sequence.

Preferably, the donor nucleic acid comprises STOP codons in the three possible frames, preferably said STOP codons in the three possible frames comprises or consists of two stop codons inserted in each frame, preferably said STOP codons in the three possible frames comprises or consists of the sequence of SEQ ID NO: 1 (TAATAAATAATAAATAATAA) or a permutation thereof. Preferably:
 the kozak consensus sequence comprises or has essentially:
  a sequence having at least 98% of identity to SEQ ID NO: 54 (gccacc) or functional fragments thereof or the sequence SEQ ID NO: 55 (gccncc) wherein n may be g or a, and/or
 the IRES sequence comprises or has essentially a sequence having at least 95% of identity to SEQ ID NO: 24 (TgACAAACTgTACATgCCgT-TAACTgTAATTTTgCgTgATTTTTTTgTAg) or SEQ ID NO: 23 (AggTggTAgCCgCAAACATAgTT-CAATACAAACTTgCTgTCTCggCgg) functional fragments thereof and/or
 the ribosomal-skipping T2A sequence comprises or has essentially a sequence having at least 80% of identity to SEQ ID NO: 32 (ggaagcggagagggcagaggaagtctgctaacatgcggtgacgtcgaggagaatcctggacct) sequence encoding for SEQ ID NO: 25-28 or functional fragments thereof and/or
 the targeting sequence comprises or has essentially a sequence having at least 95% of identity to SEQ ID NO: 29 (GCAGCCGCAGTACTACCTGG), SEQ ID NO: 30 (AGTACTGCGGATACTCAAAG), SEQ ID NO: 31 (ACAAGAGTGAGATCGCCCAT) or functional fragments thereof and/or
 the complementary strand oligonucleotide homologous to the targeting sequence comprises or has essentially a sequence having at least 95% of identity to SEQ ID NO: 56 (CCAGGTAGTACTGCGGCTGC), SEQ ID NO: 57 (CTTTGAGTATCCGCAGTACT), SEQ ID NO: 58 (ATGGGCGATCTCACTCTTGT) or functional fragments thereof.

In a preferred embodiment, the targeting sequence may comprise or have essentially a sequence having at least 95% of identity to SEQ ID NO: 56 (CCAGGTAGTACTGCGGCTGC), SEQ ID NO: 57 (CTTTGAGTATCCGCAGTACT), SEQ ID NO: 58 (ATGGGCGATCTCACTCTTGT) or functional fragments thereof and/or the complementary strand oligonucleotide homologous to the targeting sequence may comprise or have essentially a sequence having at least 95% of identity to SEQ ID NO: 29 (GCAGCCGCAGTACTACCTGG), SEQ ID NO: 30 (AGTACTGCGGATACTCAAAG), SEQ ID NO: 31 (ACAAGAGTGAGATCGCCCAT) or functional fragments thereof.

Preferably, the donor nucleic acid further comprises a polyadenylation signal, preferably a bovine growth hormone polyA.

Preferably, the targeting sequence is a sequence comprised in rhodopsin (Rho) or in a liver-expressed gene, e.g. albumin gene. Preferably, the targeting sequence is a sequence comprised in a liver-expressed gene and the donor DNA sequence is a coding sequence of a secreted therapeutic protein, e.g. arylsulfatase B (ARSB).

Preferably the targeting sequence is comprised within:
 the first exon of RHO gene, preferably from human, mouse or pig,
 the second exon of the albumin gene, preferably from human or mouse or functional fragments thereof.

Preferably, the targeting sequence is a guide RNA (gRNA) target site and said complementary strand oligonucleotide homologous to the targeting sequence is a guide RNA that hybridizes to a targeting sequence of a gene.

Said gRNA target site may comprise or have essentially sequence having at least 95% of identity to SEQ ID NO: 29 (GCAGCCGCAGTACTACCTGG), SEQ ID NO: 30 (AGTACTGCGGATACTCAAAG), SEQ ID NO: 31 (ACAAGAGTGAGATCGCCCAT) or functional fragments thereof and/or said guide RNA may comprise or have essentially a sequence having at least 95% of identity to SEQ ID NO: 29 (GCAGCCGCAGTACTACCTGG), SEQ ID NO: 30 (AGTACTGCGGATACTCAAAG), SEQ ID NO: 31 (ACAAGAGTGAGATCGCCCAT) or functional fragments thereof.

Said exogenous DNA sequence preferably comprises a reporter gene, preferably said reporter gene is selected from at least one of dicosoma red, green fluorescent protein (GFP), a red fluorescent protein (RFP), a luciferase, a β-galactosidase and a β-glucuronidase.

Said nuclease is preferably selected from: a CRISPR nuclease, a TALEN, a DNA-guided nuclease, a meganuclease, and a Zinc Finger Nuclease, preferably said nuclease is a CRISPR nuclease selected from the group consisting of: Cas9, Cpf1, Casl2b (C2cl), Casl3a (C2c2), Cas3, Csf1, Casl3b (C2c6), and C2c3 or variants thereof such as SaCas9 or VQR-Cas9-HF1.

Said complementary strand oligonucleotide, said donor nucleic acid said polynucleotide encoding the nuclease are preferably comprised in a viral or non-viral vector, preferably said viral vector being selected from: an adeno-associated virus, a lentivirus, a retrovirus and an adenovirus.

Preferably the cell is selected from the group consisting of: one or more of lymphocytes, monocytes, neutrophils, eosinophils, basophils, endothelial cells, epithelial cells, hepatocytes, osteocytes, platelets, adipocytes, cardiomyocytes, neurons, retinal cells, smooth muscle cells, skeletal muscle cells, spermatocytes, oocytes, and pancreas cells, induced pluripotent stem cells (iPScells), stem cells, hematopoietic stem cells, hematopoietic progenitor stem cells, preferably the cell is a cell of a retina of an eye or an hepatocyte of a subject.

Another object of the invention is a cell obtainable by the above defined, preferably for medical use or for use in treating a genetic disease or for use in treating dominantly inherited diseases wherein both the mutant and wildtype alleles are replaced with a correct copy of the gene provided by the donor DNA or for use in treating inherited and common diseases due to loss-of-function, preferably said diseases comprising haemophilia, diabetes, Lysosomal storage diseases comprising mucopolysaccharidoses (MPSI, MPSII, MPSIIIA, MPSIIIB, MPSIIIC, MPSIVA, MPSIVB, MPSVII), sphingolipidoses (Fabry's Disease, Gaucher Disease, Nieman-Pick Disease, GM1 Gangliosidosis), lipofuccinoses (Batten's Disese and others) and mucolipidoses; adenylosuccinate deficiency, hemophilia A and B, ALA dehydratase deficiency, adrenoleukodystrophy, Autosomal dominant. The above cell may be for use in treating dominantly inherited ocular, e.g. retinal degeneration, preferably retinitis pigmentosa, neuronal and hepatic diseases.

A further object of the invention is a system comprising:
a) a donor nucleic acid comprising:
  at least one STOP codon and a translation initiation sequence (TIS) or
  a ribosomal skipping sequence, and
  said exogenous DNA sequence
  wherein said donor nucleic acid is flanked at 5' and 3' by inverted targeting sequences;
b) a complementary strand oligonucleotide homologous to the targeting sequence and
c) a nuclease that recognizes the targeting sequence.

In a preferred embodiment the donor nucleic acid and/or the at least one STOP codon and/or a ribosomal skipping sequence and/or the translation initiation sequence (TIS) and/or the exogenous DNA sequence and/or the targeting sequences and/or the complementary strand oligonucleotide and/or the nuclease are as defined above.

Preferably, the complementary strand oligonucleotide and/or the donor nucleic acid and/or the polynucleotide encoding the nuclease are comprised in one or more viral or non-viral vector, preferably said viral vector being selected from: an adeno-associated virus, a retrovirus, an adenovirus and a lentivirus.

The system according to the invention is preferably for medical use, preferably for use in treating a genetic disease or for use in treating dominantly inherited diseases wherein both the mutant and wildtype alleles are replaced with a correct copy of the gene provided by the donor DNA or for use in treating inherited and common diseases due to loss-of-function, preferably said diseases comprising haemophilia, diabetes, Lysosomal storage diseases comprising mucopolysaccharidoses (MPSI, MPSII, MPSIIIA, MPSIIIB, MPSIIIC, MPSIVA, MPSIVB, MPSVII), sphingolipidoses (Fabry's Disease, Gaucher Disease, Nieman-Pick Disease, GM1 Gangliosidosis), lipofuccinoses (Batten's Disese and others) and mucolipidoses; adenylosuccinate deficiency, hemophilia A and B, ALA dehydratase deficiency, adrenoleukodystrophy, Autosomal dominant. The above cell may be for use in treating dominantly inherited ocular, e.g. retinal degeneration, preferably retinitis pigmentosa, neuronal and hepatic diseases.

Another object if the invention is an expression vector that comprises the system as above defined or the donor nucleic acid and/or the complementary strand oligonucle-otide homologous to the targeting sequence and/or a nuclease that recognizes the targeting sequence as above defined.

In the present invention the vector is preferably selected from the group consisting of: Adeno associated vector (AAV), adenoviral vector, lentiviral vector, retroviral vector or naked plasmid DNA vector. Another object of the invention is a host cell comprising the or an expression vector as above defined.

Another object of the invention is a viral particle that comprises the system or an expression vector s above defined.

Preferably the viral particle comprises capsid proteins of an AAV.

Preferably the viral particle comprises capsid proteins of an AAV of a serotype selected from one or more of the group consisting of AAV1, AAV2, AAV3, AAV4, AAV5, AAV6, AAV7, AAV8 AAV9 and AAV 10, preferably from the AAV2 or AAV8 serotype.

Another object of the invention is a pharmaceutical composition that comprises one of the following: system or an expression vector or a host cell or a viral particle as above defined and a pharmaceutically acceptable carrier.

Another object of the invention is a kit comprising: system or an expression vector or a host cell or a viral particle as above defined or a pharmaceutical composition as above defined in one or more containers, optionally further comprising instructions or packaging materials that describe how to administer the nucleic acid construct, vector, host cell, viral particle or pharmaceutical composition to a patient.

The system or an expression vector or a host cell or a viral particle as above defined or a pharmaceutical composition as above defined are preferably for use as a medicament, preferably for use in the treatment of retinal dystrophy, preferably the retinal dystrophy is selected from retinitis pigmentosa, Leber's congenital amaurosis, cone dystrophy or cone-rod dystrophy, Stargardt's Disease (ELOVL4), Von-Hippel Lindau, Retinoblastoma, neuronal, hepatic diseases, Lysosomal storage diseases comprising mucopolysacchari-doses (MPSI, MPSII, MPSIIIA, MPSIIIB, MPSIIIC, MPSIVA, MPSIVB, MPSVII), sphingolipidoses (Fabry's Disease, Gaucher Disease, Nieman-Pick Disease, GM1 Gangliosidosis), lipofuccinoses (Batten's Disese and others) and mucolipidoses; other diseases where the liver can be used as a factory for production and secretion of therapeutic proteins, like diabetes, adenylosuccinate deficiency, hemophilia A and B, ALA dehydratase deficiency, adrenoleukodystrophy, Autosomal dominant.

A further object of the invention is an expression vector as above defined for the production of viral particles.

Preferably, object of the invention are the sequences herein mentioned.

Preferably, the donor DNA cassette elements and/or the gRNA expression cassette elements and/or the promoter sequences and/or U6 promoter for gRNA expression and/or the gRNA and/or the gRNA target site and/or the Cas9/Cas9-2a-GFP and/or the therapeutic transgene And/or the polyA and/or the STOP SIGNAL and/or the START SIGNAL (Kozak/T2A/IRES) are the sequences depicted in the following sequences SEQ ID NOs 3-22.

In an embodiment, the methods of the invention are ex-vivo o in vitro.

In an embodiment, in the methods of the invention the cell is an isolated cell from a subject or a patient.

The inverted targeting sequences in the context of the present invention are positioned upstream and downstream of the donor DNA, which is the DNA construct that is cut and then integrated in the target genome. The inverted targeting sequences are the same exact sequences as those that recognize the guide RNA in the target genomic locus (e.g. albumin or rhodopsin) but inverted. This allows to obtain a mono-directional integration.

Preferably, when the translation initiation sequence (TIS) is a ribosomal-skipping T2A sequence or the ribosomal-skipping T2A sequence is present, the at least one STOP codon is not present. Preferably, the at least one STOP codon is selected from the group consisting of: TAG, TAA, TGA. In order to insert STOP codons in the three possible frames, two stop codons are inserted in each frame, for e.g. TAATAAATAATAAATAATAA (SEQ ID NO: 1). Any permutation or combination of the above STOP codons may be used.

The sequence of rhodopsin (Rho) is preferably disclosed with the following Accession numbers: human: AB065668.1, mouse: AC142099.3, pig: AEMK02000087.1, while the sequence of albumin is preferably described with the following Accession n. AC140220.4.

The dicosoma red has preferably the sequence of SEQ ID NO: 2

(atggatagcactgagaacgtcatcaagcccttcatgcgcttcaaggtg cacatggagggctccgtgaacggccacgagttcgagatcgagggcgagg gcgagggcaagccctacgagggcacccagaccgccaagctgcaggtgac caagggcggcccctgcccttcgcctgggacatcctgtcccccagttc cagtacggctccaaggtgtacgtgaagcacccgccgacatccccgact acaagaagctgtccttccccgagggcttcaagtgggagcgcgtgatgaa cttcgaggacggcggcgtggtgaccgtgacccaggactcctccctgcag gacggcaccttcatctaccacgtgaagttcatcggcgtgaacttcccct ccgacggccccgtaatgcagaagaagactctgggctgggagccctccac cgagcgcctgtaccccgcgacggcgtgctgaagggcgagatccacaag gcgctgaagctgaagggcggcggccactacctggtggagttcaagtcaa tctacatggccaagaagcccgtgaagctgcccggctactactacgtgga ctccaagctggacatcacctcccacaacgaggactacaccgtggtggag cagtacgagcgcgccgaggcccgccaccacctgttccag).

In the method according to the invention the exogenous DNA comprises at least one nucleotide difference compared to the genome.

In a preferred embodiment of the invention, one vector comprising IRBP and Cas9 is used together with a second vector comprising the donor DNA as defined above The donor DNA sequence is preferably flanked at 3' and 5' by the same gRNA target site that the gRNA recognizes, but inverted (e.g. an inverted target site).

The cell obtainable according to the invention expresses the exogenous sequence.

In the context of the present invention, the nuclease is preferably present in a different vector, in particular when AAV vectors are used.

Preferably AAV2/8 vectors are used.

In the present invention, a first vector comprising Cas9 or spCas9 is preferably under the control of a tissue specific promoter, e.g. a liver specific hybrid liver promoter (HLP) or a retina specific. Said vector may further comprise a short syntethic polyA (sh polyA). Preferably, a second vector comprises the gRNA expression cassette and the donor DNA as defined above. Preferably, the gRNA specific for albumin is under the U6 promoter. Preferably the donor DNA is flanked at 3' and 5' by the inverted albumin gRNA target sites, preferably comprising the PAM.

Preferably the above second vector may alternatively comprise the expression cassette for the Albumin-specific gRNA and the donor DNA comprising the coding sequence for ARSB, as defined above.

In a preferred embodiment, the gene of interest as well as the enzyme necessary for the NHEJ site specific insertion are carried by two AAV vectors, wherein due to the limited size of the element needed for the process, larger genes of interest may be employed. Inventors indeed minimized the structural parts (using e.g. insertions sites instead of homology arms) allowing to insert a longer cDNA in the vector.

In the context of the present invention the donor nucleic acid is inserted into the gene via nonhomologous end joining.

The invention also provides a pharmaceutical composition comprising the nucleic acid as defined above or the nucleotide sequence as defined above or the vector as defined above and pharmaceutically acceptable diluents and/or excipients and/or carriers.

Preferably the composition further comprising a therapeutic agent, preferably the therapeutic agent is selected from the group consisting of: enzyme replacement therapy and small molecule therapy.

Preferably the pharmaceutical composition is administered through a route selected from the group consisting of: intra cerebral spinal fluid (CSF), intrathecal, parenteral, intravenous, intralesional, intraperitoneal, intramuscular, intratumoral, subcutaneous, intraventricular, intra cisterna magna, lumbar, intracranial, intraspinal, intravenous, topical, nasal, oral, ocular, subretinal or any combination thereof.

The present invention also provides a vector comprising the above nucleic acid or nucleotide sequence for medical use, wherein said vector is administered through a route selected from the group consisting of: intra cerebral spinal fluid (CSF), intrathecal, parenteral, intravenous, intralesional, intraperitoneal, intramuscular, intratumoral, subcutaneous, intraventricular, intra cisterna magna, lumbar, intracranial, intraspinal, intravenous, topical, nasal, oral, ocular, subretinal or any combination thereof. Preferably the vector of the invention is administered through intravenous, parenteral, ocular, preferably sub retinal route.

Preferably the vector is a viral vector, preferably the viral vector is a lentiviral vector, an adeno-associated virus vector, an adenoviral vector, a retroviral vector, a polio viral vector, a murine Maloney-based viral vector, an alpha viral vector, a pox viral vector, a herpes viral vector, a vaccinia viral vector, a baculoviral vector, or a parvoviral vector, preferably the adeno-associated virus is AAV2, AAV9, AAV1, AAVSH19, AAVPHP.B, AAV8, AAV6.

Preferably said nucleotide sequence is inserted in a vector, preferably a viral vector, still preferably an adeno-associated vector.

In the present invention "at least 80% identity" means that the identity may be at least 80%, or 85% or 90% or 95% or 100% sequence identity to referred sequences. This applies to all the mentioned % of identity. In the present invention "at least 95% identity" means that the identity may be at least 95%, 96%, 97%, 98%, 99% or 100% sequence identity to referred sequences. This applies to all the mentioned % of identity. In the present invention "at least 98% identity" means that the identity may be at least 98%, 99% or 100% sequence identity to referred sequences. This applies to all the mentioned % of identity. Preferably, the % of identity relates to the full length of the referred sequence.

Included in the present invention are also nucleic acid sequences derived from the nucleotide sequences herein mentioned, e.g. functional fragments, mutants, variants, derivatives, analogues, and sequences having a % of identity of at least 80% with the sequences herein mentioned.

The invention will be now illustrated by means of non-limiting examples referring to the following figures.

BRIEF DESCRIPTION OF THE DRAWINGS

FIG. 2. In vitro testing of HITI in mRho: A) Plasmids used for transfection in HEK293 cells: yellow rectangle and blue triangle depict the two parts of the gRNA target sequence (upstream and downstream of Cas9 cleavage respectively). Cbh: chicken beta-actin hybrid promoter. STOP: STOP codons, START: translation start site, bGH: bovine Growth Hormone polyA. Cells were fixed for 15 minutes in PFA 4% and stained using a DAPI-containing mounting medium. B) Fluorescence microscopy of HEK293 cells 48 h after transfection: Cells were fixed for 15 minutes in PFA 4% and stained using a DAPI-containing mounting medium. C) Representative FACS graphs of fluorescent HEK293 cells: Cells were detached 48 h after transfection using trypsin 0.05% EDTA. 10.000 cells were counted for each sample. Q1: EGFP−/DsRed+, Q2: EGFP+/DsRed+, Q3: EGFP−/DsRed−, Q4: EGFP+/DsRed−. Red square depicts sorted cells. PE-A: DsRed fluorescence filter. FITC-A: EGFP fluorescence filter. D) Quantification of DsRed+ cells inside the EGFP+ population.

FIG. 6. NGS characterization of HITI junctions in mRho: Relative INDEL frequency in each position surrounding the cleavage site. Negative and positive numbers represent deletions and insertions respectively. +1 position regarding cleavage site is underlined with a blue line. Only INDELs with a relative frequency higher than 0.05% in their position are depicted.

FIG. 7. HITI in the suine retina: A) DsRed+ photoreceptors are only present in gRNA-treated retinae. B) Quantification of DsRed+ photoreceptors to assess HITI efficiency in the pig retina.***=p>0.001

FIG. 8. INDEL characterization in pRho. A) Surveyor Assay in the pRho locus using DNA extracted from retina or RPE: T7E: T7 Endonuclease I treatment. Sizes of PCR product and expected cleavage bands are depicted. B) TIDE analysis of the pRho locus: PCR products amplified from DNA extracted from retina or RPE were sequenced. RPE sequence was used as a template for TIDE. Chromatograms were used to deconstruct frequency and type of INDELs. A) Representative TIDE result. B) Quantification of INDEL frequency in pig retinae.

FIG. 9. Correction of RP phenotype using HITI. A) Schematic depiction of AAV vectors used for therapy in P23H+/− mice: ITRs are depicted in blue. IRBP: interphotoreceptor retinoid-binding protein promoter. shpolyA: short synthetic polyA. hRHO CDS: coding sequence of the human RHO gene, bGH: bovine growth hormone polyA. yellow rectangle and blue triangle depict the two parts of the gRNA target sequence (upstream and downstream of Cas9 cleavage). B) Improvement of ERG B-wave in P23H mice at p60. Cd.s/m2=candles per square meter. *=p<0.05

FIG. 10. Histological analysis of ONL thickness: A) Microscopy images of hematoxylin-eosin staining of retinas harvested at p120. B) Quantification of ONL thickness in the temporal region of analyzed retinas.

A) Design of the hRHO-2A-DsRed construct. B) Fluorescence microscopy shows no difference in HITI efficiency with 2 donor DNAs of different sizes. C) FACS quantification of DsRed+/GFP+ cells.

FIG. 12. Schematic depiction of HITI design for integration in the Albumin locus and of gRNA and viral vectors used: A) Design of the gRNA specific for the 2nd intron of the murine Albumin gene. PAM sequence is depicted in red and underlined. B) Schematic depiction of the AAV2/8 vectors used for HITI in the mouse liver. Donor DNA is flanked by the same gRNA target sequences. Donor DNA contains STOP codons in the 3 frames, a translation START sequence (kozak), the reporter gene DsRed and the bGH poly-A. C) Depiction of the expected HITI after Cas9 and donor DNA delivery. Scissors represent Cas9-mediated DBSs. Crossed scissors represent inability of Cas9 to recognize target sites.

One month after injection livers were harvested and imaged. A) Stereomicroscope imaging of the fresh liver shows widespread presence of DsRed+ foci only in gRNA-treated livers. B) Fluorescence microscopy of liver cryosections shows foci of DsRed+ hepatocytes. C) Quantification of DsRed+ hepatocytes. *** p<0,0001.

Figure 14:
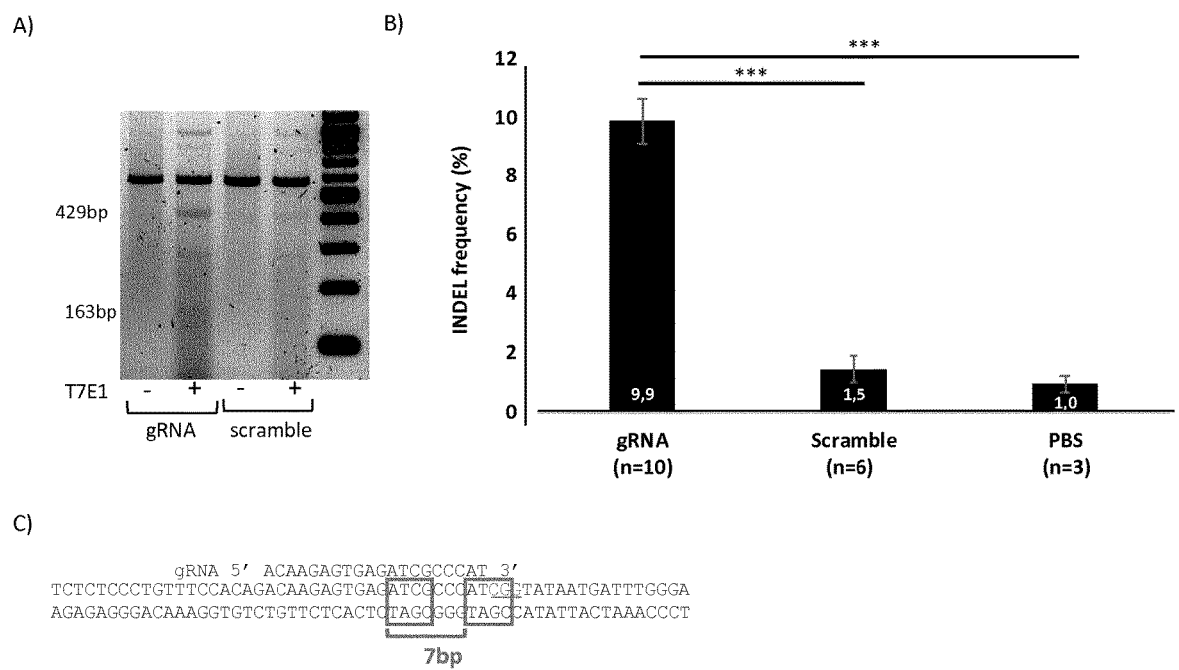

FIG. 14. INDEL characterization. A) Surveyor Assay for INDEL detection at the albumin 2° exon. DNA was extracted from liver and used for PCR amplification of the genomic region surrounding the Cas9 target sequence. A 592 bp fragment was amplified. Expected size of T7E1 digestion products is depicted. T7E1: T7 Endonuclease I treatment. B) Quantification of INDEL frequency. Not significative INDELs observed in scramble and PBS were included. C) Schematic depiction of a common 7 bp deletion due to microhomology-mediated end joining (MMEJ) DSB repair. Microhomology regions are depicted with blue squares. PAM is depicted in RED and underlined.

FIG. 15. HITI Junction amplification. A) Scheme depicting primer design to amplify 5' and 3' junctions. B) 5' junction amplification. Expected fragment size was 663 bp. PCR amplification was observed in all gRNA-treated and absent in all scramble-treated livers. C) 3' junction amplification. Expected fragment size was 455 bp. PCR amplification was observed in all gRNA-treated and absent in all scramble-treated livers.

FIG. 16. NGS of HITI junctions in the Alb locus. Distribution of Insertion and Deletion frequencies in NGS reads of HITI junctions. A) 5' junction: total reads=80.000-100.000, B) 3' junction: total reads=250.000-350.000. Negative and positive numbers represent deletions and insertions respectively. Blue bar shows the +1 position after the DSB.

Figure 17:
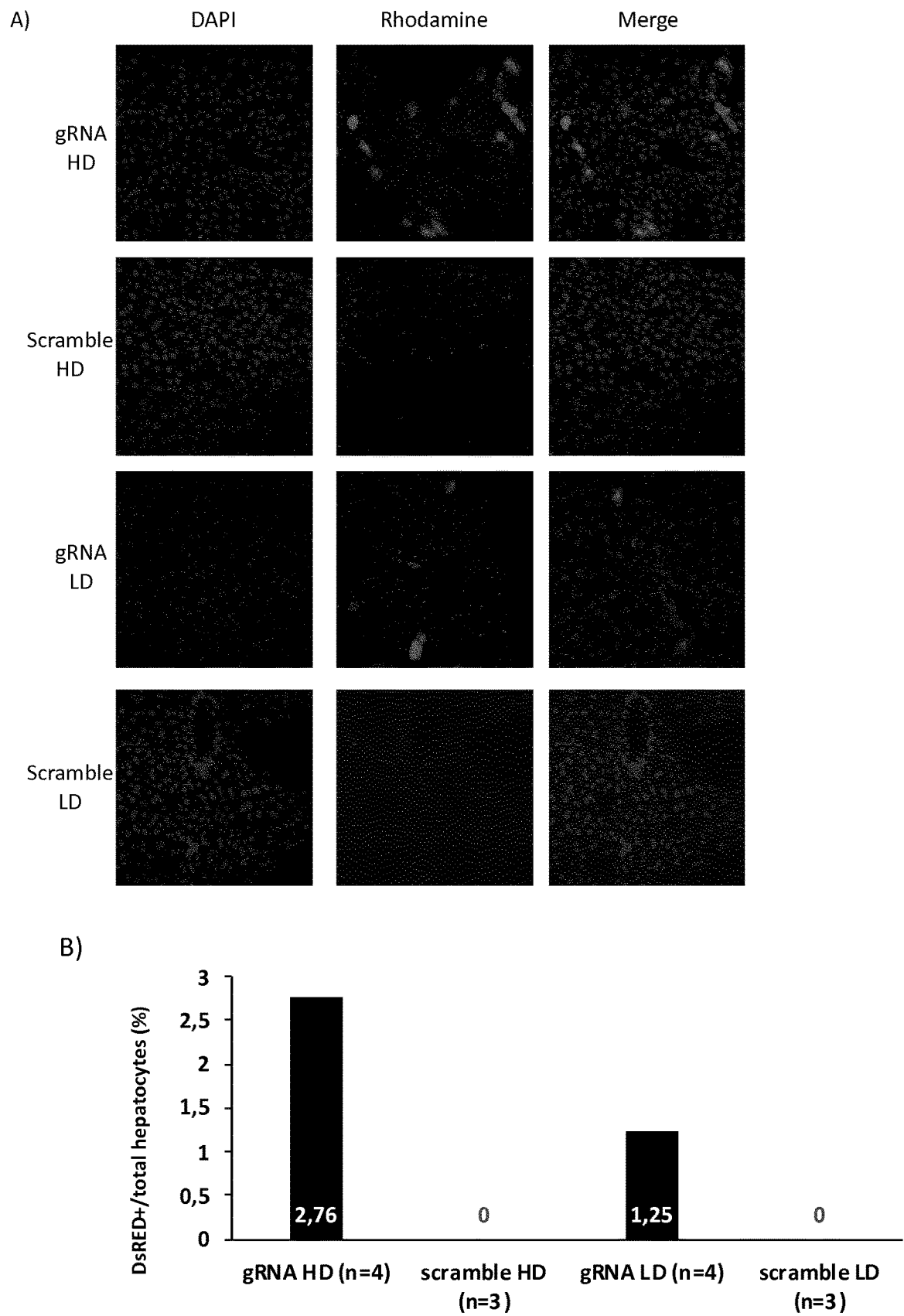

FIG. 17. HITI is efficient and dose dependent in adult mouse liver. 4-week old C57BL/6 mice were injected with $4*10^{13}$GC/Kg (High Dose, HD) or $1,3*10^{13}$GC/Kg (Low Dose, LD) of each vector. A) Fluorescence microscopy of liver cryosections. B) Quantification of DsRed+ hepatocytes.

Figure 18:
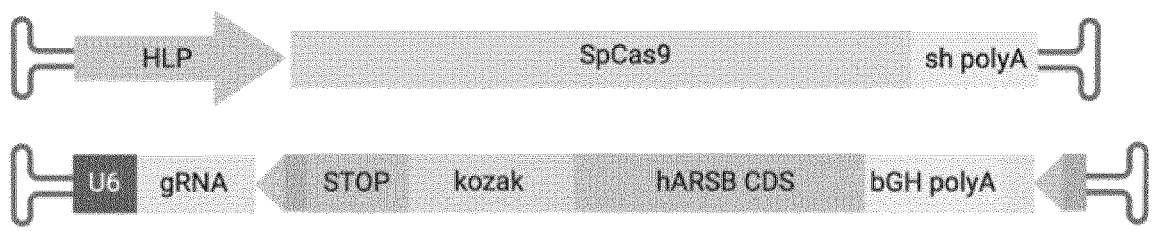

FIG. 18. Design of AAV used to integrate the ARSB coding sequence in the albumin locus of mouse hepatocytes. HLP: Hybrid liver promoter, sh polyA: Short polyA, U6: U6 promoter for RNA polymerase 3, STOP: STOP codons in 3 different frames. hARSB CDS: coding sequence of human arylsulfatase B, bGH poly-A: Bovine Growth Hormone poly-A. Stuffer DNA is depicted in grey. Yellow rectangle and blue triangle depict the two parts of the gRNA target sequence (upstream and downstream of Cas9 cleavage).

Figure 19:
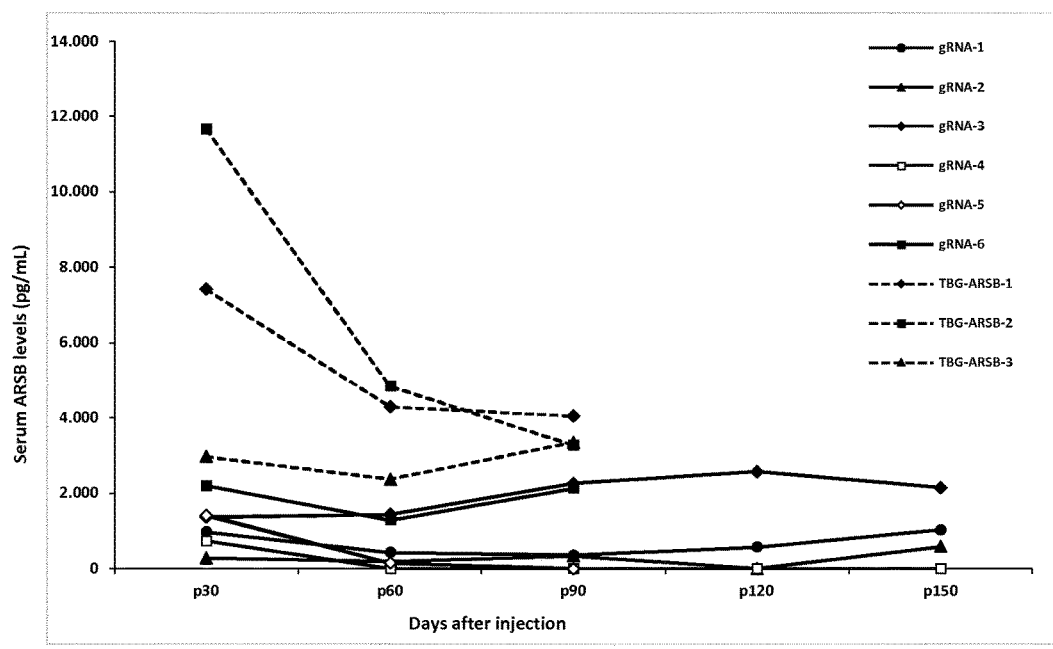

FIG. 19. ARSB levels in mouse serum. Serum ARSB was measured monthly using an immunoassay with an antibody against human ARSB. Values observed at each timepoint are represented separately for each mouse.

Figure 20:
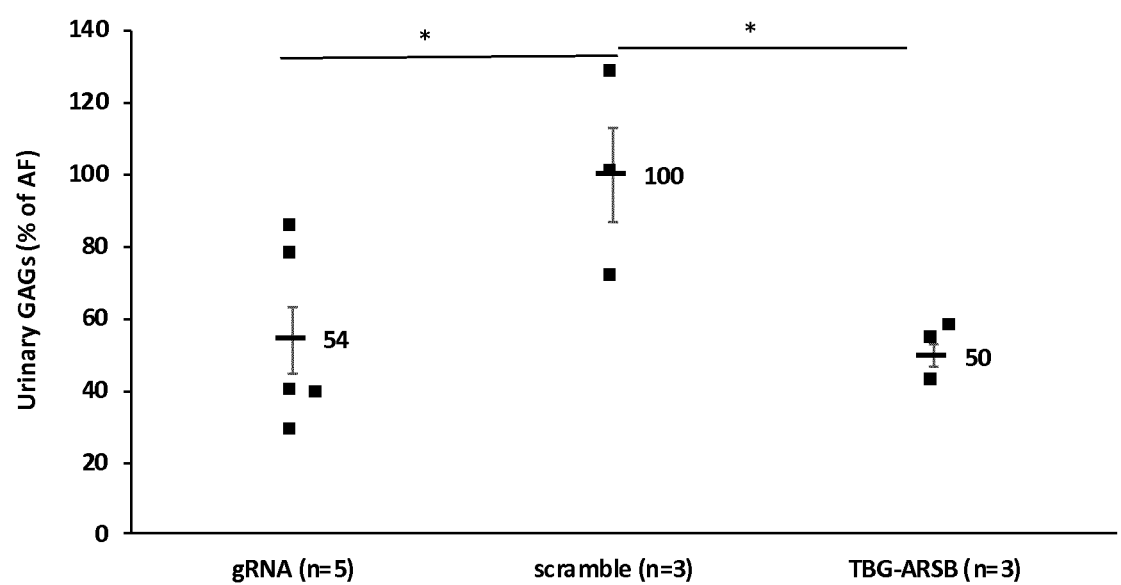

FIG. 20. Urinary GAGs are reduced 3 months after treatment. Urinary GAGs were measured from urine collected 3 months after injection. GAG levels were normalized with creatinine levels. Results are represented as percentage relative to GAG levels in control affected mice treated with scramble gRNA. Circles represent single analyzed mice. Bars represent group means and standard error.

DESCRIPTION OF THE SEQUENCES IN THE SEQUENCE LISTING

Legend:
Donor DNA cassette elements are highlighted in dark grey
gRNA expression cassette elements are highlighted in light grey
Promoter sequence are underlined
U6 promoter for gRNA expression
gRNA
gRNA target site
Cas9/Cas9-2a-GFP
therapeutic transgene
polyA
STOP SIGNAL (STOP CODONS IN DIFFERENT FRAMES)
START SIGNAL: Kozak/T2A/IRES

```
P939// pSpCas9(BB)-2A-GFP + gRNAScramble
                                                                    (SEQ ID NO: 3)
atgtgagggcctatttcccatgattccttcatatttgcatatacgatacaaggctgttagagagataattggaattaatttgactgtaaac acaaagatattagtacaaaatacgtgacgtagaaagtaataatttcttgggtagtttgcagttttaaaattatgttttaaaatggactatc atatgcttaccgtaacttgaaagtatttcgatttcttggctttatatatcttGTGGAAAGGACGAAACACCGGACTCGCGCG AGTCGAGGAGgttttagagctaGAAAtagcaagttaaaataaggctagtccgttatcaacttgaaaaagtggcaccgagtcggt gcTTTTTTgttttagagctagaaatagcaagttaaaataaggctagtccgtTTTTagcgcgtgcgccaattctgcagacaaatggct ctagaggtacccgttacataacttacggtaaatggcccgcctggctgaccgcccaacgaccccgcccattgacgtcaatagtaacgcc aatagggactttccattgacgtcaatgggtggagtatttacggtaaactgcccacttggcagtacatcaagtgtatcatatgccaagtac gccccctattgacgtcaatgacggtaaatggcccgcctggcattGtgcccagtacatgaccttatgggactttcctacttggcagtacat ctacgtattagtcatcgctattaccatggtcgaggtgagccccacgttctgcttcactctcccatctccccccctcccaccccaatttt gtatttatttattttttaattatttttgtgcagcgatggggcggggggggggggggcgcgcgccaggcggggcgggggggcgag gggcggggcgggcgaggcggagaggtgcggcggcagccaatcagagcggcgcgctccgaaagtttccttttatggcgaggcggcg gcggcggcggccctataaaaagcgaagcgcgcggggggggagtcgctgcgacgctgccttcgccccgtgcccgctccgccgccg cctcgcgccgcccgccccggctctgactgaccgcgttactcccacaggtgagcgggggacggcccttctcctccgggctgtaattagc tgagcaagaggtaagggtttaagggatggttggttggtggggtattaatgtttaattacctggagcacctgcctgaaatcacttttttttca ggttGGaccggtgccaccATGGACTATAAGGACCACGACGGAGACTACAAGGATCATGATATTGATTACAA
```

-continued

```
AGACGATGACGATAAGATGGCCCCAAAGAAGAAGCGGAAGGTCGGTATCCACGGAGTCCCAGCAGCC

GACAAGAAGTACAGCATCGGCCTGGACATCGGCACCAACTCTGTGGGCTGGGCCGTGATCACCGACG

AGTACAAGGTGCCCAGCAAGAAATTCAAGGTGCTGGGCAACACCGACCGGCACAGCATCAAGAAGAA

CCTGATCGGAGCCCTGCTGTTCGACAGCGGCGAAACAGCCGAGGCCACCCGGCTGAAGAGAACCGCC

AGAAGAAGATACACCAGACGGAAGAACCGGATCTGCTATCTGCAAGAGATCTTCAGCAACGAGATGG

CCAAGGTGGACGACAGCTTCTTCCACAGACTGGAAGAGTCCTTCCTGGTGGAAGAGGATAAGAAGCA

CGAGCGGCACCCCATCTTCGGCAACATCGTGGACGAGGTGGCCTACCACGAGAAGTACCCCACCATCT

ACCACCTGAGAAAGAAACTGGTGGACAGCACCGACAAGGCCGACCTGCGGCTGATCTATCTGGCCCTG

GCCCACATGATCAAGTTCCGGGGCCACTTCCTGATCGAGGGCGACCTGAACCCCGACAACAGCGACGT

GGACAAGCTGTTCATCCAGCTGGTGCAGACCTACAACCAGCTGTTCGAGGAAAACCCCATCAACGCCA

GCGGCGTGGACGCCAAGGCCATCCTGTCTGCCAGACTGAGCAAGAGCAGACGGCTGGAAAATCTGAT

CGCCCAGCTGCCCGGCGAGAAGAAGAATGGCCTGTTCGGAAACCTGATTGCCCTGAGCCTGGGCCTG

ACCCCCAACTTCAAGAGCAACTTCGACCTGGCCGAGGATGCCAAACTGCAGCTGAGCAAGGACACCTA

CGACGACGACCTGGACAACCTGCTGGCCCAGATCGGCGACCAGTACGCCGACCTGTTTCTGGCCGCCA

AGAACCTGTCCGACGCCATCCTGCTGAGCGACATCCTGAGAGTGAACACCGAGATCACCAAGGCCCCC

CTGAGCGCCTCTATGATCAAGAGATACGACGAGCACCACCAGGACCTGACCCTGCTGAAAGCTCTCGT

GCGGCAGCAGCTGCCTGAGAAGTACAAAGAGATTTTCTTCGACCAGAGCAAGAACGGCTACGCCGGC

TACATTGACGGCGGAGCCAGCCAGGAAGAGTTCTACAAGTTCATCAAGCCCATCCTGGAAAAGATGGA

CGGCACCGAGGAACTGCTCGTGAAGCTGAACAGAGAGGACCTGCTGCGGAAGCAGCGGACCTTCGAC

AACGGCAGCATCCCCCACCAGATCCACCTGGGAGAGCTGCACGCCATTCTGCGGCGGCAGGAAGATTT

TTACCCATTCCTGAAGGACAACCGGGAAAAGATCGAGAAGATCCTGACCTTCCGCATCCCCTACTACGT

GGGCCCTCTGGCCAGGGGAAACAGCAGATTCGCCTGGATGACCAGAAAGAGCGAGGAAACCATCACC

CCCTGGAACTTCGAGGAAGTGGTGGACAAGGGCGCTTCCGCCCAGAGCTTCATCGAGCGGATGACCA

ACTTCGATAAGAACCTGCCCAACGAGAAGGTGCTGCCCAAGCACAGCCTGCTGTACGAGTACTTCACC

GTGTATAACGAGCTGACCAAAGTGAAATACGTGACCGAGGGAATGAGAAAGCCCGCCTTCCTGAGCG

GCGAGCAGAAAAAGGCCATCGTGGACCTGCTGTTCAAGACCAACCGGAAAGTGACCGTGAAGCAGCT

GAAAGAGGACTACTTCAAGAAAATCGAGTGCTTCGACTCCGTGGAAATCTCCGGCGTGGAAGATCGGT

TCAACGCCTCCCTGGGCACATACCACGATCTGCTGAAAATTATCAAGGACAAGGACTTCCTGGACAATG

AGGAAAACGAGGACATTCTGGAAGATATCGTGCTGACCCTGACACTGTTTGAGGACAGAGAGATGAT

CGAGGAACGGCTGAAAACCTATGCCCACCTGTTCGACGACAAAGTGATGAAGCAGCTGAAGCGGCGG

AGATACACCGGCTGGGGCAGGCTGAGCCGGAAGCTGATCAACGGCATCCGGGACAAGCAGTCCGGC

AAGACAATCCTGGATTTCCTGAAGTCCGACGGCTTCGCCAACAGAAACTTCATGCAGCTGATCCACGAC

GACAGCCTGACCTTTAAAGAGGACATCCAGAAAGCCCAGGTGTCCGGCCAGGGCGATAGCCTGCACG

AGCACATTGCCAATCTGGCCGGCAGCCCCGCCATTAAGAAGGGCATCCTGCAGACAGTGAAGGTGGT

GGACGAGCTCGTGAAAGTGATGGGCCGGCACAAGCCCGAGAACATCGTGATCGAAATGGCCAGAGA

GAACCAGACCACCCAGAAGGGACAGAAGAACAGCCGCGAGAGAATGAAGCGGATCGAAGAGGGCAT

CAAAGAGCTGGGCAGCCAGATCCTGAAAGAACACCCCGTGGAAAACACCCAGCTGCAGAACGAGAAG

CTGTACCTGTACTACCTGCAGAATGGGCGGGATATGTACGTGGACCAGGAACTGGACATCAACCGGCT

GTCCGACTACGATGTGGACCATATCGTGCCTCAGAGCTTTCTGAAGGACGACTCCATCGACAACAAGG

TGCTGACCAGAAGCGACAAGAACCGGGGCAAGAGCGACAACGTGCCCTCCGAAGAGGTCGTGAAGA

AGATGAAGAACTACTGGCGGCAGCTGCTGAACGCCAAGCTGATTACCCAGAGAAAGTTCGACAATCTG
```

-continued

ACCAAGGCCGAGAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACACTAAGTACGACG
AGAATGACAAGCTGATCCGGGAAGTGAAAGTGATCACCCTGAAGTCCAAGCTGGTGTCCGATTTCCGG
AAGGATTTCCAGTTTTACAAAGTGCGCGAGATCAACAACTACCACCACGCCCACGACGCCTACCTGAAC
GCCGTCGTGGGAACCGCCCTGATCAAAAAGTACCCTAAGCTGGAAAGCGAGTTCGTGTACGGCGACTA
CAAGGTGTACGACGTGCGGAAGATGATCGCCAAGAGCGAGCAGGAAATCGGCAAGGCTACCGCCAA
GTACTTCTTCTACAGCAACATCATGAACTTTTTCAAGACCGAGATTACCCTGGCCAACGGCGAGATCCG
GAAGCGGCCTCTGATCGAGACAAACGGCGAAACCGGGGAGATCGTGTGGGATAAGGGCCGGGATTT
TGCCACCGTGCGGAAAGTGCTGAGCATGCCCCAAGTGAATATCGTGAAAAAGACCGAGGTGCAGACA
GGCGGCTTCAGCAAAGAGTCTATCCTGCCCAAGAGGAACAGCGATAAGCTGATCGCCAGAAAGAAGG
ACTGGGACCCTAAGAAGTACGGCGGCTTCGACAGCCCCACCGTGGCCTATTCTGTGCTGGTGGTGGCC
AAAGTGGAAAAGGGCAAGTCCAAGAAACTGAAGAGTGTGAAAGAGCTGCTGGGGATCACCATCATG
GAAAGAAGCAGCTTCGAGAAGAATCCCATCGACTTTCTGGAAGCCAAGGGCTACAAAGAAGTGAAAA
AGGACCTGATCATCAAGCTGCCTAAGTACTCCCTGTTCGAGCTGGAAAACGGCCGGAAGAGAATGCTG
GCCTCTGCCGGCGAACTGCAGAAGGGAAACGAACTGGCCCTGCCCTCCAAATATGTGAACTTCCTGTA
CCTGGCCAGCCACTATGAGAAGCTGAAGGGCTCCCCCGAGGATAATGAGCAGAAACAGCTGTTTGTG
GAACAGCACAAGCACTACCTGGACGAGATCATCGAGCAGATCAGCGAGTTCTCCAAGAGAGTGATCCT
GGCCGACGCTAATCTGGACAAAGTGCTGTCCGCCTACAACAAGCACCGGGATAAGCCCATCAGAGAG
CAGGCCGAGAATATCATCCACCTGTTTACCCTGACCAATCTGGGAGCCCCTGCCGCCTTCAAGTACTTT
GACACCACCATCGACCGGAAGAGGTACACCAGCACCAAAGAGGTGCTGGACGCCACCCTGATCCACCA
GAGCATCACCGGCCTGTACGAGACACGGATCGACCTGTCTCAGCTGGGAGGCGACAAAAGGCCGGCG
GCCACGAAAAAGGCCGGCCAGGCAAAAAAGAAAAAGgaattcGGCAGTGGAGAGGGCAGAGGAAGTC
TGCTAACATGCGGTGACGTCGAGGAGAATCCTGGCCCAGTGAGCAAGGGCGAGGAGCTGTTCACCGG
GGTGGTGCCCATCCTGGTCGAGCTGGACGGCGACGTAAACGGCCACAAGTTCAGCGTGTCCGGCGAG
GGCGAGGGCGATGCCACCTACGGCAAGCTGACCCTGAAGTTCATCTGCACCACCGGCAAGCTGCCCGT
GCCCTGGCCCACCCTCGTGACCACCCTGACCTACGGCGTGCAGTGCTTCAGCCGCTACCCCGACCACAT
GAAGCAGCACGACTTCTTCAAGTCCGCCATGCCCGAAGGCTACGTCCAGGAGCGCACCATCTTCTTCAA
GGACGACGGCAACTACAAGACCCGCGCCGAGGTGAAGTTCGAGGGCGACACCCTGGTGAACCGCATC
GAGCTGAAGGGCATCGACTTCAAGGAGGACGGCAACATCCTGGGGCACAAGCTGGAGTACAACTACA
ACAGCCACAACGTCTATATCATGGCCGACAAGCAGAAGAACGGCATCAAGGTGAACTTCAAGATCCGC
CACAACATCGAGGACGGCAGCGTGCAGCTCGCCGACCACTACCAGCAGAACACCCCCATCGGCGACG
GCCCCGTGCTGCTGCCCGACAACCACTACCTGAGCACCCAGTCCGCCCTGAGCAAAGACCCCAACGAG
AAGCGCGATCACATGGTCCTGCTGGAGTTCGTGACCGCCGCCGGGATCACTCTCGGCATGGACGAGCT
GTACAAGgaattctaaCTAGAGCTCGCTGATCAGCCTCGACTGTGCCTTCTAGTTGCCAGCCATCTGTTGTT
TGCCCCTCCCCCGTGCCTTCCTTGACCCTGGAAGGTGCCACTCCCACTGTCCTTTCCTAATAAAATGAGG
AAATTGCATCGCATTGTCTGAGTAGGTGTCATTCTATTCTGGGGGGTGGGGTGGGCAGGACAGCAA
GGGGGAGGATTGGGAAGAgAATAGCAGGCATGCTGGGGAgcggccgcaggaacccctagtgatggagttggcca
ctccctctctgcgcgctcgctcgctcactgaggccgggcgaccaaaggtcgcccgacgcccgggctttgcccgggcggcctcagtgagc
gagcgagcgcgcagctgcctgcaggggcgcctgatgcggtattttctccttacgcatctgtgcggtatttcacaccgcatacgtcaaagc
aaccatagtacgcgccctgtagcggcgcattaagcgcggcgggtgtggtggttacgcgcagcgtgaccgctacacttgccagcgccct -continued

```
agcgcccgctcctttcgctttcttcccttcctttctcgccacgttcgccggctttccccgtcaagctctaaatcgggggctcccttagggttc cgatttagtgctttacggcacctcgaccccaaaaaacttgatttgggtgatggttcacgtagtgggccatcgccctgatagacggttttc gcccttgacgttggagtccacgttctttaatagtggactcttgttccaaactggaacaacactcaaccctatctcgggctattcttttgatt tataagggattttgccgatttcggcctattggttaaaaaatgagctgatttaacaaaaatttaacgcgaattttaacaaaatattaacgtt tacaattttatggtgcactctcagtacaatctgctctgatgccgcatagttaagccagccccgacacccgccaacacccgctgacgcgcc ctgacgggcttgtctgctcccggcatccgcttacagacaagctgtgaccgtctccgggagctgcatgtgtcagaggttttcaccgtcatca ccgaaacgcgcgagacgaaagggcctcgtgatacgcctattttataggttaatgtcatgataataatggtttcttagacgtcaggtggc acttttcggggaaatgtgcgcggaaccccatttgtttattttctaaatacattcaaatatgtatccgctcatgagacaataaccctgata aatgcttcaataatattgaaaaaggaagagtatgagtattcaacatttccgtgtcgcccttattcccttttttgcggcattttgccttcctgt ttttgctcacccagaaacgctggtgaaagtaaaagatgctgaagatcagttgggtgcacgagtgggttacatcgaactggatctcaaca gcggtaagatccttgagagttttcgccccgaagaacgttttccaatgatgagcacttttaaagttctgctatgtggcgcggtattatcccg tattgacgccgggcaagagcaactcggtcgccgcatacactattctcagaatgacttggttgagtactcaccagtcacagaaaagcatc ttacggatggcatgacagtaagagaattatgcagtgctgccataaccatgagtgataacactgcggccaacttacttctgacaacgatc ggaggaccgaaggagctaaccgcttttttgcacaacatgggggatcatgtaactcgccttgatcgttgggaaccggagctgaatgaag ccataccaaacgacgagcgtgacaccacgatgcctgtagcaatggcaacaacgttgcgcaaactattaactggcgaactacttactct agcttcccggcaacaattaatagactggatggaggcggataaagttgcaggaccacttctgcgctcggcccttccggctggctggtttat tgctgataaatctggagccggtgagcgtgaagccgcggtatcattgcagcactggggccagatggtaagccctcccgtatcgtagtta tctacacgacggggagtcaggcaactatggatgaacgaaatagacagatcgctgagataggtgcctcactgattaagcattggtaact gtcagaccaagtttactcatatatactttagattgatttaaaacttcattttttaattaaaaggatctaggtgaagatccttttttgataatct catgaccaaaatcccttaacgtgagttttcgttccactgagcgtcagaccccgtagaaaagatcaaaggatcttcttgagatcctttttttt ctgcgcgtaatctgctgcttgcaaacaaaaaaaccaccgctaccagcggtggtttgtttgccggatcaagagctaccaactcttttttccg aaggtaactggcttcagcagagcgcagataccaaatactgtccttctagtgtagccgtagttaggccaccacttcaagaactctgtagc accgcctacatacctcgctctgctaatcctgttaccagtggctgctgccagtggcgataagtcgtgtcttaccgggttggactcaagacg atagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcg gaacaggagagcgcacgagggagcttccaggggaaacgcctggtatctttatagtcctgtcgggtttcgccacctctgacttgagcgt cgattttgtgatgctcgtcaggggggcggagcctatggaaaaacgccagcaacgcggcctttttacggttcctggccttttgctggcctt ttgctcac
``` p972// pSpCas9(BB)-2A-GFP + gRNA hRHO HITI
(SEQ ID NO: 4)

```
gtgagggcctatttcccatgattccttcatatttgcatatacgatacaaggctgttagagagataattggaattaatttgactgtaaacac aaagatattagtacaaaatacgtgacgtagaaagtaataatttcttgggtagtttgcagttttaaaattatgttttaaaatggactatcat atgcttaccgtaacttgaaagtatttcgatttcttggctttatatatcttGTGGAAAGGACGAAACACCGACACCAGGAGA CTTGGAACGgttttagagctaGAAAtagcaagttaaaataaggctagtccgttatcaacttgaaaaagtggcaccgagtcggtgc TTTTTTgttttagagctagaaatagcaagttaaaataaggctagtccgtTTTTagcgcgtgcgccaattctgcagacaaatggctcta gaggtacccgttacataacttacggtaaatggcccgcctggctgaccgcccaacgacccccgcccattgacgtcaatagtaacgccaat agggactttccattgacgtcaatgggtggagtatttacggtaaactgcccacttggcagtacatcaagtgtatcatatgccaagtacgcc ccctattgacgtcaatgacggtaaatggcccgcctggcattGtgcccagtacatgaccttatgggactttcctacttggcagtacatcta cgtattagtcatcgctattaccatggtcgaggtgagccccacgttctgcttcactctccccatctcccccccctccccacccccaatttgt atttatttattttttaattattttgtgcagcgatgggggcggggggggggggggcgcgcgccaggcggggggggcgggcgaggg gcggggcggggcgaggcggagaggtgcggcggcagccaatcagagcggcgcgctccgaaagtttccttttatggcgaggcggcggc ggcggcggccctataaaaagcgaagcgcgcggggggggagtcgctgcgacgctgccttcgccccgtgccccgctccgccgccgcct
```

-continued cgcgccgcccgccccggctctgactgaccgcgttactcccacaggtgagcgggggacggcccttctcctccgggctgtaattagctg agcaagaggtaagggtttaagggatggttggttggtggggtattaatgtttaattacctggagcacctgcctgaaatcactttttttcagg ttGGaccggtgccaccATGGACTATAAGGACCACGACGGAGACTACAAGGATCATGATATTGATTACAAAG

ACGATGACGATAAGATGGCCCCAAAGAAGAAGCGGAAGGTCGGTATCCACGGAGTCCCAGCAGCCGA

CAAGAAGTACAGCATCGGCCTGGACATCGGCACCAACTCTGTGGGCTGGGCCGTGATCACCGACGAG

TACAAGGTGCCCAGCAAGAAATTCAAGGTGCTGGGCAACACCGACCGGCACAGCATCAAGAAGAACC

TGATCGGAGCCCTGCTGTTCGACAGCGGCGAAACAGCCGAGGCCACCCGGCTGAAGAGAACCGCCAG

AAGAAGATACACCAGACGGAAGAACCGGATCTGCTATCTGCAAGAGATCTTCAGCAACGAGATGGCC

AAGGTGGACGACAGCTTCTTCCACAGACTGGAAGAGTCCTTCCTGGTGGAAGAGGATAAGAAGCACG

AGCGGCACCCCATCTTCGGCAACATCGTGGACGAGGTGGCCTACCACGAGAAGTACCCCACCATCTAC

CACCTGAGAAAGAAACTGGTGGACAGCACCGACAAGGCCGACCTGCGGCTGATCTATCTGGCCCTGG

CCCACATGATCAAGTTCCGGGGCCACTTCCTGATCGAGGGCGACCTGAACCCCGACAACAGCGACGTG

GACAAGCTGTTCATCCAGCTGGTGCAGACCTACAACCAGCTGTTCGAGGAAAACCCCATCAACGCCAG

CGGCGTGGACGCCAAGGCCATCCTGTCTGCCAGACTGAGCAAGAGCAGACGGCTGGAAAATCTGATC

GCCCAGCTGCCCGGCGAGAAGAAGAATGGCCTGTTCGGAAACCTGATTGCCCTGAGCCTGGGCCTGA

CCCCCAACTTCAAGAGCAACTTCGACCTGGCCGAGGATGCCAAACTGCAGCTGAGCAAGGACACCTAC

GACGACGACCTGGACAACCTGCTGGCCCAGATCGGCGACCAGTACGCCGACCTGTTTCTGGCCGCCAA

GAACCTGTCCGACGCCATCCTGCTGAGCGACATCCTGAGAGTGAACACCGAGATCACCAAGGCCCCCC

TGAGCGCCTCTATGATCAAGAGATACGACGAGCACCACCAGGACCTGACCCTGCTGAAAGCTCTCGTG

CGGCAGCAGCTGCCTGAGAAGTACAAAGAGATTTTCTTCGACCAGAGCAAGAACGGCTACGCCGGCT

ACATTGACGGCGGAGCCAGCCAGGAAGAGTTCTACAAGTTCATCAAGCCCATCCTGGAAAAGATGGA

CGGCACCGAGGAACTGCTCGTGAAGCTGAACAGAGAGGACCTGCTGCGGAAGCAGCGGACCTTCGAC

AACGGCAGCATCCCCCACCAGATCCACCTGGGAGAGCTGCACGCCATTCTGCGGCGGCAGGAAGATTT

TTACCCATTCCTGAAGGACAACCGGGAAAAGATCGAGAAGATCCTGACCTTCCGCATCCCCTACTACGT

GGGCCCTCTGGCCAGGGGAAACAGCAGATTCGCCTGGATGACCAGAAAGAGCGAGGAAACCATCACC

CCCTGGAACTTCGAGGAAGTGGTGGACAAGGGCGCTTCCGCCCAGAGCTTCATCGAGCGGATGACCA

ACTTCGATAAGAACCTGCCCAACGAGAAGGTGCTGCCCAAGCACAGCCTGCTGTACGAGTACTTCACC

GTGTATAACGAGCTGACCAAAGTGAAATACGTGACCGAGGGAATGAGAAAGCCCGCCTTCCTGAGCG

GCGAGCAGAAAAAGGCCATCGTGGACCTGCTGTTCAAGACCAACCGGAAAGTGACCGTGAAGCAGCT

GAAAGAGGACTACTTCAAGAAAATCGAGTGCTTCGACTCCGTGGAAATCTCCGGCGTGGAAGATCGGT

TCAACGCCTCCCTGGGCACATACCACGATCTGCTGAAAATTATCAAGGACAAGGACTTCCTGGACAATG

AGGAAAACGAGGACATTCTGGAAGATATCGTGCTGACCCTGACACTGTTTGAGGACAGAGAGATGAT

CGAGGAACGGCTGAAAACCTATGCCCACCTGTTCGACGACAAAGTGATGAAGCAGCTGAAGCGGCGG

AGATACACCGGCTGGGGCAGGCTGAGCCGGAAGCTGATCAACGGCATCCGGGACAAGCAGTCCGGC

AAGACAATCCTGGATTTCCTGAAGTCCGACGGCTTCGCCAACAGAAACTTCATGCAGCTGATCCACGAC

GACAGCCTGACCTTTAAAGAGGACATCCAGAAAGCCCAGGTGTCCGGCCAGGGCGATAGCCTGCACG

AGCACATTGCCAATCTGGCCGGCAGCCCCGCCATTAAGAAGGGCATCCTGCAGACAGTGAAGGTGGT

GGACGAGCTCGTGAAAGTGATGGGCCGGCACAAGCCCGAGAACATCGTGATCGAAATGGCCAGAGA

GAACCAGACCACCCAGAAGGGACAGAAGAACAGCCGCGAGAGAATGAAGCGGATCGAAGAGGGCAT

CAAAGAGCTGGGCAGCCAGATCCTGAAAGAACACCCCGTGGAAAACACCCAGCTGCAGAACGAGAAG

-continued

```
CTGTACCTGTACTACCTGCAGAATGGGGGATATGTACGTGGACCAGGAACTGGACATCAACCGGCT
GTCCGACTACGATGTGGACCATATCGTGCCTCAGAGCTTTCTGAAGGACGACTCCATCGACAACAAGG
TGCTGACCAGAAGCGACAAGAACCGGGGCAAGAGCGACAACGTGCCCTCCGAAGAGGTCGTGAAGA
AGATGAAGAACTACTGGCGGCAGCTGCTGAACGCCAAGCTGATTACCCAGAGAAAGTTCGACAATCTG
ACCAAGGCCGAGAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACACTAAGTACGACG
AGAATGACAAGCTGATCCGGGAAGTGAAAGTGATCACCCTGAAGTCCAAGCTGGTGTCCGATTTCCGG
AAGGATTTCCAGTTTTACAAAGTGCGCGAGATCAACAACTACCACCACGCCCACGACGCCTACCTGAAC
GCCGTCGTGGGAACCGCCCTGATCAAAAAGTACCCTAAGCTGGAAAGCGAGTTCGTGTACGGCGACTA
CAAGGTGTACGACGTGCGGAAGATGATCGCCAAGAGCGAGCAGGAAATCGGCAAGGCTACCGCCAA
GTACTTCTTCTACAGCAACATCATGAACTTTTTCAAGACCGAGATTACCCTGGCCAACGGCGAGATCCG
GAAGCGGCCTCTGATCGAGACAAACGGCGAAACCGGGGAGATCGTGTGGGATAAGGGCCGGGATTT
TGCCACCGTGCGGAAAGTGCTGAGCATGCCCCAAGTGAATATCGTGAAAAAGACCGAGGTGCAGACA
GGCGGCTTCAGCAAAGAGTCTATCCTGCCCAAGAGGAACAGCGATAAGCTGATCGCCAGAAAGAAGG
ACTGGGACCCTAAGAAGTACGGCGGCTTCGACAGCCCCACCGTGGCCTATTCTGTGCTGGTGGTGGCC
AAAGTGGAAAAGGGCAAGTCCAAGAAACTGAAGAGTGTGAAAGAGCTGCTGGGGATCACCATCATG
GAAAGAAGCAGCTTCGAGAAGAATCCCATCGACTTTCTGGAAGCCAAGGGCTACAAAGAAGTGAAAA
AGGACCTGATCATCAAGCTGCCTAAGTACTCCCTGTTCGAGCTGGAAAACGGCCGGAAGAGAATGCTG
GCCTCTGCCGGCGAACTGCAGAAGGGAAACGAACTGGCCCTGCCCTCCAAATATGTGAACTTCCTGTA
CCTGGCCAGCCACTATGAGAAGCTGAAGGGCTCCCCCGAGGATAATGAGCAGAAACAGCTGTTTGTG
GAACAGCACAAGCACTACCTGGACGAGATCATCGAGCAGATCAGCGAGTTCTCCAAGAGAGTGATCCT
GGCCGACGCTAATCTGGACAAAGTGCTGTCCGCCTACAACAAGCACCGGGATAAGCCCATCAGAGAG
CAGGCCGAGAATATCATCCACCTGTTTACCCTGACCAATCTGGGAGCCCCTGCCGCCTTCAAGTACTTT
GACACCACCATCGACCGGAAGAGGTACACCAGCACCAAAGAGGTGCTGGACGCCACCCTGATCCACCA
GAGCATCACCGGCCTGTACGAGACACGGATCGACCTGTCTCAGCTGGGAGGCGACAAAAGGCCGGCG
GCCACGAAAAAGGCCGGCCAGGCAAAAAAGAAAAAGgaattcGGCAGTGGAGAGGGCAGAGGAAGTC
TGCTAACATGCGGTGACGTCGAGGAGAATCCTGGCCCAGTGAGCAAGGGCGAGGAGCTGTTCACCGG
GGTGGTGCCCATCCTGGTCGAGCTGGACGGCGACGTAAACGGCCACAAGTTCAGCGTGTCCGGCGAG
GGCGAGGGCGATGCCACCTACGGCAAGCTGACCCTGAAGTTCATCTGCACCACCGGCAAGCTGCCCGT
GCCCTGGCCCACCCTCGTGACCACCCTGACCTACGGCGTGCAGTGCTTCAGCCGCTACCCCGACCACAT
GAAGCAGCACGACTTCTTCAAGTCCGCCATGCCCGAAGGCTACGTCCAGGAGCGCACCATCTTCTTCAA
GGACGACGGCAACTACAAGACCCGCGCCGAGGTGAAGTTCGAGGGCGACACCCTGGTGAACCGCATC
GAGCTGAAGGGCATCGACTTCAAGGAGGACGGCAACATCCTGGGGCACAAGCTGGAGTACAACTACA
ACAGCCACAACGTCTATATCATGGCCGACAAGCAGAAGAACGGCATCAAGGTGAACTTCAAGATCCGC
CACAACATCGAGGACGGCAGCGTGCAGCTCGCCGACCACTACCAGCAGAACACCCCCATCGGCGACG
GCCCCGTGCTGCTGCCCGACAACCACTACCTGAGCACCCAGTCCGCCCTGAGCAAAGACCCCAACGAG
AAGCGCGATCACATGGTCCTGCTGGAGTTCGTGACCGCCGCGGGATCACTCTCGGCATGGACGAGCT
GTACAAGgaattctaaCTAGAGCTCGCTGATCAGCCTCGACTGTGCCTTCTAGTTGCCAGCCATCTGTTGTT
TGCCCCTCCCCCGTGCCTTCCTTGACCCTGGAAGGTGCCACTCCCACTGTCCTTTCCTAATAAAATGAGG
AAATTGCATCGCATTGTCTGAGTAGGTGTCATTCTATTCTGGGGGGTGGGGTGGGCAGGACAGCAA
GGGGGAGGATTGGGAAGAgAATAGCAGGCATGCTGGGGAgcggccgcaggaaccccctagtgatggagttggcca
```

-continued ctccctctctgcgcgctcgctcgctcactgaggccgggcgaccaaaggtcgcccgacgcccgggctttgcccgggcggcctcagtgagc gagcgagcgcgcagctgcctgcaggggcgcctgatgcggtattttctccttacgcatctgtgcggtatttcacaccgcatacgtcaaagc aaccatagtacgcgccctgtagcggcgcattaagcgcggcgggtgtggtggttacgcgcagcgtgaccgctacacttgccagcgccct agcgcccgctcctttcgctttcttcccttcctttctcgccacgttcgccggctttccccgtcaagctctaaatcgggggctcccttagggttc cgatttagtgctttacggcacctcgaccccaaaaaacttgatttgggtgatggttcacgtagtgggccatcgccctgatagacggttttc gcccttgacgttggagtccacgttctttaatagtggactcttgttccaaactggaacaacactcaaccctatctcgggctattcttttgatt tataagggattttgccgatttcggcctattggttaaaaaatgagctgatttaacaaaaatttaacgcgaattttaacaaaatattaacgtt tacaattttatggtgcactctcagtacaatctgctctgatgccgcatagttaagccagccccgacacccgccaacacccgctgacgcgcc ctgacgggcttgtctgctcccggcatccgcttacagacaagctgtgaccgtctccgggagctgcatgtgtcagaggttttcaccgtcatca ccgaaacgcgcgagacgaaagggcctcgtgatacgcctatttttataggttaatgtcatgataataatggtttcttagacgtcaggtggc acttttcggggaaatgtgcgcggaacccctatttgtttatttttctaaatacattcaaatatgtatccgctcatgagacaataaccctgata aatgcttcaataatattgaaaaaggaagagtatgagtattcaacatttccgtgtcgcccttattcccttttttgcggcattttgccttcctgt ttttgctcacccagaaacgctggtgaaagtaaaagatgctgaagatcagttgggtgcacgagtgggttacatcgaactggatctcaaca gcggtaagatccttgagagttttcgccccgaagaacgttttccaatgatgagcacttttaaagttctgctatgtggcgcggtattatcccg tattgacgccgggcaagagcaactcggtcgccgcatacactattctcagaatgacttggttgagtactcaccagtcacagaaaagcatc ttacggatggcatgacagtaagagaattatgcagtgctgccataaccatgagtgataacactgcggccaacttacttctgacaacgatc ggaggaccgaaggagctaaccgcttttttgcacaacatgggggatcatgtaactcgccttgatcgttgggaaccggagctgaatgaag ccataccaaacgacgagcgtgacaccacgatgcctgtagcaatggcaacaacgttgcgcaaactattaactggcgaactacttactct agcttcccggcaacaattaatagactggatggaggcggataaagttgcaggaccacttctgcgctcggcccttccggctggctggtttat tgctgataaatctggagccggtgagcgtggaagccgcggtatcattgcagcactggggccagatggtaagccctcccgtatcgtagtta tctacacgacggggagtcaggcaactatggatgaacgaaatagacagatcgctgagataggtgcctcactgattaagcattggtaact gtcagaccaagtttactcatatatactttagattgatttaaaacttcattttaatttaaaaggatctaggtgaagatcctttttgataatct catgaccaaaatcccttaacgtgagttttcgttccactgagcgtcagaccccgtagaaaagatcaaaggatcttcttgagatcctttttt ctgcgcgtaatctgctgcttgcaaacaaaaaaaccaccgctaccagcggtggtttgtttgccggatcaagagctaccaactcttttccg aaggtaactggcttcagcagagcgcagataccaaatactgtccttctagtgtagccgtagttaggccaccacttcaagaactctgtagc accgcctacatacctcgctctgctaatcctgttaccagtggctgctgccagtggcgataagtcgtgtcttaccgggttggactcaagacg atagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcg gaacaggagagcgcacgagggagcttccaggggaaacgcctggtatctttatagtcctgtcgggtttcgccacctctgacttgagcgt cgatttttgtgatgctcgtcaggggggcggagcctatggaaaaacgccagcaacgcggcctttttacggttcctggccttttgctggcctt ttgctcacat p995/ SpCas9-2A-GFP-HITI mRHO (SEQ ID NO: 5)

tcacatgtgagggcctatttcccatgattccttcatatttgcatatacgatacaaggctgttagagagataattggaattaatttgactgta aacacaaagatattagtacaaaatacgtgacgtagaaagtaataatttcttgggtagtttgcagttttaaaattatgttttaaaatggac tatcatatgcttaccgtaacttgaaagtatttcgatttcttggctttatatatcttGTGGAAAGGACGAAACACCGCAGCCGC AGTACTACCTGGgttttagagctaGAAAtagcaagttaaaataaggctagtccgttatcaacttgaaaaagtggcaccgagtcg gtgcTTTTTTgttttagagctagaaatagcaagttaaaataaggctagtccgtTTTTagcgcgtgcgccaattctgcagacaaatgg ctctagaggtacccgttacataacttacggtaaatggcccgcctggctgaccgcccaacgacccccgcccattgacgtcaatagtaacg ccaatagggactttccattgacgtcaatgggtggagtatttacggtaaactgcccacttggcagtacatcaagtgtatcatatgccaagt acgccccctattgacgtcaatgacggtaaatggcccgcctggcattGtgcccagtacatgaccttatgggactttcctacttggcagtac -continued

```
atctacgtattagtcatcgctattaccatggtcgaggtgagcccacgttctgcttcactctccccatctccccccctccccaccccaat tttgtatttatttattttttaattattttgtgcagcgatgggggcggggggggggggggggcgcgcgccaggcgggggggcggggcg agggggggcgggcgaggcggagaggtgcggcggcagccaatcagagcggcgcgctccgaaagtttccttttatggcgaggcgg cggcggcggcgggccctataaaaagcgaagcgcgggggggggagtcgctgcgacgctgccttcgccccgtgccccgctccgccgc cgcctcgcgccgcccgccccggctctgactgaccgcgttactcccacaggtgagcggggggacggcccttctcctccgggctgtaatta gctgagcaagaggtaagggtttaagggatggttggttggtggggtattaatgtttaattacctggagcacctgcctgaaatcactttttttt caggttGGaccggtgccaccATGGACTATAAGGACCACGACGGAGACTACAAGGATCATGATATTGATTACA

AAGACGATGACGATAAGATGGCCCCAAAGAAGAAGCGGAAGGTCGGTATCCACGGAGTCCCAGCAGC

CGACAAGAAGTACAGCATCGGCCTGGACATCGGCACCAACTCTGTGGGCTGGGCCGTGATCACCGAC

GAGTACAAGGTGCCCAGCAAGAAATTCAAGGTGCTGGGCAACACCGACCGGCACAGCATCAAGAAGA

ACCTGATCGGAGCCCTGCTGTTCGACAGCGGCGAAACAGCCGAGGCCACCCGGCTGAAGAGAACCGC

CAGAAGAAGATACACCAGACGGAAGAACCGGATCTGCTATCTGCAAGAGATCTTCAGCAACGAGATG

GCCAAGGTGGACGACAGCTTCTTCCACAGACTGGAAGAGTCCTTCCTGGTGGAAGAGGATAAGAAGC

ACGAGCGGCACCCCATCTTCGGCAACATCGTGGACGAGGTGGCCTACCACGAGAAGTACCCCACCATC

TACCACCTGAGAAAGAAACTGGTGGACAGCACCGACAAGGCCGACCTGCGGCTGATCTATCTGGCCCT

GGCCCACATGATCAAGTTCCGGGGCCACTTCCTGATCGAGGGCGACCTGAACCCCGACAACAGCGACG

TGGACAAGCTGTTCATCCAGCTGGTGCAGACCTACAACCAGCTGTTCGAGGAAAACCCCATCAACGCC

AGCGGCGTGGACGCCAAGGCCATCCTGTCTGCCAGACTGAGCAAGAGCAGACGGCTGGAAAATCTGA

TCGCCCAGCTGCCCGGCGAGAAGAAGAATGGCCTGTTCGGAAACCTGATTGCCCTGAGCCTGGGCCTG

ACCCCCAACTTCAAGAGCAACTTCGACCTGGCCGAGGATGCCAAACTGCAGCTGAGCAAGGACACCTA

CGACGACGACCTGGACAACCTGCTGGCCCAGATCGGCGACCAGTACGCCGACCTGTTTCTGGCCGCCA

AGAACCTGTCCGACGCCATCCTGCTGAGCGACATCCTGAGAGTGAACACCGAGATCACCAAGGCCCCC

CTGAGCGCCTCTATGATCAAGAGATACGACGAGCACCACCAGGACCTGACCCTGCTGAAAGCTCTCGT

GCGGCAGCAGCTGCCTGAGAAGTACAAAGAGATTTTCTTCGACCAGAGCAAGAACGGCTACGCCGGC

TACATTGACGGCGGAGCCAGCCAGGAAGAGTTCTACAAGTTCATCAAGCCCATCCTGGAAAAGATGGA

CGGCACCGAGGAACTGCTCGTGAAGCTGAACAGAGAGGACCTGCTGCGGAAGCAGCGGACCTTCGAC

AACGGCAGCATCCCCCACCAGATCCACCTGGGAGAGCTGCACGCCATTCTGCGGCGGCAGGAAGATTT

TTACCCATTCCTGAAGGACAACCGGGAAAAGATCGAGAAGATCCTGACCTTCCGCATCCCCTACTACGT

GGGCCCTCTGGCCAGGGGAAACAGCAGATTCGCCTGGATGACCAGAAAGAGCGAGGAAACCATCACC

CCCTGGAACTTCGAGGAAGTGGTGGACAAGGGCGCTTCCGCCCAGAGCTTCATCGAGCGGATGACCA

ACTTCGATAAGAACCTGCCCAACGAGAAGGTGCTGCCCAAGCACAGCCTGCTGTACGAGTACTTCACC

GTGTATAACGAGCTGACCAAAGTGAAATACGTGACCGAGGGAATGAGAAAGCCCGCCTTCCTGAGCG

GCGAGCAGAAAAAGGCCATCGTGGACCTGCTGTTCAAGACCAACCGGAAAGTGACCGTGAAGCAGCT

GAAAGAGGACTACTTCAAGAAAATCGAGTGCTTCGACTCCGTGGAAATCTCCGGCGTGGAAGATCGGT

TCAACGCCTCCCTGGGCACATACCACGATCTGCTGAAAATTATCAAGGACAAGGACTTCCTGGACAATG

AGGAAAACGAGGACATTCTGGAAGATATCGTGCTGACCCTGACACTGTTTGAGGACAGAGAGATGAT

CGAGGAACGGCTGAAAACCTATGCCCACCTGTTCGACGACAAAGTGATGAAGCAGCTGAAGCGGCGG

AGATACACCGGCTGGGGCAGGCTGAGCCGGAAGCTGATCAACGGCATCCGGGACAAGCAGTCCGGC

AAGACAATCCTGGATTTCCTGAAGTCCGACGGCTTCGCCAACAGAAACTTCATGCAGCTGATCCACGAC

GACAGCCTGACCTTTAAAGAGGACATCCAGAAAGCCCAGGTGTCCGGCCAGGGCGATAGCCTGCACG

AGCACATTGCCAATCTGGCCGGCAGCCCCGCCATTAAGAAGGGCATCCTGCAGACAGTGAAGGTGGT
```

-continued

```
GGACGAGCTCGTGAAAGTGATGGGCCGGCACAAGCCCGAGAACATCGTGATCGAAATGGCCAGAGA

GAACCAGACCACCCAGAAGGGACAGAAGAACAGCCGCGAGAGAATGAAGCGGATCGAAGAGGGCAT

CAAAGAGCTGGGCAGCCAGATCCTGAAAGAACACCCCGTGGAAAACACCCAGCTGCAGAACGAGAAG

CTGTACCTGTACTACCTGCAGAATGGGCGGGATATGTACGTGGACCAGGAACTGGACATCAACCGGCT

GTCCGACTACGATGTGGACCATATCGTGCCTCAGAGCTTTCTGAAGGACGACTCCATCGACAACAAGG

TGCTGACCAGAAGCGACAAGAACCGGGGCAAGAGCGACAACGTGCCCTCCGAAGAGGTCGTGAAGA

AGATGAAGAACTACTGGCGGCAGCTGCTGAACGCCAAGCTGATTACCCAGAGAAAGTTCGACAATCTG

ACCAAGGCCGAGAGAGGCGGCCTGAGCGAACTGGATAAGGCCGGCTTCATCAAGAGACAGCTGGTG

GAAACCCGGCAGATCACAAAGCACGTGGCACAGATCCTGGACTCCCGGATGAACACTAAGTACGACG

AGAATGACAAGCTGATCCGGGAAGTGAAAGTGATCACCCTGAAGTCCAAGCTGGTGTCCGATTTCCGG

AAGGATTTCCAGTTTTACAAAGTGCGCGAGATCAACAACTACCACCACGCCCACGACGCCTACCTGAAC

GCCGTCGTGGGAACCGCCCTGATCAAAAAGTACCCTAAGCTGGAAAGCGAGTTCGTGTACGGCGACTA

CAAGGTGTACGACGTGCGGAAGATGATCGCCAAGAGCGAGCAGGAAATCGGCAAGGCTACCGCCAA

GTACTTCTTCTACAGCAACATCATGAACTTTTTCAAGACCGAGATTACCCTGGCCAACGGCGAGATCCG

GAAGCGGCCTCTGATCGAGACAAACGGCGAAACCGGGGAGATCGTGTGGGATAAGGGCCGGGATTT

TGCCACCGTGCGGAAAGTGCTGAGCATGCCCCAAGTGAATATCGTGAAAAAGACCGAGGTGCAGACA

GGCGGCTTCAGCAAAGAGTCTATCCTGCCCAAGAGGAACAGCGATAAGCTGATCGCCAGAAAGAAGG

ACTGGGACCCTAAGAAGTACGGCGGCTTCGACAGCCCCACCGTGGCCTATTCTGTGCTGGTGGTGGCC

AAAGTGGAAAAGGGCAAGTCCAAGAAACTGAAGAGTGTGAAAGAGCTGCTGGGGATCACCATCATG

GAAAGAAGCAGCTTCGAGAAGAATCCCATCGACTTTCTGGAAGCCAAGGGCTACAAAGAAGTGAAAA

AGGACCTGATCATCAAGCTGCCTAAGTACTCCCTGTTCGAGCTGGAAAACGGCCGGAAGAGAATGCTG

GCCTCTGCCGGCGAACTGCAGAAGGGAAACGAACTGGCCCTGCCCTCCAAATATGTGAACTTCCTGTA

CCTGGCCAGCCACTATGAGAAGCTGAAGGGCTCCCCCGAGGATAATGAGCAGAAACAGCTGTTTGTG

GAACAGCACAAGCACTACCTGGACGAGATCATCGAGCAGATCAGCGAGTTCTCCAAGAGAGTGATCCT

GGCCGACGCTAATCTGGACAAAGTGCTGTCCGCCTACAACAAGCACCGGGATAAGCCCATCAGAGAG

CAGGCCGAGAATATCATCCACCTGTTTACCCTGACCAATCTGGGAGCCCCTGCCGCCTTCAAGTACTTT

GACACCACCATCGACCGGAAGAGGTACACCAGCACCAAAGAGGTGCTGGACGCCACCCTGATCCACCA

GAGCATCACCGGCCTGTACGAGACACGGATCGACCTGTCTCAGCTGGGAGGCGACAAAAGGCCGGCG

GCCACGAAAAGGCCGGCCAGGCAAAAAAGAAAAAGgaattcGGCAGTGGAGAGGGCAGAGGAAGTC

TGCTAACATGCGGTGACGTCGAGGAGAATCCTGGCCCAGTGAGCAAGGGCGAGGAGCTGTTCACCGG

GGTGGTGCCCATCCTGGTCGAGCTGGACGGCGACGTAAACGGCCACAAGTTCAGCGTGTCCGGCGAG

GGCGAGGGCGATGCCACCTACGGCAAGCTGACCCTGAAGTTCATCTGCACCACCGGCAAGCTGCCCGT

GCCCTGGCCCACCCTCGTGACCACCCTGACCTACGGCGTGCAGTGCTTCAGCCGCTACCCCGACCACAT

GAAGCAGCACGACTTCTTCAAGTCCGCCATGCCCGAAGGCTACGTCCAGGAGCGCACCATCTTCTTCAA

GGACGACGGCAACTACAAGACCCGCGCCGAGGTGAAGTTCGAGGGCGACACCCTGGTGAACCGCATC

GAGCTGAAGGGCATCGACTTCAAGGAGGACGGCAACATCCTGGGGCACAAGCTGGAGTACAACTACA

ACAGCCACAACGTCTATATCATGGCCGACAAGCAGAAGAACGGCATCAAGGTGAACTTCAAGATCCGC

CACAACATCGAGGACGGCAGCGTGCAGCTCGCCGACCACTACCAGCAGAACACCCCCATCGGCGACG

GCCCCGTGCTGCTGCCCGACAACCACTACCTGAGCACCCAGTCCGCCCTGAGCAAAGACCCCAACGAG

AAGCGCGATCACATGGTCCTGCTGGAGTTCGTGACCGCCGCCGGGATCACTCTCGGCATGGACGAGCT
```

```
GTACAAGgaattctaaCTAGAGCTCGCTGATCAGCCTCGACTGTGCCTTCTAGTTGCCAGCCATCTGTTGTT

TGCCCCTCCCCCGTGCCTTCCTTGACCCTGGAAGGTGCCACTCCCACTGTCCTTTCCTAATAAAATGAGG

AAATTGCATCGCATTGTCTGAGTAGGTGTCATTCTATTCTGGGGGGGGGGTGGGGCAGGACAGCAA

GGGGGAGGATTGGGAAGAgAATAGCAGGCATGCTGGGGAgcggccgcaggaacccctagtgatggagttggcca ctccctctctgcgcgctcgctcgctcactgaggccgggcgaccaaaggtcgcccgacgcccgggctttgcccgggcggcctcagtgagc gagcgagcgcgcagctgcctgcaggggcgcctgatgcggtattttctccttacgcatctgtgcggtatttcacaccgcatacgtcaaagc aaccatagtacgcgccctgtagcggcgcattaagcgcggcgggtgtggtggttacgcgcagcgtgaccgctacacttgccagcgccct agcgcccgctccttcgctttcttcccttcctttctcgccacgttcgccggctttcccgtcaagctctaaatcggggctccctttagggttc cgatttagtgctttacggcacctcgaccccaaaaaacttgatttgggtgatggttcacgtagtgggccatcgccctgatagacggttttc gccctttgacgttggagtccacgttctttaatagtggactcttgttccaaactggaacaacactcaaccctatctcgggctattctttgatt tataagggattttgccgatttcggcctattggttaaaaaatgagctgatttaacaaaaatttaacgcgaattttaacaaaatattaacgtt tacaattttatggtgcactctcagtacaatctgctctgatgccgcatagttaagccagccccgacacccgccaacacccgctgacgcgcc ctgacggcttgtctgctcccggcatccgcttacagacaagctgtgaccgtctccggagctgcatgtgtcagaggttttcaccgtcatca ccgaaacgcgcgagacgaaagggcctcgtgatacgcctatttttataggttaatgtcatgataataatggtttcttagacgtcaggtggc acttttcggggaaatgtgcgcggaacccctatttgtttatttttctaaatacattcaaatatgtatccgctcatgagacaataaccctgata aatgcttcaataatattgaaaaaggaagagtatgagtattcaacatttccgtgtcgcccttattccctttttgcggcattttgccttcctgt ttttgctcacccagaaacgctggtgaaagtaaaagatgctgaagatcagttgggtgcacgagtgggttacatcgaactggatctcaaca gcggtaagatccttgagagttttcgccccgaagaacgttttccaatgatgagcacttttaaagttctgctatgtggcgcggtattatcccg tattgacgccgggcaagagcaactcggtcgccgcatacactattctcagaatgacttggttgagtactcaccagtcacagaaaagcatc ttacggatggcatgacagtaagagaattatgcagtgctgccataaccatgagtgataacactgcggccaacttacttctgacaacgatc ggaggaccgaaggagctaaccgcttttttgcacaacatgggggatcatgtaactcgccttgatcgttgggaaccggagctgaatgaag ccataccaaacgacgagcgtgacaccacgatgcctgtagcaatggcaacaacgttgcgcaaactattaactggcgaactacttactct agcttcccggcaacaattaatagactggatggaggcggataaagttgcaggaccacttctgcgctcggcccttccggctggctggtttat tgctgataaatctggagccggtgagcgtggaagccgcggtatcattgcagcactggggccagatggtaagccctcccgtatcgtagtta tctacacgacggggagtcaggcaactatggatgaacgaaatagacagatcgctgagataggtgcctcactgattaagcattggtaact gtcagaccaagtttactcatatatactttagattgatttaaaacttcatttttaatttaaaaggatctaggtgaagatcctttttgataatct catgaccaaaatcccttaacgtgagttttcgttccactgagcgtcagaccccgtagaaaagatcaaaggatcttcttgagatccttttttt ctgcgcgtaatctgctgcttgcaaacaaaaaaaccaccgctaccagcggtggtttgtttgccggatcaagagctaccaactcttttttccg aaggtaactggcttcagcagagcgcagataccaaatactgtccttctagtgtagccgtagttaggccaccacttcaagaactctgtagc accgcctacatacctcgctctgctaatcctgttaccagtggctgctgccagtggcgataagtcgtgtcttaccgggttggactcaagacg atagttaccggataaggcgcagcggtcgggctgaacggggggttcgtgcacacagcccagctggagcgaacgacctacaccgaact gagatacctacagcgtgagctatgagaaagcgccacgcttcccgaagggagaaaggcggacaggtatccggtaagcggcagggtcg gaacaggagagcgcacgagggagcttccaggggaaacgcctggtatctttatagtcctgtcgggtttcgccacctctgacttgagcgt cgatttttgtgatgctcgtcaggggggcggagcctatggaaaaacgccagcaacgcggcctttttacggttcctggccttttgctggcctt ttgc p1070// pSpCas9(BB)-2A-GFP-gRNAalbumin
                                                                    (SEQ ID NO: 6)
tgagggcctatttcccatgattccttcatatttgcatatacgatacaaggctgttagagagataattggaattaatttgactgtaaacaca aagatattagtacaaaatacgtgacgtagaaagtaataatttcttgggtagtttgcagttttaaaattatgttttaaaatggactatcata tgcttaccgtaacttgaaagtatttcgatttcttggctttatatatcttGTGGAAAGGACGAAACACCGACAAGAGTGAGA TCGCCCATgttttagagctaGAAAtagcaagttaaaataaggctagtccgttatcaacttgaaaaagtggcaccgagtcggtgcT TTTTTgttttagagctagaaatagcaagttaaaataaggctagtccgtTTTTAgcgcgtgcgccaattctgcagacaaatggctctag
```

-continued aggtacccgttacataacttacggtaaatggcccgcctggctgaccgcccaacgaccccgcccattgacgtcaatagtaacgccaata gggactttccattgacgtcaatgggtggagtatttacggtaaactgcccacttggcagtacatcaagtgtatcatatgccaagtacgccc cctattgacgtcaatgacggtaaatggcccgcctggcattGtgcccagtacatgaccttatgggactttcctacttggcagtacatctac gtattagtcatcgctattaccatggtcgaggtgagccccacgttctgcttcactctccccatctcccccccctcccaccccaattttgtat ttatttatttttttaattattttgtgcagcgatggggggggggggggggggggggggcgcgcgccaggcggggggggggggcgaggggc ggggcgggggcgaggcggagaggtgcggcggcagccaatcagagcggcgcgctccgaaagtttccttttatggcgaggcggcggcgg cggcggccctataaaaagcgaagcgcgcgggggggagtcgctgcgacgctgccttcgcccgtgcccgctccgccgccgcctcg cgccgcccgccccggctctgactgaccgcgttactcccacaggtgagcgggggacggcccttctcctccgggctgtaattagctgag caagaggtaagggtttaagggatggttggttggtggggtattaatgtttaattacctggagcacctgcctgaaatcacttttttttcaggtt GGaccggtgccaccATGGACTATAAGGACCACGACGGAGACTACAAGGATCATGATATTGATTACAAAGA

CGATGACGATAAGATGGCCCCAAAGAAGAAGCGGAAGGTCGGTATCCACGGAGTCCCAGCAGCCGAC

AAGAAGTACAGCATCGGCCTGGACATCGGCACCAACTCTGTGGGCTGGGCCGTGATCACCGACGAGT

ACAAGGTGCCCAGCAAGAAATTCAAGGTGCTGGGCAACACCGACCGGCACAGCATCAAGAAGAACCT

GATCGGAGCCCTGCTGTTCGACAGCGGCGAAACAGCCGAGGCCACCCGGCTGAAGAGAACCGCCAGA

AGAAGATACACCAGACGGAAGAACCGGATCTGCTATCTGCAAGAGATCTTCAGCAACGAGATGGCCA

AGGTGGACGACAGCTTCTTCCACAGACTGGAAGAGTCCTTCCTGGTGGAAGAGGATAAGAAGCACGA

GCGGCACCCCATCTTCGGCAACATCGTGGACGAGGTGGCCTACCACGAGAAGTACCCCACCATCTACC

ACCTGAGAAAGAAACTGGTGGACAGCACCGACAAGGCCGACCTGCGGCTGATCTATCTGGCCCTGGC

CCACATGATCAAGTTCCGGGGCCACTTCCTGATCGAGGGCGACCTGAACCCCGACAACAGCGACGTGG

ACAAGCTGTTCATCCAGCTGGTGCAGACCTACAACCAGCTGTTCGAGGAAAACCCCATCAACGCCAGC

GGCGTGGACGCCAAGGCCATCCTGTCTGCCAGACTGAGCAAGAGCAGACGGCTGGAAAATCTGATCG

CCCAGCTGCCCGGCGAGAAGAAGAATGGCCTGTTCGGAAACCTGATTGCCCTGAGCCTGGGCCTGACC

CCCAACTTCAAGAGCAACTTCGACCTGGCCGAGGATGCCAAACTGCAGCTGAGCAAGGACACCTACGA

CGACGACCTGGACAACCTGCTGGCCCAGATCGGCGACCAGTACGCCGACCTGTTTCTGGCCGCCAAGA

ACCTGTCCGACGCCATCCTGCTGAGCGACATCCTGAGAGTGAACACCGAGATCACCAAGGCCCCCCTG

AGCGCCTCTATGATCAAGAGATACGACGAGCACCACCAGGACCTGACCCTGCTGAAAGCTCTCGTGCG

GCAGCAGCTGCCTGAGAAGTACAAAGAGATTTTCTTCGACCAGAGCAAGAACGGCTACGCCGGCTACA

TTGACGGCGGAGCCAGCCAGGAAGAGTTCTACAAGTTCATCAAGCCCATCCTGGAAAAGATGGACGG

CACCGAGGAACTGCTCGTGAAGCTGAACAGAGAGGACCTGCTGCGGAAGCAGCGGACCTTCGACAAC

GGCAGCATCCCCCACCAGATCCACCTGGGAGAGCTGCACGCCATTCTGCGGCGGCAGGAAGATTTTTA

CCCATTCCTGAAGGACAACCGGGAAAAGATCGAGAAGATCCTGACCTTCCGCATCCCCTACTACGTGG

GCCCTCTGGCCAGGGGAAACAGCAGATTCGCCTGGATGACCAGAAAGAGCGAGGAAACCATCACCCC

CTGGAACTTCGAGGAAGTGGTGGACAAGGGCGCTTCCGCCCAGAGCTTCATCGAGCGGATGACCAAC

TTCGATAAGAACCTGCCCAACGAGAAGGTGCTGCCCAAGCACAGCCTGCTGTACGAGTACTTCACCGT

GTATAACGAGCTGACCAAAGTGAAATACGTGACCGAGGGAATGAGAAAGCCCGCCTTCCTGAGCGGC

GAGCAGAAAAAGGCCATCGTGGACCTGCTGTTCAAGACCAACCGGAAAGTGACCGTGAAGCAGCTGA

AAGAGGACTACTTCAAGAAAATCGAGTGCTTCGACTCCGTGGAAATCTCCGGCGTGGAAGATCGGTTC

AACGCCTCCCTGGGCACATACCACGATCTGCTGAAAATTATCAAGGACAAGGACTTCCTGGACAATGA

GGAAAACGAGGACATTCTGGAAGATATCGTGCTGACCCTGACACTGTTTGAGGACAGAGAGATGATC

GAGGAACGGCTGAAAACCTATGCCCACCTGTTCGACGACAAAGTGATGAAGCAGCTGAAGCGGCGGA

-continued

```
GATACACCGGCTGGGGCAGGCTGAGCCGGAAGCTGATCAACGGCATCCGGGACAAGCAGTCCGGCA

AGACAATCCTGGATTTCCTGAAGTCCGACGGCTTCGCCAACAGAAACTTCATGCAGCTGATCCACGACG

ACAGCCTGACCTTTAAAGAGGACATCCAGAAAGCCCAGGTGTCCGGCCAGGGCGATAGCCTGCACGA

GCACATTGCCAATCTGGCCGGCAGCCCCGCCATTAAGAAGGGCATCCTGCAGACAGTGAAGGTGGTG

GACGAGCTCGTGAAAGTGATGGGCCGGCACAAGCCCGAGAACATCGTGATCGAAATGGCCAGAGAG

AACCAGACCACCCAGAAGGGACAGAAGAACAGCCGCGAGAGAATGAAGCGGATCGAAGAGGGCATC

AAAGAGCTGGGCAGCCAGATCCTGAAAGAACACCCCGTGGAAAACACCCAGCTGCAGAACGAGAAGC

TGTACCTGTACTACCTGCAGAATGGGCGGGATATGTACGTGGACCAGGAACTGGACATCAACCGGCTG

TCCGACTACGATGTGGACCATATCGTGCCTCAGAGCTTTCTGAAGGACGACTCCATCGACAACAAGGT

GCTGACCAGAAGCGACAAGAACCGGGGCAAGAGCGACAACGTGCCCTCCGAAGAGGTCGTGAAGAA

GATGAAGAACTACTGGCGGCAGCTGCTGAACGCCAAGCTGATTACCCAGAGAAAGTTCGACAATCTGA

CCAAGGCCGAGAGAGGCGGCCTGAGCGAACTGGATAAGGCCGGCTTCATCAAGAGACAGCTGGTGG

AAACCCGGCAGATCACAAAGCACGTGGCACAGATCCTGGACTCCCGGATGAACACTAAGTACGACGA

GAATGACAAGCTGATCCGGGAAGTGAAAGTGATCACCCTGAAGTCCAAGCTGGTGTCCGATTTCCGGA

AGGATTTCCAGTTTTACAAAGTGCGCGAGATCAACAACTACCACCACGCCCACGACGCCTACCTGAACG

CCGTCGTGGGAACCGCCCTGATCAAAAAGTACCCTAAGCTGGAAAGCGAGTTCGTGTACGGCGACTAC

AAGGTGTACGACGTGCGGAAGATGATCGCCAAGAGCGAGCAGGAAATCGGCAAGGCTACCGCCAAG

TACTTCTTCTACAGCAACATCATGAACTTTTTCAAGACCGAGATTACCCTGGCCAACGGCGAGATCCGG

AAGCGGCCTCTGATCGAGACAAACGGCGAAACCGGGGAGATCGTGTGGGATAAGGGCCGGGATTTT

GCCACCGTGCGGAAAGTGCTGAGCATGCCCCAAGTGAATATCGTGAAAAAGACCGAGGTGCAGACAG

GCGGCTTCAGCAAAGAGTCTATCCTGCCCAAGAGGAACAGCGATAAGCTGATCGCCAGAAAGAAGGA

CTGGGACCCTAAGAAGTACGGCGGCTTCGACAGCCCCACCGTGGCCTATTCTGTGCTGGTGGTGGCCA

AAGTGGAAAAGGGCAAGTCCAAGAAACTGAAGAGTGTGAAAGAGCTGCTGGGGATCACCATCATGG

AAAGAAGCAGCTTCGAGAAGAATCCCATCGACTTTCTGGAAGCCAAGGGCTACAAAGAAGTGAAAAA

GGACCTGATCATCAAGCTGCCTAAGTACTCCCTGTTCGAGCTGGAAAACGGCCGGAAGAGAATGCTGG

CCTCTGCCGGCGAACTGCAGAAGGGAAACGAACTGGCCCTGCCCTCCAAATATGTGAACTTCCTGTAC

CTGGCCAGCCACTATGAGAAGCTGAAGGGCTCCCCCGAGGATAATGAGCAGAAACAGCTGTTTGTGG

AACAGCACAAGCACTACCTGGACGAGATCATCGAGCAGATCAGCGAGTTCTCCAAGAGAGTGATCCTG

GCCGACGCTAATCTGGACAAAGTGCTGTCCGCCTACAACAAGCACCGGGATAAGCCCATCAGAGAGCA

GGCCGAGAATATCATCCACCTGTTTACCCTGACCAATCTGGGAGCCCCTGCCGCCTTCAAGTACTTTGA

CACCACCATCGACCGGAAGAGGTACACCAGCACCAAAGAGGTGCTGGACGCCACCCTGATCCACCAGA

GCATCACCGGCCTGTACGAGACACGGATCGACCTGTCTCAGCTGGGAGGCGACAAAAGGCCGGCGGC

CACGAAAAAGGCCGGCCAGGCAAAAAAGAAAAAGgaattcGGCAGTGGAGAGGGCAGAGGAAGTCTG

CTAACATGCGGTGACGTCGAGGAGAATCCTGGCCCAGTGAGCAAGGGCGAGGAGCTGTTCACCGGGG

TGGTGCCCATCCTGGTCGAGCTGGACGGCGACGTAAACGGCCACAAGTTCAGCGTGTCCGGCGAGGG

CGAGGGCGATGCCACCTACGGCAAGCTGACCCTGAAGTTCATCTGCACCACCGGCAAGCTGCCCGTGC

CCTGGCCCACCCTCGTGACCACCCTGACCTACGGCGTGCAGTGCTTCAGCCGCTACCCCGACCACATGA

AGCAGCACGACTTCTTCAAGTCCGCCATGCCCGAAGGCTACGTCCAGGAGCGCACCATCTTCTTCAAGG

ACGACGGCAACTACAAGACCCGCGCCGAGGTGAAGTTCGAGGGCGACACCCTGGTGAACCGCATCGA

GCTGAAGGGCATCGACTTCAAGGAGGACGGCAACATCCTGGGGCACAAGCTGGAGTACAACTACAAC

AGCCACAACGTCTATATCATGGCCGACAAGCAGAAGAACGGCATCAAGGTGAACTTCAAGATCCGCCA
```

-continued

```
CAACATCGAGGACGGCAGCGTGCAGCTCGCCGACCACTACCAGCAGAACACCCCCATCGGCGACGGC

CCCGTGCTGCTGCCCGACAACCACTACCTGAGCACCCAGTCCGCCCTGAGCAAAGACCCCAACGAGAA

GCGCGATCACATGGTCCTGCTGGAGTTCGTGACCGCCGCCGGGATCACTCTCGGCATGGACGAGCTGT

ACAAGgaattctaaCTAGAGCTCGCTGATCAGCCTCGACTGTGCCTTCTAGTTGCCAGCCATCTGTTGTTTG

CCCCTCCCCCGTGCCTTCCTTGACCCTGGAAGGTGCCACTCCCACTGTCCTTTCCTAATAAAATGAGGAA

ATTGCATCGCATTGTCTGAGTAGGTGTCATTCTATTCTGGGGGGTGGGGTGGGGCAGGACAGCAAGG

GGGAGGATTGGGAAGAgAATAGCAGGCATGCTGGGGAgcggccgcaggaaccccctagtgatggagttggccactc cctctctgcgcgctcgctcgctcactgaggccgggcgaccaaaggtcgcccgacgcccgggctttgcccgggcggcctcagtgagcga gcgagcgcgcagctgcctgcaggggcgcctgatgcggtattttctccttacgcatctgtgcggtatttcacaccgcatacgtcaaagcaa ccatagtacgcgccctgtagcggcgcattaagcgcggcgggtgtggtggttacgcgcagcgtgaccgctacacttgccagcgccctagc gcccgctcctttcgctttcttcccttcctttctcgccacgttcgccggctttccccgtcaagctctaaatcgggggctcccttttagggttccga tttagtgctttacggcacctcgaccccaaaaaacttgatttgggtgatggttcacgtagtgggccatcgccctgatagacggttttttcgcc ctttgacgttggagtccacgttctttaatagtggactcttgttccaaactggaacaacactcaaccctatctcgggctattcttttgatttat aagggattttgccgatttcggcctattggttaaaaaatgagctgatttaacaaaaatttaacgcgaattttaacaaaatattaacgtttac aattttatggtgcactctcagtacaatctgctctgatgccgcatagttaagccagccccgacacccgccaacacccgctgacgcgccctg acgggcttgtctgctcccggcatccgcttacagacaagctgtgaccgtctccgggagctgcatgtgtcagaggttttcaccgtcatcacc gaaacgcgcgagacgaaagggcctcgtgatacgcctatttttataggttaatgtcatgataataatggtttcttagacgtcaggtggcac ttttcggggaaatgtgcgcggaacccctatttgtttatttttctaaatacattcaaatatgtatccgctcatgagacaataaccctgataaa tgcttcaataatattgaaaaaggaagagtatgagtattcaacatttccgtgtcgcccttattcccttttttgcggcattttgccttcctgttttt gctcacccagaaacgctggtgaaagtaaaagatgctgaagatcagttgggtgcacgagtgggttacatcgaactggatctcaacagc ggtaagatccttgagagttttcgccccgaagaacgttttccaatgatgagcacttttaaagttctgctatgtggcgcggtattatcccgtat tgacgccgggcaagagcaactcggtcgccgcatacactattctcagaatgacttggttgagtactcaccagtcacagaaaagcatctta cggatggcatgacagtaagagaattatgcagtgctgccataaccatgagtgataacactgcggccaacttacttctgacaacgatcgg aggaccgaaggagctaaccgcttttttgcacaacatgggggatcatgtaactcgccttgatcgttgggaaccggagctgaatgaagcc ataccaaacgacgagcgtgacaccacgatgcctgtagcaatggcaacaacgttgcgcaaactattaactggcgaactacttactctag cttcccggcaacaattaatagactggatggaggcggataaagttgcaggaccacttctgcgctcggcccttccggctggctggtttattg ctgataaatctggagccggtgagcgtggaagccgcggtatcattgcagcactggggccagatggtaagccctcccgtatcgtagttatc tacacgacggggagtcaggcaactatggatgaacgaaatagacagatcgctgagataggtgcctcactgattaagcattggtaactgt cagaccaagtttactcatatatactttagattgatttaaaacttcattttaattaaaaggatctaggtgaagatcctttttgataatctca tgaccaaaatcccttaacgtgagttttcgttccactgagcgtcagaccccgtagaaaagatcaaaggatcttcttgagatcctttttttct gcgcgtaatctgctgcttgcaaacaaaaaaaccaccgctaccagcggtggtttgtttgccggatcaagagctaccaactcttttccgaa ggtaactggcttcagcagagcgcagataccaaatactgtccttctagtgtagccgtagttaggccaccacttcaagaactctgtagcac cgcctacatacctcgctctgctaatcctgttaccagtggctgctgccagtggcgataagtcgtgtcttaccgggttggactcaagacgata gttaccggataaggcgcagcggtcgggctgaacggggggttcgtgcacacagcccagcttggagcgaacgacctacaccgaactgag atacctacagcgtgagctatgagaaagcgccacgcttcccgaagggagaaaggcggacaggtatccggtaagcggcagggtcggaa caggagagcgcacgagggagcttccaggggaaacgcctggtatctttatagtcctgtcgggtttcgccacctctgacttgagcgtcga tttttgtgatgctcgtcaggggggcggagcctatggaaaaacgccagcaacgcggcctttttacggttcctggccttttgctggccttttg ctcacatg
```

-continued p946// pAAV-IRBP-SpCas9

(SEQ ID NO: 7)

tgcagctggcacgacaggtttcccgactggaaagcgggcagtgagcgcaacgcaattaatgtgagttagctcactcattaggcacccc aggctttacactttatgcttccggctcgtatgttgtgtggaattgtgagcggataacaatttcacacaggaaacagctatgaccatgatta cgccagatttaattaaggctgcgcgctcgctcgctcactgaggccgcccgggcaaagcccgggcgtcgggcgacctttggtcgcccggc ctcagtgagcgagcgagcgcgcagagagggagtggccaactccatcactagggggttccttgtagttaatgattaacccgccatgctact tatctacgtagccatgctctaggaagatcggaattcgcccttaagctagtagcacagtgtctggcatgtagcaggaactaaaataatgg cagtgattaatgttatgatatgcagacacaacacagcaagataagatgcaatgtaccttctgggtcaaaccaccctggccactcctccc cgatacccagggttgatgtgcttgaattagacaggattaaaggcttactggagctggaagccttgccccaactcaggagtttagcccca gaccttctgtccaccagcgcggccgaccggccaagggcgaattctgcagatatccatcacactggcggccgatcccgggtaccggtg ccaccatgtacccatacgatgttccagattacgcttcgccgaagaaaaagcgcaaggtcgaagcgtccgacaagaagtacagcatcg gcctggacatcggcaccaactctgtgggctgggccgtgatcaccgacgagtacaaggtgcccagcaagaaattcaaggtgctgggca acaccgaccggcacagcatcaagaagaacctgatcggagccctgctgttcgacagcggcgaaacagccgaggccacccggctgaag agaaccgccagaagaagatacaccagacggaagaaccggatctgctatctgcaagagatcttcagcaacgagatggccaaggtgga cgacagcttcttccacagactggaagagtccttcctggtggaagaggataagaagcacgagcggcaccccatcttcggcaacatcgtg gacgaggtggcctaccacgagaagtaccccaccatctaccacctgagaaagaaactggtggacagcaccgacaaggccgacctgcg gctgatctatctggccctggcccacatgatcaagttccggggccacttcctgatcgagggcgacctgaaccccgacaacagcgacgtgg acaagctgttcatccagctggtgcagacctacaaccagctgttcgaggaaaaccccatcaacgccagcggcgtggacgccaaggccat cctgtctgccagactgagcaagagcagacggctggaaaatctgatcgcccagctgcccggcgagaagaagaatggcctgttcggcaa cctgattgccctgagcctgggcctgacccccaacttcaagagcaacttcgacctggccgaggatgccaaactgcagctgagcaaggac acctacgacgacgacctggacaacctgctggcccagatcggcgaccagtacgccgacctgttcctggccgccaagaacctgtccgacg ccatcctgctgagcgacatcctgagagtgaacaccgagatcaccaaggcccccctgagcgcctctatgatcaagagatacgacgagca ccaccaggacctgaccctgctgaaagctctcgtgcggcagcagctgcctgagaagtacaaagagattttcttcgaccagagcaagaac ggctacgccggctacattgacggcggagccagccaggaagagttctacaagttcatcaagcccatcctggaaaagatggacggcacc gaggaactgctcgtgaagctgaacagagaggacctgctgcggaagcagcggaccttcgacaacggcagcatcccccaccagatccac ctgggagagctgcacgccattctgcggcggcaggaagattttttacccattcctgaaggacaaccgggaaaagatcgagaagatcctga ccttccgcatcccctactacgtgggccctctggccaggggaaacagcagattcgcctggatgaccagaaagagcgaggaaaccatcac ccctggaacttcgaggaagtggtggacaagggcgcttccgcccagagcttcatcgagcggatgaccaacttcgataagaacctgccc aacgagaaggtgctgcccaagcacagcctgctgtacgagtacttcaccgtgtataacgagctgaccaaagtgaaatacgtgaccgag ggaatgagaaagcccgcctcctgagcggcgagcagaaaaaggccatcgtggacctgctgttcaagaccaaccggaaagtgaccgtg aagcagctgaaagaggactacttcaagaaaatcgagtgcttcgactccgtggaaatctccggcgtggaagatcggttcaacgcctccc tgggcacataccacgatctgctgaaaattatcaaggacaaggacttcctggacaatgaggaaaacgaggacattctggaagatatcgt gctgaccctgacactgtttgaggacagagagatgatcgaggaacggctgaaaacctatgcccacctgttcgacgacaaagtgatgaa gcagctgaagcggcggagatacaccggctggggcaggctgagccggaagctgatcaacggcatccgggacaagcagtccggcaaga caatcctggatttcctgaagtccgacggcttcgccaacagaaacttcatgcagctgatccacgacgacagcctgacctttaaagaggac atccagaaagcccaggtgtccggccagggcgatagcctgcacgagcacattgccaatctggccggcagccccgccattaagaagggc atcctgcagacagtgaaggtggtggacgagctcgtgaaagtgatgggccggcacaagcccgagaacatcgtgatcgaaatggccaga gagaaccagaccacccagaagggacagaagaacagccgcgagagaatgaagcggatcgaagagggcatcaaagagctgggcagc cagatcctgaaagaacaccccgtggaaaacacccagctgcagaacgagaagctgtacctgtactacctgcagaatgggggggatatg tacgtggaccaggaactggacatcaaccggctgtccgactacgatgtggaccatatcgtgcctcagagctttctgaaggacgactccat cgacaacaaggtgctgaccagaagcgacaagaaccggggcaagagcgacaacgtgccctccgaagaggtcgtgaagaagatgaag -continued

```
aactactggcggcagctgctgaacgccaagctgattacccagagaaagttcgacaatctgaccaaggccgagagaggcggcctgagc gaactggataaggccggcttcatcaagagacagctggtggaaacccggcagatcacaaagcacgtggcacagatcctggactcccgg atgaacactaagtacgacgagaatgacaagctgatccgggaagtgaaagtgatcaccctgaagtccaagctggtgtccgatttccgga aggatttccagttttacaaagtgcgcgagatcaacaactaccaccacgcccacgacgcctacctgaacgccgtcgtgggaaccgccct gatcaaaaagtaccctaagctggaaagcgagttcgtgtacggcgactacaaggtgtacgacgtgcggaagatgatcgccaagagcga gcaggaaatcggcaaggctaccgccaagtacttcttctacagcaacatcatgaacttttttcaagaccgagattaccctggccaacggcg agatccggaagcggcctctgatcgagacaaacggcgaaaccggggagatcgtgtgggataagggccggattttgccaccgtgcgga aagtgctgagcatgccccaagtgaatatcgtgaaaaagaccgaggtgcagacaggcggcttcagcaaagagtctatcctgcccaaga ggaacagcgataagctgatcgccagaagaaggactgggaccctaagaagtacggcggcttcgacagccccaccgtggcctattctg tgctggtggtggccaaagtggaaaagggcaagtccaagaaactgaagagtgtgaaagagctgctggggatcaccatcatggaaaga agcagcttcgagaagaatcccatcgactttctggaagccaagggctacaaagaagtgaaaaaggacctgatcatcaagctgcctaag tactcccctgttcgagctggaaaacggccggaagagaatgctggcctctgccggcgaactgcagaagggaaacgaactggccctgccct ccaaatatgtgaacttcctgtacctggccagccactatgagaagctgaagggctcccccgaggataatgagcagaaacagctgtttgtg gaacagcacaagcactacctggacgagatcatcgagcagatcagcgagttctccaagagagtgatcctggccgacgctaatctggac aaagtgctgtccgcctacaacaagcacgggataagcccatcagagagcaggccgagaatatcatccacctgtttaccctgaccaatc tgggagcccctgccgccttcaagtactttgacaccaccatcgaccggaagaggtacaccagcaccaaagaggtgctggacgccaccct gatccaccagagcatcaccggcctgtacgagacacgatcgacctgtctcagctgggaggcgacagccccaagaagaagagaaagg tggaggccagctaagaattcaataaaagatctttattttcattagatctgtgtgttggttttttgtgtgcggccgcaggaaccctagtgat ggagttggccactccctctctgcgcgctcgctcgctcactgaggccgggcgaccaaaggtcgcccgacgcccgggctttgcccgggcgg cctcagtgagcgagcgagcgcgcagctgcctgcaggggcgcctgatgcggtattttctccttacgcatctgtgcggtatttcacaccgca tacgtcaaagcaaccatagtacgcgccctgtagcggcgcattaagcgcggcgggtgtggtggttacgcgcagcgtgaccgctacactt gccagcgccctagcgcccgctcctttcgctttcttcccttcctttctcgccacgttcgccggctttccccgtcaagctctaaatcgggggctc cctttagggttccgatttagtgctttacggcacctcgaccccaaaaaacttgatttgggtgatggttcacgtagtgggccatcgccctgat agacggttttttcgccctttgacgttggagtccacgttctttaatagtggactcttgttccaaactggaacaacactcaaccctatctcgggc tattcttttgatttataagggattttgccgatttcggcctattggttaaaaaatgagctgatttaacaaaaatttaacgcgaattttaacaa aatattaacgtttacaatttttatggtgcactctcagtacaatctgctctgatgccgcatagttaagccagccccgacacccgccaacacc cgctgacgcgccctgacgggcttgtctgctcccggcatccgcttacagacaagctgtgaccgtctccgggagctgcatgtgtcagaggtt ttcaccgtcatcaccgaaacgcgcgagacgaaagggcctcgtgatacgcctatttttataggttaatgtcatgataataatggtttcttag acgtcaggtggcacttttcggggaaatgtgcgcggaacccctatttgtttatttttctaaatacattcaaatatgtatccgctcatgagac aataaccctgataaatgcttcaataatattgaaaaaggaagagtatgagtattcaacatttccgtgtcgcccttattcccttttttgcggc attttgccttcctgtttttgctcacccagaaacgctggtgaaagtaaaagatgctgaagatcagttgggtgcacgagtgggttacatcga actggatctcaacagcggtaagatccttgagagttttcgccccgaagaacgttttccaatgatgagcacttttaaagttctgctatgtggc gcggtattatcccgtattgacgccgggcaagagcaactcggtcgccgcatacactattctcagaatgacttggttgagtactcaccagtc acagaaaagcatcttacggatggcatgacagtaagagaattatgcagtgctgccataaccatgagtgataacactgcggccaacttac ttctgacaacgatcggaggaccgaaggagctaaccgcttttttgcacaacatggggatcatgtaactcgccttgatcgttgggaaccg gagctgaatgaagccataccaaacgacgagcgtgacaccacgatgcctgtagcaatggcaacaacgttgcgcaaactattaactggc gaactacttactctagcttcccggcaacaattaatagactggatggaggcggataaagttgcaggaccacttctgcgctcggcccttccg gctggctggtttattgctgataaatctggagccggtgagcgtggaagccgcggtatcattgcagcactggggccagatggtaagccctc ccgtatcgtagttatctacacgacggggagtcaggcaactatggatgaacgaaatagacagatcgctgagataggtgcctcactgatt aagcattggtaactgtcagaccaagtttactcatatatactttagattgatttaaaacttcatttttaatttaaaaggatctaggtgaagat cctttttgataatctcatgaccaaaatcccttaacgtgagttttcgttccactgagcgtcagaccccgtagaaaagatcaaaggatcttct
```

-continued

```
tgagatcctttttttctgcgcgtaatctgctgcttgcaaacaaaaaaaccaccgctaccagcggtggtttgtttgccggatcaagagctac caactctttttccgaaggtaactggcttcagcagagcgcagataccaaatactgtccttctagtgtagccgtagttaggccaccacttca agaactctgtagcaccgcctacatacctcgctctgctaatcctgttaccagtggctgctgccagtggcgataagtcgtgtcttaccgggtt ggactcaagacgatagttaccggataaggcgcagcggtcgggctgaacggggggttcgtgcacacagcccagcttggagcgaacgac ctacaccgaactgagatacctacagcgtgagctatgagaaagcgccacgcttcccgaagggagaaaggcggacaggtatccggtaag cggcagggtcggaacaggagagcgcacgagggagcttccaggggggaaacgcctggtatctttatagtcctgtcgggtttcgccacctct gacttgagcgtcgatttttgtgatgctcgtcaggggggcggagcctatggaaaaacgccagcaacgcggcctttttacggttcctggcct tttgctggccttttgctcacatgttctttcctgcgttatcccctgattctgtggataaccgtattaccgcctttgagtgagctgataccgctcg ccgcagccgaacgaccgagcgcagcgagtcagtgagcgaggaagcggaagagcgcccaatacgcaaaccgcctctccccgcgcgtt ggccgattcattaa
``` p1139_pAAV2.1._HLP_SpCas9(HA)_spA (SEQ ID NO: 8)

```
ataacaatttcacacaggaaacagctatgaccatgattacgccagatttaattaaggctgcgcgctcgctcgctcactgaggccgcccg ggcaaagcccgggcgtcgggcgacctttggtcgcccggcctcagtgagcgagcgagcgcgcagagagggagtggccaactccatcac taggggttccttgtagttaatgattaacccgccatgctacttatctacgtagccatgctctaggaagatcggaattcgcccGAATTC GCCCTTAAgcggccgcaagcCTTAAGTGTTTGCTGCTTGCAATGTTTGCCCATTTTAGGGTGGACACAGGA

CGCTGTGGTTTCTGAGCCAGGGGGCGACTCAGATCCCAGCCAGTGGACTTAGCCCCTGTTTGCTCCTCC

GATAACTGGGGTGACCTTGGTTAATATTCACCAGCAGCCTCCCCCGTTGCCCCTCTGGATCCACTGCTT

AAATACGGACGAGGACAGGGCCCTGTCTCCTCAGCTTCAGGCACCACCACTGACCTGGGACAGTGAAT

CACCGGTacCTGCTTTTGCTCGCTTGGATCCCCGGTGCCACCATGTccggtgccaccatgtacccatacgatgttcc agattacgcttcgccgaagaaaaagcgcaaggtcgaagcgtccgacaagaagtacagcatcggcctggacatcggcaccaactctgt gggctgggccgtgatcaccgacgagtacaaggtgcccagcaagaaattcaaggtgctgggcaacaccgaccggcacagcatcaaga agaacctgatcggagccctgctgttcgacagcggcgaaacagccgaggccaccggctgaagagaaccgccagaagaagatacacc agacggaagaaccggatctgctatctgcaagagatcttcagcaacgagatggccaaggtggacgacagcttcttccacagactggaa gagtccttcctggtggaagaggataagaagcacgagcggcaccccatcttcggcaacatcgtggacgaggtggcctaccacgagaag taccccaccatctaccacctgagaaagaaactggtggacagcaccgacaaggccgacctgcggctgatctatctggccctggcccaca tgatcaagttccggggccacttcctgatcgagggcgacctgaaccccgacaacagcgacgtggacaagctgttcatccagctggtgca gacctacaaccagctgttcgaggaaaaccccatcaacgccagcggcgtggacgccaaggccatcctgtctgccagactgagcaagag cagacggctggaaaatctgatcgcccagctgcccggcgagaagaagaatggcctgttcggcaacctgattgccctgagcctgggcctg accccaacttcaagagcaacttcgacctggccgaggatgccaaactgcagctgagcaaggacacctacgacgacgacctggacaac ctgctggcccagatcggcgaccagtacgccgacctgtttctggccgccaagaacctgtccgacgccatcctgctgagcgacatcctgag agtgaacaccgagatcaccaaggcccccctgagcgcctctatgatcaagagatacgacgagcaccaccaggacctgacccTgctgaa agctctcgtgcggcagcagctgcctgagaagtacaaagagatttttcttcgaccagagcaagaacggctacgccggctacattgacggc ggagccagccaggaagagttctacaagttcatcaagcccatcctggaaaagatggacggcaccgaggaactgctcgtgaagctgaac agagaggacctgctgcggaagcagcggaccttcgacaacggcagcatcccccaccagatccacctgggagagctgcacgccattctg cggcggcaggaagattttttacccattcctgaaggacaacgggaaaagatcgagaagatcctgaccttccgcatcccctactacgtgg gccctctggccagggggaaacagcagattcgcctggatgaccagaaagagcgaggaaaccatcacccccctggaacttcgaggaagtg gtggacaagggcgcttccgcccagagcttcatcgagcggatgaccaacttcgataagaacctgcccaacgagaaggtgctgcccaag cacagcctgctgtacgagtacttcaccgtgtataacgagctgaccaaagtgaaatacgtgaccgagggaatgagaaagcccgccttcc tgagcggcgagcagaaaaaggccatcgtggacctgctgttcaagaccaaccggaaagtgaccgtgaagcagctgaaagaggactac ttcaagaaaatcgagtgcttcgactccgtggaaatctccggcgtggaagatcggttcaacgcctcccctgggcacataccacgatctgct
```

-continued

```
gaaaattatcaaggacaaggacttcctggacaatgaggaaaacgaggacattctggaagatatcgtgctgaccctgacactgtttgag
gacagagagatgatcgaggaacggctgaaaacctatgcccacctgttcgacgacaaagtgatgaagcagctgaagcggcggagata
caccggctggggcaggctgagccggaagctgatcaacggcatccgggacaagcagtccggcaagacaatcctggatttcctgaagtc
cgacggcttcgccaacagaaacttcatgcagctgatccacgacgacagcctgacctttaaagaggacatccagaaagcccaggtgtcc
ggccagggcgatagcctgcacgagcacattgccaatctggccggcagccccgccattaagaagggcatcctgcagacagtgaaggtg
gtggacgagctcgtgaaagtgatgggccggcacaagcccgagaacatcgtgatcgaaatggccagagagaaccagaccacccagaa
gggacagaagaacagccgcgagagaatgaagcggatcgaagagggcatcaaagagctgggcagccagatcctgaaagaacacccc
gtggaaaacacccagctgcagaacgagaagctgtacctgtactacctgcagaatggggggatatgtacgtggaccaggaactggac
atcaaccggctgtccgactacgatgtggaccatatcgtgcctcagagctttctgaaggacgactccatcgacaacaaggtgctgaccag
aagcgacaagaaccggggcaagagcgacaacgtgccctccgaagaggtcgtgaagaagatgaagaactactggcggcagctgctg
aacgccaagctgattacccagagaaagttcgacaatctgaccaaggccgagagaggcggcctgagcgaactggataaggccggcttc
atcaagagacagctggtggaaacccggcagatcacaaagcacgtggcacagatcctggactcccggatgaacactaagtacgacga
gaatgacaagctgatccgggaagtgaaagtgatcaccctgaagtccaagctggtgtccgatttccggaaggatttccagttttacaaag
tgcgcgagatcaacaactaccaccacgcccacgacgcctacctgaacgccgtcgtgggaaccgccctgatcaaaaagtaccctaagct
ggaaagcgagttcgtgtacggcgactacaaggtgtacgacgtgcggaagatgatcgccaagagcgagcaggaaatcggcaaggcta
ccgccaagtacttcttctacagcaacatcatgaacttttttcaagaccgagattaccctggccaacggcgagatccggaagcggcctctg
atcgagacaaacggcgaaaccggggagatcgtgtgggataagggccggattttgccaccgtgcggaaagtgctgagcatgccccaa
gtgaatatcgtgaaaaagaccgaggtgcagacaggcggcttcagcaaagagtctatcctgcccaagaggaacagcgataagctgatc
gccagaaagaaggactgggaccctaagaagtacggcggcttcgacagccccaccgtggcctattctgtgctggtggtggccaaagtgg
aaaagggcaagtccaagaaactgaagagtgtgaaagagctgctggggatcaccatcatggaaagaagcagcttcgagaagaatccc
atcgactttctggaagccaagggctacaaagaagtgaaaaaggacctgatcatcaagctgcctaagtactccctgttcgagctggaaa
acggccggaagagaatgctggcctctgccggcgaactgcagaagggaaacgaactggccctgccctccaaatatgtgaacttcctgta
cctggccagccactatgagaagctgaagggctcccccgaggataatgagcagaaacagctgtttgtggaacagcacaagcactacct
ggacgagatcatcgagcagatcagcgagttctccaagagagtgatcctggccgacgctaatctggacaaagtgctgtccgcctacaac
aagcaccgggataagcccatcagagagcaggccgagaatatcatccacctgtttaccctgaccaatctgggagccctgccgccttca
agtactttgacaccaccatcgaccggaagaggtacaccagcaccaaagaggtgctggacgccaccctgatccaccagagcatcaccg
gcctgtacgagacacgatcgacctgtctcagctgggaggcgacagccccaagaagaagagaaaggtggaggccagctaagaattc
aataaaagatctttattttcattagatctgtgtgttggttttttgtgtgcggccgcaggaacccctagtgatggagttggccactccctctct
gcgcgctcgctcgctcactgaggccgggcgaccaaaggtcgcccgacgcccgggctttgcccgggcggcctcagtgagcgagcgagc
gcgcagctgcctgcaggggcgcctgatgcggtattttctccttacgcatctgtgcggtatttcacaccgcatacgtcaaagcaaccatag
tacgcgccctgtagcggcgcattaagcgcggcgggtgtggtggttacgcgcagcgtgaccgctacacttgccagcgccctagcgcccgc
tcctttcgctttcttcccttcctttctcgccacgttcgccggctttccccgtcaagctctaaatcggggggctcccctttagggttccgatttagt
gctttacggcacctcgaccccaaaaaacttgatttgggtgatggttcacgtagtgggccatcgccctgatagacggttttcgccctttga
cgttggagtccacgttctttaatagtggactcttgttccaaactggaacaacactcaaccctatctcgggctattcttttgatttataaggg
attttgccgatttcggcctattggttaaaaaatgagctgatttaacaaaaatttaacgcgaattttaacaaaatattaacgtttacaattttt
atggtgcactctcagtacaatctgctctgatgccgcatagttaagccagccccgacacccgccaacacccgctgacgcgccctgacggg
cttgtctgctcccggcatccgcttacagacaagctgtgaccgtctccgggagctgcatgtgtcagaggttttcaccgtcatcaccgaaac
gcgcgagacgaaagggcctcgtgatacgcctatttttataggttaatgtcatgataataatggtttcttagacgtcaggtggcacttttcg
gggaaatgtgcgcggaacccctatttgtttatttttctaaatacattcaaatatgtatccgctcatgagacaataaccctgataaatgctt
caataatattgaaaaggaagagtatgagtattcaacatttccgtgtcgcccttattccctttttttgcggcattttgccttcctgttttttgctc
acccagaaacgctggtgaaagtaaaagatgctgaagatcagttgggtgcacgagtgggttacatcgaactggatctcaacagcggta
```

-continued agatccttgagagttttcgccccgaagaacgttttccaatgatgagcacttttaaagttctgctatgtggcgcggtattatcccgtattgac gccgggcaagagcaactcggtcgccgcatacactattctcagaatgacttggttgagtactcaccagtcacagaaaagcatcttacgg atggcatgacagtaagagaattatgcagtgctgccataaccatgagtgataacactgcggccaacttacttctgacaacgatcggagg accgaaggagctaaccgcttttttgcacaacatggggatcatgtaactcgccttgatcgttgggaaccggagctgaatgaagccatac caaacgacgagcgtgacaccacgatgcctgtagcaatggcaacaacgttgcgcaaactattaactggcgaactacttactctagcttcc cggcaacaattaatagactggatggaggcggataaagttgcaggaccacttctgcgctcggcccttccggctggctggtttattgctgat aaatctggagccggtgagcgtggaagccgcggtatcattgcagcactggggccagatggtaagccctcccgtatcgtagttatctacac gacggggagtcaggcaactatggatgaacgaaatagacagatcgctgagataggtgcctcactgattaagcattggtaactgtcagac caagtttactcatatatactttagattgatttaaaacttcattttaatttaaaaggatctaggtgaagatcctttttgataatctcatgacc aaaatcccttaacgtgagttttcgttccactgagcgtcagacccccgtagaaaagatcaaaggatcttcttgagatccttttttttctgcgcg taatctgctgcttgcaaacaaaaaaaccaccgctaccagcggtggtttgtttgccggatcaagagctaccaactctttttccgaaggtaa ctggcttcagcagagcgcagataccaaatactgtccttctagtgtagccgtagttaggccaccacttcaagaactctgtagcaccgccta catacctcgctctgctaatcctgttaccagtggctgctgccagtggcgataagtcgtgtcttaccgggttggactcaagacgatagttacc ggataaggcgcagcggtcgggctgaacggggggtcgtgcacacagcccagcttggagcgaacgacctacaccgaactgagatacct acagcgtgagctatgagaaagcgccacgcttcccgaagggagaaaggcggacaggtatccggtaagcggcagggtcggaacagga gagcgcacgagggagcttccaggggaaacgcctggtatctttatagtcctgtcgggtttcgccacctctgacttgagcgtcgatttttgt gatgctcgtcaggggggcggagcctatggaaaaacgccagcaacgcggcctttttacggttcctggccttttgctggccttttgctcaca tgttctttcctgcgttatcccctgattctgtggataaccgtattaccgcctttgagtgagctgataccgctcgccgcagccgaacgaccga gcgcagcgagtcagtgagcgaggaagcggaagagcgcccaatacgcaaaccgcctctccccgcgcgttggccgattcattaatgcag ctggcacgacaggtttcccgactggaaagcgggcagtgagcgcaacgcaattaatgtgagttagctcactcattaggcaccccaggctt tacactttatgcttccggctcgtatgttgtgtggaattgtgagcgg p1135// pAAV2.1 mRHOgRNA-mRHO HITI (kozak-dsRED)_hVmd2-EGFP (SEQ ID NO: 9)

ttaatgtgagttagctcactcattaggcaccccaggctttacactttatgcttccggctcgtatgttgtgtggaattgtgagcggataacaa tttcacacaggaaacagctatgaccatgattacgccagatttaattaaggctgcgcgctcgctcgctcactgaggccgcccgggcaaag cccgggcgtcgggcgacctttggtcgcccggcctcagtgagcgagcgagcgcgcagagagggagtggccaactccatcactaggggtt ccttgtagttaatgattaacccgccatgctacttatctacgtagccatgctctaggaagatcggaattcgcccttaaccactagtaacggc cgccagtgtgctggaattcgcccttttcgagggcctatttcccatgattccttcatatttgcatatacgatacaaggctgttagagagataa ttggaattaatttgactgtaaacacaaagatattagtacaaaatacgtgacgtagaaagtaataatttcttgggtagtttgcagttttaa aattatgttttaaaatggactatcatatgcttaccgtaacttgaaagtatttcgatttcttggctttatatatcttgtggaaaggacgaaac accggcagccgcagtactacctgggttttagagctagaaatagcaagttaaaataaggctagtccgttatcaacttgaaaaagtggca ccgagtcggtgcttttttgttttagagctagaaatagcaagctcgagcagcctgaattctgcagatatccatcacactggcggccttaact cggatccactagtaacggccgccagtgtgctggaattcaggccgccaggtagtactgcggctgctaataaataataagccaccatgga tagcactgagaacgtcatcaagcccttcatgcgcttcaaggtgcacatggagggctccgtgaacggccacgagttcgagatcgagggc gagggcgagggcaagccctacgagggcacccagaccgccaagctgcaggtgaccaagggcggccccctgcccttcgcctgggacatc ctgtcccccagttccagtacggctccaaggtgtacgtgaagcaccccgccgacatccccgactacaagaagctgtccttccccgaggg cttcaagtgggagcgcgtgatgaacttcgaggacggcggcgtggtgaccgtgacccaggactcctccctgcaggacggcaccttcatct accacgtgaagttcatcggcgtgaacttcccctccgacggccccgtaatgcagaagaagactctgggctgggagccctccaccgagcg cctgtaccccgcgacggcgtgctgaagggcgagatccacaaggcgctgaagctgaagggcggcggccactacctggtggagttcaa gtcaatctacatggccaagaagcccgtgaagctgccggctactactacgtggactccaagctggacatcacctcccacaacgaggac tacaccgtggtggagcagtacgagcgcgccgaggcccgccaccacctgttccagtagcggccgcgactctagaattccaactgagcgc -continued

```
cggtcgctaccattaccaacttgtctggtgtcaaaaataataggcctactagagtcgacctgcagaagcttggatctgcctcgactgtgc
cttctagttgccagccatctgttgtttgcccctccccgtgccttccttgaccctggaaggtgccactcccactgtcctttcctaataaaatg
aggaaattgcatcgcattgtctgagtaggtgtcattctattctggggggtggggtggggcaggacagcaaggggggaggattgggaaga
caatagcaggcatgctggggaccgccaggtagtactgcggctgcaagggcgaattctgcagatatccatcacactggcgttaagcgtc
agcatatgcagaattctgtcattttactagggtgatgaaattcccaagcaacaccatccttttcagataagggcactgaggctgagaga
ggagctgaaacctaccggggtcaccacacaggtggcaaggctgggaccagaaaccaggactgttgactgcagcccggtattcat
tctttccatagcccacagggctgtcaaagaccccagggcctagtcagaggctcctccttcctggagagttcctggcacagaagttgaag
ctcagcacagcccctaaccccaactctctctgcaaggcctcagggggtcagaacactggtggagcagatccctttagcctctggattttta
gggccatggtagagggggtgttgccctaaattccagccctggtctcagcccaacaccctccaagaagaaattagaggggccatggcca
ggctgtgctagccgttgcttctgagcagattacaagaagggactaagacaaggactcctttgtggaggtcctggcttagggagtcaagt
gacggcggctcagcactcacgtgggcagtgccagcctctaagagtgggcaggggcactggccacagagtcccaggagtcccaccag
cctagtcgccagaccttctgtgggcggccgccatggtgagcaagggcgaggagctgttcaccggggtggtgcccatcctggtcgagctg
gacggcgacgtaaacggccacaagttcagcgtgtccggcgagggcgagggcgatgccacctacggcaagctgaccctgaagttcatc
tgcaccaccggcaagctgcccgtgccctggcccaccctcgtgaccaccctgacctacggcgtgcagtgcttcagccgctaccccgacca
catgaagcagcacgacttcttcaagtccgccatgcccgaaggctacgtccaggagcgcaccatcttcttcaaggacgacggcaactac
aagacccgcgccgaggtgaagttcgagggcgacaccctggtgaaccgcatcgagctgaagggcatcgacttcaaggaggacggcaa
catcctggggcacaagctggagtacaactacaacagccacaacgtctatatcatggccgacaagcagaagaacggcatcaaggtgaa
cttcaagatccgccacaacatcgaggacggcagcgtgcagctcgccgaccactaccagcagaacacccccatcggcgacggccccgt
gctgctgcccgacaaccactacctgagcacccagtccgccctgagcaaagacccaacgagaagcgcgatcacatggtcctgctgga
gttcgtgaccgccgccgggatcactctcggcatggacgagctgtacaagtaataagcttggatccaatcaacctctggattacaaaattt
gtgaaagattgactggtattcttaactatgttgctccttttacgctatgtggatacgctgctttaatgcctttgtatcatgctattgcttcccg
tatggctttcattttctcctccttgtataaatcctggttgctgtctctttatgaggagttgtggcccgttgtcaggcaacgtggcgtggtgtgc
actgtgtttgctgacgcaaccccactggttgggcattgccaccacctgtcagctcctttccgggactttcgctttcccctcctattgcc
acggcggaactcatcgccgcctgccttgcccgctgctggacaggggctcggctgttgggcactgacaattccgtggtgttgtcggggaa
gctgacgtccttccatggctgctcgcctgtgttgccacctggattctgcgcgggacgtcctctgctacgtcccttcggccctcaatccag
cggaccttccttcccgcggcctgctgccggctctgcggcctcttccgcgtcttcgagatctgcctcgactgtgccttctagttgccagccat
ctgttgtttgcccctccccgtgccttccttgaccctggaaggtgccactcccactgtcctttcctaataaaatgaggaaattgcatcgcat
tgtctgagtaggtgtcattctattctggggggggggtggggcaggacagcaaggggggaggattgggaagacaatagcaggcatgctg
gggactcgagttaagggcgaattcccgattaggatcttcctagagcatggctacgtagataagtagcatggcgggttaatcattaacta
caaggaaccccagtgatggagttggccactccctctctgcgcgctcgctcgctcactgaggccgggcgaccaaaggtcgcccgacgcc
cgggctttgcccgggcggcctcagtgagcgagcgagcgcgcagccttaattaacctaattcactggccgtcgttttacaacgtcgtgact
gggaaaaccctggcgttacccaacttaatcgccttgcagcacatccccctttcgccagctggcgtaatagcgaagaggcccgcaccgat
cgcccttcccaacagttgcgcagcctgaatggcgaatgggacgcgccctgtagcggcgcattaagcgcggcgggtgtggtggttacgc
gcagcgtgaccgctacacttgccagcgccctagcgcccgctcctttcgctttcttcccttcctttctcgccacgttcgccggctttccccgtc
aagctctaaatcggggggctccctttagggttccgatttagtgctttacggcacctcgaccccaaaaaacttgattagggtgatggttcac
gtagtgggccatcgccccgatagacggtttttcgccctttgacgctggagttcacgttcctcaatagtggactcttgttccaaactggaac
aacactcaaccctatctcggtctattcttttgatttataagggattttccgatttcggcctattggttaaaaaatgagctgatttaacaaa
aatttaacgcgaattttaacaaaatattaacgtttataaatttcaggtggcatctttcgggaaatgtgcgcggaacccctatttgtttattt
ttctaaatacattcaaatatgtatccgctcatgagacaataaccctgataaatgcttcaataatattgaaaaaggaagagtatgagtatt
caacatttccgtgtcgcccttattccctttttgcggcattttgccttcctgtttttgctcacccagaaacgctggtgaaagtaaaagatgct
gaagatcagttgggtgcacgagtgggttacatcgaactggatctcaatagtggtaagatccttgagagttttcgccccgaagaacgtttt
```

-continued ccaatgatgagcacttttaaagttctgctatgtggcgcggtattatcccgtattgacgccgggcaagagcaactcggtcgccgcatacac tattctcagaatgacttggttgagtactcaccagtcacagaaaaagcatcttacggatggcatgacagtaagagaattatgcagtgctgc cataaccatgagtgataacactgcggccaacttacttctgacaacgatcggaggaccgaaggagctaaccgcttttttgcacaacatgg gggatcatgtaactcgccttgatcgttgggaaccggagctgaatgaagccataccaaacgacgagcgtgacaccacgatgcctgtagt aatggtaacaacgttgcgcaaactattaactggcgaactacttactctagcttcccggcaacaattaatagactggatggaggcggata aagttgcaggaccacttctgcgctcggcccttccggctggctggtttattgctgataaatctggagccggtgagcgtgggtctcgcggtat cattgcagcactggggccagatggtaagccctcccgtatcgtagttatctacacgacggggagtcaggcaactatggatgaacgaaat agacagatcgctgagataggtgcctcactgattaagcattggtaactgtcagaccaagtttactcatatactttagattgatttaaaa cttcattttttaattttaaaaggatctaggtgaagatcctttttgataatctcatgaccaaaatcccttaacgtgagttttcgttccactgagc gtcagaccccgtagaaaagatcaaaggatcttcttgagatcctttttttctgcgcgtaatctgctgcttgcaaacaaaaaaaccaccgct accagcggtggtttgtttgccggatcaagagctaccaactctttttccgaaggtaactggcttcagcagagcgcagataccaaatactgt ccttctagtgtagccgtagttaggccaccacttcaagaactctgtagcaccgcctacatacctcgctctgctaatcctgttaccagtggct gctgccagtggcgataagtcgtgtcttaccgggttggactcaagacgatagttaccggataaggcgcagcggtcgggctgaacgggg gttcgtgcacacagcccagcttggagcgaacgacctacaccgaactgagatacctacagcgtgagctatgagaaagcgccacgcttcc cgaagggagaaaggcggacaggtatccggtaagcggcagggtcggaacaggagagcgcacgagggagcttccaggggaaacgc ctggtatctttatagtcctgtcgggtttcgccacctctgacttgagcgtcgatttttgtgatgctcgtcaggggggcggagcctatggaaa aacgccagcaacgcggcctttttacggttcctggccttttgctgcggttttgctcacatgttctttcctgcgttatcccctgattctgtggata accgtattaccgcctttgagtgagctgataccgctcgccgcagccgaacgaccgagcgcagcgagtcagtgagcgaggaagcggaag ggccgattcattaatgcagctggcacgacaggtttcccgactggaaagcgggcagtgagcgcaacgcaa p1116// pAAV_Scramble_mRHO HITI(kozak-dsRED)_hVmd2-EGFP (SEQ ID NO: 10)

ggaaacagctatgaccatgattacgccagatttaattaaggctgcgcgctcgctcgctcactgaggccgcccgggcaaagcccgggcg tcgggcgacctttggtcgcccggcctcagtgagcgagcgagcgcgcagagagggagtggccaactccatcactaggggttccttgtag ttaatgattaacccgccatgctacttatctacgtagccatgctctaggaagatcggaattcgcccttaaccactagtaacggccgccagt gtgctggaattcgcccttcgagggcctatttcccatgattccttcatatttgcatatacgatacaaggctgttagagagataattggaatt aatttgactgtaaacacaaagatattagtacaaaatacgtgacgtagaaagtaataatttcttgggtagtttgcagttttaaaattatgtt ttaaaatggactatcatatgcttaccgtaacttgaaagtatttcgatttcttggctttatatatcttgtggaaaggacgaaacaccgGAC TCGCGCGAGTCGAGGAGgttttagagctagaaatagcaagttaaaataaggctagtccgttatcaacttgaaaaagtggcacc gagtcggtgcttttttgttttagagctagaaatagcaagctcgagcagcctgaattctgcagatatccatcacactggcggccttaactcg gatccactagtaacggccgccagtgtgctggaattcgaggccgccaggtagtactgcggctgctaataaataataagccaccatggat agcactgagaacgtcatcaagcccttcatgcgcttcaaggtgcacatggagggctccgtgaacggccacgagttcgagatcgagggcg agggcgaggcaagccctacgagggcacccagaccgccaagctgcaggtgaccaagggcggccccctgcccttcgcctgggacatcc tgtcccccagttccagtacggctccaaggtgtacgtgaagcaccccgccgacatccccgactacaagaagctgtccttccccgagggc ttcaagtgggagcgcgtgatgaacttcgaggacggcggcgtggtgaccgtgacccaggactcctccctgcaggacgcaccttcatcta ccacgtgaagttcatcggcgtgaacttcccctccgacggccccgtaatgcagaagaagactctgggctgggagccctccaccgagcgc ctgtaccccgcgacgcgtgctgaagggcgagatccacaaggcgctgaagctgaagggcggcggccactacctggtggagttcaag tcaatctacatggccaagaagcccgtgaagctgcccggctactactacgtggactccaagctggacatcacctcccacaacgaggact acaccgtggtggagcagtacgagcgcgccgaggcccgccaccacctgttccagtagcggccgcgactctagaattccaactgagcgcc ggtcgctaccattaccaacttgtctggtgtcaaaaataataggcctactagagtcgacctgcagaagcttggatctgcctcgactgtgcc ttctagttgccagccatctgttgtttgcccctcccccgtgccttccttgaccctggaaggtgccactcccactgtcctttcctaataaaatga ggaaattgcatcgcattgtctgagtaggtgtcattctattctggggggtggggggggcaggacagcaaggggaggattgggaagac -continued

```
aatagcaggcatgctggggaccgccaggtagtactgcggctgcaagggcgaattctgcagatatccatcacactggcgttaagcgtca gcatatgcagaattctgtcatttttactagggtgatgaaattcccaagcaacaccatccttttcagataagggcactgaggctgagagag gagctgaaacctacccgggggtcaccacacacaggtggcaaggctgggaccagaaaccaggactgttgactgcagcccggtattcattc tttccatagcccacagggctgtcaaagaccccagggcctagtcagaggctcctccttcctggagagttcctggcacagaagttgaagct cagcacagcccctaaccccccaactctctctgcaaggcctcaggggtcagaacactggtggagcagatcctttagcctctggattttag ggccatggtagaggggggtgttgccctaaattccagccctggtctcagcccaacaccctccaagaagaaattagaggggccatggccag gctgtgctagccgttgcttctgagcagattacaagaagggactaagacaaggactcctttgtggaggtcctggcttagggagtcaagtg acggcggctcagcactcacgtgggcagtgccagcctctaagagtgggcaggggcactggccacagagtcccaggagtcccaccagc ctagtcgccagaccttctgtgggcggccgccatggtgagcaagggcgaggagctgttcaccggggtggtgcccatcctggtcgagctgg acggcgacgtaaacggccacaagttcagcgtgtccggcgagggcgagggcgatgccacctacggcaagctgaccctgaagttcatct gcaccaccggcaagctgcccgtgccctggcccaccctcgtgaccaccctgacctacggcgtgcagtgcttcagccgctaccccgaccac atgaagcagcacgacttcttcaagtccgccatgcccgaaggctacgtccaggagcgcaccatcttcttcaaggacgacggcaactaca agacccgcgccgaggtgaagttcgagggcgacaccctggtgaaccgcatcgagctgaagggcatcgacttcaaggaggacggcaac atcctggggcacaagctggagtacaactacaacagccacaacgtctatatcatggccgacaagcagaagaacggcatcaaggtgaac ttcaagatccgccacaacatcgaggacggcagcgtgcagctcgccgaccactaccagcagaacacccccatcggcgacggccccgtg ctgctgcccgacaaccactacctgagcacccagtccgccctgagcaaagaccccaacgagaagcgcgatcacatggtcctgctggagt tcgtgaccgccgccgggatcactctcggcatggacgagctgtacaagtaataagcttggatccaatcaacctctggattacaaaatttgt gaaagattgactggtattcttaactatgttgctccttttacgctatgtggatacgctgctttaatgcctttgtatcatgctattgcttcccgta tggctttcattttctcctccttgtataaatcctggttgctgtctctttatgaggagttgtggcccgttgtcaggcaacgtggcgtggtgtgca ctgtgtttgctgacgcaaccccactggttggggcattgccaccacctgtcagctccttcc gggactttcgctttccccctccctattgcca cggcggaactcatcgccgcctgccttgcccgctgctggacagggggctcggctgttgggcactgacaattccgtggtgttgtcggggaag ctgacgtcctttccatggctgctcgcctgtgttgccacctggattctgcgcgggacgtccttctgctacgtcccttcggccctcaatccagc ggaccttccttcccgcggcctgctgccggctctgcggcctcttccgcgtcttcgagatctgcctcgactgtgccttctagttgccagccatc tgttgtttgcccctcccccgtgccttccttgaccctggaaggtgccactcccactgtcctttcctaataaaatgaggaaattgcatcgcatt gtctgagtaggtgtcattctattctggggggggggtggggcaggacagcaagggggaggattgggaagacaatagcaggcatgctg gggactcgagttaagggcgaattcccgattaggatcttcctagagcatggctacgtagataagtagcatggcgggttaatcattaacta caaggaacccctagtgatggagttggccactccctctctgcgcgctcgctcgctcactgaggccgggcgaccaaaggtcgcccgacgcc cgggctttgcccgggcggcctcagtgagcgagcgagcgcgcagccttaattaacctaattcactggccgtcgttttacaacgtcgtgact gggaaaaccctggcgttacccaacttaatcgccttgcagcacatccccctttcgccagctggcgtaatagcgaagaggcccgcaccgat cgcccttcccaacagttgcgcagcctgaatggcgaatgggacgcgccctgtagcggcgcattaagcgcggcgggtgtggtggttacgc gcagcgtgaccgctacacttgccagcgccctagcgcccgctcctttcgctttcttcccttcctttctcgccacgttcgccggctttccccgtc aagctctaaatcggggggctccctttagggttccgatttagtgctttacggcacctcgaccccaaaaaacttgattagggtgatggttcac gtagtgggccatcgccccgatagacggttttt cgccctttgacgctggagttcacgttcctcaatagtggactcttgttccaaactggaac aacactcaaccctatctcggtctattcttttgatttataagggattttt ccgatttcggcctattggttaaaaaatgagctgatttaacaaa aatttaacgcgaattttaacaaaatattaacgtttataatttcaggtggcatctttcggggaaatgtgcgcggaaccccctatttgtttattt ttctaaatacattcaaatatgtatccgctcatgagacaataaccctgataaatgcttcaataatattgaaaaaggaagagtatgagtatt caacatttccgtgtcgcccttattccctttttt gcggcattttgccttcctgtttttgctcacccagaaacgctggtgaaagtaaaagatgct gaagatcagttgggtgcacgagtgggttacatcgaactggatctcaatagtggtaagatccttgagagttttcgccccgaagaacgtttt ccaatgatgagcacttttaaagttctgctatgtggcgcggtattatcccgtattgacgccgggcaagagcaactcggtcgccgcatacac tattctcagaatgacttggttgagtactcaccagtcacagaaaagcatcttacggatggcatgacagtaagagaattatgcagtgctgc cataaccatgagtgataacactgcggccaacttacttctgacaacgatcggaggaccgaaggagctaaccgcttttttgcacaacatgg
```

-continued gggatcatgtaactcgccttgatcgttgggaaccggagctgaatgaagccataccaaacgacgagcgtgacaccacgatgcctgtagt aatggtaacaacgttgcgcaaactattaactggcgaactacttactctagcttcccggcaacaattaatagactggatggaggcggata aagttgcaggaccacttctgcgctcggcccttccggctggctggtttattgctgataaatctggagccggtgagcgtgggtctcgcggtat cattgcagcactggggccagatggtaagccctcccgtatcgtagttatctacacgacggggagtcaggcaactatggatgaacgaaat agacagatcgctgagataggtgcctcactgattaagcattggtaactgtcagaccaagtttactcatatatactttagattgatttaaaa cttcattttttaatttaaaaggatctaggtgaagatcctttttgataatctcatgaccaaaatcccttaacgtgagttttcgttccactgagc gtcagaccccgtagaaaagatcaaaggatcttcttgagatccttttttctgcgcgtaatctgctgcttgcaaacaaaaaaaccaccgct accagcggtggtttgtttgccggatcaagagctaccaactcttttccgaaggtaactggcttcagcagagcgcagataccaaatactgt ccttctagtgtagccgtagttaggccaccacttcaagaactctgtagcaccgcctacatacctcgctctgctaatcctgttaccagtggct gctgccagtggcgataagtcgtgtcttaccgggttggactcaagacgatagttaccggataaggcgcagcggtcgggctgaacggggg gttcgtgcacacagcccagcttggagcgaacgacctacaccgaactgagatacctacagcgtgagctatgagaaagcgccacgcttcc cgaagggagaaaggcggacaggtatccggtaagcggcagggtcggaacaggagagcgcacgagggagcttccaggggaaacgc ctggtatctttatagtcctgtcgggtttcgccacctctgacttgagcgtcgatttttgtgatgctcgtcaggggggagcctatggaaa aacgccagcaacgcggcctttttacggttcctggccttttgctgcggttttgctcacatgttctttcctgcgttatcccctgattctgtggata accgtattaccgcctttgagtgagctgataccgctcgccgcagccgaacgaccgagcgcagcgagtcagtgagcgaggaagcggaag ggccgattcattaatgcagctggcacgacaggtttcccgactggaaagcgggcagtgagcgcaacgcaattaatgtgagttagctcact cattaggcaccccaggctttacactttatgcttccggctcgtatgttgtgtggaattgtgagcggataacaatttcacaca p1048// pAAV2.1-Scramble-mRHO HITI(IRESdsRED)-Vmd2-EGFP (SEQ ID NO: 11)

acacaggaaacagctatgaccatgattacgccagatttaattaaggctgcgcgctcgctcgctcactgaggccgcccgggcaaagccc gggcgtcgggcgacctttggtcgcccggcctcagtgagcgagcgagcgcgcagagagggagtggccaactccatcactaggggttcct tgtagttaatgattaacccgccatgctacttatctacgtagccatgctctaggaagatcggaattcgcccttaaccactagtaacggccg ccagtgtgctggaattcgcccttcgagggcctatttcccatgattccttcatatttgcatatacgatacaaggctgttagagagataattg gaattaatttgactgtaaacacaaagatattagtacaaaatacgtgacgtagaaagtaataatttcttgggtagtttgcagttttaaaat tatgttttaaaatggactatcatatgcttaccgtaacttgaaagtatttcgatttcttggctttatatatcttgtggaaaggacgaaacacc gGACTCGCGCGAGTCGAGGAGgttttagagctagaaatagcaagttaaaataaggctagtccgttatcaacttgaaaaagtg gcaccgagtcggtgcttttttgttttagagctagaaatagcaagctcgagcagcctgaattctgcagatatccatcacactggcggcctt aactcggatccactagtaacggccgccagtgtgctggaattcgcccttccgccaggtagtactgcggctgctaataaataataaTgAC AAACTgTACATgCCgTTAACTgTAATTTTTgCgTgATTTTTTTgTAgatggatagcactgagaacgtcatcaagcccttca tgcgcttcaaggtgcacatggagggctccgtgaacgccacgagttcgagatcgagggcgagggcgaggcaagccctacgagggc acccagaccgccaagctgcaggtgaccaagggcggcccctgcccttcgcctgggacatcctgtcccccagttccagtacggctccaa ggtgtacgtgaagcaccccgccgacatccccgactacaagaagctgtccttccccgagggcttcaagtgggagcgcgtgatgaacttc gaggacggcggcgtggtgaccgtgacccaggactcctccctgcaggacggcaccttcatctaccacgtgaagttcatcggcgtgaactt cccctccgacggccccgtaatgcagaagaagactctgggctgggagccctccaccgagcgcctgtaccccgcgacggcgtgctgaag ggcgagatccacaaggcgctgaagctgaagggcggcggccactacctggtggagttcaagtcaatctacatggccaagaagcccgtg aagctgcccggctactactacgtggactccaagctggacatcacctcccacaacgaggactacaccgtggtggagcagtacgagcgcg ccgaggcccgccaccacctgttccagtagcggccgcgactctagaattccaactgagcgccggtcgctaccattaccaacttgtctggtg tcaaaaataataggcctactagagtcgacctgcagaagcttggatctgcctcgactgtgccttctagttgccagccatctgttgtttgccc ctcccccgtgccttccttgaccctggaaggtgccactcccactgtcctttcctaataaaatgaggaaattgcatcgcattgtctgagtagg tgtcattctattctggggggggggtggggcaggacagcaaggggaggattgggaagacaatagcaggcatgctggggaccgccag gtagtactgcggctgcaagggcgaattctgcagatatccatcacactggcgttaagcgtcagcatatgcagaattctgtcattttactag -continued

```
ggtgatgaaattcccaagcaacaccatcctttcagataagggcactgaggctgagagaggagctgaaacctacccggggtcaccac
acacaggtggcaaggctgggaccagaaaccaggactgttgactgcagcccggtattcattctttccatagcccacagggctgtcaaag
accccagggcctagtcagaggctcctccttcctggagagttcctggcacagaagttgaagctcagcacagcccctaaccccaactct
ctctgcaaggcctcaggggtcagaacactggtggagcagatcctttagcctctggattttagggccatggtagagggggtgttcccta
aattccagccctggtctcagcccaacaccctccaagaagaaattagaggggccatggccaggctgtgctagccgttgcttctgagcaga
ttacaagaagggactaagacaaggactcctttgtggaggtcctggcttagggagtcaagtgacggcggctcagcactcacgtgggcag
tgccagcctctaagagtgggcaggggcactggccacagagtcccagggagtcccaccagcctagtcgccagaccttctgtgggcggcc
gccatggtgagcaagggcgaggagctgttcaccggggtggtgcccatcctggtcgagctggacggcgacgtaaacggccacaagttc
agcgtgtccggcgagggcgagggcgatgccacctacggcaagctgaccctgaagttcatctgcaccaccggcaagctgcccgtgccct
ggcccaccctcgtgaccaccctgacctacggcgtgcagtgcttcagccgctaccccgaccacatgaagcagcacgacttcttcaagtcc
gccatgcccgaaggctacgtccaggagcgcaccatcttcttcaaggacgacggcaactacaagacccgcgccgaggtgaagttcgag
ggcgacaccctggtgaaccgcatcgagctgaagggcatcgacttcaaggaggacggcaacatcctggggcacaagctggagtacaa
ctacaacagccacaacgtctatatcatggccgacaagcagaagaacggcatcaaggtgaacttcaagatccgccacaacatcgagga
cggcagcgtgcagctcgccgaccactaccagcagaacacccccatcggcgacggccccgtgctgctgcccgacaaccactacctgagc
acccagtccgccctgagcaaagaccccaacgagaagcgcgatcacatggtcctgctggagttcgtgaccgccgccgggatcactctcg
gcatggacgagctgtacaagtaataagcttggatccaatcaacctctggattacaaaatttgtgaaagattgactggtattcttaactat
gttgctccttttacgctatgtggatacgctgctttaatgcctttgtatcatgctattgcttcccgtatggctttcattttctcctccttgtataa
atcctggttgctgtctctttatgaggagttgtggcccgttgtcaggcaacgtggcgtggtgtgcactgtgtttgctgacgcaaccccactg
gttggggcattgccaccacctgtcagctcctttccgggactttcgctttccccctccctattgccacggcggaactcatcgccgcctgcctt
gcccgctgctggacaggggctcggctgttgggcactgacaattccgtggtgttgtcggggaagctgacgtcctttccatggctgctcgcc
tgtgttgccacctggattctgcgcgggacgtccttctgctacgtcccttcggccctcaatccagcggaccttccttcccgcggcctgctgcc
ggctctgcggcctcttccgcgtcttcgagatctgcctcgactgtgccttctagttgccagccatctgttgtttgcccctcccccgtgccttcct
tgaccctggaaggtgccactcccactgtcctttcctaataaaatgaggaaattgcatcgcattgtctgagtaggtgtcattctattctggg
gggtggggggcaggacagcaagggggaggattgggaagacaatagcaggcatgctggggactcgagttaagggcgaattcccg
attaggatcttcctagagcatggctacgtagataagtagcatggcgggttaatcattaactacaaggaacccctagtgatggagttggc
cactccctctctgcgcgctcgctcgctcactgaggccgggcgaccaaaggtcgcccgacgcccgggctttgcccgggcggcctcagtga
gcgagcgagcgcgcagccttaattaacctaattcactggccgtcgttttacaacgtcgtgactgggaaaaccctggcgttacccaactta
atcgccttgcagcacatccccctttcgccagctggcgtaatagcgaagaggcccgcaccgatcgcccttcccaacagttgcgcagcctg
aatggcgaatgggacgcgccctgtagcggcgcattaagcgcggcgggtgtggtggttacgcgcagcgtgaccgctacacttgccagcg
ccctagcgcccgctccttttcgctttcttcccttcctttctcgccacgttcgccggctttccccgtcaagctctaaatcggggggctcccttag
ggttccgatttagtgctttacggcacctcgaccccaaaaaacttgattagggtgatggttcacgtagtgggccatcgccccgatagacgg
tttttcgccctttgacgctggagttcacgttcctcaatagtggactcttgttccaaactggaacaacactcaaccctatctcggtctattctt
ttgatttataagggattttccgatttcggcctattggttaaaaaatgagctgatttaacaaaaatttaacgcgaattttaacaaaatatta
acgtttataatttcaggtggcatcttcggggaaatgtgcgcggaaccccctatttgtttattttctaaatacattcaaatatgtatccgctc
atgagacaataaccctgataaatgcttcaataatattgaaaaaggaagagtatgagtattcaacatttccgtgtcgcccttattccctttt
ttgcggcattttgccttcctgtttttgctcacccagaaacgctggtgaaagtaaaagatgctgaagatcagttgggtgcacgagtgggtt
acatcgaactggatctcaatagtggtaagatccttgagagttttcgccccgaagaacgttttccaatgatgagcacttttaaagttctgct
atgtggcgcggtattatcccgtattgacgccgggcaagagcaactcggtcgccgcatacactattctcagaatgacttggttgagtactc
accagtcacagaaaagcatcttacggatggcatgacagtaagagaattatgcagtgctgccataaccatgagtgataacactgcggcc
aacttacttctgacaacgatcggaggaccgaaggagctaaccgcttttttgcacaacatggggatcatgtaactcgccttgatcgttgg
gaaccggagctgaatgaagccataccaaacgacgagcgtgacaccacgatgcctgtagtaatggtaacaacgttgcgcaaactatta
```

-continued

```
actggcgaactacttactctagcttcccggcaacaattaatagactggatggaggcggataaagttgcaggaccacttctgcgctcggc ccttccggctggctggtttattgctgataaatctggagccggtgagcgtgggtctcgcggtatcattgcagcactggggccagatggtaa gccctcccgtatcgtagttatctacacgacggggagtcaggcaactatggatgaacgaaatagacagatcgctgagataggtgcctca ctgattaagcattggtaactgtcagaccaagtttactcatatatactttagattgatttaaaacttcatttttaatttaaaaggatctaggt gaagatcctttttgataatctcatgaccaaaatcccttaacgtgagttttcgttccactgagcgtcagaccccgtagaaaagatcaaagg atcttcttgagatcctttttttctgcgcgtaatctgctgcttgcaaacaaaaaaaccaccgctaccagcggtggtttgtttgccggatcaag agctaccaactctttttccgaaggtaactggcttcagcagagcgcagataccaaatactgtccttctagtgtagccgtagttaggccacc acttcaagaactctgtagcaccgcctacatacctcgctctgctaatcctgttaccagtggctgctgccagtggcgataagtcgtgtcttac cgggttggactcaagacgatagttaccggataaggcgcagcggtcgggctgaacggggggttcgtgcacacagcccagcttggagcg aacgacctacaccgaactgagatacctacagcgtgagctatgagaaagcgccacgcttcccgaagggagaaaggcggacaggtatc cggtaagcggcagggtcggaacaggagagcgcacgagggagcttccagggggaaacgcctggtatctttatagtcctgtcgggtttcg ccacctctgacttgagcgtcgatttttgtgatgctcgtcaggggggcggagcctatggaaaaacgccagcaacgcggcctttttacggtt cctggccttttgctgcggttttgctcacatgttctttcctgcgttatcccctgattctgtggataaccgtattaccgcctttgagtgagctgat accgctcgccgcagccgaacgaccgagcgcagcgagtcagtgagcgaggaagcggaagggccgattcattaatgcagctggcacga caggtttcccgactggaaagcgggcagtgagcgcaacgcaattaatgtgagttagctcactcattaggcaccccaggctttacactttat gcttccggctcgtatgttgtgtggaattgtgagcggataacaatttc
``` p1047// pAAV2.1-mRHOgRNA-mRHOHITI(IRESdsRED)-hVDM2-EGFP (SEQ ID NO: 12)

```
cgtatgttgtgtggaattgtgagcggataacaatttcacacaggaaacagctatgaccatgattacgccagatttaattaaggctgcgc gctcgctcgctcactgaggccgcccgggcaaagcccgggcgtcgggcgacctttggtcgcccggcctcagtgagcgagcgagcgcgca gagagggagtggccaactccatcactaggggttccttgtagttaatgattaacccgccatgctacttatctacgtagccatgctctagga agatcggaattcgcccttaaccactagtaacggccgccagtgtgctggaattcgcccttcgagggcctatttcccatgattccttcatat ttgcatatacgatacaaggctgttagagagataattggaattaatttgactgtaaacacaaagatattagtacaaaatacgtgacgtag aaagtaataatttcttgggtagtttgcagttttaaaattatgttttaaaatggactatcatatgcttaccgtaacttgaaagtatttcgattt cttggctttatatatcttgtggaaaggacgaaacaccgcagccgcagtactacctgggttttagagctagaaatagcaagttaaaataa ggctagtccgttatcaacttgaaaaagtggcaccgagtcggtgcttttttgttttagagctagaaatagcaagctcgagcagcctgaatt ctgcagatatccatcacactggcggccttaactcggatccactagtaacggccgccagtgtgctggaattcaggccgccaggtagtact gcggctgctaataaataataatgacaaactgtacatgccgttaactgtaattttgcgtgattttttgtagatggatagcactgagaacgt catcaagcccttcatgcgcttcaaggtgcacatggagggctccgtgaacggccacgagttcgagatcgagggcgagggcgagggcaa gccctacgagggcacccagaccgccaagctgcaggtgaccaagggcggccccctgcccttcgcctgggacatcctgtccccccagttc cagtacggctccaaggtgtacgtgaagcaccccgccgacatccccgactacaagaagctgtccttccccgagggcttcaagtgggagc gcgtgatgaacttcgaggacggcggcgtggtgaccgtgacccaggactcctccctgcaggacggcaccttcatctaccacgtgaagttc atcggcgtgaacttccccctccgacggccccgtaatgcagaagaagactctgggctgggagccctccaccgagcgcctgtaccccgcg acggcgtgctgaagggcgagatccacaaggcgctgaagctgaagggcggcggccactacctggtggagttcaagtcaatctacatgg ccaagaagcccgtgaagctgcccggctactactacgtggactccaagctggacatcacctcccacaacgaggactacaccgtggtgga gcagtacgagcgcgccgaggccgccaccacctgttccagtagcggccgcgactctagaattccaactgagcgccggtcgctaccatt accaacttgtctggtgtcaaaaataataggcctactagagtcgacctgcagaagcttggatctgcctcgactgtgccttctagttgccag ccatctgttgtttgcccctcccccgtgccttccttgaccctggaaggtgccactcccactgtcctttcctaataaaatgaggaaattgcatc gcattgtctgagtaggtgtcattctattctggggggtggggtggggcaggacagcaaggggaggattgggaagacaatagcaggcat gctgggaccgccaggtagtactgcggctgcaagggcgaattctgcagatatccatcacactggcgttaagcgtcagcatatgcagaa ttctgtcattttactagggtgatgaaattcccaagcaacaccatcctttttcagataagggcactgaggctgagagaggagctgaaacct
```

-continued

```
acccggggtcaccacacacaggtggcaaggctgggaccagaaaccaggactgttgactgcagcccggtattcattctttccatagccc acagggctgtcaaagacccccagggcctagtcagaggctcctccttcctggagagttcctggcacagaagttgaagctcagcacagccc cctaaccccccaactctctctgcaaggcctcaggggtcagaacactggtggagcagatcctttagcctctggattttagggccatggtaga gggggtgttgccctaaaattccagccctggtctcagcccaacaccctccaagaagaaattagaggggccatggccaggctgtgctagcc gttgcttctgagcagattacaagaagggactaagacaaggactcctttgtggaggtcctggcttagggagtcaagtgacggcggctca gcactcacgtgggcagtgccagcctctaagagtgggcaggggcactggccacagagtcccagggagtcccaccagcctagtcgccag accttctgtgggcggccgccatggtgagcaagggcgaggagctgttcaccggggtggtgcccatcctggtcgagctggacggcgacgt aaacggccacaagttcagcgtgtccggcgagggcgagggcgatgccacctacggcaagctgaccctgaagttcatctgcaccaccgg caagctgcccgtgccctggcccaccctcgtgaccaccctgacctacggcgtgcagtgcttcagccgctaccccgaccacatgaagcagc acgacttcttcaagtccgccatgcccgaaggctacgtccaggagcgcaccatcttcttcaaggacgacggcaactacaagacccgcgc cgaggtgaagttcgagggcgacaccctggtgaaccgcatcgagctgaagggcatcgacttcaaggaggacggcaacatcctgggca caagctggagtacaactacaacagccacaacgtctatatcatggccgacaagcagaagaacggcatcaaggtgaacttcaagatccg ccacaacatcgaggacggcagcgtgcagctcgccgaccactaccagcagaacacccccatcggcgacggccccgtgctgctgcccga caaccactacctgagcacccagtccgccctgagcaaagaccccaacgagaagcgcgatcacatggtcctgctggagttcgtgaccgcc gccgggatcactctcggcatggacgagctgtacaagtaataagcttggatccaatcaacctctggattacaaaatttgtgaaagattga ctggtattcttaactatgttgctccttttacgctatgtggatacgctgctttaatgcctttgtatcatgctattgcttcccgtatggctttcattt tctcctccttgtataaatcctggttgctgtctctttatgaggagttgtggcccgttgtcaggcaacgtggcgtggtgtgcactgtgtttgctg acgcaaccccactggttggggcattgccaccacctgtcagctcctttccgggactttcgctttccccctccctattgccacggcggaact catcgccgcctgccttgcccgctgctggacagggctcggctgttggcactgacaattccgtggtgttgtcggggaagctgacgtcctt ccatggctgctcgcctgtgttgccacctggattctgcgcgggacgtccttctgctacgtcccttcggccctcaatccagcggaccttcctt ccgcggcctgctgccggctctgcggcctcttccgcgtcttcgagatctgcctcgactgtgccttctagttgccagccatctgttgtttgcccc tcccccgtgccttccttgaccctggaaggtgccactcccactgtcctttcctaataaaatgaggaaattgcatcgcattgtctgagtaggt gtcattctattctggggggtgggtggggcaggacagcaaggggaggattgggaagacaatagcaggcatgctggggactcgagtt aagggcgaattcccgattaggatcttcctagagcatggctacgtagataagtagcatggcgggttaatcattaactacaaggaaccccct agtgatggagttggccactccctctctgcgcgctcgctcgctcactgaggccgggcgaccaaaggtcgcccgacgcccgggctttgccc gggcggcctcagtgagcgagcgagcgcgcagccttaattaacctaattcactggccgtcgttttacaacgtcgtgactgggaaaaccct ggcgttacccaacttaatcgccttgcagcacatccccctttcgccagctggcgtaatagcgaagaggcccgcaccgatcgcccttccca acagttgcgcagcctgaatggcgaatgggacgcgccctgtagcggcgcattaagcgcggcgggtgtggtggttacgcgcagcgtgacc gctacacttgccagcgccctagcgcccgctcctttcgctttcttcccttcctttctcgccacgttcgccggctttccccgtcaagctctaaat cggggggctccctttagggttccgatttagtgctttacggcacctcgaccccaaaaaacttgattagggtgatggttcacgtagtgggcca tcgccccgatagacggtttttcgccctttgacgctggagttcacgttcctcaatagtggactcttgttccaaactggaacaacactcaacc ctatctcggtctattcttttgatttataagggattttccgatttcggcctattggttaaaaaatgagctgatttaacaaaaatttaacgcga attttaacaaaatattaacgtttataatttcaggtggcatctttcggggaaatgtgcgcggaacccctatttgtttatttttctaaatacatt caaatatgtatccgctcatgagacaataaccctgataaatgcttcaataatattgaaaaaggaagagtatgagtattcaactttccgt gtcgcccttattcccttttttgcggcattttgccttcctgttttgctcacccagaaacgctggtgaaagtaaaagatgctgaagatcagtt gggtgcacgagtgggttacatcgaactggatctcaatagtggtaagatccttgagagttttcgccccgaagaacgttttccaatgatgag cacttttaaagttctgctatgtggcgcggtattatcccgtattgacgccgggcaagagcaactcggtcgccgcatacactattctcagaat gacttggttgagtactcaccagtcacagaaaagcatcttacggatggcatgacagtaagagaattatgcagtgctgccataaccatga gtgataacactgcggccaacttacttctgacaacgatcggaggaccgaaggagctaaccgcttttttgcacaacatggggatcatgta actcgccttgatcgttgggaaccggagctgaatgaagccataccaaacgacgagcgtgacaccacgatgcctgtagtaatggtaacaa cgttgcgcaaactattaactggcgaactacttactctagcttcccggcaacaattaatagactggatggaggcggataaagttgcagga
```

-continued ccacttctgcgctcggcccttccggctggctggtttattgctgataaatctggagccggtgagcgtgggtctcgcggtatcattgcagcac tggggccagatggtaagccctcccgtatcgtagttatctacacgacggggagtcaggcaactatggatgaacgaaatagacagatcgc tgagataggtgcctcactgattaagcattggtaactgtcagaccaagtttactcatatatactttagattgatttaaaacttcatttttaatt taaaaggatctaggtgaagatcctttttgataatctcatgaccaaaatcccttaacgtgagttttcgttccactgagcgtcagacccgta gaaaagatcaaaggatcttcttgagatcctttttttctgcgcgtaatctgctgcttgcaaacaaaaaaaccaccgctaccagcggtggtt tgtttgccggatcaagagctaccaactctttttccgaaggtaactggcttcagcagagcgcagataccaaatactgtccttctagtgtag ccgtagttaggccaccacttcaagaactctgtagcaccgcctacatacctcgctctgctaatcctgttaccagtggctgctgccagtggc gataagtcgtgtcttaccgggttggactcaagacgatagttaccggataaggcgcagcggtcgggctgaacggggggttcgtgcacac agcccagcttggagcgaacgacctacaccgaactgagatacctacagcgtgagctatgagaaagcgccacgcttcccgaagggagaa aggcggacaggtatccggtaagcggcagggtcggaacaggagagcgcacgagggagcttccaggggaaacgcctggtatctttat agtcctgtcgggtttcgccacctctgacttgagcgtcgatttttgtgatgctcgtcaggggggcggagcctatggaaaaacgccagcaac gcggcctttttacggttcctggccttttgctgcggttttgctcacatgttctttcctgcgttatcccctgattctgtggataaccgtattaccgc ctttgagtgagctgataccgctcgccgcagccgaacgaccgagcgcagcgagtcagtgagcgaggaagcggaagggccgattcatta atgcagctggcacgacaggtttcccgactggaaagcgggcagtgagcgcaacgcaattaatgtgagttagctcactcattaggcaccc caggctttacactttatgcttccggct p1138// pAAV-mRHO HITI (kozak-hRHO-T2A-dsRED) + mRHO gRNA (SEQ ID NO: 13)

cggataacaatttcacacaggaaacagctatgaccatgattacgccagatttaattaaggctgcgcgctcgctcgctcactgaggccgc ccgggcaaagcccgggcgtcgggcgacctttggtcgcccggcctcagtgagcgagcgagcgcgcagagagggagtggccaactccat cactaggggttccttgtagttaatgattaacccgccatgctacttatctacgtagcccgccgccagtgtgatggatgccgccagtgtgatg gatatctgcagaattcaggctgctcgagcttgctattctagctctaaaacAAAAAgcaccgactcggtgccacttttttcaagttgat aacggactagccttattttaacttgctaTTTCtagctctaaaacccaggtagtactgcggctgccGGTGTTTCGTCCTTTCCACa agatatataaagccaagaaatcgaaatactttcaagttacggtaagcatatgatagtccattttaaaacataattttaaaactgcaaac tacccaagaaattattactttctacgtcacgtattttgtactaatatctttgtgtttacagtccaaattaattccaattatctctctaacagcc ttgtatcgtatatgcaaatatgaaggaatcatgggaaactcgaggtcagcctgaattccagcacactggcggccgttactagtatctgc agaattcgcccttGCAGCCGCAGTACTACCTGGCGGtccccagcatgcctgctattgtcttcccaatcctcccccttgctgtcct gccccaccccaccccccagaatagaatgacacctactcagacaatgcgatgcaatttcctcattttattaggaaaggacagtgggagtg gcaccttccagggtcaaggaaggcacgggggaggggcaaacaacagatggctggcaactagaaggcacagtcgaggcagatctcg aagacgcggaagaggccgcagagccggcagcaggccgcgggaaggaaggtccgctggattgagggccgaagggacgtagcagaa ggacgtcccgcgcagaatccaggtggcaacacaggcgagcagccatggaaaggacgtcagcttccccgacaacaccacggaattgtc agtgcccaacagccgagcccctgtccagcagcgggcaaggcaggcggcgatgagttccgccgtggcaatagggggggaaagcga aagtcccggaaaggagctgacaggtggtggcaatgccccaaccagtgggggttgcgtcagcaaacacagtgcacaccacgccacgtt gcctgacaacgggccacaactcctcataaagagacagcaaccaggatttatacaaggaggagaaatgaaagccatacgggaagca atagcatgatacaaaggcattaaagcagcgtatccacatagcgtaaaaggagcaacatagttaagaataccagtcaatctttcacaaa ttttgtaatccagaggttgattggatcctactggaacaggtggtggcgggcctcggcgcgctcgtactgctccaccacggtgtagtcctc gttgtgggaggtgatgtccagcttggagtccacgtagtagtagccgggcagcttcacgggcttcttggccatgtagattgacttgaactc caccaggtagtggccgccgcccttcagcttcagcgccttgtggatctcgcccttcagcacgccgtcgcggggtacaggcgctcggtgg agggctcccagcccagagtcttcttctgcattacggggccgtcggaggggaagttcacgccgatgaacttcacgtggtagatgaaggtg ccgtcctgcagggaggagtcctgggtcacggtcaccacgccgccgtcctcgaagttcatcacgcgctcccacttgaagccctcggggaa ggacagcttcttgtagtcggggatgtcggcggggtgcttcacgtacaccttggagccgtactggaactgggggacaggatgtcccagg cgaagggcaggggccgcccttggtcacctgcagcttggcggtctgggtgccctcgtagggcttgccctcgccctcgccctcgatctcga -continued

```
actcgtggccgttcacggagccctccatgtgcaccttgaagcgcatgaagggcttgatgacgttctcagtgctatccataggtccaggat tctcctcgacgtcaccgcatgttagcagacttcctctgccctctccgcttccggccggggccacctggctcgtctccgtcttggacacggta gcagaggcctcatcgtcacccagtgggttcttgccgcagcagatggtggtgagcatgcagttccggaactgcttgttcatcatgatatag atgacagggttgtagatggcggcgctcttggcaaagaacgctgggatggtcatgaagatgggaccgaagttggagccctggtgggtga agatgtagaatgccacgctggcgtagggcacccagcagatcaggaaagcgatgaccatgatgatgaccatgcgggtgacctccttctc tgccttctgtggtggctgactcctgctgctgggcagcggcctccttgacggtgaagacgagctgcccatagcagaaaaagatgataa tcatggggatggtgaagtggaccacgaacatgtagatgacaaaagactcgttgttgacctccggcttgagcgtgtagtagtcgattcca cacgagcactgcaggccctcggggatgtacctggaccagccggcgagtgggggtgcggcgcaggccagcgccatgacccaggtgaa ggcaacgcccatgatggcatggttctccccgaagcggaagttgctcatgggcttacacaccaccacgtaccgctcgatggccaggacc accaaggaccacagggcaatttcaccgcccagggtggcaaagaagccctccaaattgcatcctgtgggcccgaagacgaagtatcca tgcagagaggtgtagagggtgctggtgaagccacctaggaccatgaagagtcagccacggctaggttgagcaggatgtagttgaga ggcgtgcgcagcttcttgtgctggacggtgacgtagagcgtgaggaagttgatgggaagcccagcacgatcagcagaaacatgtag gcggccagcatggagaactgccatggctcagccaggtagtactgtgggtactcgaaggggctgcgtaccacaccgtcgcattggaga agggcacgtagaagttagggccttctgtgccattcatggtggcttattatttattagcagccgcagtactacctggcggaagggcgaatt ccagcacactggcggccgttactaggaattccgatcttcctagagcataattcccgattaggatcttcctagagcatggctacgtagata agtagcatggcgggttaatcattaactacaaggaacccctagtgatggagttggccactccctctctgcgcgctcgctcgctcactgagg ccgggcgaccaaaggtcgcccgacgcccgggctttgcccgggcggcctcagtgagcgagcgagcgcgcagccttaattaacctaattc actggccgtcgttttacaacgtcgtgactgggaaaaccctggcgttacccaacttaatcgccttgcagcacatcccccttcgccagctg gcgtaatagcgaagaggcccgcaccgatcgcccttcccaacagttgcgcagcctgaatggcgaatgggacgcgcctgtagcggcgc attaagcgcggcgggtgtggtggttacgcgcagcgtgaccgctacacttgccagcgccctagcgcccgctcctttcgctttcttcccttcc tttctcgccacgttcgccggctttccccgtcaagctctaaatcggggctccctttagggttccgatttagtgctttacggcacctcgaccc caaaaaacttgattagggtgatggttcacgtagtgggccatcgccccgatagacggttttcgccctttgacgctggagttcacgttcctc aatagtggactcttgttccaaactggaacaacactcaaccctatctcggtctattcttttgatttataagggattttccgatttcggcctat tggttaaaaaatgagctgatttaacaaaaatttaacgcgaattttaacaaaatattaacgtttataatttcaggtggcatctttcgggga aatgtgcgcggaacccctatttgtttatttttctaaatacattcaaatatgtatccgctcatgagacaataaccctgataaatgcttcaata atattgaaaaaggaagagtatgagtattcaacatttccgtgtcgcccttattcccttttttgcggcattttgccttcctgtttttgctcaccca gaaacgctggtgaaagtaaaagatgctgaagatcagttgggtgcacgagtgggttacatcgaactggatctcaatagtggtaagatcc ttgagagttttcgccccgaagaacgttttccaatgatgagcacttttaaagttctgctatgtggcgcggtattatcccgtattgacgccgg gcaagagcaactcggtcgccgcatacactattctcagaatgacttggttgagtactcaccagtcacagaaaagcatcttacggatggca tgacagtaagagaattatgcagtgctgccataaccatgagtgataacactgcggccaacttacttctgacaacgatcggaggaccgaa ggagctaaccgcttttttgcacaacatggggatcatgtaactcgccttgatcgttgggaaccggagctgaatgaagccataccaaacg acgagcgtgacaccacgatgcctgtagtaatggtaacaacgttgcgcaaactattaactggcgaactacttactctagcttcccggcaa caattaatagactggatggaggcggataaagttgcaggaccacttctgcgctcggcccttccggctggctggtttattgctgataaatct ggagccggtgagcgtgggtctcgcggtatcattgcagcactggggccagatggtaagccctcccgtatcgtagttatctacacgacggg gagtcaggcaactatggatgaacgaaatagacagatcgctgagataggtgcctcactgattaagcattggtaactgtcagaccaagtt tactcatatatactttagattgatttaaaacttcatttttaatttaaaaggatctaggtgaagatcctttttgataatctcatgaccaaaatc ccttaacgtgagttttcgttccactgagcgtcagaccccgtagaaaagatcaaaggatcttcttgagatcctttttttctgcgcgtaatctg ctgcttgcaaacaaaaaaaccaccgctaccagcggtggtttgtttgccggatcaagagctaccaactcttttccgaaggtaactggctt cagcagagcgcagataccaaatactgtccttctagtgtagccgtagttaggccaccacttcaagaactctgtagcaccgcctacatacc tcgctctgctaatcctgttaccagtggctgctgccagtggcgataagtcgtgtcttaccgggttggactcaagacgatagttaccggata aggcgcagcggtcgggctgaacggggggttcgtgcacacagcccagcttggagcgaacgacctacaccgaactgagatacctacagc
```

-continued gtgagctatgagaaagcgccacgcttcccgaagggagaaaggcggacaggtatccggtaagcggcagggtcggaacaggagagcg cacgagggagcttccaggggaaacgcctggtatctttatagtcctgtcgggtttcgccacctctgacttgagcgtcgattttgtgatgc tcgtcagggggcggagcctatggaaaaacgccagcaacgcggccttttttacggttcctggccttttgctgcggttttgctcacatgttct ttcctgcgttatcccctgattctgtggataaccgtattaccgcctttgagtgagctgataccgctcgccgcagccgaacgaccgagcgca gcgagtcagtgagcgaggaagcggaagagcgcccaatacgcaaaccgcctctccccgcgcgttggccgattcattaatgcagctggc acgacaggtttcccgactggaaagcgggcagtgagcgcaacgcaattaatgtgagttagctcactcattaggcaccccaggctttacac tttatgcttccggctcgtatgttgtgtggaattgtgag p1118// pAAV_Scramble_sRHO HITI(kozak-dsRED)_hVmd2-EGFP (SEQ ID NO: 14)

tatgaccatgattacgccagatttaattaaggctgcgcgctcgctcgctcactgaggccgcccgggcaaagcccgggcgtcgggcgacc tttggtcgcccggcctcagtgagcgagcgagcgcgcagagagggagtggccaactccatcactagggggttccttgtagttaatgattaa cccgccatgctacttatctacgtagccatgctctaggaagatcggaattcgcccttaaccactagtaacggccgccagtgtgctggaatt cgccctttcgagggcctatttcccatgattccttcatatttgcatatacgatacaaggctgttagagagataattggaattaatttgactgt aaacacaaagatattagtacaaaatacgtgacgtagaaagtaataatttcttgggtagtttgcagttttaaaattatgttttaaaatgga ctatcatatgcttaccgtaacttgaaagtatttcgatttcttggctttatatatcttgtggaaaggacgaaacaccgGACTCGCGCGA GTCGAGGAGgttttagagctagaaatagcaagttaaaataaggctagtccgttatcaacttgaaaaagtggcaccgagtcggtgct ttttgttttagagctagaaatagcaagtcgagcagccgaattctgcagatatccatcacactggcggccttaactcggatccactagt aacggccgccagtgtgctggaattcaggCCCCTTTGAGTATCCGCAGTACTtccccagcatgcctgctattgtcttcccaatcc tcccccttgctgtcctgccccaccccacccccagaataagaatgacacctactcagacaatgcgatgcaatttcctcattttattaggaaa ggacagtgggagtggcaccttccagggtcaaggaaggcacggggaggggcaaacaacagatggctggcaactagaaggcacagt cgaggcagatccaagcttctgcaggtcgactctagtaggcctattattttttgacaccagacaagttggtaatggtagcgaccggcgctc agttggaattctagagtcgcggccgctactggaacaggtggtgggggcctcggcgcgctcgtactgctccaccacggtgtagtcctcg ttgtgggaggtgatgtccagcttggagtccacgtagtagtagccgggcagcttcacgggcttcttggccatgtagattgacttgaactcc accaggtagtggccgccgcccttcagcttcagcgccttgtggatctcgcccttcagcacgccgtcgcgggggtacaggcgctcggtgga gggctcccagcccagagtcttcttctgcattacggggccgtcggaggggaagttcacgccgatgaacttcacgtggtagatgaaggtgc cgtcctgcagggaggagtcctgggtcacggtcaccacgccgcgtcctcgaagttcatcacgcgctcccacttgaagccctcggggaag gacagcttcttgtagtcggggatgtcggcggggtgcttcacgtacaccttggagccgtactggaactggggggacaggatgtcccagc gaagggcaggggccgcccttggtcacctgcagcttggcggtctgggtgccctcgtagggcttgccctcgccctcgccctcgatctcgaa ctcgtggccgttcacggagccctccatgtgcaccttgaagcgcatgaagggcttgatgacgttctcagtgctatccatggtggcttattat ttattaCCCCTTTGAGTATCCGCAGTACTaagggcgaattctgcagatatccatcacactggcgttaagcgtcagcatatgca gaattctgtcatttttactagggtgatgaaattcccaagcaacaccatccttttcagataagggcactgaggctgagagaggagctgaaa cctaccggggtcaccacacacaggtggcaaggctgggaccagaaaccaggactgttgactgcagcccggtattcattctttccatagc ccacagggctgtcaaagaccccagggcctagtcagaggctcctccttcctggagagttcctggcacagaagttgaagctcagcacagc cccctaaccccaactctctctgcaaggcctcaggggtcagaacactggtggagcagatcctttagcctctggattttagggccatggta gaggggggtgttgccctaaattccagccctggtctcagcccaacaccctccaagaagaaattagaggggccatggccaggctgtgctag ccgttgcttctgagcagattacaagaagggactaagacaaggactccttttgtggaggtcctggcttagggagtcaagtgacggcggctc agcactcacgtgggcagtgccagcctctaagagtgggcaggggcactggccacagagtcccagggagtcccaccagcctagtcgcca gaccttctgtgggcggccgccatggtgagcaagggcgaggagctgttcaccggggggtgcccatcctggtcgagctggacgcgacg taaacggccacaagttcagcgtgtccggcgagggcgagggcgatgccacctacggcaagctgaccctgaagttcatctgcaccaccgg caagctgcccgtgccctggcccaccctcgtgaccaccctgacctacggcgtgcagtgcttcagccgctaccccgaccacatgaagcagc acgacttcttcaagtccgccatgcccgaaggctacgtccaggagcgcaccatcttcttcaaggacgacggcaactacaagacccgcgc -continued

```
cgaggtgaagttcgagggcgacaccctggtgaaccgcatcgagctgaagggcatcgacttcaaggaggacggcaacatcctggggca
caagctggagtacaactacaacagccacaacgtctatatcatggccgacaagcagaagaacggcatcaaggtgaacttcaagatccg
ccacaacatcgaggacggcagcgtgcagctcgccgaccactaccagcagaacacccccatcggcgacggccccgtgctgctgcccga
caaccactacctgagcacccagtccgccctgagcaaagaccccaacgagaagcgcgatcacatggtcctgctggagttcgtgaccgcc
gccgggatcactctcggcatggacgagctgtacaagtaataagcttggatccaatcaacctctggattacaaaatttgtgaaagattga
ctggtattcttaactatgttgctccttttacgctatgtggatacgctgctttaatgcctttgtatcatgctattgcttcccgtatggctttcattt
tctcctccttgtataaatcctggttgctgtctctttatgaggagttgtggcccgttgtcaggcaacgtggcgtggtgtgcactgtgtttgctg
acgcaaccccactggttggggcattgccaccacctgtcagctcctttccgggactttcgctttccccctcccattgccacggcggaact
catcgccgcctgccttgcccgctgctggacaggggctcggctgttgggcactgacaattccgtggtgttgtcggggaagctgacgtccttt
ccatggctgctcgcctgtgttgccacctggattctgcgcgggacgtccttctgctacgtcccttcggccctcaatccagcggaccttccttc
ccgcggcctgctgccggctctgcggcctcttccgcgtcttcgagatctgcctcgactgtgccttctagttgccagccatctgttgtttgcccc
tcccccgtgccttccttgaccctggaaggtgccactcccactgtcctttcctaataaaatgaggaaattgcatcgcattgtctgagtaggt
gtcattctattctggggggtggggtggggcaggacagcaaggggggaggattgggaagacaatagcaggcatgctggggactcgagtt
aagggcgaattcccgattaggatcttcctagagcatggctacgtagataagtagcatggggggttaatcattaactacaaggaacccct
agtgatggagttggccactccctctctgcgcgctcgctcgctcactgaggccgggcgaccaaaggtcgcccgacgcccgggctttgccc
gggcggcctcagtgagcgagcgagcgcgcagccttaattaacctaattcactggccgtcgttttacaacgtcgtgactgggaaaaccct
ggcgttacccaacttaatcgccttgcagcacatccccctttcgccagctggcgtaatagcgaagaggcccgcaccgatcgcccttccca
acagttgcgcagcctgaatggcgaatgggacgcgccctgtagcggcgcattaagcgcggcgggtgtggtggttacgcgcagcgtgacc
gctacacttgccagcgccctagcgcccgctcctttcgctttcttcccttcctttctcgccacgttcgccggctttccccgtcaagctctaaat
cggggggctccctttagggttccgatttagtgctttacggcacctcgaccccaaaaaacttgattagggtgatggttcacgtagtgggcca
tcgccccgatagacggtttttcgccctttgacgctggagttcacgttcctcaatagtggactcttgttccaaactggaacaacactcaacc
ctatctcggtctattcttttgatttataagggattttccgatttcggcctattggttaaaaaatgagctgatttaacaaaaatttaacgcga
attttaacaaaatattaacgtttataatttcaggtggcatctttcggggaaatgtgcgcggaacccctatttgtttatttttctaaatacatt
caaatatgtatccgctcatgagacaataaccctgataaatgcttcaataatattgaaaaaggaagagtatgagtattcaacatttccgt
gtcgcccttattcccttttttgcggcattttgccttcctgtttttgctcacccagaaacgctggtgaaagtaaaagatgctgaagatcagtt
gggtgcacgagtgggttacatcgaactggatctcaatagtggtaagatccttgagagttttcgccccgaagaacgttttccaatgatgag
cacttttaaagttctgctatgtggcgcggtattatcccgtattgacgccgggcaagagcaactcggtcgccgcatacactattctcagaat
gacttggttgagtactcaccagtcacagaaaagcatcttacggatggcatgacagtaagagaattatgcagtgctgccataaccatga
gtgataacactgcggccaacttacttctgacaacgatcggaggaccgaaggagctaaccgcttttttgcacaacatgggggatcatgta
actcgccttgatcgttgggaaccggagctgaatgaagccataccaaacgacgagcgtgacaccacgatgcctgtagtaatggtaacaa
cgttgcgcaaactattaactggcgaactacttactctagcttcccggcaacaattaatagactggatggaggcggataaagttgcagga
ccacttctgcgctcggcccttccggctggctggtttattgctgataaatctggagccggtgagcgtgggtctcgcggtatcattgcagcac
tggggccagatggtaagccctcccgtatcgtagttatctacacgacggggagtcaggcaactatggatgaacgaaatagacagatcgc
tgagataggtgcctcactgattaagcattggtaactgtcagaccaagtttactcatatatactttagattgatttaaaacttcattttttaatt
taaaaggatctaggtgaagatcctttttgataatctcatgaccaaaatcccttaacgtgagttttcgttccactgagcgtcagaccccgta
gaaaagatcaaaggatcttcttgagatcctttttttctgcgcgtaatctgctgcttgcaaacaaaaaaaccaccgctaccagcggtggtt
tgtttgccggatcaagagctaccaactctttttccgaaggtaactggcttcagcagagcgcagataccaaatactgtccttctagtgtag
ccgtagttaggccaccacttcaagaactctgtagcaccgcctacatacctcgctctgctaatcctgttaccagtggctgctgccagtggc
gataagtcgtgtcttaccgggttggactcaagacgatagttaccggataaggcgcagcggtcgggctgaacggggggttcgtgcacac
agcccagcttggagcgaacgacctacaccgaactgagatacctacagcgtgagctatgagaaagcgccacgcttcccgaagggagaaa
aggcggacaggtatccggtaagcggcagggtcggaacaggagagcgcacgagggagcttccagggggaaacgcctggtatctttat
```

-continued agtcctgtcgggtttcgccacctctgacttgagcgtcgattttgtgatgctcgtcagggggcggagcctatggaaaaacgccagcaac gcggcctttttacggttcctggccttttgctgcggttttgctcacatgttctttcctgcgttatcccctgattctgtggataaccgtattaccgc ctttgagtgagctgataccgctcgccgcagccgaacgaccgagcgcagcgagtcagtgagcgaggaagcggaagggccgattcatta atgcagctggcacgacaggtttcccgactggaaagcgggcagtgagcgcaacgcaattaatgtgagttagctcactcattaggcaccc caggctttacactttatgcttccggctcgtatgttgtgtggaattgtgagcggataacaatttcacacaggaaacagc p1126// pAAV_sRHOgRNA_sRHO HITI(kozak-dsRED)_hVmd2-EGFP (SEQ ID NO: 15)

tcgtatgttgtgtggaattgtgagcggataacaatttcacacaggaaacagctatgaccatgattacgccagatttaattaaggctgcgc gctcgctcgctcactgaggccgcccgggcaaagcccgggcgtcgggcgacctttggtcgcccggcctcagtgagcgagcgagcgcgca gagagggagtggccaactccatcactagggggttccttgtagttaatgattaacccgccatgctacttatctacgtagccatgctctagga agatcggaattcgcccttaaccactagtaacggccgccagtgtgctggaattcgcccttcgagggcctatttcccatgattccttcatat ttgcatatacgatacaaggctgttagagagataattggaattaatttgactgtaaacacaaagatattagtacaaaatacgtgacgtag aaagtaataatttcttgggtagtttgcagttttaaaattatgttttaaaatggactatcatatgcttaccgtaacttgaaagtatttcgatttt cttggctttatatatcttgtggaaaggacgaaacaccgAGTACTGCGGATACTCAAAGgttttagagctagaaatagcaagtt aaaataaggctagtccgttatcaacttgaaaaagtggcaccgagtcggtgcttttttgttttagagctagaaatagcaagctcgagcag cctgaattctgcagatatccatcacactggcggccttaactcggatccactagtaacggccgccagtgtgctggaattcgcccttAGTA CTGCGGATACTCAAAGGGGtaataaataataagccaccatggatagcactgagaacgtcatcaagcccttcatgcgcttcaa ggtgcacatggagggctccgtgaacggccacgagttcgagatcgagggcgagggcgagggcaagccctacgagggcacccagaccg ccaagctgcaggtgaccaagggcggccccctgcccttcgcctgggacatcctgtcccccagttccagtacggctccaaggtgtacgtg aagcaccccgccgacatccccgactacaagaagctgtccttccccgagggcttcaagtgggagcgcgtgatgaacttcgaggacggcg gcgtggtgaccgtgacccaggactcctccctgcaggacggcaccttcatctaccacgtgaagttcatcggcgtgaacttcccctccgacg gccccgtaatgcagaagaagactctgggctgggagccctccaccgagcgcctgtaccccgcgacggcgtgctgaagggcgagatcc acaaggcgctgaagctgaagggcggcggccactacctggtggagttcaagtcaatctacatggccaagaagcccgtgaagctgcccg gctactactacgtggactccaagctggacatcaccctcccacaacgaggactacaccgtggtggagcagtacgagcgcgccgaggcc gccaccacctgttccagtagcggccgcgactctagaattccaactgagcgccggtcgctaccattaccaacttgtctggtgtcaaaaata ataggcctactagagtcgacctgcagaagcttggatctgcctcgactgtgccttctagttgccagccatctgttgtttgcccctcccccgtg ccttccttgaccctggaaggtgccactcccactgtcctttcctaataaaatgaggaaattgcatcgcattgtctgagtaggtgtcattctat tctgggggtggggtggggcaggacagcaaggggaggattgggaagacaatagcaggcatgctgggaAGTACTGCGGATA CTCAAAGGGGaagggcgaattctgcagatatccatcacactggcgttaagcgtcagcatatgcagaattctgtcattttactagggt gatgaaattcccaagcaacaccatccttttcagataagggcactgaggctgagagaggagctgaaacctacccgggtcaccacaca caggtggcaaggctgggaccagaaaccaggactgttgactgcagcccggtattcattctttccatagcccacagggctgtcaaagacc ccagggcctagtcagaggctcctccttcctgagagttcctggcacagaagttgaagctcagcacagcccctaaccccaactctctct gcaaggcctcaggggtcagaacactggtggagcagatcctttagcctctggattttagggccatggtagagggggtgttgccctaaatt ccagcccctggtctcagcccaacaccctccaagaagaaattagaggggccatggccaggctgtgctagccgttgcttctgagcagattac aagaagggactaagacaaggactccttttgtggaggtcctggcttagggagtcaagtgacggcggctcagcactcacgtgggcagtgcc agcctctaagagtgggcaggggcactggccacagagtcccagggagtcccaccagcctagtcgccagaccttctgtgggcggccgcca tggtgagcaagggcgaggagctgttcaccggggtggtgcccatcctggtcgagctggacggcgacgtaaacggccacaagttcagcgt gtccggcgagggcgagggcgatgccacctacggcaagctgaccctgaagttcatctgcaccaccggcaagctgcccgtgccctggccc accctcgtgaccaccctgacctacggcgtgcagtgcttcagccgctaccccgaccacatgaagcagcacgacttcttcaagtccgccat gcccgaaggctacgtccaggagcgcaccatcttcttcaaggacgacggcaactacaagacccgcgccgaggtgaagttcgagggcga caccctggtgaaccgcatcgagctgaagggcatcgacttcaaggaggacggcaacatcctggggcacaagctggagtacaactacaa -continued

```
cagccacaacgtctatatcatggccgacaagcagaagaacggcatcaaggtgaacttcaagatccgccacaacatcgaggacggca
gcgtgcagctcgccgaccactaccagcagaacacccccatcggcgacggccccgtgctgctgcccgacaaccactacctgagcaccca
gtccgccctgagcaaagaccccaacgagaagcgcgatcacatggtcctgctggagttcgtgaccgccgcgggatcactctcggcatg
gacgagctgtacaagtaataagcttggatccaatcaacctctggattacaaaatttgtgaaagattgactggtattcttaactatgttgct
ccttttacgctatgtggatacgctgctttaatgcctttgtatcatgctattgcttcccgtatggctttcattttctcctccttgtataaatcctg
gttgctgtctctttatgaggagttgtggcccgttgtcaggcaacgtggcgtggtgtgcactgtgtttgctgacgcaaccccactggtgg
ggcattgccaccacctgtcagctccttccgggactttcgctttcccctccctattgccacggcggaactcatcgccgcctgccttgcccg
ctgctggacaggggctcggctgttgggcactgacaattccgtggtgttgtcggggaagctgacgtccttccatggctgctcgcctgtgtt
gccacctggattctgcgcgggacgtccttctgctacgtcccttcggccctcaatccagcggaccttcttcccgcggcctgctgccggctc
tgcggcctcttccgcgtcttcgagatctgcctcgactgtgccttctagttgccagccatctgttgtttgccctcccccgtgccttccttgacc
ctggaaggtgccactcccactgtccttcctaataaaatgaggaaattgcatcgcattgtctgagtaggtgtcattctattctgggggtg
gggtggggcaggacagcaaggggggaggattgggaagacaatagcaggcatgctgggactcgagttaagggcgaattcccgattag
gatcttcctagagcatggctacgtagataagtagcatgggggttaatcattaactacaaggaaccctagtgatggagttggccactc
cctctctgcgcgctcgctcgctcactgaggccgggcgaccaaaggtcgcccgacgcccgggctttgcccgggcggcctcagtgagcga
gcgagcgcgcagccttaattaacctaattcactggccgtcgttttacaacgtcgtgactgggaaaaccctggcgttacccaacttaatcg
ccttgcagcacatccccctttcgccagctggcgtaatagcgaagaggcccgcaccgatcgcccttcccaacagttgcgcagcctgaatg
gcgaatgggacgcgccctgtagcggcgcattaagcgcggcgggtgtggtggttacgcgcagcgtgaccgctacacttgccagcgccct
agcgcccgctcctttcgctttcttcccttcctttctcgccacgttcgccggctttccccgtcaagctctaaatcggggctccctttagggttc
cgatttagtgctttacggcacctcgaccccaaaaaacttgattagggtgatggttcacgtagtgggccatcgccccgatagacggttttt
cgccctttgacgctggagttcacgttcctcaatagtggactcttgttccaaactggaacaacactcaaccctatctcggtctattcttttga
tttataagggattttttccgatttcggcctattggttaaaaaatgagctgatttaacaaaaatttaacgcgaattttaacaaaatattaacg
tttataatttcaggtggcatctttcggggaaatgtgcgcggaacccctatttgtttattttctaaatacattcaaatatgtatccgctcatg
agacaataaccctgataaatgcttcaataatattgaaaaaggaagagtatgagtattcaacatttccgtgtcgcccttattcccttttttg
cggcattttgccttcctgtttttgctcacccagaaacgctggtgaaagtaaaagatgctgaagatcagttgggtgcacgagtgggttaca
tcgaactggatctcaatagtggtaagatccttgagagttttcgccccgaagaacgttttccaatgatgagcacttttaaagttctgctatg
tggcgcggtattatcccgtattgacgccgggcaagagcaactcggtcgccgcatacactattctcagaatgacttggttgagtactcacc
agtcacagaaaagcatcttacggatggcatgacagtaagagaattatgcagtgctgccataaccatgagtgataacactgcggccaac
ttacttctgacaacgatcggaggaccgaaggagctaaccgcttttttgcacaacatgggggatcatgtaactcgccttgatcgttgggaa
ccggagctgaatgaagccataccaaacgacgagcgtgacaccacgatgcctgtagtaatggtaacaacgttgcgcaaactattaactg
gcgaactacttactctagcttcccggcaacaattaatagactggatggaggcggataaagttgcaggaccacttctgcgctcggcccttc
cggctggctggtttattgctgataaatctggagccggtgagcgtgggtctcgcggtatcattgcagcactggggccagatggtaagccct
cccgtatcgtagttatctacacgacggggagtcaggcaactatggatgaacgaaatagacagatcgctgagataggtgcctcactgatt
aagcattggtaactgtcagaccaagtttactcatatatactttagattgatttaaaacttcatttttaatttaaaaggatctaggtgaagat
cctttttgataatctcatgaccaaaatcccttaacgtgagttttcgttccactgagcgtcagaccccgtagaaaagatcaaaggatcttct
tgagatcctttttttctgcgcgtaatctgctgcttgcaaacaaaaaaaccaccgctaccagcggtggtttgtttgccggatcaagagctac
caactctttttccgaaggtaactggcttcagcagagcgcagataccaaatactgtccttctagtgtagccgtagttaggccaccacttca
agaactctgtagcaccgcctacatacctcgctctgctaatcctgttaccagtggctgctgccagtggcgataagtcgtgtcttaccgggtt
ggactcaagacgatagttaccggataaggcgcagcggtcgggctgaacggggggttcgtgcacacagcccagcttggagcgaacgac
ctacaccgaactgagatacctacagcgtgagctatgagaaagcgccacgcttcccgaagggagaaaggcggacaggtatccggtaag
cggcagggtcggaacaggagagcgcacgagggagcttccaggggaaacgcctggtatctttatagtcctgtcgggtttcgccacctct
gacttgagcgtcgatttttgtgatgctcgtcaggggggcggagcctatggaaaaacgccagcaacgcggcctttttacggttcctggcct
```

-continued tttgctgcggttttgctcacatgttctttcctgcgttatccctgattctgtggataaccgtattaccgcctttgagtgagctgataccgctcg ccgcagccgaacgaccgagcgcagcgagtcagtgagcgaggaagcggaagggccgattcattaatgcagctggcacgacaggtttcc cgactggaaagcgggcagtgagcgcaacgcaattaatgtgagttagctcactcattaggcaccccaggctttacactttatgcttccgg c p1222// pAAV2.1_sRHOgRNA + sRHO HITI (IRES-dsRED)_Vmd2_GFP (SEQ ID NO: 16)

caggaaacagctatgaccatgattacgccagatttaattaaggctgcgcgctcgctcgctcactgaggccgcccgggcaaagcccggg cgtcgggcgacctttggtcgcccggcctcagtgagcgagcgagcgcgcagagagggagtggccaactccatcactaggggttccttgt agttaatgattaacccgccatgctacttatctacgtagccatgctctaggaagatcggaattcgcccttaaccactagtaacggccgcca gtgtgctggaattcgcccttttcgagggcctatttcccatgattccttcatatttgcatatacgatacaaggctgttagagagataattgga attaatttgactgtaaacacaaagatattagtacaaaatacgtgacgtagaaagtaataatttcttgggtagtttgcagttttaaaattat gttttaaaatggactatcatatgcttaccgtaacttgaaagtatttcgatttcttggctttatatatcttgtggaaaggacgaaacaccgG ACTCGCGCGAGTCGAGGAGgttttagagctagaaatagcaagttaaaataaggctagtccgttatcaacttgaaaaagtggc accgagtcggtgcttttttgttttagagctagaaatagcaagctcgagcagcctgaattctgcagatatccatcacactggcggccttaa ctcggatccactagtaacggccgccagtgtgctggaattcaggCCCCTTTGAGTATCCGCAGTACTccccagcatgcctgct attgtcttcccaatcctccccttgctgtcctgccccaccccacccccagaatagaatgacacctactcagacaatgcgatgcaatttcc tcattttattaggaaaggacagtgggagtggcaccttccagggtcaaggaaggcacgggggaggggcaaacaacagatggctggca actagaaggcacagtcgaggcagatccaagcttctgcaggtcgactctagtaggcctattattttttgacaccagacaagttggtaatgg tagcgaccggcgctcagttggaattctagagtcgcggccgctactggaacaggtggtggcgggcctcggcgcgctcgtactgctccacc acggtgtagtcctcgttgtgggaggtgatgtccagcttggagtccacgtagtagtagccgggcagcttcacgggcttcttggccatgtag attgacttgaactccaccaggtagtggccgccgcccttcagcttcagcgccttgtggatctcgcccttcagcacgccgtcgcggggtac aggcgctcggtggagggctcccagcccagagtcttcttctgcattacggggccgtcggagggaagttcacgccgatgaacttcacgtg gtagatgaaggtgccgtcctgcagggaggagtcctgggtcacggtcaccacgccgccgtcctcgaagttcatcacgcgctcccacttga agccctcggggaaggacagcttcttgtagtcgggatgtcggcggggtgcttcacgtacaccttggagccgtactggaactgggggga caggatgtcccaggcgaagggcaggggccgcccttggtcacctgcagcttggcggtctgggtgcctcgtagggcttgccctcgccct cgccctcgatctcgaactcgtggccgttcacggagccctccatgtgcaccttgaagcgcatgaagggcttgatgacgttctcagtgctat ccatcTAcAAAAAATcAcGcAAAATTAcAGTTAAcGGcATGTAcAGTTTGTcAttattatttattaCCCCTTTGA GTATCCGCAGTACTaagggcgaattctgcagatatccatcacactggcgttaagcgtcagcatatgcagaattctgtcatttttact agggtgatgaaattcccaagcaacaccatccttttcagataagggcactgaggctgagagaggagctgaaacctacccggggtcacc acacacaggtggcaaggctgggaccagaaaccaggactgttgactgcagcccggtattcattctttccatagcccacagggctgtcaa agaccccagggcctagtcagaggctcctccttcctggagagttcctggcacagaagttgaagctcagcacagcccctaaccccaact ctctctgcaaggcctcaggggtcagaacactggtggagcagatccttagcctctggattttagggccatggtagaggggtgttgccct aaattccagccctggtctcagcccaacaccctccaagaagaaattagaggggccatggccaggctgtgctagccgttgcttctgagcag attcaagaagggactaagacaaggactccttgtggaggtcctggcttagggagtcaagtgacggcggctcagcactcacgtgggca gtgccagcctctaagagtgggcaggggcactggccacagagtcccagggagtcccaccagcctagtcgccagaccttctgtgggggc cgccatggtgagcaagggcgaggagctgttcaccggggggtgcccatcctggtcgagctggacggcgacgtaaacgccacaagtt cagcgtgtccggcgagggcgagggcgatgccacctacggcaagctgaccctgaagttcatctgcaccaccggcaagctgcccgtgccc tggcccaccctcgtgaccaccctgacctacggcgtgcagtgcttcagccgctaccccgaccacatgaagcagcacgacttcttcaagtc cgccatgcccgaaggctacgtccaggagcgcaccatcttcttcaaggacgacggcaactacaagacccgcgccgaggtgaagttcga gggcgacaccctggtgaaccgcatcgagctgaagggcatcgacttcaaggaggacggcaacatcctggggcacaagctggagtaca actacaacagccacaacgtctatatcatggccgacaagcagaagaacggcatcaaggtgaacttcaagatccgccacaacatcgagg -continued

```
acggcagcgtgcagctcgccgaccactaccagcagaacaccccatcggcgacggccccgtgctgctgcccgacaaccactacctga gcacccagtccgccctgagcaaagaccccaacgagaagcgcgatcacatggtcctgctggagttcgtgaccgccgccgggatcactct cggcatggacgagctgtacaagtaataagcttggatccaatcaacctctggattacaaaatttgtgaaagattgactggtattcttaact atgttgctccttttacgctatgtggatacgctgctttaatgcctttgtatcatgctattgcttcccgtatggctttcattttctcctccttgtata aatcctggttgctgtctctttatgaggagttgtggcccgttgtcaggcaacgtggcgtggtgtgcactgtgtttgctgacgcaacccccac tggttggggcattgccaccacctgtcagctcctttccgggactttcgctttccccctccctattgccacggcggaactcatcgccgcctgcc ttgcccgctgctggacaggggctcggctgttgggcactgacaattccgtggtgttgtcggggaagctgacgtcctttccatggctgctcgc ctgtgttgccacctggattctgcgcgggacgtccttctgctacgtcccttcggccctcaatccagcggaccttccttcccgcggcctgctgc cggctctgcggcctcttccgcgtcttcgagatctgcctcgactgtgccttctagttgccagccatctgttgtttgccctccccgtgccttc cttgaccctggaaggtgccactcccactgtcctttcctaataaaatgaggaaattgcatcgcattgtctgagtaggtgtcattctattctgg ggggtggggtggggcaggacagcaaggggggaggattgggaagacaatagcaggcatgctggggactcgagttaagggcgaattccc gattaggatcttcctagagcatggctacgtagataagtagcatggcgggttaatcattaactacaaggaaccctagtgatggagttgg ccactccctctctgcgcgctcgctcgctcactgaggccgggcgaccaaaggtcgcccgacgcccgggctttgcccggcggcctcagtg agcgagcgagcgcgcagccttaattaacctaattcactggccgtcgttttacaacgtcgtgactgggaaaaccctggcgttacccaactt aatcgccttgcagcacatccccctttcgccagctggcgtaatagcgaagaggcccgcaccgatcgcccttcccaacagttgcgcagcct gaatggcgaatgggacgcgccctgtagcggcgcattaagcgcggcgggtgtggtggttacgcgcagcgtgaccgctacacttgccagc gccctagcgcccgctcctttcgctttcttcccttcctttctcgccacgttcgccggctttccccgtcaagctctaaatcgggggctcccttta gggttccgatttagtgctttacggcacctcgaccccaaaaaacttgattagggtgatggttcacgtagtgggccatcgccccgatagacg gtttttcgccctttgacgctggagttcacgttcctcaatagtggactcttgttccaaactggaacaacactcaaccctatctcggtctattct tttgatttataagggattttttccgatttcggcctattggttaaaaaatgagctgatttaacaaaaatttaacgcgaattttaacaaaatatt aacgtttataatttcaggtggcatctttcggggaaatgtgcgcggaacccctatttgtttattttctaaatacattcaaatatgtatccgct catgagacaataaccctgataaatgcttcaataatattgaaaaaggaagagtatgagtattcaacatttccgtgtcgcccttattcccttt tttgcggcattttgccttcctgttttgctcacccagaaacgctggtgaaagtaaaagatgctgaagatcagttgggtgcacgagtgggtt acatcgaactggatctcaatagtggtaagatccttgagagttttcgccccgaagaacgttttccaatgatgagcacttttaaagttctgct atgtggcgcggtattatcccgtattgacgccgggcaagagcaactcggtcgccgcatacactattctcagaatgacttggttgagtactc accagtcacagaaaagcatcttacggatggcatgacagtaagagaattatgcagtgctgccataaccatgagtgataacactgcggcc aacttacttctgacaacgatcggaggaccgaaggagctaaccgcttttttgcacaacatgggggatcatgtaactcgccttgatcgttgg gaaccggagctgaatgaagccataccaaacgacgagcgtgacaccacgatgcctgtagtaatggtaacaacgttgcgcaaactatta actggcgaactacttactctagcttcccggcaacaattaatagactggatggaggcggataaagttgcaggaccacttctgcgctcggc ccttccggctggctggtttattgctgataaatctggagccggtgagcgtgggctcgcggtatcattgcagcactggggccagatggtaa gccctcccgtatcgtagttatctacacgacggggagtcaggcaactatggatgaacgaaatagacagatcgctgagataggtgcctca ctgattaagcattggtaactgtcagaccaagtttactcatatatactttagattgatttaaaacttcatttttaatttaaaaggatctaggt gaagatcctttttgataatctcatgaccaaaatcccttaacgtgagttttcgttccactgagcgtcagacccgtagaaaagatcaaagg atcttcttgagatccttttttttctgcgcgtaatctgctgcttgcaaacaaaaaaaccaccgctaccagcggtggtttgtttgccggatcaag agctaccaactctttttccgaaggtaactggcttcagcagagcgcagataccaaatactgtccttctagtgtagccgtagttaggccacc acttcaagaactctgtagcaccgcctacatacctcgctctgctaatcctgttaccagtggctgctgccagtggcgataagtcgtgtcttac cgggttggactcaagacgatagttaccggataaggcgcagcggtcgggctgaacggggggttcgtgcacacagcccagcttggagcg aacgacctacaccgaactgagatacctacagcgtgagctatgagaaagcgccacgcttcccgaagggagaaaggcggacaggtatc cggtaagcggcagggtcggaacaggagagcgcacgagggagcttccaggggaaacgcctggtatctttatagtcctgtcgggtttcg ccacctctgacttgagcgtcgatttttgtgatgctcgtcaggggggcggagcctatggaaaaacgccagcaacgcggcctttttacggtt cctggccttttgctgcggttttgctcacatgttctttcctgcgttatcccctgattctgtggataaccgtattaccgcctttgagtgagctgat
```

```
accgctcgccgcagccgaacgaccgagcgcagcgagtcagtgagcgaggaagcggaagggccgattcattaatgcagctggcacga caggtttcccgactggaaagcgggcagtgagcgcaacgcaattaatgtgagttagctcactcattaggcaccccaggctttacactttat gcttccggctcgtatgttgtgtggaattgtgagcggataacaatttcaca
``` p1227// pAAV2.1_sRHOgRNA + sRHO HITI (IRES-dsRED)_Vmd2_GFP (SEQ ID NO: 17)

```
attacgccagatttaattaaggctgcgcgctcgctcgctcactgaggccgcccgggcaaagcccgggcgtcgggcgacctttggtcgcc cggcctcagtgagcgagcgagcgcgcagagagggagtggccaactccatcactagggttccttgtagttaatgattaacccgccatg ctacttatctacgtagccatgctctaggaagatcggaattcgcccttaaccactagtaacggccgccagtgtgctggaattcgccctttcg agggcctatttcccatgattccttcatatttgcatatacgatacaaggctgttagagagataattggaattaatttgactgtaaacacaaa gatattagtacaaaatacgtgacgtagaaagtaataatttcttgggtagtttgcagttttaaaattatgttttaaaatggactatcatatg cttaccgtaacttgaaagtatttcgatttcttggctttatatatcttgtggaaaggacgaaacaccgAGTACTGCGGATACTCAA AGgttttagagctagaaatagcaagttaaaataaggctagtccgttatcaacttgaaaaagtggcaccgagtcggtgcttttttgtttta gagctagaaatagcaagctcgagcagcctgaattctgcagatatccatcacactggcggccttaactcggatccactagtaacggccg ccagtgtgctggaattcaggCCCCTTTGAGTATCCGCAGTACTccccagcatgcctgctattgtcttcccaatcctcccccttg ctgtcctgccccaccccacccccagaatagaatgacacctactcagacaatgcgatgcaatttcctcattttattaggaaaggacagtg ggagtggcaccttccagggtcaaggaaggcacggggagggcaaacaacagatggctggcaactagaaggcacagtcgaggcag atccaagcttctgcaggtcgactctagtaggcctattatttttgacaccagacaagttggtaatggtagcgaccggcgctcagttggaat tctagagtcgcggccgctactggaacaggtggtggcgggcctcggcgcgctcgtactgctccaccacggtgtagtcctcgttgtgggag gtgatgtccagcttggagtccacgtagtagtagccgggcagcttcacgggcttcttggccatgtagattgacttgaactccaccaggtag tggccgccgcccttcagcttcagcgccttgtggatctcgcccttcagcacgccgtcgcggggtacaggcgctcggtggagggctccca gcccagagtcttcttctgcattacggggccgtcggaggggaagttcacgccgatgaacttcacgtggtagatgaaggtgccgtcctgca gggaggagtcctgggtcacggtcaccacgccgccgtcctcgaagttcatcacgcgctcccacttgaagccctcggggaaggacagctt cttgtagtcggggatgtcggcggggtgcttcacgtacaccttggagccgtactggaactgggggacaggatgtcccaggcgaagggc aggggccgcccttggtcacctgcagcttggcggtctgggtgccctcgtagggcttgccctcgccctcgccctcgatctcgaactcgtgg ccgttcacggagccctccatgtgcaccttgaagcgcatgaagggcttgatgacgttctcagtgctatccatcTAcAAAAAAATcAc GcAAAATTAcAGTTAAcGGcATGTAcAGTTTGTcAttattatttattaCCCCTTTGAGTATCCGCAGTACTaagg gcgaattctgcagatatccatcacactggcgttaagcgtcagcatatgcagaattctgtcattttactagggtgatgaaattcccaagca acaccatccttttcagataagggcactgaggctgagagaggagctgaaacctacccggggtcaccacacacaggtggcaaggctggg accagaaaccaggactgttgactgcagcccggtattcattctttccatagcccacagggctgtcaaagaccccagggcctagtcagagg ctcctccttcctggagagttcctggcacagaagttgaagctcagcacagcccctaaccccaactctctctgcaaggcctcaggggtca gaacactggtggagcagatcctttagcctctggattttagggcatggtagagggggtgttgccctaaattccagccctggtctcagccc aacaccctccaagaagaaattagagggggccatggccaggctgtgctagccgttgcttctgagcagattacaagaagggactaagaca aggactcctttgtggaggtcctggcttagggagtcaagtgacggcggctcagcactcacgtgggcagtgccagcctctaagagtgggc aggggcactggccacagagtcccagggagtcccaccagcctagtcgccagacttctgtgggcggccgccatggtgagcaagggcga ggagctgttcaccggggggtgcccatcctggtcgagctggacggcgacgtaaacggccacaagttcagcgtgtccggcgagggcgag ggcgatgccacctacggcaagctgaccctgaagttcatctgcaccaccggcaagctgcccgtgccctggcccaccctcgtgaccaccct gacctacggcgtgcagtgcttcagccgctaccccgaccacatgaagcagcacgacttcttcaagtccgccatgcccgaaggctacgtcc aggagcgcaccatcttcttcaaggacgacggcaactacaagacccgcgccgaggtgaagttcgagggcgacaccctggtgaaccgca tcgagctgaagggcatcgacttcaaggaggacggcaacatcctggggcacaagctggagtacaactacaacagccacaacgtctata tcatggccgacaagcagaagaacggcatcaaggtgaacttcaagatccgccacaacatcgaggacggcagcgtgcagctcgccgac cactaccagcagaacacccccatcggcgacggccccgtgctgctgcccgacaaccactacctgagcacccagtccgccctgagcaaa
```

-continued

```
gaccccaacgagaagcgcgatcacatggtcctgctggagttcgtgaccgccgcgggatcactctcggcatggacgagctgtacaagt
aataagcttggatccaatcaacctctggattacaaaatttgtgaaagattgactggtattcttaactatgttgctccttttacgctatgtgg
atacgctgctttaatgcctttgtatcatgctattgcttcccgtatggctttcattttctcctccttgtataaatcctggttgctgtctctttatga
ggagttgtggcccgttgtcaggcaacgtggcgtggtgtgcactgtgtttgctgacgcaaccccactggttgggcattgccaccacctg
tcagctcctttccgggactttcgctttcccctcccattgccacggcggaactcatcgccgcctgccttgcccgctgctggacaggggctc
ggctgttgggcactgacaattccgtggtgttgtcggggaagctgacgtcctttccatggctgctcgcctgtgttgccacctggattctgcg
cgggacgtccttctgctacgtcccttcggccctcaatccagcggaccttccttcccgcggcctgctgccggctctgcggcctcttccgcgtc
ttcgagatctgcctcgactgtgccttctagttgccagccatctgttgtttgcccctccccgtgccttccttgaccctggaaggtgccactcc
cactgtcctttcctaataaaatgaggaaattgcatcgcattgtctgagtaggtgtcattctattctggggggtggggggggcaggacag
caaggggaggattgggaagacaatagcaggcatgctgggactcgagttaagggcgaattcccgattaggatcttcctagagcatg
gctacgtagataagtagcatggcgggttaatcattaactacaccttaattaacctaattcactggccgtcgttttacaacgtcgtgactgg
gaaaaccctggcgttacccaacttaatcgccttgcagcacatcccccttttcgccagctggcgtaatagcgaagaggcccgcaccgatcg
cccttcccaacagttgcgcagcctgaatggcgaatgggacgcgccctgtagcggcgcattaagcgcggcgggtgtggtggttacgcgc
agcgtgaccgctacacttgccagcgccctagcgcccgctcctttcgctttcttcccttcctttctcgccacgttcgccggctttccccgtcaa
gctctaaatcggggggctccctttagggttccgatttagtgctttacggcacctcgaccccaaaaaacttgattagggtgatggttcacgta
gtgggccatcgccccgatagacggtttttcgccctttgacgctggagttcacgttcctcaatagtggactcttgttccaaactggaacaac
actcaacccctatctcggtctattcttttgatttataagggattttttccgatttcggcctattggttaaaaaatgagctgatttaacaaaaatt
taacgcgaattttaacaaaatattaacgtttataatttcaggtggcatcttttcggggaaatgtgcgcggaacccctatttgtttattttttct
aaatacattcaaatatgtatccgctcatgagacaataaccctgataaatgcttcaataatattgaaaaaggaagagtatgagtattcaa
catttccgtgtcgcccttattcccttttttgcggcattttgccttcctgttttttgctcacccagaaacgctggtgaaagtaaaagatgctgaa
gatcagttgggtgcacgagtgggttacatcgaactggatctcaatagtggtaagatccttgagagttttcgccccgaagaacgttttcca
atgatgagcacttttaaagttctgctatgtggcgcggtattatcccgtattgacgccgggcaagagcaactcggtcgccgcatacactat
tctcagaatgacttggttgagtactcaccagtcacagaaaagcatcttacggatggcatgacagtaagagaattatgcagtgctgccat
aaccatgagtgataacactgcggccaacttacttctgacaacgatcggaggaccgaaggagctaaccgcttttttgcacaacatgggg
gatcatgtaactcgccttgatcgttgggaaccggagctgaatgaagccataccaaacgacgagcgtgacaccacgatgcctgtagtaa
tggtaacaacgttgcgcaaactattaactggcgaactacttactctagcttcccggcaacaattaatagactggatggaggcggataaa
gttgcaggaccacttctgcgctcggcccttccggctggctggtttattgctgataaatctggagccggtgagcgtgggtctcgcggtatca
ttgcagcactggggccagatggtaagccctcccgtatcgtagttatctacacgacggggagtcaggcaactatggatgaacgaaatag
acagatcgctgagataggtgcctcactgattaagcattggtaactgtcagaccaagtttactcatatatactttagattgatttaaaactt
cattttttaatttaaaaggatctaggtgaagatcctttttgataatctcatgaccaaaatcccttaacgtgagttttcgttccactgagcgtc
agaccccgtagaaaagatcaaaggatcttcttgagatcctttttttctgcgcgtaatctgctgcttgcaaacaaaaaaaccaccgctacc
agcggtggtttgtttgccggatcaagagctaccaactctttttccgaaggtaactggcttcagcagagcgcagataccaaatactgtcct
tctagtgtagccgtagttaggccaccacttcaagaactctgtagcaccgcctacatacctcgctctgctaatcctgttaccagtggctgct
gccagtggcgataagtcgtgtcttaccgggttggactcaagacgatagttaccggataaggcgcagcggtcgggctgaacggggggtt
cgtgcacacagcccagcttggagcgaacgacctacaccgaactgagatacctacagcgtgagctatgagaaagcgccacgcttcccg
aagggagaaaggcggacaggtatccggtaagcggcagggtcggaacaggagagcgcacgagggagcttccaggggaaacgcctg
gtatctttatagtcctgtcgggtttcgccacctctgacttgagcgtcgatttttgtgatgctcgtcaggggggcggagcctatggaaaaac
gccagcaacgcggcctttttacggttcctggccttttgctgcggttttgctcacatgttctttcctgcgttatcccctgattctgtggataacc
gtattaccgcctttgagtgagctgataccgctcgccgcagccgaacgaccgagcgcagcgagtcagtgagcgaggaagcggaagggc
```

-continued cgattcattaatgcagctggcacgacaggtttcccgactggaaagcgggcagtgagcgcaacgcaattaatgtgagttagctcactcat taggcacccaggctttacactttatgcttccggctcgtatgttgtgtggaattgtgagcggataacaatttcacacaggaaacagctat gaccatg p1160//pAAV_Alb5'HITI(kozak-dsRED) + gRNA mAlb 5'

(SEQ ID NO: 18)

ttacgccagatttaattaaggctgcgcgctcgctcgctcactgaggccgcccgggcaaagcccgggcgtcgggcgacctttggtcgccc ggcctcagtgagcgagcgagcgcgcagagagggagtggccaactccatcactagggggttccttgtagttaatgattaacccgccatgc tacttatctacgtagccatgctctaggaagatcggaattactagtaacggccgccagtgtgctggcacaagagtgagatcgcccatcgg tccccagcatgcctgctattgtcttcccaatcctccccccttgctgtcctgccccaccccaccccccagaatagaatgacacctactcagac aatgcgatgcaatttcctcatttattaggaaaggacagtgggagtggcaccttccagggtcaaggaaggcacggggagggcaaa caacagatggctggcaactagaaggcacagtcgaggcagatccaagcttctgcaggtcgactctagtaggcctattattttgtgacacca gacaagttggtaatggtagcgaccggcgctcagttggaattctagagtcgcggccgctactggaacaggtggtggcgggcctcggcgc gctcgtactgctccaccacggtgtagtcctcgttgtgggaggtgatgtccagcttggagtccacgtagtagtagccgggcagcttcacgg gcttcttggccatgtagattgacttgaactccaccaggtagtggccgccgcccttcagcttcagcgccttgtggatctcgcccttcagcac gccgtcgcgggggtacaggcgctcggtggagggctcccagcccagtgtcttcttctgcattacggggccgtcggaggggaagttcacg ccgatgaacttcacgtggtagatgaaggtgccgtcctgcaggaggagtcctgggtcacggtcaccacgccgccgtcctcgaagttcat cacgcgctcccacttgaagccctcggggaaggacagcttcttgtagtcggggatgtcggcggggtgcttcacgtacaccttggagccgt actggaactgggggacaggatgtcccaggcgaagggcaggggccgcccttggtcacctgcagcttggcggtctgggtgccctcgta gggcttgccctcgccctcgccctcgatctcgaactcgtggccgttcacggagcccctccatgtgcaccttgaagcgcatgaagggcttgat gacgttctcagtgctatccatggtggcttattatttattatttattaacaagagtgagatcgcccatcgggaattgccgccagtgtgatgg atatctgcagaattcaggctgctcgagcttgctatttctagctctaaaacaaaaaagcaccgactcggtgccactttttcaagttgataac ggactagccttattttaacttgctatttctagctctaaaacCTCCTCGACTCGCGCGAGTCcggtgtttcgtccttttccacaagat atataaagccaagaaatcgaaatactttcaagttacggtaagcatatgatagtccattttaaaacataatttttaaaactgcaaactacc caagaaattattactttctacgtcacgtatttttgtactaatatctttgtgtttacagtccaaattaattccaattatctctctaacagccttgt atcgtatatgcaaatatgaaggaatcatgggaaactcgaggtcagcctgaattaattcccgattaggatcttcctagagcatggctacg tagataagtagcatggcgggttaatcattaactacaaggaaccccctagtgatggagttggccactccctctctgcgcgctcgctcgctca ctgaggccgggcgaccaaaggtcgcccgacgcccgggctttgcccgggcggcctcagtgagcgagcgagcgcgcagccttaattaac ctaattcactggccgtcgttttacaacgtcgtgactgggaaaaccctggcgttacccaacttaatcgccttgcagcacatccccctttcgc cagctggcgtaatagcgaagaggcccgcaccgatcgcccttcccaacagttgcgcagcctgaatggcgaatgggacgcgccctgtagc ggcgcattaagcgcggcgggtgtggtggttacgcgcagcgtgaccgctacacttgccagcgccctagcgcccgctcctttcgctttcttc ccttcctttctcgccacgttcgccggctttccccgtcaagctctaaatcgggggctcccctttagggttccgatttagtgctttacggcacctc gaccccaaaaaacttgattagggtgatggttcacgtagtgggccatcgccccgatagacggtttttcgccctttgacgctggagttcacg ttcctcaatagtggactcttgttccaaactggaacaacactcaaccctatctcggtctattcttttgatttataagggattttccgatttcg gcctattggttaaaaaatgagctgatttaacaaaaatttaacgcgaattttaacaaaatattaacgtttataatttcaggtggcatctttc ggggaaatgtgcgcggaaccccctatttgtttatttttctaaatacattcaaatatgtatccgctcatgagacaataaccctgataaatgct tcaataatattgaaaaaggaagagtatgagtattcaacatttccgtgtcgcccttattcccttttttgcggcattttgccttcctgtttttgct cacccagaaacgctggtgaaagtaaaagatgctgaagatcagttgggtgcacgagtgggttacatcgaactggatctcaatagtggta agatccttgagagttttcgccccgaagaacgttttccaatgatgagcacttttaaagttctgctatgtggcgcggtattatcccgtattgac gccgggcaagagcaactcggtcgccgcatacactattctcagaatgacttggttgagtactcaccagtcacagaaaagcatcttacgg atggcatgacagtaagagaattatgcagtgctgccataaccatgagtgataacactgcggccaacttacttctgacaacgatcggagg accgaaggagctaaccgcttttttgcacaacatgggggatcatgtaactcgccttgatcgttgggaaccggagctgaatgaagccatac -continued caaacgacgagcgtgacaccacgatgcctgtagtaatggtaacaacgttgcgcaaactattaactggcgaactacttactctagcttcc cggcaacaattaatagactggatggaggcggataaagttgcaggaccacttctgcgctcggcccttccggctggctggtttattgctgat aaatctggagccggtgagcgtgggtctcgcggtatcattgcagcactggggccagatggtaagccctcccgtatcgtagttatctacac gacggggagtcaggcaactatggatgaacgaaatagacagatcgctgagataggtgcctcactgattaagcattggtaactgtcagac caagtttactcatatatactttagattgatttaaaacttcattttaatttaaaaggatctaggtgaagatcctttttgataatctcatgacc aaatcccttaacgtgagttttcgttccactgagcgtcagacccgtagaaaagatcaaaggatcttcttgagatccttttttctgcgcg taatctgctgcttgcaaacaaaaaaaccaccgctaccagcggtggtttgtttgccggatcaagagctaccaactcttttccgaaggtaa ctggcttcagcagagcgcagataccaaatactgtccttctagtgtagccgtagttaggccaccacttcaagaactctgtagcaccgccta catacctcgctctgctaatcctgttaccagtggctgctgccagtggcgataagtcgtgtcttaccgggttggactcaagacgatagttacc ggataaggcgcagcggtcgggctgaacggggggttcgtgcacacagcccagcttggagcgaacgacctacaccgaactgagatacct acagcgtgagctatgagaaagcgccacgcttcccgaagggagaaaggcggacaggtatccggtaagcggcagggtcggaacagga gagcgcacgagggagcttccaggggaaacgcctggtatctttatagtcctgtcgggtttcgccacctctgacttgagcgtcgattttgt gatgctcgtcaggggggcggagcctatggaaaaacgccagcaacgcggcctttttacggttcctggccttttgctgcggttttgctcaca tgttctttcctgcgttatcccctgattctgtggataaccgtattaccgcctttgagtgagctgataccgctcgccgcagccgaacgaccga gcgcagcgagtcagtgagcgaggaagcggaagagcgcccaatacgcaaaccgcctctccccgcgcgttggccgattcattaatgcag ctggcacgacaggtttcccgactggaaagcgggcagtgagcgcaacgcaattaatgtgagttagctcactcattaggcaccccaggctt tacactttatgcttccggctcgtatgttgtgtggaattgtgagcggataacaatttcacacaggaaacagctatgaccatga p1161//pAAV_Alb5'HITI(kozak-dsRED) + scramble (SEQ ID NO: 19)

cacaggaaacagctatgaccatgattacgccagatttaattaaggctgcgcgctcgctcgctcactgaggccgcccgggcaaagcccg ggcgtcgggcgacctttggtcgcccggcctcagtgagcgagcgagcgcgcagagagggagtggccaactccatcactaggggttcctt gtagttaatgattaacccgccatgctacttatctacgtagccatgctctaggaagatcggaattactagtaacgccgccagtgtgctgg cacaagagtgagatcgcccatcggtccccagcatgcctgctattgtcttcccaatcctccccttgctgtcctgccccacccccaccccca gaatagaatgacacctactcagacaatgcgatgcaatttcctcattttattaggaaaggacagtgggagtggcacttccagggtcaag gaaggcacggggagggcaaacaacagatggctggcaactagaaggcacagtcgaggcagatccaagcttctgcaggtcgactct agtaggcctattatttttgacaccagacaagttggtaatggtagcgaccggcgctcagttggaattctagagtcgcggccgctactgga acaggtggtggcgggcctcggcgcgctcgtactgctccaccacggtgtagtcctcgttgtgggaggtgatgtccagcttggagtccacgt agtagtagccgggcagcttcacgggcttcttggccatgtagattgacttgaactccaccaggtagtggccgccgcccttcagcttcagcg ccttgtggatctcgcccttcagcacgccgtcgcggggtacaggcgctcggtggagggctcccagcccagagtcttcttctgcattacgg ggccgtcggaggggaagttcacgccgatgaacttcacgtggtagatgaaggtgccgtcctgcagggaggagtcctgggtcacggtcac cacgccgccgtcctcgaagttcatcacgcgctcccacttgaagccctcggggaaggacagcttcttgtagtcggggatgtcggcgggt gcttcacgtacaccttggagccgtactggaactgggggacaggatgtcccaggcgaagggcaggggccgcccttggtcacctgcag cttggcggtctgggtgccctcgtagggcttgccctcgccctcgccctcgatctcgaactcgtggccgttcacggagccctccatgtgcacc ttgaagcgcatgaagggcttgatgacgttctcagtgctatccatggtggcttattatttattatttattaacaagagtgagatcgcccatc gggaattgccgccagtgtgatggatatctgcagaattcaggctgctcgagcttgctatttctagctctaaaacaaaaaagcaccgactc ggtgccacttttcaagttgataacggactagccttatttaacttgctatttctagctctaaaacatgggcgatctcactcttgtcggtgtt tcgtcctttccacaagatatataaagccaagaaatcgaaatactttcaagttacggtaagcatatgatagtccatttaaaacataatttt aaaactgcaaactacccaagaaattattactttctacgtcacgtattttgtactaatatctttgtgtttacagtccaaattaattccaattat ctctctaacagccttgtatcgtatatgcaaatatgaaggaatcatgggaaactcgaggtcagcctgaattaattcccgattaggatcttc ctagagcatggctacgtagataagtagcatggcgggttaatcattaactacaaggaaccccctagtgatggagttggccactccctctct gcgcgctcgctcgctcactgaggccgggcgaccaaaggtcgcccgacgcccgggctttgcccgggcggcctcagtgagcgagcgagc gcgcagccttaattaacctaattcactggccgtcgttttacaacgtcgtgactgggaaaaccctggcgttacccaacttaatcgccttgca -continued

```
gcacatccccctttcgccagctggcgtaatagcgaagaggcccgcaccgatcgcccttcccaacagttgcgcagcctgaatggcgaatg ggacgcgccctgtagcggcgcattaagcgcggcgggtgtggtggttacgcgcagcgtgaccgctacacttgccagcgccctagcgccc gctcctttcgctttcttcccttcctttctcgccacgttcgccggctttccccgtcaagctctaaatcggggggctccctttagggttccgattta gtgctttacggcacctcgaccccaaaaaacttgattagggtgatggttcacgtagtgggccatcgccccgatagacggttttcgccctt gacgctggagttcacgttcctcaatagtggactcttgttccaaactggaacaacactcaaccctatctcggtctattcttttgatttataag ggattttccgatttcggcctattggttaaaaaatgagctgatttaacaaaaatttaacgcgaatttaacaaaatattaacgtttataatt tcaggtggcatcttcggggaaatgtgcgcggaacccctatttgtttatttttctaaatacattcaaatatgtatccgctcatgagacaata accctgataaatgcttcaataatattgaaaaaggaagagtatgagtattcaacatttccgtgtcgcccttattcccttttttgcggcatttt gccttcctgtttttgctcacccagaaacgctggtgaaagtaaaagatgctgaagatcagttgggtgcacgagtgggttacatcgaactg gatctcaatagtggtaagatccttgagagttttcgccccgaagaacgttttccaatgatgagcacttttaaagttctgctatgtggcgcgg tattatcccgtattgacgccgggcaagagcaactcggtcgccgcatacactattctcagaatgacttggttgagtactcaccagtcacag aaaagcatcttacggatggcatgacagtaagagaattatgcagtgctgccataaccatgagtgataacactgcggccaacttacttctg acaacgatcggaggaccgaaggagctaaccgcttttttgcacaacatgggggatcatgtaactcgccttgatcgttgggaaccggagct gaatgaagccataccaaacgacgagcgtgacaccacgatgcctgtagtaatggtaacaacgttgcgcaaactattaactggcgaacta cttactctagcttcccggcaacaattaatagactggatggaggcggataaagttgcaggaccacttctgcgctcggcccttccggctggc tggtttattgctgataaatctggagccggtgagcgtgggtctcgcggtatcattgcagcactggggccagatggtaagccctcccgtatc gtagttatctacacgacggggagtcaggcaactatggatgaacgaaatagacagatcgctgagataggtgcctcactgattaagcatt ggtaactgtcagaccaagtttactcatatatactttagattgatttaaaacttcattttaatttaaaaggatctaggtgaagatcctttttg ataatctcatgaccaaaatcccttaacgtgagttttcgttccactgagcgtcagaccccgtagaaaagatcaaaggatcttcttgagatc ctttttttctgcgcgtaatctgctgcttgcaaacaaaaaaaccaccgctaccagcggtggtttgtttgccggatcaagagctaccaactct ttttccgaaggtaactggcttcagcagagcgcagataccaaatactgtccttctagtgtagccgtagttaggccaccacttcaagaactc tgtagcaccgcctacatacctcgctctgctaatcctgttaccagtggctgctgccagtggcgataagtcgtgtcttaccgggttggactca agacgatagttaccggataaggcgcagcggtcgggctgaacggggggttcgtgcacacagcccagcttggagcgaacgacctacacc gaactgagatacctacagcgtgagctatgagaaagcgccacgcttcccgaagggagaaaggcggacaggtatccggtaagcggcag ggtcggaacaggagagcgcacgagggagcttccagggggaaacgcctggtatctttatagtcctgtcgggtttcgccacctctgacttg agcgtcgatttttgtgatgctcgtcaggggggcggagcctatggaaaaacgccagcaacgcggcctttttacggttcctggccttttgct gcggttttgctcacatgttcttcctgcgttatcccctgattctgtggataaccgtattaccgcctttgagtgagctgataccgctcgccgca gccgaacgaccgagcgcagcgagtcagtgagcgaggaagcggaagagcgcccaatacgcaaaccgcctctccccgcgcgttggccg attcattaatgcagctggcacgacaggtttcccgactggaaagcgggcagtgagcgcaacgcaattaatgtgagttagctcactcatta ggcaccccaggctttacactttatgcttccggctcgtatgttgtgtggaattgtgagcggataacaatttca
``` p1336// pAAV_mAlb5' HITI(kozak-ARSB) + Stuffer DNA + gRNA (SEQ ID NO: 20)

```
cacaggaaacagctatgaccatgattacgccagatttaattaaggctgcgcgctcgctcgctcactgaggccgcccgggcaaagcccg ggcgtcgggcgacctttggtcgcccggcctcagtgagcgagcgagcgcgcagagagggagtggccaactccatcactaggggttcctt gtagttaatgattaacccgccatgctacttatctacgtagccatgctctaggaagatcggaattcgcccttaaactagtaacggccgcca gtgtgctggaattcaggctgacctcgagtttcccatgattccttcatatttgcatatacgatacaaggctgttagagagataattggaatt aatttggactgtaaacacaaagatatagtacaaaatacgtgacgtagaaagtaataatttcttgggtagtttgcagttttaaaattatg ttttaaaatggactatcatatgcttaccgtaacttgaaagtatttcgatttcttggctttatatatcttGTGGAAAGGACGAAACAC CgacaagagtgagatcgcccattgttttagagctaGAAAtagcaagttaaaataaggctagtccgttatcaacttgaaaaagtggca ccgagtcggtgcTTTTTTgttttagagctagaaatagcaagctcgagcagcctgaattctgcagatatccatcacactggcggcttaa gctagcactagtaacggccgccagtgtgctggaattcgcccttacaagagtgagatcgcccatcgggactacaagaagctgtccttccc
```

-continued cgagggcttcaagtgggagcgcgtgattccccagcatgcctgctattgtcttcccaatcctcccccttgctgtcctgccccaccccacccc ccagaatagaatgacacctactcagacaatgcgatgcaatttcctcattttattaggaaaggacagtgggagtggcaccttccagggtc aaggaaggcacggggaggggcaaacaacagatggctggcaactagaaggcacagtcgaggcagatctactagaatcgataagctt gattcgagctacatccaagggccccacacccagtggccttgggatcacagcgggggtcctgtgcagggaagtacacggggactgagt gtttatggtagaactgtaggcgggacaggagctttgtgacgatgtgaggatattctctggacaggtcatgtctttcttcagggtcccgatc aatatcaaagagccagagggtcttggttggtgggtctgatgagggtatctcagaaacattgtattgagacggtggagggaaccagtaa ccacagcctgggtagcccgtgaggagtttccaatttccatgtctaattgcagcatggacagatgtgttaaaggctgaatattctggaaga gaagagtcatcctttgctggagccatgctgttcctgggacacggtgaagagtccacgaagttcgggtcaatattatgcagcagctcaatt ctgggggatgggcttccttcactgatggttttccacacgtcgaagccatccagaggctttgtgccattggtgtgtccctggccagcttca cgagtgttggcagccagtcagagatgtggatgagctcccggttcttcacgcccttctgcttcagcaaggggcttgccacaaagcccacc cctcggacgcctccttcccacaggctccattttcttcctcgaaggggccagttattaccccctgccaaagtctgccctccgttatctgtaga aaagatgaacaccgtgttgttccagagcccactgcttttttaaagctgcagtgacatttcctactgcttcatccataagggacaccattcct gcatagtgatgcctgttcttgtcttggataaagtcatatggcttcaagtattcctcagggacctgaaggggctcatgcacagactggaga gcaaggtagagaaacagaggcttctctggtggatggttagttatgagggctatagccttttggtgaatatgtttgttgaatacatattt tatatcctgttgcaacttcttcgccatctcgaaaatcaagagcacatcgtgtgacattcagagcgtcaattaatgtacagcgttcatggg aataataatcttcactacccaggagatatccaaagtaggtatcaaatcctcggcgggttggaaggcattcttccggtacattcccaggt gccattttccgaccatatgggtagtataacctgcttcttttaggagctggggcaggagttttttcatccagaggaacacagctgggctgac agggccagattatttggtgctgtaaacctgtacggatctggtagcggccagtgagcagctggctccgcgacggcgtgcacagcggctgc gtgtagtagttgtccaggagcaccccgccggccgccagcgcgtccaggtgcggcgtgcggatgcgggagccgtggaagccgacgtcgt tccagcctaggtcgtctgccagcaagaagaccaggtggggcggccggctggccccggcgcccgagcccggcggcgccaacaacagc agcagcagcagcggaggacgacggggaggagcagccgccgaggtccggggcctcggggcaagctcgccgcgccgcgcggaccca tggtggcttattatttattatttattaacaagagtgagatcgcccatcgGAAGGGCgaattctgcagatatccatcacactggcggcc tcgagttaagggcgaattcccgattaggatcttcctagagcatggctacgtagataagtagcatggcgggttaatcattaactacaagg aaccctagtgatggagttggccactccctctctgcgcgctcgctcgctcactgaggccgggcgaccaaaggtcgcccgacgcccgggc tttgcccggcggcctcagtgagcgagcgagcgcgcagccttaattaacctaattcactggccgtcgttttacaacgtcgtgactgggaa aaccctggcgttacccaacttaatcgccttgcagcacatccccctttcgccagctggcgtaatagcgaagaggcccgcaccgatcgccc ttcccaacagttgcgcagcctgaatggcgaatgggacgcgccctgtagcggcgcattaagcgcggcgggtgtggtggttacgcgcagc gtgaccgctacacttgccagcgccctagcgcccgctcctttcgctttcttcccttcctttctcgccacgttcgccggctttccccgtcaagct ctaaatcggggctccctttagggttccgatttagtgctttacggcacctcgacccaaaaaacttgattagggtgatggttcacgtagtg ggccatcgccccgatagacggtttttcgccctttgacgctggagttcacgttcctcaatagtggactcttgttccaaactggaacaacact caacccctatctcggtctattcttttgatttataagggattttttccgatttcggcctattggttaaaaaatgagctgatttaacaaaaatttaa cgcgaattttaacaaaatattaacgtttataatttcaggtggcatctttcggggaaatgtgcgcggaacccctatttgtttattttttctaaa tacattcaaatatgtatccgctcatgagacaataaccctgataaatgcttcaataatattgaaaaaggaagagtatgagtattcaacatt tccgtgtcgcccttattcccttttttgcggcattttgccttcctgtttttgctcacccagaaacgctggtgaaagtaaaagatgctgaagatc agttgggtgcacgagtgggttacatcgaactggatctcaatagtggtaagatccttgagagttttcgccccgaagaacgttttccaatga tgagcacttttaaagttctgctatgtggcgcggtattatcccgtattgacgccgggcaagagcaactcggtcgccgcatacactattctca gaatgacttggttgagtactcaccagtcacagaaaagcatcttacggatggcatgacagtaagagaattatgcagtgctgccataacc atgagtgataacactgcggccaacttacttctgacaacgatcggaggaccgaaggagctaaccgcttttttgcacaacatggggggatc atgtaactcgccttgatcgttgggaaccggagctgaatgaagccataccaaacgacgagcgtgacaccacgatgcctgtagtaatggt aacaacgttgcgcaaactattaactggcgaactacttactctagcttcccggcaacaattaatagactggatggaggcggataaagttg caggaccacttctgcgctcggcccttccggctggctggtttattgctgataaatctggagccggtgagcgtgggtctcgcggtatcattgc -continued agcactggggccagatggtaagccctcccgtatcgtagttatctacacgacggggagtcaggcaactatggatgaacgaaatagaca
gatcgctgagataggtgcctcactgattaagcattggtaactgtcagaccaagtttactcatatactttagattgatttaaaacttcatt
tttaatttaaaaggatctaggtgaagatcctttttgataatctcatgaccaaaatcccttaacgtgagttttcgttccactgagcgtcagac
cccgtagaaaagatcaaaggatcttcttgagatcctttttttctgcgcgtaatctgctgcttgcaaacaaaaaaaccaccgctaccagcg
gtggtttgtttgccggatcaagagctaccaactctttttccgaaggtaactggcttcagcagagcgcagataccaaatactgtccttctag
tgtagccgtagttaggccaccacttcaagaactctgtagcaccgcctacatacctcgctctgctaatcctgttaccagtggctgctgccag
tggcgataagtcgtgtcttaccgggttggactcaagacgatagttaccggataaggcgcagcggtcgggctgaacggggggttcgtgc
acacagcccagcttggagcgaacgacctacaccgaactgagatacctacagcgtgagctatgagaaagcgccacgcttcccgaaggg
agaaaggcggacaggtatccggtaagcggcagggtcggaacaggagagcgcacgagggagcttccaggggaaacgcctggtatct
ttatagtcctgtcgggtttcgccacctctgacttgagcgtcgatttttgtgatgctcgtcaggggggcggagcctatggaaaaacgccag
caacgcggccttttacggttcctggccttttgctgcggttttgctcacatgttctttcctgcgttatcccctgattctgtggataaccgtatt
accgcctttgagtgagctgataccgctcgccgcagccgaacgaccgagcgcagcgagtcagtgagcgaggaagcggaagagcgccc
aatacgcaaaccgcctctccccgcgcgttggccgattcattaatgcagctggcacgacaggtttcccgactggaaagcgggcagtgag
cgcaacgcaattaatgtgagttagctcactcattaggcaccccaggctttacactttatgcttccggctcgtatgttgtgtggaattgtga
gcggataacaatttca p1240// pAAV2.1_mAlb5' HITI (kozak-ARSB) NEW + Scramble (SEQ ID NO: 21)
atgaccatgattacgccagatttaattaaggctgcgcgctcgctcgctcactgaggccgcccgggcaaagcccgggcgtcgggcgacct
ttggtcgcccggcctcagtgagcgagcgagcgcgcagagagggagtggccaactccatcactaggggttccttgtagttaatgattaac
ccgccatgctacttatctacgtagccatgctctaggaagatcggaattcgcccttaaactagtaacggccgccagtgtgctggaattcag
gctgacctcgagtttcccatgattccttcatatttgcatatacgatacaaggctgttagagagataattggaattaatttggactgtaaac
acaaagatattagtacaaaatacgtgacgtagaaagtaataatttcttgggtagtttgcagttttaaaattatgttttaaaatggactatc
atatgcttaccgtaacttgaaagtatttcgatttcttggcttatatatcttGTGGAAAGGACGAAACACCgGACTCGCGCG
AGTCGAGGAGtgttttagagctaGAAAtagcaagttaaaataaggctagtccgttatcaacttgaaaaagtggcaccgagtcgg
tgcTTTTTTgttttagagctagaaatagcaagctcgagcagcctgaattctgcagatatccatcacactggcggcttaagctagcact
agtaacggccgccagtgtgctggaattcgcccttacaagagtgagatcgcccatcggtcccagcatgcctgctattgtcttcccaatcc
tccccttgctgtcctgccccaccccaccccccagaatagaatgacacctactcagacaatgcgatgcaatttcctcattttattaggaaa
ggacagtgggagtggcaccttccagggtcaaggaaggcacggggagggcaaacaacagatggctggcaactagaaggcacagt
cgaggcagatctactagaatcgataagcttgattcgagctacatccaagggccccacaccccagtggccttgggatcacagcggggt
cctgtgcagggaagtacacggggactgagtgtttatggtagaactgtaggcgggacaggagctttgtgacgatgtgaggatattctctg
gacaggtcatgtctttcttcagggtcccgatcaatatcaaagagccagagggtcttggttggtgggtctgatgagggtatctcagaaaca
ttgtattgagacggtggagggaaccagtaaccacagcctgggtagcccgtgaggagtttccaatttccatgtctaattgcagcatggac
agatgtgttaaaggctgaatattctggaagagaagagtcatcctttgctggagccatgctgttcctgggacacggtgaagagtccacga
agttcgggtcaatattatgcagcagctcaattctggggatgggcttccttcactgatggttttccacacgtcgaagccatccagaggctt
tgtgccattggtgtgtccctggccagcttcacgagtgttggcagccagtcagagatgtggatgagctcccggttcttcacgcccttctgc
ttcagcaaggggcttgcccacaaagcccacccctcggacgcctccttcccacaggctccattttcttcctcgaaggggccagttattccc
cctgccaaagtctgccctccgttatctgtagaaaagatgaacaccgtgttgttccagagcccactgcttttaaagctgcagtgacatttc
ctactgcttcatccataagggacaccattcctgcatagtgatgcctgttcttgtcttggataaagtcatatggcttcaagtattcctcaggg
acctgaaggggctcatgcacagactggagagcaaggtagagaaacagaggcttctctggtggatggttagttatgagggctatagccc
ttttggtgaatatgtttgttgaatacatattttatatcctgttgcaacttcttcgccatctcgaaaatcaagagcacatcgtgtgacattca
gagcgtcaattaatgtacagcgttcatgggaataataatcttcactacccaggagatatccaaagtaggtatcaaatcctcggcgggtt -continued

```
ggaaggcattctttccggtacattcccaggtgccattttccgaccatatgggtagtataacctgcttcttttaggagctggggcaggagtt
tttcatccagaggaacacagctgggctgacagggccagattatttggtgctgtaaacctgtacggatctggtagcggccagtgagcagc
tggctccgcgacggcgtgcacagcggctgcgtgtagtagttgtccaggagcaccccgccggccgccagcgcgtccaggtgcggcgtgc
ggatgcgggagccgtggaagccgacgtcgttccagcctaggtcgtctgccagcaagaagaccaggtggggcggccggctggccccgg
cgcccgagcccggcggcgccaacaacagcagcagcagcagcgggaggacgacggggaggagcagccgccgaggtccggggcctcg
gggcaagctcgccgcgccgcgcggacccatggtggcttattatttattatttattaacaagagtgagatcgcccatcgGAAGGGCga
attctgcagatatccatcacactggcggcctcgagttaagggcgaattcccgattaggatcttcctagagcatggctacgtagataagta
gcatggcgggttaatcattaactacaaggaaccccctagtgatggagttggccactccctctctgcgcgctcgctcgctcactgaggccgg
gcgaccaaaggtcgcccgacgcccgggctttgcccgggcggcctcagtgagcgagcgagcgcgcagccttaattaacctaattcactg
gccgtcgttttacaacgtcgtgactgggaaaaccctggcgttacccaacttaatcgccttgcagcacatcccctttcgccagctggcgt
aatagcgaagaggcccgcaccgatcgcccttcccaacagttgcgcagcctgaatggcgaatgggacgcgccctgtagcggcgcattaa
gcgcggcgggtgtggtggttacgcgcagcgtgaccgctacacttgccagcgccctagcgcccgctcctttcgctttcttcccttcctttctc
gccacgttcgccggctttccccgtcaagctctaaatcgggggctcccttttagggttccgatttagtgctttacggcacctcgaccccaaaa
aacttgattagggtgatggttcacgtagtgggccatcgccccgatagacggtttttcgccctttgacgctggagttcacgttcctcaatag
tggactcttgttccaaactggaacaacactcaaccctatctcggtctattcttttgatttataagggattttccgatttcggcctattggtt
aaaaaatgagctgatttaacaaaaatttaacgcgaattttaacaaaatattaacgtttataatttcaggtggcatctttcggggaaatgt
gcgcggaacccctatttgtttatttttctaaatacattcaaatatgtatccgctcatgagacaataaccctgataaatgcttcaataatatt
gaaaaaggaagagtatgagtattcaacatttccgtgtcgcccttattcccttttttgcggcattttgccttcctgtttttgctcacccagaaa
cgctggtgaaagtaaaagatgctgaagatcagttgggtgcacgagtgggttacatcgaactggatctcaatagtggtaagatccttgag
agttttcgccccgaagaacgttttccaatgatgagcacttttaaagttctgctatgtggcgcggtattatcccgtattgacgccgggcaag
agcaactcggtcgccgcatacactattctcagaatgacttggttgagtactcaccagtcacagaaaagcatcttacggatggcatgaca
gtaagagaattatgcagtgctgccataaccatgagtgataacactgcggccaacttacttctgacaacgatcggaggaccgaaggagc
taaccgcttttttgcacaacatgggggatcatgtaactcgccttgatcgttgggaaccggagctgaatgaagccataccaaacgacgag
cgtgacaccacgatgcctgtagtaatggtaacaacgttgcgcaaactattaactggcgaactacttactctagcttcccggcaacaatta
atagactggatggaggcggataaagttgcaggaccacttctgcgctcggcccttccggctggctggtttattgctgataaatctggagcc
ggtgagcgtgggtctcgcggtatcattgcagcactggggccagatggtaagccctcccgtatcgtagttatctacacgacggggagtca
ggcaactatggatgaacgaaatagacagatcgctgagataggtgcctcactgattaagcattggtaactgtcagaccaagtttactcat
atatactttagattgatttaaaacttcattttttaatttaaaaggatctaggtgaagatcctttttgataatctcatgaccaaaatcccttaac
gtgagttttcgttccactgagcgtcagaccccgtagaaaagatcaaaggatcttcttgagatcctttttttctgcgcgtaatctgctgcttg
caaacaaaaaaaccaccgctaccagcggtggtttgtttgccggatcaagagctaccaactctttttccgaaggtaactggcttcagcag
agcgcagataccaaatactgtccttctagtgtagccgtagttaggccaccacttcaagaactctgtagcaccgcctacatacctcgctct
gctaatcctgttaccagtggctgctgccagtggcgataagtcgtgtcttaccgggttggactcaagacgatagttaccggataaggcgc
agcggtcgggctgaacggggggttcgtgcacacagcccagcttggagcgaacgacctacaccgaactgagatacctacagcgtgagc
tatgagaaagcgccacgcttcccgaagggagaaaggcggacaggtatccggtaagcggcagggtcggaacaggagagcgcacgag
ggagcttccaggggggaaacgcctggtatctttatagtcctgtcgggtttcgccacctctgacttgagcgtcgatttttgtgatgctcgtcag
gggggcggagcctatggaaaaacgccagcaacgcggcctttttacggttcctggccttttgctgcggttttgctcacatgttctttcctgc
gttatcccctgattctgtggataaccgtattaccgcctttgagtgagctgataccgctcgccgcagccgaacgaccgagcgcagcgagtc
```

-continued agtgagcgaggaagcggaagagcgcccaatacgcaaaccgcctctccccgcgcgttggccgattcattaatgcagctggcacgacag gtttcccgactggaaagcgggcagtgagcgcaacgcaattaatgtgagttagctcactcattaggcaccccaggctttacactttatgct tccggctcgtatgttgtgtggaattgtgagcggataacaatttcacacaggaaacagct p1239//pAAV2.1_mAlb5' HITI (kozak-ARSB) NEW + gRNA (SEQ ID NO: 22)

gatttaattaaggctgcgcgctcgctcgctcactgaggccgcccgggcaaagcccgggcgtcgggcgacctttggtcgcccggcctcag tgagcgagcgagcgcgcagagagggagtggccaactccatcactaggggttccttgtagttaatgattaacccgccatgctacttatct acgtagccatgctctaggaagatcggaattcgcccttaaactagtaacggccgccagtgtgctggaattcaggctgacctcgagtttccc atgattccttcatatttgcatatacgatacaaggctgttagagagataattggaattaatttggactgtaaacacaaagatattagtaca aaatacgtgacgtagaaagtaataatttcttgggtagtttgcagttttaaaattatgttttaaaatggactatcatatgcttaccgtaactt gaaagtatttcgatttcttggctttatatatcttGTGGAAAGGACGAAACACCgacaagagtgagatcgcccattgttttagagc taGAAAtagcaagttaaaataaggctagtccgttatcaacttgaaaaagtggcaccgagtcggtgcTTTTTTgttttagagctagaa atagcaagctcgagcagcctgaattctgcagatatccatcacactggcggcttaagctagcactagtaacggccgccagtgtgctggaa ttcgcccttacaagagtgagatcgcccatcggtccccagcatgcctgctattgtcttcccaatcctccccttgctgtcctgccccacccca cccccagaatagaatgacacctactcagacaatgcgatgcaatttcctcattttattaggaaaggacagtgggagtggcaccttccag ggtcaaggaaggcacggggagggcaaacaacagatggctggcaactagaaggcacagtcgaggcagatctactagaatcgata agcttgattcgagctacatccaagggcccacaccccagtggccttgggatcacagcgggggtcctgtgcagggaagtacacggggac tgagtgtttatggtagaactgtaggcgggacaggagctttgtgacgatgtgaggatattctctggacaggtcatgtctttcttcagggtcc cgatcaatatcaaagagccagagggtcttggttggtgggtctgatgagggtatctcagaaacattgtattgagacggtggagggaacc agtaaccacagcctgggtagcccgtgaggagtttccaatttccatgtctaattgcagcatggacagatgtgttaaaggctgaatattctg gaagagaagagtcatccttgctggagccatgctgttcctgggacaggtgaagagtccacgaagttcgggtcaatattatgcagcagc tcaattctggggatgggcttccttcactgatggttttccacacgtcgaagccatccagaggctttgtgccattggtgtgtcccctggcca gcttcacgagtgttggcagccagtcagagatgtggatgagctcccggttcttcacgcccttctgcttcagcaaggggcttgccacaaagc ccaccccctcggacgcctccttcccacaggctccattttcttcctcgaaggggccagttattacccctgccaaagtctgcctccgttatct gtagaaaagatgaacaccgtgttgttccagagcccactgcttttaaagctgcagtgacatttcctactgcttcatccataagggacacc attcctgcatagtgatgcctgttcttgtcttggataaagtcatatgcttcaagtattcctcagggacctgaaggggctcatgcacagact ggagagcaaggtagagaaacagaggcttctctggtggatggttagttatgagggctatagcccttttggtgaatatgtttgttgaataca tatttttatatcctgttgcaacttcttcgccatctcgaaaatcaagagcacatcgtgtgacattcagagcgtcaattaatgtacagcgttca tgggaataataatcttcactacccaggagatatccaaagtaggtatcaaatcctcgggggttggaaggcattctttccggtacattccc aggtgccattttccgaccatatgggtagtataacctgcttcttttaggagctggggcaggagttttcatccagaggaacacagctgggc tgacagggccagattatttggtgctgtaaacctgtacggatctggtagcggccagtgagcagctggctccgcgacggcgtgcacagcg gctgcgtgtagtagttgtccaggagcaccccgccggccgccagcgcgtccaggtgcggcgtgcggatgcgggagccgtggaagccga cgtcgttccagcctaggtcgtctgccagcaagaagaccaggtggggcggccggctggccccggcgcccgagcccggcggcgccaaca acagcagcagcagcggaggacgacgggaggagcagccgccgaggtccggggcctcggggcaagctcgccgcgccgcgcgg acccatggtggcttattatttattatttattaacaagagtgagatcgcccatcgGAAGGGCgaattctgcagatatccatcacactgg cggcctcgagttaagggcgaattcccgattaggatcttcctagagcatggctacgtagataagtagcatggcgggttaatcattaacta caaggaaccctagtgatggagttggccactccctctctgcgcgctcgctcgctcactgaggccgggcgaccaaaggtcgcccgacgcc cgggctttgcccggcggcctcagtgagcgagcgagcgcgcagccttaattaacctaattcactggccgtcgttttacaacgtcgtgact gggaaaaccctggcgttacccaacttaatcgccttgcagcacatccccctttcgccagctggcgtaatagcgaagaggcccgcaccgat cgcccttcccaacagttgcgcagcctgaatgcgaatgggacgcgccctgtagcggcgcattaagcgcggcgggtgtggtggttacgc gcagcgtgaccgctacacttgccagcgccctagcgcccgctcctttcgctttcttcccttcctttctcgccacgttcgccggctttccccgtc

```
aagctctaaatcggggctccctttagggttccgatttagtgctttacggcacctcgaccccaaaaaacttgattagggtgatggttcac gtagtgggccatcgccccgatagacggttttttcgcccttttgacgctggagttcacgttcctcaatagtggactcttgttccaaactggaac aacactcaaccctatctcggtctattcttttgatttataagggattttttccgatttcggcctattggttaaaaaatgagctgatttaacaaa aatttaacgcgaattttaacaaaatattaacgtttataatttcaggtggcatctttcggggaaatgtgcgcggaaccccctatttgtttattt ttctaaatacattcaaatatgtatccgctcatgagacaataaaccctgataaatgcttcaataatattgaaaaaggaagagtatgagtatt caacatttccgtgtcgcccttattcccttttttgcggcattttgccttcctgtttttgctcacccagaaacgctggtgaaagtaaaagatgct gaagatcagttgggtgcacgagtgggttacatcgaactggatctcaatagtggtaagatccttgagagttttcgccccgaagaacgttttt ccaatgatgagcacttttaaagttctgctatgtggcgcggtattatcccgtattgacgccgggcaagagcaactcggtcgccgcatacac tattctcagaatgacttggttgagtactcaccagtcacagaaaagcatcttacggatggcatgacagtaagagaattatgcagtgctgc cataaccatgagtgataacactgcggccaacttacttctgacaacgatcggaggaccgaaggagctaaccgcttttttgcacaacatgg gggatcatgtaactcgccttgatcgttgggaaccggagctgaatgaagccataccaaacgacgagcgtgacaccacgatgcctgtagt aatggtaacaacgttgcgcaaactattaactggcgaactacttactctagcttcccggcaacaattaatagactggatggaggcggata aagttgcaggaccacttctgcgctcggcccttccggctggctggtttattgctgataaatctggagccggtgagcgtgggtctcgcggtat cattgcagcactggggccagatggtaagccccccgtatcgtagttatctacacgacggggagtcaggcaactatggatgaacgaaat agacagatcgctgagataggtgcctcactgattaagcattggtaactgtcagaccaagtttactcatatactttagattgatttaaaa cttcattttttaatttaaaaggatctaggtgaagatcctttttgataatctcatgaccaaaatcccttaacgtgagttttcgttccactgagc gtcagaccccgtagaaaagatcaaaggatcttcttgagatccttttttttctgcgcgtaatctgctgcttgcaaacaaaaaaaccaccgct accagcggtggtttgtttgccggatcaagagctaccaactctttttccgaaggtaactggcttcagcagagcgcagataccaaatactgt ccttctagtgtagccgtagttaggccaccacttcaagaactctgtagcaccgcctacatacctcgctctgctaatcctgttaccagtggct gctgccagtggcgataagtcgtgtcttaccgggttggactcaagacgatagttaccggataaggcgcagcggtcgggctgaacggggg gttcgtgcacacagcccagcttggagcgaacgacctacaccgaactgagatacctacagcgtgagctatgagaaagcgccacgcttcc cgaagggagaaaggcggacaggtatccggtaagcggcagggtcggaacaggagagcgcacgagggagcttccaggggaaacgc ctggtatctttatagtcctgtcgggtttcgccacctctgacttgagcgtcgatttttgtgatgctcgtcaggggggcggagcctatggaaa aacgccagcaacgcggcctttttacggttcctggccttttgctggccttttgctcacatgttctttcctgcgttatcccctgattctgtggata accgtattaccgcctttgagtgagctgataccgctcgccgcagccgaacgaccgagcgcagcgagtcagtgagcgaggaagcggaag agcgcccaatacgcaaaccgcctctccccgcgcgttggccgattcattaatgcagctggcacgacaggtttcccgactggaaagcggg cagtgagcgcaacgcaattaatgtgagttagctcactcattaggcaccccaggctttacactttatgcttccggctcgtatgttgtgtgga attgtgagcggataacaatttcacacaggaaacagctatgaccatgattacgcca
```

Plasmids of the Invention:

TABLE 1

Plasmids of the invention

| Plasmid | Gene of Interest |
| --- | --- |
| P939// pSpCas9(BB)-2A-GFP + gRNAScramble | GFP |
| p972// pSpCas9(BB)-2A-GFP + gRNA hRHO HITI | hRHO |
| p995/ SpCas9-2A-GFP-HITI mRHO | GFP |
| p1070// pSpCas9(BB)-2A-GFP-gRNAalbumin | GFP |
| p946// pAAV-IRBP-SpCas9 | Cas9 |
| p1139_pAAV2.1._HLP_SpCas9(HA)_spA | Cas9 |
| p1135// pAAV2.1 mRHOgRNA-mRHO HITI (kozak-dsRED)_hVmd2-EGFP | mRHO |
| p1116// pAAV_Scramble_mRHO HITI(kozak-dsRED)_hVmd2-EGFP | mRHO |
| p1048// pAAV2.1-Scramble-mRHO HITI(IRESdsRED)-Vmd2-EGFP | mRHO |
| p1047// pAAV2.1-mRHOgRNA-mRHOHITI(IRESdsRED)-hVDM2-EGFP | mRHO |

TABLE 1-continued

Plasmids of the invention

| Plasmid | Gene of Interest |
| --- | --- |
| p1138// pAAV-mRHO HITI (kozak-hRHO-T2A-dsRED) + mRHO gRNA | mRHO |
| p1118// pAAV_Scramble_sRHO HITI(kozak-dsRED)_hVmd2-EGFP | mRHO |
| p1126// pAAV_sRHOgRNA_sRHO HITI(kozak-dsRED)_hVmd2-EGFP | mRHO |
| P1222// pAAV2.1_sRHOgRNA + sRHO HITI (IRES-dsRED)_Vmd2_GFP | mRHO |
| P1227// pAAV2.1_sRHOgRNA + sRHO HITI (IRES-dsRED)_Vmd2_GFP | mRHO |
| p1160//pAAV_Alb5'HITI(kozak-dsRED) + gRNA mAlb 5' | Alb |
| p1161//pAAV_Alb5'HITI(kozak-dsRED) + scramble | Alb |
| p1336// pAAV_mAlb5' HITI(kozak-ARSB) + Stuffer DNA + gRNA | Alb-ARSB |

TABLE 1-continued

Plasmids of the invention

| Plasmid | Gene of Interest |
|---|---|
| p1240// pAAV2.1_mAlb5' HITI (kozak-ARSB) NEW + Scramble | Alb-ARSB |
| p1239//pAAV2.1_mAlb5' HITI (kozak-ARSB) NEW + gRNA | Alb-ARSB |

Definitions

Exogenous DNA Sequences

Exogenous DNA sequences mentioned above comprise a fragment of DNA to be incorporated into genomic DNA of a target genome. In some embodiments, the exogenous DNA comprises at least a portion of a gene. The exogenous DNA may comprise a coding sequence e.g. a cDNA related to a wild type gene or to a "codon optimized" sequence for the factor that has to be expressed. In some embodiments, the exogenous DNA comprises at least an exon of a gene and/or at least one intron of a gene. In some embodiments, the exogenous DNA comprises an enhancer element or a promoter element of a gene. In some embodiments, the exogenous DNA comprises a discontinuous sequence of a gene comprising a 5' portion of the gene fused to the 3' portion of the gene. In some embodiments, the exogenous DNA comprises a wild type gene sequence. In some embodiments, the exogenous DNA comprises a mutated gene sequence. In some embodiments, the exogenous DNA comprises a wild type gene sequence. In some embodiments, the exogenous DNA sequence comprises a reporter gene. In some embodiments, the reporter gene is selected from at least one of a green fluorescent protein (GFP), a red fluorescent protein (RFP), a luciferase, a β-galactosidase, and a β-glucuronidase. In some embodiments, the exogenous DNA sequence comprises a gene transcription regulatory element which may e.g. comprise a promoter sequence or an enhancer sequence. In some embodiments, the exogenous DNA sequence comprises one or more exons or fragments thereof. In some embodiments, the exogenous DNA sequence comprises one or more introns or fragments thereof. In some embodiments, the exogenous DNA sequence comprises at least a portion of a 3' untranslated region or a 5' untranslated region. In some embodiments, the exogenous DNA sequence comprises an artificial DNA sequence. In some embodiments, the exogenous DNA sequence comprises a nuclear localization sequence and/or a nuclear export sequence. An exogenous DNA sequence, in some embodiments, comprises a segment of nucleic acid to be integrated at a target genomic locus. The exogenous DNA sequence, in some embodiments, comprises one or more polynucleotides of interest. The exogenous DNA sequence in some embodiments comprises one or more expression cassettes. Such an expression cassette, in some embodiments, comprises an exogenous DNA sequence of interest, a polynucleotide encoding a selection marker and/or a reporter gene, and regulatory components that influence expression. The exogenous DNA sequence, in some embodiments, comprises a genomic nucleic acid. The genomic nucleic acid is derived from an animal, a mouse, a human, a non-human, a rodent, a non-human, a rat, a hamster, a rabbit, a pig, a bovine, a deer, a sheep, a goat, a chicken, a cat, a dog, a ferret, a primate (e.g., marmoset, rhesus monkey), domesticated mammal or an agricultural mammal, an avian, a bacterium, an archaeon, a virus, or any other organism of interest or a combination thereof. Exogenous DNA sequences of any suitable size are integrated into a target genome. In some embodiments, the exogenous DNA sequence integrated into a genome is less than 3, about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 kilobases (kb) in length. In some embodiments, the exogenous DNA sequence integrated into a genome is at least about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 (kb) in length.

Targeting Sequences

In some embodiments, the targeting construct (which comprises the donor nucleic acid flanked at 5' and 3' by the inverted targeting sequences) comprises at least two targeting sequences. Targeting sequences herein are nucleic acid sequences recognized and cleaved by a nuclease. In some embodiments, the targeting sequence is about 9 to about 12 nucleotides in length, from about 12 to about 18 nucleotides in length, from about 18 to about 21 nucleotides in length, from about 21 to about 40 nucleotides in length, from about 40 to about 80 nucleotides in length, or any combination of subranges (e.g., 9-18, 9-21, 9-40, and 9-80 nucleotides). In some embodiments, the targeting sequence comprises a nuclease binding site. In some embodiments the targeting sequence comprises a nick/cleavage site. In some embodiments, the targeting sequence comprises a protospacer adjacent motif (PAM) sequence. In some embodiments, the target nucleic acid sequence (e.g., protospacer) is 20 nucleotides. In some embodiments, the target nucleic acid is less than 20 nucleotides. In some embodiments, the target nucleic acid is at least 5, 10, 15, 16, 17, 18, 19, 20, 21, 22, 23, 24, 25, 30 or more nucleotides. The target nucleic acid, in some embodiments, is at most 5, 10, 15, 16, 17, 18, 19, 20, 21, 22, 23, 24, 25, 30 or more nucleotides. In some embodiments, the target nucleic acid sequence is 16, 17, 18, 19, 20, 21, 22, or 23 bases immediately 5' of the first nucleotide of the PAM. In some embodiments, the target nucleic acid sequence is 16, 17, 18, 19, 20, 21, 22, or 23 bases immediately 3' of the last nucleotide of the PAM. In some embodiments, the target nucleic acid sequence is 20 bases immediately 5' of the first nucleotide of the PAM. In some embodiments, the target nucleic acid sequence is 20 bases immediately 3' of the last nucleotide of the PAM. In some embodiments, the target nucleic acid sequence is 5' or 3' of the PAM. A targeting sequence, in some embodiments includes nucleic acid sequences present in a target nucleic acid to which a nucleic acid-targeting segment of a complementary strand nucleic acid binds. For example, targeting sequences, in some embodiments, include sequences to which a complementary strand nucleic acid is designed to have base pairing. A targeting sequence in some embodiments comprises any polynucleotide, which is located, for example, in the nucleus or cytoplasm of a cell or within an organelle of a cell, such as a mitochondrion or chloroplast. Targeting sequences include cleavage sites for nucleases. A targeting sequence, in some embodiments, is adjacent to cleavage sites for nucleases. The nuclease cleaves the nucleic acid, in some embodiments, at a site within or outside of the nucleic acid sequence present in the target nucleic acid to which the nucleic acid-targeting sequence of the complementary strand binds. The cleavage site, in some embodiments, includes the position of a nucleic acid at which a nuclease produces a single-strand break or a double-strand break. For example, formation of a nuclease complex comprising a complementary strand nucleic acid hybridized to a protease recognition sequence and complexed with a protease results in cleavage of one or both strands in or near (e.g., within 1, 2, 3, 4, 5, 6, 7, 8, 9, 10, 19, 20, 23, 50, or more base pairs from) the nucleic acid sequence present in a target nucleic acid to which a spacer region of a complementary strand nucleic acid binds. The cleavage site, in some embodiments, is on only one strand or on both strands of a nucleic acid. In some embodiments, cleavage sites are at the same position on both strands of the nucleic acid (producing blunt ends) or are at different sites on each strand (producing staggered ends). Staggered ends, in some embodiments, are 5' or 3' overhang sticky-ends. Staggered ends, in some embodiments, are produced by sticky-end producing nucleases (e.g., Cpf1). In some embodiments, staggered ends are produced, for example, by using two nucleases, each of which produces a single-strand break at a different cleavage site on each strand, thereby producing a double-strand break. For example, a first nickase creates a single-strand break on the first strand of double-stranded DNA (dsDNA), and a second nickase creates a single-strand break on the second strand of dsDNA such that overhanging sequences are created. In some cases, the nuclease recognition sequence of the nickase on the first strand is separated from the nuclease recognition sequence of the nickase on the second strand by at least 2, 3, 4, 5, 6, 7, 8, 9, 10, 15, 20, 25, 30, 40, 50, 75, 100, 250, 500, or 1000 base pairs. Site-specific cleavage of a target nucleic acid by a nuclease, in some embodiments, occurs at locations determined by base-pairing complementarity between the complementary strand nucleic acid and the target nucleic acid. Site-specific cleavage of a target nucleic acid by a nuclease protein, in some embodiments, occurs at locations determined by a short motif, called the protospacer adjacent motif (PAM), in the target nucleic acid. For example, the PAM flanks the nuclease recognition sequence at the 3' end of the recognition sequence. For example, the cleavage site of the nuclease, in some embodiments, is about 1 to about 25, or about 2 to about 5, or about 19 to about 23 base pairs (e.g., 3 base pairs) upstream or downstream of the PAM sequence. In some embodiments, the cleavage site of the nuclease is 3 base pairs upstream of the PAM sequence. In some embodiments, the cleavage site of the nuclease is 19 bases on the (+) strand and 23 base on the (−) strand, producing a 5' overhang 5 nucleotides (nt) in length. In some cases, the cleavage produces blunt ends. In some cases, the cleavage produces staggered or sticky ends with 5' overhangs. In some cases, the cleavage produces staggered or sticky ends with 3' overhangs. Orthologs of various nuclease proteins utilize different PAM sequences. For example different Cas proteins, in some embodiments, recognize different PAM sequences. For example, in S. pyogenes, the PAM is a sequence in the target nucleic acid that comprises the sequence 5'-XRR-3', where R is either A or G, where X is any nucleotide and X is immediately 3' of the target nucleic acid sequence targeted by the spacer sequence. The PAM sequence of S. pyogenes Cas9 (SpyCas9) is 5'-XGG-3', where X is any DNA nucleotide and is immediately 3' of the nuclease recognition sequence of the non-complementary strand of the target DNA. The PAM of Cpf1 is 5'-TTX-3', where X is any DNA nucleotide and is immediately 5' of the nuclease recognition sequence. Preferably, The Cas9/sgRNA complex introduces DSBs 3 base pairs upstream of the PAM sequence in the genomic target sequence, resulting in two blunt ends. The exact same Cas9/sgRNA target sequence is loaded onto the donor DNA in the reverse direction. Targeted genomic loci, as well as the donor DNA, are cleaved by Cas9/gRNA and the linearized donor DNAs are integrated into target sites via the NHEJ DSB repair pathway. If donor DNA is integrated in the correct orientation, junction sequences are protected from further cleavage by Cas9/gRNA. If donor DNA integrates in the reverse orientation, Cas9/gRNA will excise the integrated donor DNA due to the presence of intact Cas9/gRNA target sites.

Complementary Strand Nucleic Acids

A complementary strand nucleic acid, for example, a complementary strand oligonucleotide or a complementary strand RNA, refers to a nucleic acid that hybridizes to another nucleic acid, for example, the target nucleic acid in genome of a cell. A complementary strand nucleic acid may be e.g. RNA or DNA. A complementary strand nucleic acid, in some embodiments, comprises a nucleotide analog and/or a modified nucleotide. The complementary strand nucleic acid, in some embodiments, is programmed or designed to bind to a sequence of nucleic acid site-specifically. A complementary strand nucleic acid, in some embodiments, comprises one or more modifications to provide the nucleic acid with a new or enhanced feature. In some embodiments, a complementary strand nucleic acid comprises a nucleic acid affinity tag and/or synthetic nucleotide, synthetic nucleotide analog, nucleotide derivatives, and/or modified nucleotides. The complementary strand nucleic acid, in some embodiments, comprises a nucleotide sequence (e.g., a spacer), for example, at or near the 5' end or 3' end, that hybridizes to a sequence in a target nucleic acid. In some embodiments, the spacer of a complementary strand nucleic acid interacts with a target nucleic acid in a sequence-specific manner via hybridization (i.e., base pairing). In some embodiments, the spacer sequence hybridizes to a target nucleic acid (e.g., protospacer sequence) that is located 5' or 3' of protospacer adjacent motif (PAM). In some embodiments, a complementary strand nucleic acid comprises two separate nucleic acid molecules, which is referred to as a double complementary strand nucleic acid. In some embodiments, a complementary strand nucleic acid comprises a single nucleic acid molecule, which is referred to as a single complementary strand nucleic acid. In some embodiments, the complementary strand nucleic acid is a single complementary strand nucleic acid comprising a crRNA. In some embodiments, the complementary strand nucleic acid is a single complementary strand nucleic acid comprising a fused construct. The nucleic acid-targeting region of a complementary strand nucleic acid, in some embodiments, comprises a nucleotide sequence that is complementary to a sequence in a target nucleic acid. The nucleic acid-targeting region, in some embodiments, comprises the spacer region. The nucleotide sequence of a spacer region varies and determines the location within the target nucleic acid with which the complementary strand nucleic acid interacts. The spacer region of a complementary strand nucleic acid, in some embodiments, is modified to hybridize to any desired sequence within a target nucleic acid. Complementarity is alternatively perfect or substantial/sufficient. Perfect complementarity between two nucleic acids means that the two nucleic acids form a duplex in which every base in the duplex is bonded to a complementary base by Watson-Crick pairing. Substantial or sufficient complementarity means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. In some embodiments, the nucleic acid-targeting region of a complementary strand nucleic acid (e.g., spacer region) is between 18 to 72 nucleotides in length. The nucleic acid-targeting region of a complementary strand nucleic acid (e.g., spacer region) has a length of from about 12 nucleotides to about 100 nucleotides. For example, the nucleic acid-targeting region of a complementary strand nucleic acid (e.g., spacer region) has a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, from about 12 nt to about 19 nt, from about 12 nt to about 18 nt, from about 12 nt to about 17 nt, from about 12 nt to about 16 nt, or from about 12 nt to about 15 nt. Alternatively, the DNA-targeting segment has a length of from about 18 nt to about 20 nt, from about 18 nt to about 25 nt, from about 18 nt to about 30 nt, from about 18 nt to about 35 nt, from about 18 nt to about 40 nt, from about 18 nt to about 45 nt, from about 18 nt to about 50 nt, from about 18 nt to about 60 nt, from about 18 nt to about 70 nt, from about 18 nt to about 80 nt, from about 18 nt to about 90 nt, from about 18 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

In some embodiments, the nucleic acid-targeting region of a complementary strand nucleic acid (e.g., spacer region) is 20 nucleotides in length. In some embodiments, the nucleic acid-targeting region of a complementary strand nucleic acid (e.g., spacer region) is 19 nucleotides in length. In some embodiments, the nucleic acid-targeting region of a complementary strand nucleic acid (e.g., spacer region) is 18 nucleotides in length. In some embodiments, the nucleic acid-targeting region of a complementary strand nucleic acid (e.g., spacer region) is 17 nucleotides in length. In some embodiments, the nucleic acid-targeting region of a complementary strand nucleic acid (e.g., spacer region) is 16 nucleotides in length. In some embodiments, the nucleic acid-targeting region of a complementary strand nucleic acid (e.g., spacer region) is 21 nucleotides in length. In some embodiments, the nucleic acid-targeting region of a complementary strand nucleic acid (e.g., spacer region) is 22 nucleotides in length. A protospacer sequence, in some embodiments, is identified by identifying a PAM within a region of interest and selecting a region of a desired size upstream or downstream of the PAM as the protospacer. A corresponding spacer sequence is designed by determining the complementary sequence of the protospacer region. A spacer sequence, in some embodiments, is identified using a computer program (e.g., machine readable code). The computer program, in some embodiments, uses variables such as predicted melting temperature, secondary structure formation, and predicted annealing temperature, sequence identity, genomic context, chromatin accessibility, % GC, frequency of genomic occurrence, methylation status, presence of S Ps, and the like. The percent complementarity between the nucleic acid-targeting sequence (e.g., spacer sequence) and the nuclease recognition sequence within the target nucleic acid (e.g., protospacer), in some embodiments, is at least 60%, at least 70%, at least 75%, at least 80%, at least 85%, at least 90%, at least 95%, at least 97%, at least 98%, at least 99%, or 100%. The percent complementarity between the nucleic acid-targeting sequence and the nuclease recognition sequence within the target nucleic acid, in some embodiments, is at least 60% over about 20 contiguous nucleotides.

In some embodiments, complementary strand nucleic acids include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); or a modification or sequence that provides a binding site for proteins (e.g., proteins that act on DNA, including transcriptional activators, transcriptional repressors, DNA methyl transferases, DNA demethylases, histone acetyltransferases, histone deacetylases, and combinations thereof). Complementary strand nucleic acids are provided in any form, e.g. in the form of RNA, either as two molecules (e.g., separate crRNA and tracrRNA) or as one molecule (e.g., sgRNA). In some embodiments, the complementary strand nucleic acid is provided in the form of a complex with a nuclease protein. Alternatively, the complementary strand nucleic acid is also provided in the form of DNA encoding the RNA. The DNA encoding the complementary strand nucleic acid alternatively encodes a single complementary strand nucleic acid (e.g., sgRNA) or separate RNA molecules (e.g., separate crRNA and tracrRNA). In the latter case, the DNA encoding the complementary strand nucleic acid is provided as separate DNA molecules encoding the crRNA and tracrRNA, respectively. In some embodiments, DNAs encoding complementary strand nucleic acid are stably integrated in the genome of the cell and, optionally, operably linked to a promoter active in the cell. DNAs encoding complementary strand nucleic acids, in some embodiments, are operably linked to a promoter in an expression construct. Complementary strand nucleic acids are prepared by any suitable method. For example, complementary strand nucleic acids are prepared by in vitro transcription using, for example, T7 RNA polymerase. In some embodiments, complementary strand nucleic acids are also synthetically produced molecules prepared by chemical synthesis.

Nucleases.

Nucleases recognizing a targeting sequence are known by those of skill in the art and include, but are not limited to, zinc finger nucleases (ZFN), transcription activator-like effector nucleases (TALEN), clustered regularly interspaced short palindromic repeats (CRISPR) nucleases, and meganucleases. Nucleases found in compositions and useful in methods disclosed herein are described in more detail below.

Zinc Finger Nucleases (ZFNs)

"Zinc finger nucleases" or "ZFNs" are a fusion between the cleavage domain of FokI and a DNA recognition domain containing 3 or more zinc finger motifs. The heterodimerization at a particular position in the DNA of two individual ZFNs in precise orientation and spacing leads to a double-strand break in the DNA. In some cases, ZFNs fuse a cleavage domain to the C-terminus of each zinc finger domain. In order to allow the two cleavage domains to dimerize and cleave DNA, the two individual ZFNs bind opposite strands of DNA with their C-termini at a certain distance apart. In some cases, linker sequences between the zinc finger domain and the cleavage domain require the 5' edge of each binding site to be separated by about 5-7 bp. Exemplary ZFNs that are useful in the present invention include, but are not limited to, those described in Urnov et al., Nature Reviews Genetics, 2010, 11:636-646; Gaj et al., Nat Methods, 2012, 9 (8): 805-7; U.S. Pat. Nos. 6,534,261; 6,607,882; 6,746,838; 6,794,136; 6,824,978; 6,866,997; 6,933, 113; 6,979,539; 7,013,219; 7,030,215; 7,220,719; 7,241,573; 7,241,574; 7,585,849; 7,595,376; 6,903,185; 6,479,626; and U.S. Application Publication Nos. 2003/0232410 and 2009/0203140. In some embodiments, a ZFN is a zinc finger nickase which, in some embodiments, is an engineered ZFN that induces site-specific single-strand DNA breaks or nicks. Descriptions of zinc finger nickases are found, e.g., in Ramirez et al., Nucl Acids Res, 2012, 40 (12): 5560-8; Kim et al., Genome Res, 2012, 22 (7): 1327-33.

TALENS

"TALENs" or "TAL-effector nucleases" are engineered transcription activator-like effector nucleases that contain a central domain of DNA-binding tandem repeats, a nuclear localization signal, and a C-terminal transcriptional activation domain. In some instances, a DNA-binding tandem repeat comprises 33-35 amino acids in length and contains two hypervariable amino acid residues at positions 12 and 13 that recognize one or more specific DNA base pairs. TALENS are produced by fusing a TAL effector DNA binding domain to a DNA cleavage domain. For instance, a TALE protein may be fused to a nuclease such as a wild-type or mutated FokI endonuclease or the catalytic domain of FokI. Several mutations to FokI have been made for its use in TALENs, which, for example, improve cleavage specificity or activity. Such TALENs are engineered to bind any desired DNA sequence. TALENs are often used to generate gene modifications by creating a double-strand break in a target DNA sequence, which in turn, undergoes NHEJ or HDR. In some cases, a single-stranded donor DNA repair template is provided to promote HDR. Detailed descriptions of TALENs and their uses for gene editing are found, e.g., in U.S. Pat. Nos. 8,440,431; 8,440,432; 8,450,471; 8,586, 363; and U.S. Pat. No. 8,697,853; Scharenberg et al., Curr Gene Ther, 2013, 13 (4): 291-303; Gaj et al., Nat Methods, 2012, 9 (8): 805-7; Beurdeley et al., Nat Commun, 2013, 4:1762; and Joung and Sander, Nat Rev Mol Cell Biol, 2013, 14 (I): 49-55. DNA Guided Nucleases "DNA guided nucleases" are nucleases that use a single stranded DNA complementary nucleotide to direct the nuclease to the correct place in the genome by hybridizing to another nucleic acid, for example, the target nucleic acid in the genome of a cell. In some embodiments, the DNA guided nuclease comprises an Argonaute nuclease. In some embodiments, the DNA guided nuclease is selected from TtAgo, PfAgo, and NgAgo. In some embodiments, the DNA guided nuclease is NgAgo.

Meganucleases

"Meganucleases" are rare-cutting endonucleases or homing endonucleases that, in certain embodiments, are highly specific, recognizing DNA target sites ranging from at least 12 base pairs in length, e.g., from 12 to 40 base pairs or 12 to 60 base pairs in length.

Any meganuclease is contemplated to be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIiP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, 1-PobIP, I-PorI, I-PorIIP, I-PbpIP, I-SpBetaIP, I-ScaI, I-SexIP, 1-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, 1-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-THII, I-CreI meganuclease, I-CeuI meganuclease, I-MsoI meganuclease, I-SceI meganuclease, or any active variants, fragments, mutants or derivatives thereof.

CRISPR

The CRISPR (Clustered Regularly Interspaced Short Palindromic Repeats)/Cas (CRISPR-associated protein) nuclease system is an engineered nuclease system based on a bacterial system that is used for genome engineering. It is based in part on the adaptive immune response of many bacteria and archaea. When a virus or plasmid invades a bacterium, segments of the invader's DNA are converted into CRISPR RNAs (crRNA) by the "immune" response. The crRNA then associates, through a region of partial complementarity, with another type of RNA called tracrRNA to guide the Cas (e.g., Cas9) nuclease to a region homologous to the crRNA in the target DNA called a "protospacer." The Cas (e.g., Cas9) nuclease cleaves the DNA to generate blunt ends at the double-strand break at sites specified by a 20-nucleotide complementary strand sequence contained within the crRNA transcript. The Cas (e.g., Cas9) nuclease, in some embodiments, requires both the crRNA and the tracrRNA for site-specific DNA recognition and cleavage. This system has now been engineered such that, in certain embodiments, the crRNA and tracrRNA are combined into one molecule (the "single guide RNA" or "sgRNA"), and the crRNA equivalent portion of the single guide RNA is engineered to guide the Cas (e.g., Cas9) nuclease to target any desired sequence (see, e.g., Jinek et al. (2012) Science 337:816-821; Jinek et al. (2013) eLife 2: e00471; Segal (2013) eLife 2: e00563). Thus, the CRISPR/Cas system can be engineered to create a double-strand break at a desired target in a genome of a cell, and harness the cell's endogenous mechanisms to repair the induced break by homology-directed repair (HDR) or nonhomologous end-joining (NHEJ). In some embodiments, the Cas nuclease has DNA cleavage activity. The Cas nuclease, in some embodiments, directs cleavage of one or both strands at a location in a target DNA sequence. For example, in some embodiments, the Cas nuclease is a nickase having one or more inactivated catalytic domains that cleaves a single strand of a target DNA sequence. Non-limiting examples of Cas nucleases include Cas1, Cas1B, Cas2, Cas3, Cas4, Cas5, Cas6, Cas7, Cas8, Cas9 (also known as Csn1 and Csx12), Cas10, Cpf1, C2c3, C2c2 and C2c1Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Cpf1, Csb1, Csb2, Csb3, Csx17, Csx14, CsxIO, Csx16, CsaX, Csx3, Csx1, Csx15, Csf1, Csf2, Csf3, Csf4, homologs thereof, variants thereof, mutants thereof, and derivatives thereof. There are three main types of Cas nucleases (type I, type II, and type III), and 10 subtypes including 5 type 1, 3 type II, and 2 type III proteins (see, e.g., Hochstrasser and Doudna, Trends Biochem Sci, 2015: 40 (I): 58-66). Type II Cas nucleases include, but are not limited to, Cas1, Cas2, Csn2, and Cas9. These Cas nucleases are known to those skilled in the art. For example, the amino acid sequence of the *Streptococcus pyogenes* wild-type Cas9 polypeptide is set forth, e.g., in NBCl Ref. Seq. No. NP 269215, and the amino acid sequence of *Streptococcus thermophilus* wild-type Cas9 polypeptide is set forth, e.g., in NBCl Ref. Seq. No. WP_011681470. Cas nucleases, e.g., Cas9 polypeptides, in some embodiments, are derived from a variety of bacterial species. "Cas9" refers to an RNA-guided double-stranded DNA-binding nuclease protein or nickase protein. Wild-type Cas9 nuclease has two functional domains, e.g., RuvC and HNH, that cut different DNA strands. Cas9 can induce double-strand breaks in genomic DNA (target DNA) when both functional domains are active. The Cas9 enzyme, in some embodiments, comprises one or more catalytic domains of a Cas9 protein derived from bacteria belonging to the group consisting of Corynebacter, Sutterella, Legionella, Treponema, Filif actor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, and Campylobacter. In some embodiments, the Cas9 is a fusion protein, e.g. the two catalytic domains are derived from different bacteria species. Useful variants of the Cas9 nuclease include a single inactive catalytic domain, such as a RuvC⁻ or HNH⁻ enzyme or a nickase. A Cas9 nickase has only one active functional domain and, in some embodiments, cuts only one strand of the target DNA, thereby creating a single strand break or nick. In some embodiments, the mutant Cas9 nuclease having at least a D10A mutation is a Cas9 nickase. In other embodiments, the mutant Cas9 nuclease having at least a H840A mutation is a Cas9 nickase. Other examples of mutations present in a Cas9 nickase include, without limitation, N854A and N863 A. A double-strand break is introduced using a Cas9 nickase if at least two DNA-targeting RNAs that target opposite DNA strands are used. A double-nicked induced double-strand break is repaired by NHEJ or HDR. This gene editing strategy favors HDR and decreases the frequency of indel mutations at off-target DNA sites. The Cas9 nuclease or nickase, in some embodiments, is codon-optimized for the target cell or target organism. In some embodiments, the Cas nuclease is a Cas9 polypeptide that contains two silencing mutations of the RuvCl and HNH nuclease domains (D10A and H840A), which is referred to as dCas9. In one embodiment, the dCas9 polypeptide from *Streptococcus pyogenes* comprises at least one mutation at position D10, G12, G17, E762, H840, N854, N863, H982, H983, A984, D986, A987, or any combination thereof. Descriptions of such dCas9 polypeptides and variants thereof are provided in, for example, International Patent Publication No. WO 2013/176772. The dCas9 enzyme in some embodiments, contains a mutation at D10, E762, H983, or D986, as well as a mutation at H840 or N863. In some instances, the dCas9 enzyme contains a D10A or DION mutation. Also, the dCas9 enzyme alternatively includes a mutation H840A, H840Y, or H840N. In some embodiments, the dCas9 enzyme of the present invention comprises D10A and H840A; D10A and H840Y; D10A and H840N; DION and H840A; DION and H840Y; or DION and H840N substitutions. The substitutions are alternatively conservative or non-conservative substitutions to render the Cas9 polypeptide catalytically inactive and able to bind to target DNA. For genome editing methods, the Cas nuclease in some embodiments comprises a Cas9 fusion protein such as a polypeptide comprising the catalytic domain of the type IIS restriction enzyme, Fokl, linked to dCas9. The Fokl-dCas9 fusion protein (fCas9) can use two guide RNAs to bind to a single strand of target DNA to generate a double-strand break.

Delivery

The gene delivery vehicles of the present invention may be administered to a patient. Said administration may be an "in vivo" administration or an "ex vivo" administration. A skilled worker would be able to determine appropriate dosage rates. The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors etc as described above. Non-viral delivery systems include DNA transfection such as electroporation, lipid mediated transfection, compacted DNA-mediated transfection; liposomes, immunoliposomes, lipofectin, cationic facial amphiphiles (CFAs) and combinations thereof. The delivery of one or more therapeutic genes by a vector system according to the present invention may be used alone or in combination with other treatments or components of the treatment.

Any suitable delivery method is contemplated to be used for delivering the compositions of the disclosure. The individual components of the HITI system (e.g., nuclease and/or the exogenous DNA sequence), in some embodiments, are delivered simultaneously or temporally separated. The choice of method of genetic modification is dependent on the type of cell being transformed and/or the circumstances under which the transformation is taking place (e.g., in vitro, ex vivo, or in vivo). A general discussion of these methods is found in Ausubel, et al., Short Protocols in Molecular Biology, 3rd ed., Wiley & Sons, 1995.

The term "contacting the cell" comprises all the delivery method herein discloses. In some embodiments, a method as disclosed herein involves contacting a target DNA or introducing into a cell (or a population of cells) one or more nucleic acids comprising nucleotide sequences encoding a complementary strand nucleic acid (e.g., gRNA), a site-directed modifying polypeptide (e.g., Cas protein), and/or a exogenous DNA sequence. Suitable nucleic acids comprising nucleotide sequences encoding a complementary strand nucleic acid and/or a site-directed modifying polypeptide include expression vectors, where an expression vector comprising a nucleotide sequence encoding a complementary strand nucleic acid and/or a site-directed modifying polypeptide is a recombinant expression vector. Non-limiting examples of delivery methods or transformation include, for example, viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, and nanoparticle-mediated nucleic acid delivery (see, e.g., Panyam et., al Adv Drug Deliv Rev. 2012 Sep. 13. pii: 50169-409X (12) 00283-9. doi: 10.1016/j.addr.2012.09.023). In some aspects, the present invention provides methods comprising delivering one or more polynucleotides, such as or one or more vectors as described herein, one or more transcripts thereof, and/or one or proteins transcribed therefrom, to a host cell. In some aspects, the disclosure further provides cells produced by such methods, and organisms (such as animals, plants, or fungi) comprising or produced from such cells. In some embodiments, a nuclease protein in combination with, and optionally complexed with, a complementary strand sequence is delivered to a cell. Conventional viral and non-viral based gene transfer methods are contemplated to be used to introduce nucleic acids in mammalian cells or target tissues. Such methods are used to administer nucleic acids encoding components of a HITI system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems can include DNA and RNA viruses, which can have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon. TIBTECH 11:167-175 (1993); Miller, Nature 357:455-460 (1992); Van Brunt, Biotechnology 6 (10): 1149-1154 (1988); Vigne, Restorative Neurology and Neuroscience 8:35-36 (1995); Kremer & Perricaudet, British Medical Bulletin 51 (1): 31-44 (1995); Haddada et al., in Current Topics in Microbiology and Immunology Doerfler and Bohm (eds) (1995); and Yu et al., Gene Therapy 1:13-26 (1994). Methods of non-viral delivery of nucleic acids can include lipofection, nucleofection, microinjection, electroporation, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam.™. and Lipofectin.™.). Cationic and neutral lipids that are suitable for efficient receptor-recognition lipofection of polynucleotides include those of Feigner, WO 91/17424; WO 91/16024. Delivery is contemplated to be to cells (e.g. in vitro or ex vivo administration) or target tissues (e.g. in vivo administration). The preparation of lipid: nucleic acid complexes, including targeted liposomes such as immunolipid complexes, is well known (see, e.g., Crystal, Science 270: 404-410 (1995); Blaese et al., Cancer Gene Ther. 2:291-297 (1995): Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). RNA or DNA viral based systems are used to target specific cells in the body and trafficking the viral payload to the nucleus of the cell. Viral vectors are alternatively administered directly (in vivo) or they are used to treat cells in vitro, and the modified cells are optionally be administered (ex vivo). Viral based systems include, but are not limited to, retroviral, lentivirus, adenoviral, adeno-associated, and herpes simplex virus vectors for gene transfer. Integration in the host genome, in some embodiments, occurs with the retrovirus, lentivirus, and adeno-associated virus gene transfer methods, which results in long term expression of the inserted transgene, in some embodiments. High transduction efficiencies are observed in many different cell types and target tissues. In some embodiments, adenoviral-based systems are used. Adenoviral-based systems, in some embodiments, lead to transient expression of the transgene. Adenoviral based vectors are capable of high transduction efficiency in cells and in some embodiments do not require cell division. High titer and levels of expression are possible with adenoviral based vectors. In some embodiments, adeno-associated virus ("AAV") vectors are used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Packaging cells, in some embodiments, are used to form virus particles capable of infecting a host cell. Such cells include but are not limited to 293 cells, (e.g., for packaging adenovirus), and .psi.2 cells or PA317 cells (e.g., for packaging retrovirus). Viral vectors are generated by producing a cell line that packages a nucleic acid vector into a viral particle. In some cases, the vectors contain the minimal viral sequences required for packaging and subsequent integration into a host. In some cases, the vectors contain other viral sequences being replaced by an expression cassette for the polynucleotide(s) to be expressed. In some embodiments, the missing viral functions are supplied in trans by the packaging cell line. For example, in some embodiments, AAV vectors comprise ITR sequences from the AAV genome which are required for packaging and integration into the host genome. Viral DNA is packaged in a cell line, which contains a helper plasmid encoding the other AAV genes, namely rep and cap, while lacking ITR sequences. Alternatively, the cell line is infected with adenovirus as a helper. The helper virus promotes replication of the AAV vector and expression of AAV genes from the helper plasmid. Contamination with adenovirus is reduced by, e.g., heat treatment, to which adenovirus is more sensitive than AAV.

AAV Serotypes

To date, dozens of different AAV variants (serotypes) have been identified and classified (Srivastava A, Curr Opin Virol. 2016 December; 21:75-80). All of the known serotypes can infect cells from multiple diverse tissue types. Tissue specificity is determined by the capsid serotype and pseudotyping of AAV vectors to alter their tropism range will likely be important to their use in therapy. Pseudotyped AAV vectors are those which contain the genome of one AAV serotype in the capsid of a second AAV serotype; for example an AAV2/8 vector contains the AAV8 capsid and the AAV 2 genome (Auricchio et al. (2001) Hum. Mol. Genet. 10 (26): 3075-81). Such vectors are also known as chimeric vectors Serotype 2

Serotype 2 (AAV2) has been the most extensively examined so far. AAV2 presents natural tropism towards skeletal muscles, neurons, vascular smooth muscle cells and hepatocytes. Three cell receptors have been described for AAV2: heparan sulfate proteoglycan (HSPG), avß5 integrin and fibroblast growth factor receptor 1 (FGFR-1). The first functions as a primary receptor, while the latter two have a co-receptor activity and enable AAV to enter the cell by receptor-mediated endocytosis. These study results have been disputed by Qiu, Handa, et al., HSPG functions as the primary receptor, though its abundance in the extracellular matrix can scavenge AAV particles and impair the infection efficiency.

Other Serotypes

Although AAV2 is the most popular serotype in various AAV-based research, it has been shown that other serotypes can be more effective as gene delivery vectors. For instance AAV6 appears much better in infecting airway epithelial cells, AAV7 presents very high transduction rate of murine skeletal muscle cells (similarly to AAV1 and AAV5), AAV8 is superb in transducing hepatocytes and photoreceptors, AAV1 and 5 were shown to be very efficient in gene delivery to vascular endothelial cells. In the brain, most AAV serotypes show neuronal tropism, while AAV5 also transduces astrocytes. AAV6, a hybrid of AAV1 and AAV2, also shows lower immunogenicity than AAV2. Serotypes can differ with the respect to the receptors they are bound to. For example AAV4 and AAV5 transduction can be inhibited by soluble sialic acids (of different form for each of these serotypes), and AAV5 was shown to enter cells via the platelet-derived growth factor receptor. Novel AAV variants such as quadruple tyrosine mutants or AAV 2/7m8 were shown to transduce the outer retina from the vitreous in small animal models (Dalkara D et al., Sci Transl Med. 2013 Jun. 12; 5 (189): 189ra76; Petrs-Silva H et al., Mol Ther. 2011 February; 19 (2): 293-301). Another AAV mutant named ShH10, an AAV6 variant with improved glial tropism after intravitreal administration (Klimczak R R et al., PLOS One. 2009 Oct. 14;4 (10): e7467.). A further AAV mutant with particularly advantageous tropism for the retina is the AAV2 (quad Y-F) (Hickey D G et al., Gene Ther. 2017 December; 24 (12): 787-800). Within the meaning of the present invention, an AAV viral particle comprises capsid proteins of an AAV of a serotype selected from one or more of the group consisting of AAV1, AAV2, AAV3, AAV4, AAV5, AAV6, AAV7, AAV8 AAV9 and AAV 10, preferably from the AAV2 or AAV8 serotype.

Any suitable vector compatible with the host cell is contemplated to be used with the methods of the invention. Non-limiting examples of vectors for eukaryotic host cells include pXTI, pSG5, pSVK3, pBPV, pMSG, and pSVLSV40. In some embodiments, a nucleotide sequence encoding a complementary strand nucleic acid and/or a site-directed modifying polypeptide is operably linked to a control element, e.g., a transcriptional control element, such as a promoter. The transcriptional control element is functional, in some embodiments, in either a eukaryotic cell, e.g., a mammalian cell, or a prokaryotic cell (e.g., bacterial or archaeal cell). In some embodiments, a nucleotide sequence encoding a complementary strand nucleic acid and/or a site-directed modifying polypeptide is operably linked to multiple control elements that allow expression of the nucleotide sequence encoding a complementary strand nucleic acid and/or a site-directed modifying polypeptide in prokaryotic and/or eukaryotic cells. Depending on the host/vector system utilized, any of a number of suitable transcription and translation control elements, including constitutive and inducible promoters, transcription enhancer elements, transcription terminators, etc. may be used in the expression vector (e.g., U6 promoter, HI promoter, etc.; see above) (see e.g., Bitter et al. (1987) Methods in Enzymology, 153:516-544). In some embodiments, a complementary strand nucleic acid and/or a site-directed modifying polypeptide is provided as RNA. In such cases, the complementary strand nucleic acid and/or the RNA encoding the site-directed modifying polypeptide is produced by direct chemical synthesis or may be transcribed in vitro from a DNA encoding the complementary strand nucleic acid. The complementary strand nucleic acid and/or the RNA encoding the site-directed modifying polypeptide are synthesized in vitro using an RNA polymerase enzyme (e.g., T7 polymerase, T3 polymerase, SP6 polymerase, etc.). Once synthesized, the RNA directly contacts a target DNA or is introduced into a cell using any suitable technique for introducing nucleic acids into cells (e.g., microinjection, electroporation, transfection, etc). Nucleotides encoding a complementary strand nucleic acid (introduced either as DNA or RNA) and/or a site-directed modifying polypeptide (introduced as DNA or RNA) and/or an exogenous DNA sequence are provided to the cells using a suitable transfection technique; see, e.g. Angel and Yanik (2010) PLOS ONE 5 (7): el 1756, and the commercially available TransMessenger.RTM. reagents from Qiagen, Stemfect.™. RNA Transfection Kit from Stemgent, and TransIT.RTM.-mRNA Transfection Kit from Minis Bio LLC. Nucleic acids encoding a complementary strand nucleic acid and/or a site-directed modifying polypeptide and/or a chimeric site-directed modifying polypeptide and/or an exogenous DNA sequence may be provided on DNA vectors. Many vectors, e.g., plasmids, cosmids, minicircles, phage, viruses, etc., useful for transferring nucleic acids into target cells are available. The vectors comprising the nucleic acid(s) in some embodiments are maintained episomally, e.g. as plasmids, minicircle DNAs, viruses such cytomegalovirus, adenovirus, etc., or they are integrated into the target cell genome, through homologous recombination or random integration, e.g. retrovirus-derived vectors such as MMLV, HIV-1, and ALV.

Methods of Making Changes to Genomic DNA

Provided herein are homology-independent targeted integration (HITI) methods and compositions for making changes to nucleic acid, such as genomic DNA, including genomic DNA in non-dividing or terminally differentiated cells that do not divide. Methods herein, at least in some embodiments, are homology independent, using non-homologous end-joining to insert exogenous DNA into a target DNA, such as a genomic DNA of a cell, such as a non-dividing or terminally differentiated cell. In some embodiments, methods herein comprise a method of integrating an exogenous DNA sequence into a genome of a non-dividing cell comprising contacting the non-dividing cell with a composition comprising a targeting construct comprising the exogenous DNA sequence and a targeting sequence, a complementary strand oligonucleotide homologous to the targeting sequence, and a nuclease, wherein the exogenous DNA sequence comprises at least one nucleotide difference compared to the genome and the targeting sequence is recognized by the nuclease. In some embodiments of HITI methods disclosed herein, exogenous DNA sequences are fragments of DNA containing the desired sequence to be inserted into the genome of the target cell or host cell. At least a portion of the exogenous DNA sequence has a sequence homologous to a portion of the genome of the target cell or host cell and at least a portion of the exogenous DNA sequence has a sequence not homologous to a portion of the genome of the target cell or host cell. For example, in some embodiments, the exogenous DNA sequence may comprise a portion of a host cell genomic DNA sequence with a mutation therein. Therefore, when the exogenous DNA sequence is integrated into the genome of the host cell or target cell, the mutation found in the exogenous DNA sequence is carried into the host cell or target cell genome. In some embodiments of HITI methods disclosed herein, the exogenous DNA sequence is flanked by at least one targeting sequence. In some embodiments, the exogenous DNA sequence is flanked by two targeting sequences. The targeting sequence comprises a specific DNA sequence that is recognized by at least one nuclease. In some embodiments, the targeting sequence is recognized by the nuclease in the presence of a complementary strand oligonucleotide having a homologous sequence to the targeting sequence. In some embodiments, in HITI methods disclosed herein, a targeting sequence comprises a nucleotide sequence that is recognized and cleaved by a nuclease. Nucleases recognizing a targeting sequence are known by those of skill in the art and include but are not limited to zinc finger nucleases (ZFN), transcription activator-like effector nucleases (TALEN), and clustered regularly interspaced short palindromic repeats (CRISPR) nucleases. ZFNs, in some embodiments, comprise a zinc finger DNA-binding domain and a DNA cleavage domain, fused together to create a sequence specific nuclease. TALENs, in some embodiments, comprise a TAL effector DNA binding domain and a DNA cleavage domain, fused together to create a sequence specific nuclease. CRISPR nucleases, in some embodiments, are naturally occurring nucleases that recognize DNA sequences homologous to clustered regularly interspaced short palindromic repeats, commonly found in prokaryotic DNA. CRISPR nucleases include, but are not limited to, Cas9 Cpfl, C2c3, C2c2, and C2cl. Conveniently, a Cas 9 of tehe present invention is a variant with reduced off target activity as SpCas9 D10A (Ran, F. A., et al., Genome engineering using the CRISPR-Cas9 system. Nat Protoc, 2013. 8 (11): p. 2281-2308. (with Inactivation of RuvC domain cleavage activity), SpCas9 N863A (Ran, F. A., et al., *Genome engineering using the CRISPR-Cas9 system*. Nat Protoc, 2013. 8 (11): p. 2281-2308) (Inactivation of HNH domain cleavage activity), SpCas9-HF1 (Kleinstiver, B. P., et al., *High-fidelity CRISPR-Cas9 nucleases with no detectable genome-wide off-target effects*. Nature, 2016. 529 (7587): p. 490-5) (Reduction of Cas9 binding energy by protein engineering), eSpCas9 (laymaker, I. M., et al., *Rationally engineered Cas9 nucleases with improved specificity*. Science, 2016. 351 (6268): p. 84-8) (Reduction of positive charge of Cas9), EvoCas9 (asini, A., et al., *A highly specific SpCas9 variant is identified by in vivo screening in yeast*. Nat Biotechnol, 2018. 36 (3): p. 265-271) (Mutagenesis of REC3 domain), KamiCas9 (Merienne, N., et al., *The Self-Inactivating Kami-Cas9 System for the Editing of CNS Disease Genes*. Cell Rep, 2017. 20 (12): p. 2980-2991) (Knockout of Cas9 after expression) HITI methods disclosed herein, in some embodiments, are capable of introducing mutations into a host genome or a target genome as well as repairing mutations in a host genome or a target genome. Mutations or wild-type sequences, in some embodiments of the methods described herein, are found in the exogenous DNA sequence to be inserted into the host genome or target genome. Mutations are known by those of skill in the art and include single base-pair changes or point mutations, insertions, and deletions. In some embodiments, a single base-pair change results in a missense mutation which creates a codon that encodes a different amino acid in transcribed mRNA than the wild-type sequence. In some embodiments, a single base-pair change results in a nonsense mutation which encodes for a stop codon in transcribed mRNA. In some embodiments, a stop codon in transcribed RNA results in early truncation of a protein translated from the mRNA. In some embodiments, a single base-pair change results in a silent mutation that does not result in any change in amino acids encoded by a mRNA transcribed from the host genome or the target genome. In some embodiments, a silent mutation is in an intron. In some embodiments, a silent mutation is in an exon and creates a codon encoding for the same amino acid as the wild-type sequence. In some embodiments, a silent mutation, is in a promoter, an enhancer, a 5' UTR, a 3' UTR, or other non-coding region of the host genome or target genome. In some embodiments, a silent mutation results in aberrant splicing of an mRNA transcript. In some embodiments, a silent mutation disrupts a RNA splice donor or splice acceptor site. In some embodiments, a silent mutation results in aberrant RNA export. In some embodiments, a silent mutation results in aberrant or reduced translation of an mRNA. In some embodiments, a silent mutation results in aberrant or reduced transcription of an RNA. In some embodiments, mutations comprise insertions into the host genome or target genome. In some embodiments, insertions comprise a specific number of nucleotides ranging from 1 to 4,700 base pairs, for example 1-10, 5-20, 15-30, 20-50, 40-80, 50-100, 100-1000, 500-2000, 1000-4,700 base pairs. In some embodiments, the method comprises eliminating at least one gene, or fragment thereof, from the host genome or target genome. In some embodiments, the method comprises introducing an exogenous gene (herein also defined as Eexogenous DNA sequence or gene of interest), or fragment thereof, into the host genome or target genome. In some embodiments, the method comprises replacing a mutated gene, or fragment thereof, in the host genome or target genome with a wild-type gene, or fragment thereof. In some embodiments the host gene is silenced and replaced by a wild-type gene or coding sequence thereof. In some embodiments, the method changes at least one nucleotide of a host genome or target genome resulting in increased expression of a gene. In some embodiments, the method changes at least one nucleotide of a host genome or target genome resulting in decreased expression of a gene. In some embodiments, the method introduces an exogenous promoter into the host genome or target genome resulting in altered expression of a gene. In some embodiments, the promoter is an inducible promoter. HITI methods disclosed herein have increased capabilities in making changes to genomic DNA in non-dividing cells. Non-dividing cells include, but are not limited to: cells in the central nervous system including neurons, oligodendrocytes, microglia and ependymal cells; sensory transducer cells; autonomic neuron cells; sense organ and peripheral neuron supporting cells; cells in the retina including photoreceptors, rods and cones; cells in the kidney including parietal cells, glomerulus podocytes, proximal tubule brush border cells, loop of henle thin segment cells, distal tubule cells, collecting duct cells; cells in the hematopoietic lineage including lymphocytes, monocytes, neutrophils, eosinophils, basophils, thrombocytes; cells of liver including hepatocytes, stellate cells, the Kupffer cells and the liver endothelial cells; pancreatic endocrine cells including alpha, beta, delta, gamma, and epsilon cells; cells of the respiratory epithelium including ciliated cells, basal cells, goblet cells and alveolar cells, germ cells including oogonium/oocyte, spermatid, spermatocyte, spermatogonium cell and spermatozoon; cells of the bone including osteocytes, osteoclasts and osteoblasts; cells of the heart including cardiomyocytes and cardiac pacemaker cells; follicular cells in the thyroid; cells in the upper digestive tract including serous cells, mucous cells and taste buds; cells in the stomach including parietal cells, chief cells, enteroendocrine cells; endothelial cells, epithelial cells, adipocytes, bone marrow cells, inner ear cells, dermis cells, smooth muscle cells, skeletal muscle cells. In some embodiments, HITI methods disclosed herein provide a method of making changes to genomic DNA in dividing cells, wherein the method has higher efficiency than previous methods disclosed in the art. Dividing cells include, but are not limited to, hematopoietic stem cells, mesenchymal stem cells, neural stem cells, liver stem cells, muscle satellite cells, epidermis cells, glial cells, and astrocytes. In some embodiments, the targeting construct, the complementary strand oligonucleotides, and/or a polynucleotide encoding the nuclease for HITI methods described herein are introduced into the target cell or the host cell by a virus. Viruses, in some embodiments, infect the target cell and express the targeting construct, the complementary strand oligonucleotides, and the nuclease, which allows the exogenous DNA of the targeting construct to be integrated into the host genome. In some embodiments, the virus comprises a sendai virus, a retrovirus, a lentivirus, a baculovirus, an adenovirus, or an adeno-associated virus. In some embodiments the virus is a pseudotyped virus. In some embodiments, the targeting construct, the complementary strand oligonucleotides, and/or a polynucleotide encoding the nuclease for HITI methods described herein are introduced into the target cell or the host cell by a non-viral gene delivery method. Non-viral gene delivery methods, in some embodiments, deliver the genetic materials (including DNA, RNA and protein) into the target cell and express the targeting construct, the complementary strand oligonucleotides, and the nuclease, which allows the exogenous DNA of the targeting construct to be integrated into the host genome. In some embodiments, the non-viral method comprises transfection reagent (including nanoparticles) for DNA mRNA or protein, or electroporation.

Methods of Treating Disease

Also provided herein are methods and compositions for treating disease, such as genetic disease. Genetic diseases are those that are caused by mutations in inherited DNA. In some embodiments, genetic diseases are caused by mutations in genomic DNA. Genetic mutations are known by those of skill in the art and include, single base-pair changes or point mutations, insertions, and deletions. In some embodiments, methods provided herein include a method of treating a genetic disease in a subject in need thereof, wherein the genetic disease results from a mutated gene having at least one changed nucleotide compared to a wild-type gene, wherein the method comprises contacting at least one cell of the subject with a composition comprising a targeting construct comprising a DNA sequence homologous to the wild-type gene and a targeting sequence, a complementary strand oligonucleotide homologous to the targeting sequence, and a nuclease, wherein the targeting sequence is recognized by the nuclease such that the mutated gene, or fragment thereof, is replaced with the wild-type gene, or fragment thereof. Genetic diseases that are treated by methods disclosed herein include but are not limited to Lysosomal storage diseases comprising mucopolysaccharidoses (MPSI, MPSII, MPSIIIA, MPSIIIB, MPSIIIC, MPSIVA, MPSIVB, MPSVII), sphingolipidoses (Fabry's Disease, Gaucher Disease, Nieman-Pick Disease, GM1 Gangliosidosis), lipofuccinoses (Batten's Disese and others) and mucolipidoses; other diseases where the liver can be used as a factory for production and secretion of therapeutic proteins, like diabetes, adenylosuccinate deficiency, hemophilia A and B, ALA dehydratase deficiency, adrenoleukodystrophy, Autosomal dominant. Retinal diseases that can be treated in the present invention are e.g. retinitis pigmentosa (due to mutations in RHO, AlPL1, IMPDH1, RDS, PDE6B or other genes), cone-rod dystrophy (CRX), Stargardt's Disease (ELOVL4), Von-Hippel Lindau and Retinoblastoma.

Methods of treating genetic disease disclosed herein employ exogenous DNA sequences comprising at least a portion of a wild type DNA sequence that corresponds to the DNA sequence of mutated gene, so that in the method, the mutated DNA sequence is replaced with the wild type DNA sequence.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth. The term "genome editing" refers to a type of genetic engineering in which DNA is inserted, replaced, or removed from a target DNA, e.g. the genome of a cell, using one or more nucleases and/or nickases. The nucleases create specific double-strand breaks (DSBs) at desired locations in the genome, and harness the cell's endogenous mechanisms to repair the induced break by nonhomologous end joining (NHEJ). The nickases create specific single-strand breaks at desired locations in the genome. In one non-limiting example, two nickases can be used to create two single strand breaks on opposite strands of a target DNA, thereby generating a blunt or a sticky end. Any suitable nuclease can be introduced into a cell to induce genome editing of a target DNA sequence including, but not limited to, CRISPR-associated protein (Cas) nucleases, zinc finger nucleases (ZFNs), transcription activator-like effector nucleases (TALENs), meganucleases, other endo- or exo-nucleases, variants thereof, fragments thereof, and combinations thereof. The term "nonhomologous end joining" or "NHEJ" refers to a pathway that repairs double-strand DNA breaks in which the break ends are directly ligated without the need for a homologous template. The term "polynucleotide," "oligonucleotide", "nucleic acid", "nucleotide" and "nucleic acid molecule" may be used interchangeably refers to deoxyribonucleic acids (DNA), ribonucleic acids (RNA) and polymers thereof in either single, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic, or derivatized nucleotide bases. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing non nucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. In some embodiments, a nucleic acid can comprise a mixture of DNA, RNA, and analogs thereof. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with gene, cDNA, and mRNA encoded by a gene. The term "gene" or "nucleotide sequence encoding a polypeptide" means the segment of DNA involved in producing a polypeptide chain. The DNA segment may include regions preceding and following the coding region (leader and trailer) involved in the transcription/translation of the gene product and the regulation of the transcription/translation, as well as intervening sequences (introns) between individual coding segments (exons). The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds. A "recombinant expression vector" is a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators), as well as those that confer certain binding affinity or antigenicity to the recombinant protein produced from the expression vector. The term "single nucleotide polymorphism" or "SNP" refers to a change of a single nucleotide with a polynucleotide, including within an allele. This can include the replacement of one nucleotide by another, as well as deletion or insertion of a single nucleotide. Most typically, SNPs are biallelic markers although tri- and tetra-allelic markers can also exist. By way of non-limiting example, a nucleic acid molecule comprising SNP A\C may include a C or A at the polymorphic position. The terms "subject," "patient," and "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance. As used herein, the term "administering" includes oral administration, topical contact, administration as a suppository, intravenous, intraperitoneal, intramuscular, intralesional, intrathecal, intranasal, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. The term "treating" refers to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. The term "effective amount" or "sufficient amount" refers to the amount of an agent (e.g., DNA nuclease, etc.) that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried. The term "pharmaceutically acceptable carrier" refers to a substance that aids the administration of an agent (e.g., DNA nuclease, etc.) to a cell, an organism, or a subject. "Pharmaceutically acceptable carrier" refers to a carrier or excipient that can be included in a composition or formulation and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical carriers are useful in the present invention.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

As used herein, the term "derivatives" also refers to longer or shorter polynucleotides/proteins and/or having e.g. a percentage of identity of at least 85%, 86%, 87%, 88%, 89%, 90%, 91%, 92%, 93%, 94%, 95%, 96%, 97%, 98%, more preferably of at least 99% with the sequences herein disclosed. In the present invention "at least 70% identity" means that the identity may be at least 70%, or 75%, or 80%, or 85% or 90% or 95% or 100% sequence identity to referred sequences. This applies to all the mentioned % of identity. Preferably, the % of identity relates to the full length of the referred sequence. The derivative of the invention also includes "functional mutants" of the polypeptides or polynucleotide, which are polypeptides or polynuclotide that may be generated by mutating one or more amino acids or nucleotide in their sequences and that maintain their activity. In the present invention "functional" is intended for example as "maintaining their activity". Also within the scope of the subject invention are polynucleotides which have the same nucleotide sequences of a polynucleotide exemplified herein except for nucleotide substitutions, additions, or deletions within the sequence of the polynucleotide, as long as these variant polynucleotides retain substantially the same relevant functional activity as the polynucleotides specifically exemplified herein (e.g., they encode a protein having the same amino acid sequence or the same functional activity as encoded by the exemplified polynucleotide). Thus, the polynucleotides disclosed herein should be understood to include mutants, derivatived, variants and fragments, as discussed above, of the specifically exemplified sequences. The subject invention also contemplates those polynucleotide molecules having sequences which are sufficiently homologous with the polynucleotide sequences of the invention so as to permit hybridization with that sequence under standard stringent conditions and standard methods (Maniatis, T. et al, 1982).

Internal Ribosome Entry Sites (IRES)

Internal ribosome entry site (IRES) elements are cis-acting RNA regions that promote internal initiation of translation using a cap-independent mechanism. Average size of IRES elements is 500 bp. Conveniently, small artificial IRES elements maintaining the activity have been reported. For instance describes two 50nt long IRES elements:

(SEQ. ID NO: 23)
AggTggTAgCCgCAAACATAgTTCAATACAAACTTgCTgTCTCggCgg

And (SEQ. ID NO: 24)
TgACAAACTgTACATgCCgTTAACTgTAATTTTgCgTgATTTTTTTgT
Ag

Kozak Consensus Sequence

Kozak sequence is a motif that functions as translation initiation site in most RNA transcripts, as is recognized by the ribosome as the translational start site, from which a protein is coded by that mRNA molecule. In vivo, this site is often not matched exactly on different mRNAs and the amount of protein synthesized from a given mRNA is dependent on the strength of the Kozak sequence. Some nucleotides in this sequence are more important than others: the AUG is most important because it is the actual initiation codon encoding a methionine amino acid at the N-terminus of the protein. (Rarely, GUG is used as an initiation codon, but methionine is still the first amino acid as it is the met-tRNA in the initiation complex that binds to the mRNA.) The A nucleotide of the "AUG" is referred to as number 1. For a 'strong' consensus, the nucleotides at positions +4 (i.e. G in the consensus) and −3 (i.e. either A or G in the consensus) relative to the number 1 nucleotide must both match the consensus (there is no number 0 position). An 'adequate' consensus has only 1 of these sites, while a 'weak' consensus has neither. The cc at −1 and −2 are not as conserved, but contribute to the overall strength. 2A self-cleaving peptides 2A peptides, are 18-22 aa-long peptides which can induce the cleaving of recombinant proteins in the cell. 2A peptides are derived from the 2A region in the genome of virus. Four members of 2A peptides family are frequently used in life science research. They are P2A, E2A, F2A and T2A. F2A is derived from foot-and-mouth disease virus 18; E2A is derived from equine rhinitis A virus; P2A is derived from porcine teschovirus-1 2A; T2A is derived from thosea asigna virus 2

| Name | Sequence |
|---|---|
| T2A | (GSG) E G R G S L L T C G D V E E N P G P (SEQ ID NO: 25) |
| P2A | (GSG) A T N E S L L K Q A G D V E E N P G P (SEQ ID NO: 26) |
| E2A | (GSG) Q C T N Y A L L K L A G D V E S N P G P (SEQ ID NO: 27) |
| F2A | (GSG) V K Q T L N F D L L K L A G D V E S N P G P (SEQ ID NO: 28) |

Stop Codon:

A stop codon is a trinucleotide sequence within a messenger RNA (mRNA) molecule that signals a halt to protein synthesis. There are three stop codons in the genetic code, TAG, TAA, TGA. Within the meaning of the present inventions, in order to insert STOP codons in the three possible frames, two stop codons are inserted in each frame, for instance TAATAAATAATAAATAATAA (SEQ ID NO:1) or a permutation or combination thereof

EXAMPLES

Materials & Methods

Plasmid Constructs:

Generation of AAV Vector Plasmids

The plasmids used for AAV vector production derived from the pAAV2.1 [36] plasmid that contains the ITRs of AAV serotype 2. Specifically, I used a pAAV2.1 plasmid generated by our group for a previous publication.

The kozak-DsRed and IRES-DsRed donor DNA vectors were generated by PCR-amplification of Discosoma red fluorescent protein (DsRed) CDS (675 bp) and the bovine growth hormone polyadenylation signal (bGHpA), from the plasmids generated in a previous publication from our group [37], adding the kozak or IRES sequences, as well as the 5' and 3' gRNA target sites, as PCR primer overhangs. PCR fragments were subcloned in PCR-Blunt II-TOPO (Invitrogen, Carlsbad, California, United States) before cloning in the pAAV2.1 plasmid by Infusion (Takara, Kusatsu, Japan) using an AflIII restriction site.

mRho-gRNA, pRHO-gRNA, mAlb-gRNA (see Table 2) were designed using Benchling gRNA design tool (www.benchling.com), selecting the gRNAs with higher predicted on-target and off-target score targeting the first exon of each gene. gRNAs were then generated as Fwd and Rev oligonucleotides (Table 3), annealed and cloned in PX458 (pCbh-SpCas9-2A-GFP) as described by Zhang's lab [35]. gRNA expression cassettes (including scramble gRNA described above) were PCR-amplified and subcloned in PCR-Blunt II-TOPO (Invitrogen, Carlsbad, California, United States) before cloning in the pAAV2.1 plasmid by In-Fusion cloning (Takara, Kusatsu, Japan) using a NheI restriction site.

TABLE 2 gRNAs sequences used to target Cas9
to the rhodopsin and albumin locus in
different species.

| gRNA target | gRNA sequence | Endogenous PAM | Target Strand |
|---|---|---|---|
| murine Rho (mRho) | GCAGCCGCAGTACTACCTGG (SEQ ID NO: 29) | CGG | Fwd |
| porcine RHO (pRHO) | AGTACTGCGGATACTCAAAG (SEQ ID NO: 30) | GGG | Rev |
| Murine Alb (mAlb) | ACAAGAGTGAGATCGCCCAT (SEQ ID NO: 31) | CGG | Fwd |
| scramble (scr) | GACTCGCGCGAGTCGAGGAG (SEQ ID NO: 33) | NGG | — | pAAV2.1-IRBP-SpCas9-spA plasmid was generated by cloning the interphotoreceptor retinol-binding protein (IRBP) promoter to the commercial pAAV-pMecp2-SpCas9-spA (Addgene PX551 [39]) using HindIII and AgeI restriction sites and conventional ligation. The pAAV2.1-IRBP-VQRCas9HF1-SpA plasmid was generated by Daniela Benati and Clarissa Patrizi (University of Modena and Regio Emilia) following a similar ligation strategy.

pAAV2.1-HLP-SpCas9-spA plasmid was generated in collaboration with Hristiana Lyubenova from the Auricchio group by substituting the IRBP promoter in the previous primer with the hybrid liver promoter HLP) using AflII and AgeI restriction sites and In-Fusion cloning (Takara, Kusatsu, Japan).

Plasmids Used as Cas9 Templates
AAV Vector Production and Characterization

AAV vectors were produced by the TIGEM AAV Vector Core by triple transfection of HEK293 cells followed by two rounds of CsCl$^2$ purification [40]. For each viral preparation, physical titers (GC/mL) were determined by averaging the titer achieved by dot-blot analysis and by PCR quantification using TaqMan (Applied Biosystems, Carlsbad, CA, USA) [40]. The probes used for dot-blot and PCR analyses were designed to anneal with the IRBP promoter for the pAAV2.1-IRBP-SpCas9-spA vector, the HLP promoter for the pAAV2.1-HLP-SpCas9-spA vector and the bGHpA region for the donor DNA vectors. The length of probes varied between 200 and 700 bp.

Culture and Transfection of HEK293 Cells

HEK293 cells were maintained in DMEM containing 10% fetal bovine serum (FBS) and 2 mM L-glutamine (Gibco, Thermo Fisher Scientific, Waltham, MA, USA). Cells were plated in 6-well plates (1*10$^6$cells/well), and transfected 16 hr later with the plasmids encoding for Cas9 and the different gRNAs and donor DNAs, using the calcium phosphate method (1 to 2 mg/1*106cells); medium was replaced 4 hr later. Maximum material transfected was 3 ug. In all cases, quantity of plasmid DNA was equilibrated between wells, using an empty vector when necessary.

Cytofluorimetric Analysis

HEK293 cells, plated in 6-well plates, were washed once with PBS, detached with trypsin 0.05% EDTA (Thermo Fisher Scientific, Waltham, MA USA), washed twice with PBS, and resuspended in sorting solution containing PBS, 5% FBS and 2.5 mM EDTA. Cells were analyzed on a BD FACS ARIA III (BD Biosciences, San Jose, CA, USA) equipped with BD FACSDiva software (BD Biosciences) using appropriate excitation and detection settings for EGFP and DsRed. Thresholds for fluorescence detection were set on untransfected cells, and a minimum of 10,000 cells/sample were analyzed. A minimum of 50,000 GFP+ or GFP+/DsRed+ cells/sample were sorted and used for DNA extraction.

Animal Models

Mice were housed at the TIGEM animal house (Pozzuoli, Italy) and maintained under a 12-hr light/dark cycle. C57BL/6J mice were purchased from Envigo Italy SRL (Udine, Italy). P347S mice were kindly provided by Enrico Surace. P347S transgenic mice were maintained as F0 by crossing them with themselves, and were crossed with C57BL/6 mice to generate experimental mice. Rho-P23H knock-in (referred as P23H) mice were imported from The Jackson Laboratory. Mice were maintained by crossing homozygous females and males. The P23H mouse is a knock-in for the P23H mutation in the 1$^{st}$ exon of the murine Rho gene, inserted together with a Neomicin cassette. Experimental heterozygous animals were generated by crossing homozygous P23H mice with C57BL/6 mice. The genotype of mice was confirmed by PCR analysis on genomic DNA (extracted from the mouse phalanx tip). Homozygous mice presented a 530 bp PCR product, while heterozygous mice presented a 530 bp and a 399 bp product. Wildtype mice presented only a 399 bp PCR product. The primers used for the PCR amplification are as follows:

Fwd:
(SEQ. ID NO: 34)
5'-TGGAAGGTCAATGAGGCTCT-3'

Rev:
(SEQ. ID NO: 35)
5'-GACCCCACAGAGACAAGCTC-3

The MPSVI mouse is a knock-out for the ARSB gene and a transgenic that expresses a truncated human ARSB, which generates tolerance for the therapeutic ARSB protein. This recapitulates the immunological state of MPSVI patients. MPSVI mice were maintained as heterozygotes and crossed to produce homozygote knock-out experimental mice. The genotype of mice was confirmed by PCR analysis on genomic DNA (extracted from the mouse phalanx tip). Knockout mice presented a 1400 bp PCR product, while heterozygous mice presented both the 1400 bp and another 234 bp band. Wildtype mice presented only the 234 bp band. The primers used for the PCR amplification are as follows:

Fwd:
(SEQ ID NO: 36)
5'-TGGGCAGACTAGGTCTGG-3'

Rev:
(SEQ ID NO: 37)
5'-TGTCTTCCACATGTTGAAGC-3'

The Large White female pigs (Azienda Agricola Pasotti, Imola, Italy) used in this study were registered as purebred in the LWHerd Book of the Italian National Pig Breeders' Association and were housed at the Centro di Biotecnologie A.O.R.N. Antonio Cardarelli (Naples, Italy) and maintained under a 12-hr light/dark cycle.

Subretinal Injection of AAV Vectors in Mice and Pigs

This study was carried out in accordance with the Association for Research in Vision and Ophthalmology Statement for the Use of Animals in Ophthalmic and Vision Research and with the Italian Ministry of Health regulation for animal procedures (Ministry of Health authorization number 147/2015-PR). Surgery was performed under general anesthesia, and all efforts were made to minimize animal suffering.

Mice (1 to 4 weeks old) were anesthetized with an intraperitoneal injection of 2 mL/100 g of body weight of ketamine/xylazine, then AAV2/8 vectors were delivered subretinally via a trans-scleral trans-choroidal approach, as described by Liang et al [42]. Eyes were injected with 1 μL of vector solution. The AAV2/8 dose (GC/eye) was between $1*10^9$ and $2,5*10^9$ GC of each vector/eye; thus, co-injection resulted in a maximum of $5*10^9$ GC/eye.

Subretinal delivery of AAV2/8 vectors to the pig retina was performed as previously described [43]. Eyes (n=3) were injected with two blebs of 100 μL of AAV2/8 vector solution. The AAV2/8 dose was $2*10^{11}$ GC of each vector/bleb; thus, co-injection of triple AAV vectors resulted in a total of $4*10^{11}$ GC/bleb and $8*10^{11}$ GC/eye.

Neonatal Intravenous Injection Via the Temporal Vein p1-p2 neonatal mice were injected following the protocol published by Gombash Lampe et al. [44]. Total volume was 35 μL. The dose injected was $4*10^{13}$ GC/Kg of each vector, for a total dose of $8*10^{13}$ GC/Kg.

Intravenous Injection Via the Retroorbital Plexus 4-week old C57BL/6 mice were injected via the retroorbital plexus with a total volume of 360 uL Injection dose was $1,3*10^{13}$ or $4*10^{13}$ GC/Kg for each vector.

Electrophysiological Recordings

For electroretinographic analyses, P347S or P23H mice were dark-adapted for 3 hr. Mice were anesthetized and positioned in a stereotaxic apparatus, under dim red light. Pupils were dilated with a drop of 0.5% tropicamide (Visufarma, Rome, Italy), and body temperature was maintained at 37.5 degrees Light flashes were generated by a Ganzfeld stimulator (CSO, Costruzione Strumenti Oftalmici, Florence, Italy). The electrophysiological signals were recorded through gold-plate electrodes inserted under the lower eyelids in contact with the cornea. The electrodes in each eye were referred to a needle electrode inserted subcutaneously at the level of the corresponding frontal region. The different electrodes were connected to a two-channel amplifier. After completion of responses obtained in dark-adapted conditions (scotopic), the recording session continued with the purpose of dissecting the cone pathway mediating the light response (photopic). To minimize the noise, different responses evoked by light were averaged for each luminance step. The maximal scotopic response of rods and cones was measured in dark conditions (scotopic) with two flashes of 0.7 Hz and a light intensity of 20 cd s/m2, photopic cone responses were isolated in light conditions with a continuous background white light of 50 cd s/m2, with 10 flashes of 0.7 Hz and a light intensity of 20 cd s/m2.

Assay for ARSB Enzymatic Activity Evaluation in Serum

Serum ARSB activity was measured by an immune capture assay based on the use of a specific anti-hARSB polyclonal antibody (Covalab), as previously described [26]. Briefly, 96-well plates (Nunclon) were coated with 5 μg/ml in 0.1 M NaHCO₃ (100 μL/well) and incubated overnight (O/N) at 4° C. The following day, plates were blocked with 1% milk; after 2 hr of incubation, 50 μL standard and unknown samples (diluted 1:10) was added to each well. Plates were incubated at 4° C. O/N. The following day, 100 uL 5 mM 4-methylumbelliferylsulfate potassium salt (4-MUS; Sigma-Aldrich) substrate was added to each well and then incubated at 37° C. for 4 hr. The reaction was stopped by the addition of 100 uL stop solution/well (0.2 M glycine). Plates were shaken for 10 min at room temperature and fluorescence was read (excitation of 365 nm/emission of 460 nm) on a multiplate fluorimeter (Infinite F200; TECAN). Serum ARSB was determined based on a rhARSB (Naglazyme; BioMarin Europe) standard curve and is expressed as picograms per milliliter.

Quantitative Analysis of GAG Accumulation in Urine

Urine samples were diluted 1:50 in water to measure GAG content. was used for the GAG assay, as previously described [45]. GAG concentrations were determined on the basis of a dermatan sulfate standard curve (Sigma-Aldrich). Tissue GAGs were expressed as micrograms of GAG per milligram of protein. Urinary GAGs were normalized to creatinine content, which was measured with a creatinine assay kit (Quidel, San Diego, USA). Thus, the units of urinary GAGs are given in micrograms of GAG per micromole of creatinine. Urinary GAGs are reported as the percentage of AF control mice. At the latest time point of observation, the urinary GAG levels were averaged for each group.

Serum Albumin Quantification

Serum samples were analyzed with the mouse albumin ELISA kit (Abcam, Cambridge, UK) following manufacturer's instructions. Samples were diluted 30.000 times and albumin was determined on the basis of the competition of biotinylated albumin to bind to the plate. Serum albumin was expressed as milligrams of albumin per milliliter of serum.

Retinal Dissection

To isolate the temporal and nasal regions of the retina, after mice sacrifice, the temporal area of the eye was cauterized. After eye harvesting, eyes were dissected under a Leica M205FA Stereomicroscope (Leica, Wetzlar, Germany) to confirm GFP fluorescence of the temporal area. Temporal and nasal areas were dissected in two separate tubes.

Histology and Light and Fluorescence Microscopy

In Vitro Fluorescence Imaging

To evaluate DsRed expression after HITI in vitro, HEK293 cells, plated in 6-wells at a density of $1*10^6$ were transfected as previously described. Forty-eight hours post-transfection, cells were washed once with PBS, fixed for 10 min with 4% paraformaldehyde (PFA) in PBS, washed three times with PBS, and mounted with Vectashield with DAPI (Vector Lab, Peterborough, UK). Cells were analyzed under an Axio Observer Z1 (Carl Zeiss, Oberkochen, Germany) equipped with ZEN software (Carl Zeiss) and using appropriate excitation and detection settings for EGFP, DsRed, and DAPI.

Retinal Cryosections and Fluorescence Imaging

To evaluate DsRed expression in the retina after HITI in histological sections, C57BL/6J mice and large white pigs were injected subretinally with IRBP-Cas9 and donor DNA AAV vectors. One month later, mice and pigs were sacrificed and eyes were fixed in 4% paraformaldehyde overnight and infiltrated with 30% sucrose overnight; the cornea and the lens were then dissected, and the eyecups were embedded in optimal cutting temperature compound (O.C.T. matrix; Kaltek, Padua, Italy). Ten-micrometer-thick serial retinal cryosections were cut along the horizontal meridian, progressively distributed on slides, and mounted with Vectashield with DAPI (Vector Lab, Peterborough, UK). Then, cryosections were analyzed under the confocal LSM-700 microscope (Carl Zeiss, Oberkochen, Germany), using appropriate excitation and detection settings. For assessment of HITI efficiency in mouse retinal cryosections following AAV administration, the highest transduced area of two sections/eye was selected and acquired at 40 magnification and then analyzed using ImageJ software (http://rsbweb.nih.gov/ij/). A minimum of 500 PRs, identified by DAPI staining, were counted for each image. PRs with signal compatible with DsRed expression were unequivocally identified based on their shape as observed in z-stacks of the analyzed sections, as well as the presence of DsRed+ outer segments.

Evaluation of Retinal Outer Nuclear Layer Thickness

To evaluate retinal outer nuclear layer thickness after HITI treatment, P23H mice were injected subretinally with IRBP-Cas9 and donor DNA AAV vectors. Three months later, mice were sacrificed and eyes were fixed in Davidson's fixative (deionized water, 10% acetic acid, % 20% formalin, 35% ethanol) overnight dehydration in serial ethanols and then embedded in paraffin blocks. Ten-micrometer thick microsections were cut along the horizontal meridian, progressively distributed on slides and stained with hematoxylin-eosin. Then, the sections were analyzed under the microscope (Leica Microsystems GmbH; DM5000) and acquired at 20× magnification. For each eye one image from the temporal injected side of a slice in the central region of the eye was used for the analysis. Three measurements of the ONL thickness were taken in each image, masked to the genotype/treatment group, using the "freehand line" tool of the ImageJ software.

Liver Cryosections and Fluorescence Imaging

To evaluate DsRed expression in the liver after HITI, C57BL/6J mice were injected either at p2 or at 4 weeks of age, and sacrificed one month after injection by cardiac perfusion. Liver was harvested and photographed in a Leica Stereomicroscope (Leica, Wetzlar, Germany) at a 25× magnification. Then, a small piece of each lobe was dissected, and all pieces were fixed in 4% paraformaldehyde overnight and infiltrated with 15% sucrose overday and 30% sucrose overnight before being included in O.C.T. matrix (Kaltek, Padua, Italy) for cryosectioning. Five-micrometer-thick retinal cryosections were cut and distributed on slides, and mounted with Vectashield with DAPI (Vector Lab, Peterborough, UK). Then, cryosections were analyzed under the confocal LSM-700 microscope (Carl Zeiss, Oberkochen, Germany), using appropriate excitation and detection settings. For assessment of HITI efficiency in mouse liver cryosections, 3 images of each liver were acquired ad 20 magnification and then analyzed using ImageJ software (http://rsbweb.nih.gov/ij/). A minimum of 850 hepatocytes, identified by DAPI staining of the nucleus, was counted for each image. Hepatocytes with signal compatible with DsRed expression were unequivocally identified based on their shape.

DNA Cleavage Analysis

DNA Extraction

Samples (GFP+ or GFP+/DsRed+ sorted HEK293 cells, retinal tissue or liver tissue) were lysed in commercial lysis buffer (GeneArt™ Genomic Cleavage Detection Kit, Invitrogen, Carlsbad, California, United States) or conventional lysis buffer for DNA extraction from tissue (400 mM NaCl, 1% SDS, 20 mM TRIS-CL (pH 8.0), 5 mM EDTA (pH 8.0)) respectively. Lysis buffers were supplemented with proteinase K, which was inactivated after lysis for 15 minutes at 80 degrees. 50 to 200 ng of DNA were used for PCR amplification of the region comprising the Cas9 target site (the first exon of RHO) from the pCMV-mRho-P23H plasmid or from the mouse genome, respectively. Primers used are shown in Table 4:

TABLE 4

Primers used to generate PCR fragments for Surveyor Assay and sequencing of INDELs.

| Primer name | Sequence | Sequence ID NO: |
|---|---|---|
| pCMV-mRho-Indel Fwd: | 5' CCATGGTGATGCGGTTTTGG 3' | 38 |
| pCMV-mRho-Indel Rev: | 5' ATGTAGTTGAGGGGTGTGCG 3' | 39 |
| mRho-HITI-Indel Fwd: | 5' CAGTGCCTGGAGTTGCGCTG 3' | 40 |
| mRho-HITI-Indel Rev: | 5' GGGCCCAAAGACGAAGTAGCC 3' | 41 |
| pRHO-Indel-Fwd: | 5' AGGCCTCAGCAGCATCCTTG 3' | 42 |
| pRHO-Indel-Rev: | 5' GTGGTGGTGAAGCCTCCGAA 3' | 43 |
| mAlb-HITI-Indel Fwd: | 5' ATTACGGTCTCATAGGGCCTGC 3' | 44 |
| mAlb-HITI-Indel Rev: | 5' GCACACATTTCTACTGGACAGCA 3' | 45 |

P347S-Indel primers produced a 444 bp PCR product. pCMV-mRho-Indel primers produced a 634 bp PCR product. mRho-HITI-Indel primers produced a 426 bp PCR product. pRHO-Indel primers produced a 341 bp PCR product. mAlb-HITI-Indel primers produced a 592 bp PCR product.

Surveyor Assay 1-3 uL of the PCR products (according to PCR efficiency) was used for Surveyor Assay, following the GeneArt™ Genomic Cleavage Detection Kit manufacturer's recommendations. In short, DNA was de-annealed at 99° C. and re-annealed by a slow temperature gradient in a thermocycler. After re-annealing, 1 µL of Detection Enzyme (T7Endonuclease) was added, and samples were incubated for an hour at 37 degrees. After incubation, samples were run in a 2% agarose gel in order to detect DNA cleavage products resulting from INDEL presence.

Tracking of INDELs by Decomposition mRho-HITI-Indel, pRHO-Indel and mAlb-HITI-Indel PCR products were also used for Sanger sequencing. Sequences were then used for TIDE software (https://tide.deskgen.com/) analysis of INDEL frequency.

HITI Junction Characterization

Junction PCR Amplification

DNA extracted from retina or liver tissue was used for PCR amplification of HITI junctions. Both 5' and 3' junctions of integration were amplified. For the 5' junction, I used a forward primer recognizing the region upstream the first exon of the mRho or mAlb gene and a reverse primer recognizing the DsRed coding sequence. For the 3' junction we designed a forward primer recognizing the bGH polyA sequence of the donor DNA, and a reverse primer recognizing the first Exon of mRho or the second exon of mAlb, after the cleavage site. Table 5 shows the primers used.

TABLE 5

Primers used for HITI junction amplification.

| Primer name | Sequence | Sequence ID NO |
|---|---|---|
| mRho HITI 5' junction Fwd | 5' CAGTGCCTGGAGTTGCGCTG 3' | 46 |
| mRho HITI 5' junction Rev | 5' GGCTTGATGACGTTCTCAGTGC 3' | 47 |
| mRho HITI 3' junction Fwd | 5' CGACCTGCAGAAGCTTGGATCT 3' | 48 |
| mRho HITI 3' junction Rev | 5' GGGCCCAAAGACGAAGTAGCC 3' | 49 |
| mAlb HITI 5' junction Fwd | 5' GCCTGCTCGACCATGCTATACT 3' | 50 |
| mAlb HITI 5' junction Rev | 5' CCTTGGAGCCGTACTGGAACTG 3' | 51 |
| mAlb HITI 3' junction Fwd | 5' CGACCTGCAGAAGCTTGGATCT 3' | 52 |
| mAlb HITI 3' junction Rev | 5' TCTCTGGCTGCCACATTGCT 3' | 53 |

5' junction primers produced a 663 bp PCR product. 3' junction primers produced a 455 bp PCR product. Both PCR products were cloned into PCR-Blunt II-TOPO (Invitrogen, Carlsbad, California, United States) and single clones were sequenced to confirm the identity of the PCR products before NGS analysis.

Library Preparation and Next-Generation Sequencing:

For library preparation a total of 47.5 ng of DNA from HITI junction PCR products was used as input for the synthesis of a DNA library with the SMART-Seq v4 Ultra Low Input RNA Kit for sequencing (Takara Bio USA, Mountain View, CA, USA). Manufacturer suggested protocol was followed, with minor modifications. Seventyfive pg of cDNA generated with SMART-Seq v4 Kit were used for library preparation using the NEXTERA XT DNA Library Preparation kit (Illumina, San Diego, CA, USA), following the suggested protocol. Quality of libraries was assessed by using Bioanalyzer DNA Analysis on a DNA high sensitivity chip (Agilent Technologies, Santa Clara, CA, USA), and quantified by using Qubit 4 Fluorometer (Thermo Fisher Scientific, Waltham, MA, USA). Samples were sequenced using NextSeq 500/550 Mid Output v2 kit in a 150+150 paired-end run. The data were deposited in GEO: GSE10717. Illumina base call raw data were converted in fastq file through bcl2fastq software (version v2.20.0.422, Illumina, San Diego, USA). Sequence reads were trimmed using Cutadapt software to reduce reads length from 600 bp to 350 bp. The custom reference sequence was built by predicting the NHEJ-mediated integration mediated by Cas9 in the locus of interest. The cleaved donor DNA sequence was inserted between the 3 and 4 bases of the gRNA sequence. All sequencing reads were aligned with their respective reference sequence using BWASW software and INDELs at each position respective to the cleavage site were quantified. Alignment was performed using BWA-SW software (MIT, Boston, USA). Total number of indel and specific nucleotide counts contained in aligned bam files were estimated with deepSNV package. Length of INDELs was obtained from BAM CIGAR strings through an ad-hoc R algorithm. INDELs with a frequency lower than 0.5% of reads were not included in graphical representations of INDEL length.

Example 1: HITI in the Retina

Gene Therapy of Dominant Retinitis Pigmentosa by HITI in Photoreceptors

Figure 1:
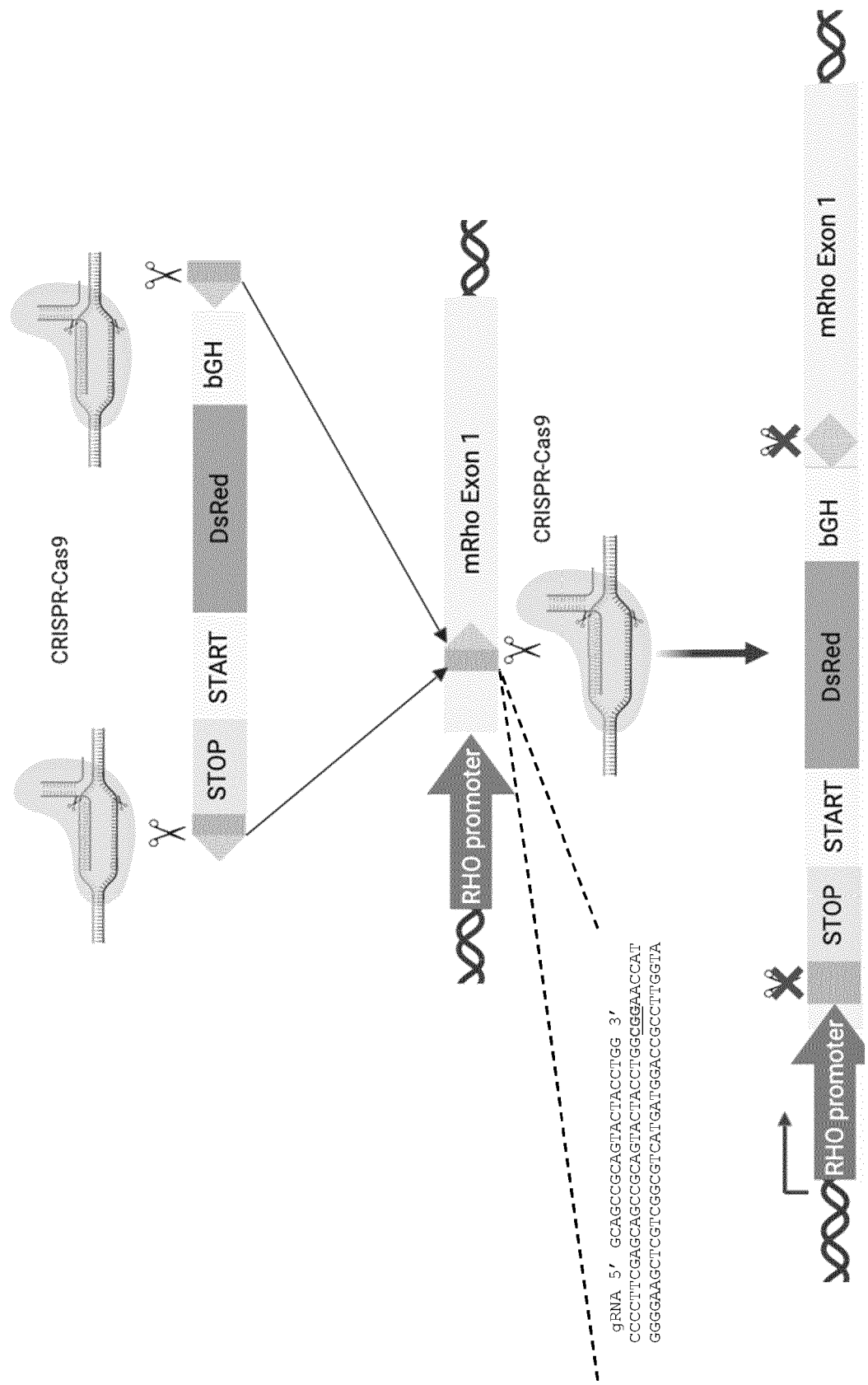
FIG. 1. HITI design to target the RHO locus: yellow rectangle and blue triangle depict the two parts of the gRNA target sequence (upstream and downstream of Cas9 cleavage). Scissors represent Cas9-mediated DSBs. Crossed scissors represent inability of Cas9 to recognize and cleave the sequence. PAM sequence is depicted in red and underlined. STOP: STOP codons, START: translation start site, bGH: bovine Growth Hormone polyA.

Most efforts have been historically focused on using AAV to supply a correct copy of the otherwise mutated gene in recessive conditions due to a loss of function. However, in adRP due to RHO mutations (RP4), knockout of the RHO mutant allele rather than addition a correct RHO copy is required to achieve a therapeutic effect [47, 48]. Different strategies have been used to knock down mutant RHO in an allele-independent or allele-specific manner. Allele-independent strategies include RHO silencing with short hairpin RNAs coupled with AAV-mediated RHO expression [49-51] and RHO silencing using an inactive transcription factor [21]. Allele-specific strategies include allele-specific silencing and allele-specific genome editing. Genome editing with CRISPR/Cas9 (Cas9) has emerged in the last years as a versatile and efficient strategy for the treatment of dominant IRDs [4, 48]. Since PRs are terminally-differentiated cells, the efficiency of HDR correction after cleavage is low [10, 52]. NHEJ, on the other hand, is the main DNA repair mechanism in PRs. The resulting INDELs are normally used to knock out a targeted gene [3]. This has been used to induce allele-specific RHO knockout in the retina of various models of Retinitis Pigmentosa. Two different groups targeted the prevalent P23H mutation in the mRho and the RHO locus respectively. In both cases, allele-specific genome editing in the retina of mouse models achieved partial correction of RP4 [23, 53]. Similarly, Bakondi et al. targeted the Ser334-Ter mutation in mRho in a transgenic rat model [22]. Yu et al. targeted the NRL locus and observed prevention of retinal degeneration in mice [54]. This method has also been used ex vivo by Burnright et al. to generate gene-corrected induced pluripotent stem cells, which could potentially be used for retinal therapy [55]. However, this approach is limited by both the availability of gRNA/PAM combinations at the GOF allele, and is mutation-specific, which limits its clinical applicability due to the genetic heterogeneity of RP4 [19, 48]. Considering the limitations of allele-specific knock-out for the treatment of diseases caused by gain of function mutations like for example Dominant Retinitis Pigmentosa, the present inventors aimed at developing an allele-independent approach, aimed at silencing both endogenous alleles and replacing them with a functional coding sequence. This would result particularly advantageous when targeting non-dividing cells. The inventors decided to achieve gene correction in photoreceptors as proof of concept for the strategy. As HDR is expected to be very inefficient in differentiated neurons, the inventors developed a HITI system to replace the mutant rhodopsin with a WT one. For this, the inventors designed a gRNA against the $1^{st}$ exon of mRHO that would recognize both mutant and WT alleles. Then, the inventors generated a donor DNA sequence carrying STOP codons in the 3 possible frames, a translation initiation sequence (TIS), the reporter gene dsRED and the BgH polyA. This donor DNA sequence is flanked at 5' and 3' by the same gRNA target site that the gRNA against mRHO recognizes, but inverted (eg an inverted target site) (FIG. 1). This allows directional integration, because in the case that the donor DNA was integrated in the opposite direction Cas9 would be able to recognize again its target site and cleave it. Upon integration in the correct orientation, Cas9 would no longer be able to cleave the target site.

The present inventors decided to test both the kozak and the IRES sequences in vivo in a mouse model. To test HITI in the mRho locus in vitro the present inventors generated plasmids encoding for two versions of the donor DNA with different TIS: one carried a kozak sequence while the other carried a small synthetic 50 bp IRES. Each donor DNA was cloned with the Rho-specific gRNA and a scramble gRNA that doesn't recognize any sequence in the mouse genome. This plasmid was transfected together with the CBh-Sp-Cas9-2A-EGFP plasmid, as well as another plasmid encoding for mRhoP23H under control of the CMV promoter (FIG. 2A). This CMV-mRhoP23H plasmid was used as a template for Cas9 cleavage and donor DNA integration. The present inventors expected that, after HITI occurred, DsRed would be expressed due to the promotorial action of CMV. Forty-eight hours after transfection, fluorescence microscopy showed abundant presence of DsRed+ cells only in those cells treated with the gRNA and none in those treated with scramble (FIG. 2B).

Since Cas9-transfected cells expressed EGFP+, the present inventors used FACS sorting to determine the ratio between DsRed+ and EGFP+ cells in order to assess whether kozak or IRES achieved a higher expression of DsRed or a higher efficiency of integration (FIG. 2C). No significant differences were found between kozak and IRES, although kozak seemed to perform slightly better (47% compared to 34%) (FIG. 2D). Again, FACS demonstrated no presence of DsRed+ cells in those treated with scramble, confirming that DsRed positivity was dependent on gRNA presence.

Figure 3:
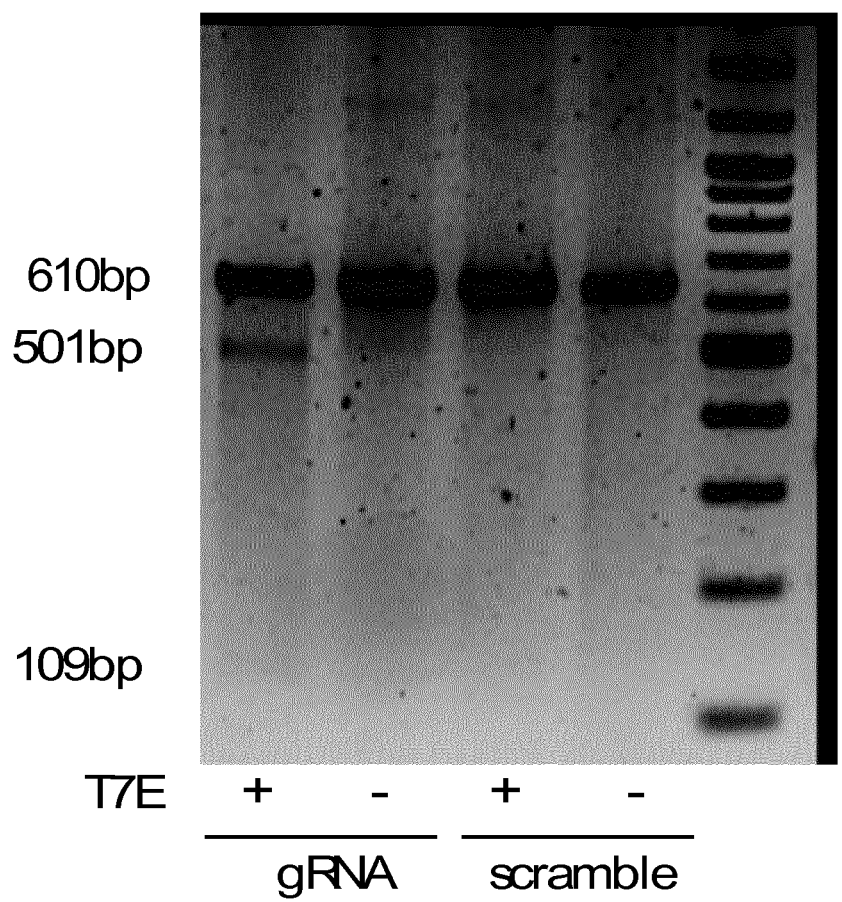
FIG. 3: Surveyor assay in the mRho gene: Expected band sizes are depicted. T7E: T7 Endonuclease I treatment.

To confirm that DsRed expression was a result of Cas9 cleavage in the template CMV-RhoP23H plasmid, the present inventors extracted DNA from EGFP+ sorted cells and PCR-amplified the region of the plasmid around the gRNA target site. Surveyor Assay showed presence of INDELs only in cells treated with gRNA (FIG. 3), which correlated with DsRed expression.

Figure 11:
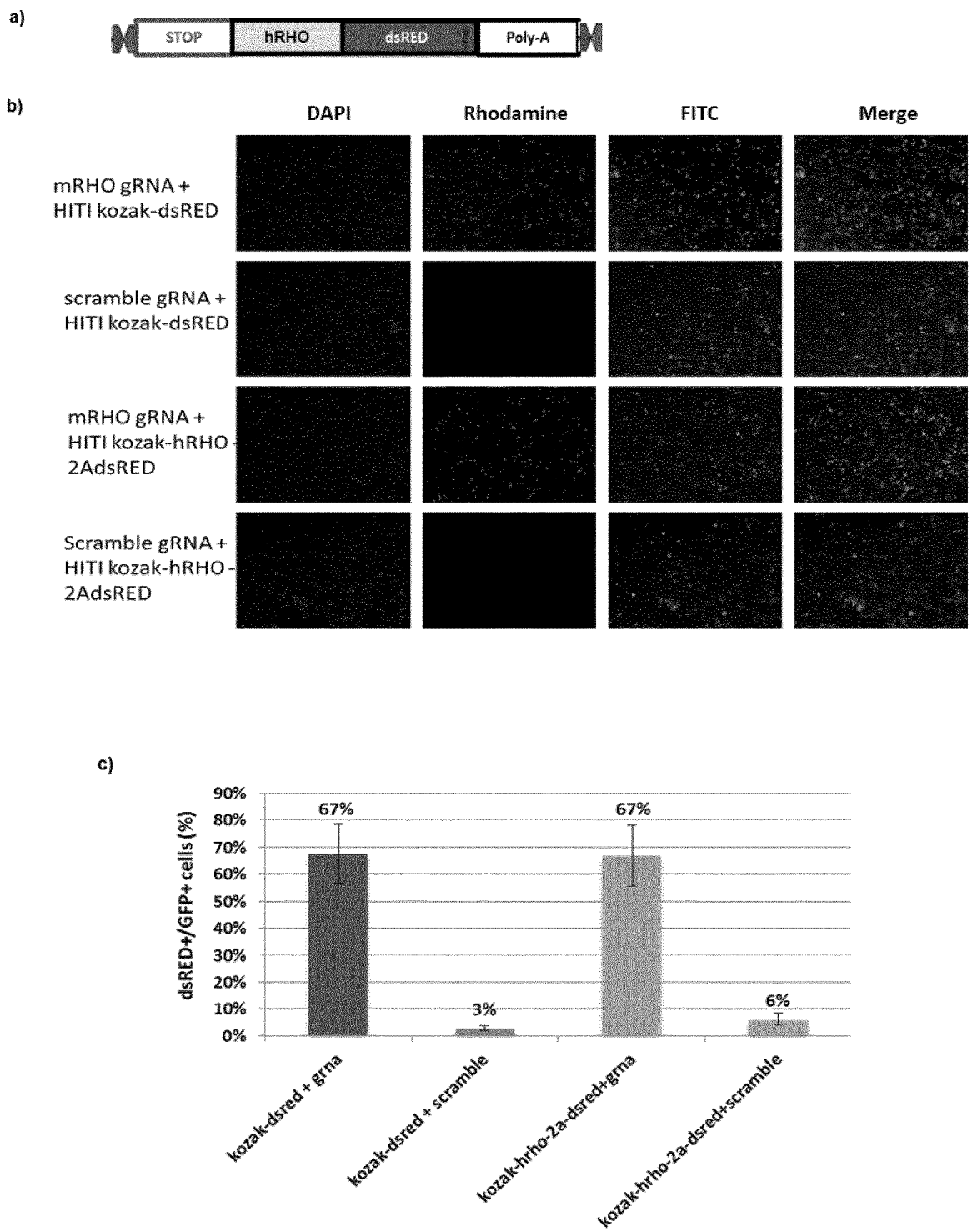
FIG. 11. Size of construct and T2A sequence don't affect efficiency of in vitro HITI.

The present inventors also generated a donor DNA carrying hRHO-T2A-dsRED (FIG. 11A). This donor DNA should be able to replace the mRho gene with a copy of the human rhodopsin, as well as produce the expression of dsRED in the corrected photoreceptors. The present inventors tested this donor DNA in vitro comparing it to the original dsRED donor DNA, in order to determine whether the efficiency of HITI varies with the different of size of the insert. Even if hRHO-T2A-dsRED donor DNA is twice the length of the dsRED donor (2.4 kB instead of 1.2 kB), fluorescence imaging (FIG. 11B) and FACS sorting (FIG. 11C) showed exactly the same efficiency of integration with both inserts (67%), and again no integration when the Scramble was used instead of the mRho-specific gRNA.

Figure 4:
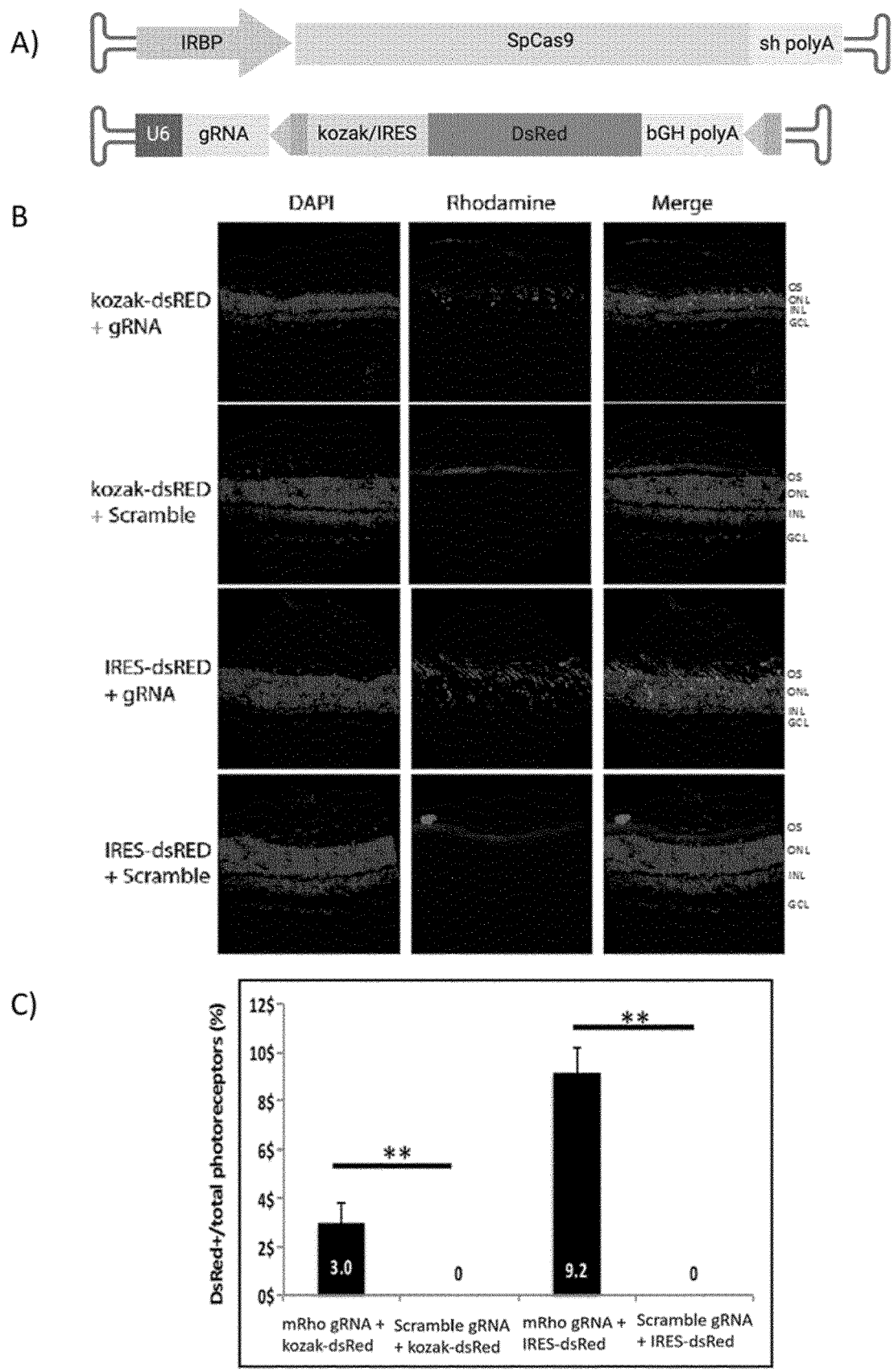
FIG. 4. In vivo HITI in the mouse retina. A) Schematic depiction of AAVs used for HITI in the mouse retina: IRBP: interphotoreceptor retinoid-binding protein promoter. shpolyA: short synthetic polyA. bGH: bovine growth hormone polyA. yellow rectangle and blue triangle depict the two parts of the gRNA target sequence (upstream and downstream of Cas9 cleavage). ITR sequences are depicted as blue loops. B) Fluorescence microscopy of retinal cryosections: Eyes were harvested 30 days after injection and fixed overnight in 4% PFA. Eyes were treated with 30% sucrose for 6 h and then included in optimal cooling medium. 10 μm sections were made and stained with DAPI-containing mounting medium. C) Quantification of DsRed+ photoreceptors to assess HITI efficiency. **=p<0.01

In order to assess whether HITI is feasible in mouse photoreceptors, the present inventors generated AAV2/8 vectors carrying the donor DNA with the kozak or the IRES sequence, as well as the gRNA expression cassette for the mRho-specific gRNA or the scramble gRNA (FIG. 4A). These vectors were injected together with the already described IRBP-SpCas9-shpolyA vector. Subretinal injection of $2,5*10^9$ GC/eye of each vector was performed in 4-week old C57BL/6 mice. One month after injection, fluorescence microscopy of retinal cryosections showed presence of DsRed+ photoreceptors near the area of injection only in gRNA-treated retinae and not in scramble- treated retinae. Interestingly, IRES seemed to perform significantly better than kozak in vivo (9,2% compared to 3%) (FIG. 4B,C).

Figure 5:
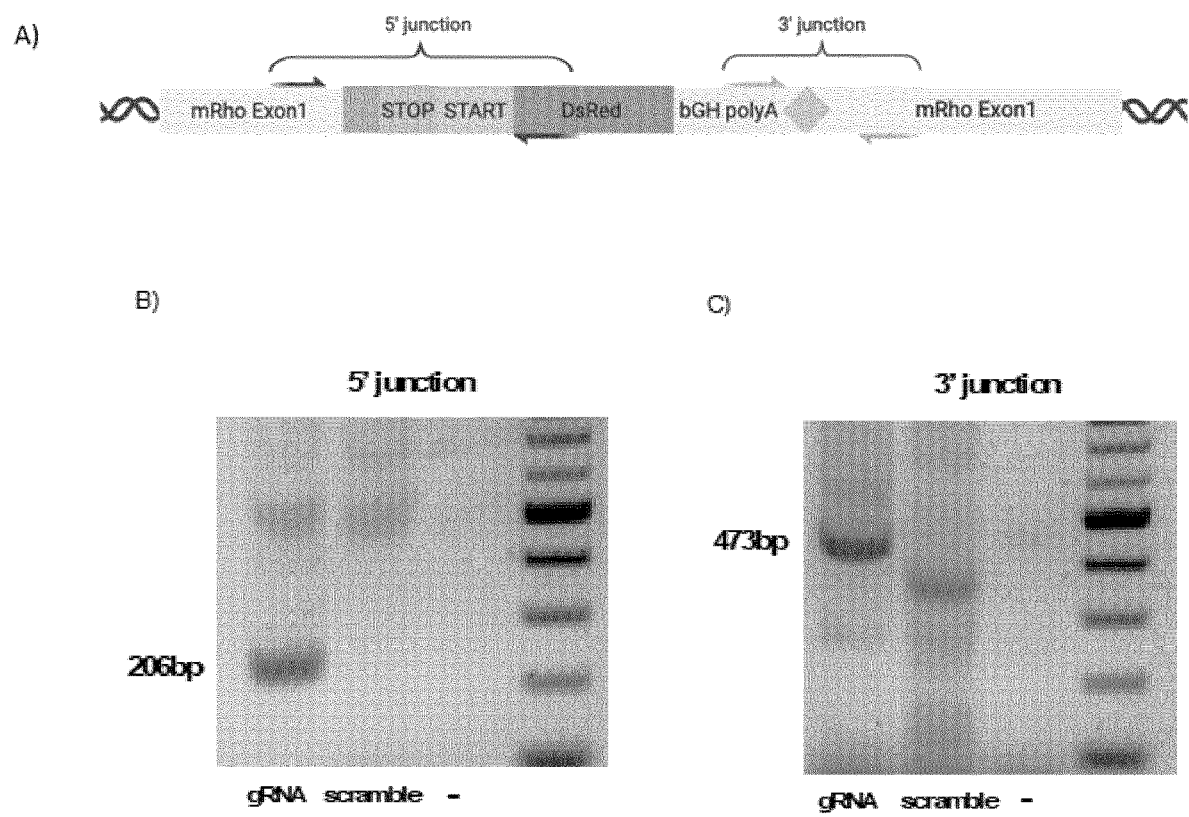
FIG. 5. HITI Junction amplification. DNA was extracted from the temporal side of the retina and used for PCR amplification of the HITI junctions. A) Scheme depicting primer design to amplify 5' and 3' junctions. B) 5' junction amplification. Expected fragment size was 206 bp. PCR amplification was observed only in one gRNA-treated retina. C) 3' junction amplification. Expected fragment size was 473 bp. PCR amplification was observed only in one gRNA-treated retina.

Characterization of HITI in Photoreceptors:

In order to better understand how precise HITI can be in photoreceptors, the present inventors designed two primer pairs to amplify the 5' and 3' junctions of integration (FIG. 5A). Both primer pairs were able to amplify a PCR product of the expected size only in DNA extracted from a gRNA-treated retina, and not in the DNA from a scramble-treated retina. (FIG. 5B). These PCR fragments were subsequently used for NGS analysis. Between 1,5 and 3 million reads were obtained for each junction. Analysis of NGS reads showed low presence of insertions (5%) and deletions (15%) in the 5' junction, especially in the Cas9 cleavage site (position 1) (FIG. 6). Most common deletions ranged between 1 and 9 bp. Interestingly, the present inventors observed two common insertions of 40 bp and 48 bp sequences that the present inventors identified as being part of the AAV ITR sequences (FIG. 6). Differently, the 3' junction presented surprisingly abundant 1 bp insertions (71%), which were mostly cytosine or thymine, some 2 bp insertions and almost no presence of deletions (FIG. 6).

Additionally, DNA extracted from mouse retinas was used for NGS analysis of potential off-target HITI integrations. Probes targeting DsRed were used to enrich for sequences in the genome that included the donor DNA. Surprisingly, no genomic sequences containing the full donor DNA were found, even in the RHO locus. This could be explained by the low number of reads and the low efficiency of integration observed, as well as the inability to select only DsRed+ photoreceptors for DNA extraction, thus diluting the edited genomes in the total DNA extracted.

HITI is Efficient in Pig Photoreceptors:

In order to characterize HITI efficiency in an animal model that better recapitulates the anatomy of the human eye, the present inventors decided to use the pig eye, which is a relevant preclinical model. For this, the present inventors designed a gRNA specific for the first exon of the pig rhodopsin (pRho) gene, and donor DNAs identical to the ones used in previous experiments but flanked by pRho target sites. With these, the present inventors generated the same types of vectors depicted in FIG. 14. Subretinal injection of $2,5*10^{11}$GC/bleb of each vector was performed in 3-month-old large white pigs in 2 blebs per each retina. One month after injection, fluorescence microscopy of retinal cryosections showed presence of DsRed+ photoreceptors in the area of injection in gRNA-treated retinae and not in scramble-treated retinae (FIG. 7A). Again, IRES performed significantly better than kozak (FIG. 7B).

In order to determine whether DsRed expression correlated to Cas9-mediated DSBs in the pRho gene, the present inventors extracted genomic DNA from pig retinae and RPE and performed Surveyor Assay. The present inventors observed presence of INDELs only in gRNA-treated retinae and not in scramble-treated retinae. As the present inventors expected, INDELs were present only in the retina and absent in the RPE, which is consistent with photoreceptor-specific expression of Cas9 by the IRBP promoter (FIG. 8A). In order to better characterize the efficiency of cleavage, the inventors used TIDE analysis, for which the same PCR fragments used for Surveyor Assay were used for SANGER sequencing. Resulting chromatograms were used as input for the TIDE software. The chromatogram from an RPE sample was used as a negative control, and other chromatograms were compared to it. TIDE showed 22% efficiency of cleavage in gRNA-treated retinae and negligible INDELs in scramble-treated retinae (FIG. 8B)

HITI at the mRho Locus Partially Restores Vision in a Mouse Model of AdRP:

To assess whether HITI efficiency was enough to correct the AdRP phenotype, the present inventors generated two AAV2/8 vectors carrying a donor DNA with the IRES sequence and the coding sequence of the hRHO gene (hRHO CDS), as well as the mRho or scramble gRNA (FIG. 9A). These vectors were injected together with the AAV2/8-IRBP-SpCas9 vector. Twenty-day old P23H+/− mice received subretinal injection of $2,5*10^9$GC of each vector. At p60, ERG analysis showed small but significant improvement at the two highest light stimuli analyzed (FIG. 9B). However, the observed improvement was only transient and disappeared at p90, suggesting that the efficiency of correction was not enough to counteract the fast retinal degeneration observed in this animal model. Indeed, histological analysis at p120 showed no significant difference in retinal outer nuclear layer (ONL) thickness between gRNA and scramble groups (FIG. 10A,B). This is consistent with reports that degeneration of the surrounding retinal structure can cause the death of functioning photoreceptors [56].

HITI can be Performed on the Human RHO Gene:

An important issue with our approach is that the present inventors have targeted murine and porcine Rho sequences. For clinical applicability, the human RHO gene should be targeted. The present inventors developed a gRNA and donor DNA to target the human RHO gene. The present inventors tested this approach in vitro in HEK-293 cells. In order to optimize the translation of dsRED from the mRNA the inventors tested two different translation initiation sequences: a kozak sequence and a small 50-bp IRES sequence [38]. The inventors also tested the ribosomal-skipping T2A sequence (FIG. 11A). HEK293 cells were transfected with a plasmid encoding hRHO under control of the CMV promoter, a second plasmid encoding Cas9-GFP with the hRHO-specific gRNA and a third plasmid carrying the donor DNA. Fluorescence microscopy and FACS sorting 72 hours after transfection showed that both IRES and T2A modestly outperform kozak (39,4% and 40,3% against 35,6%), especially regarding the intensity of dsRED (FIG. 11B, C).

Hiti in the Albumin Locus for Stable Liver Expression of Therapeutic Proteins

Figure 12:
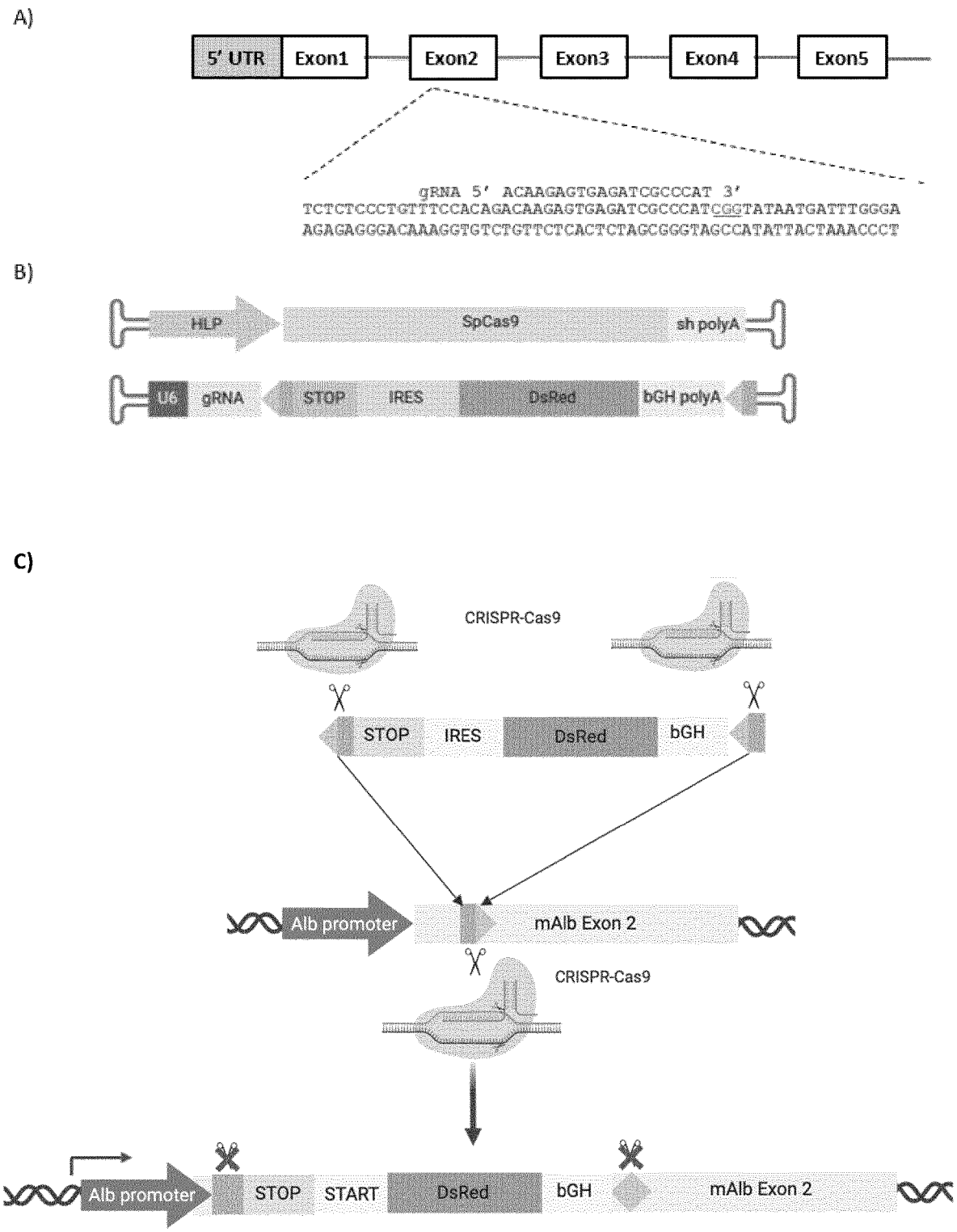
FIG. 12. Schematic depiction of HITI design for integration in the Albumin locus and of gRNA and viral vectors used: A) Design of the gRNA specific for the 2nd intron of the murine Albumin gene. PAM sequence is depicted in red. B) Schematic depiction of the AAV2/8 vectors used for HITI in the mouse liver. Donor DNA is flanked by the same gRNA target sequences. Donor DNA contains STOP codons in the 3 frames, a translation START sequence (kozak), the reporter gene DsRed and the bGH poly-A. C) Depiction of the expected HITI after Cas9 and donor DNA delivery. Scissors represent Cas9-mediated DBSs. Crossed scissors represent inability of Cas9 to recognize target sites.

Liver-directed gene therapy with AAVs has some limitations due to vector dilution during hepatocyte cell division. This prevents neonatal or pediatric treatment of several inherited diseases, which could avoid or at least modulate some of the most severe symptoms. For this and other reasons, the field of genome editing has focused on developing strategies to achieve stable expression of transgenes from the liver. Two clinical trials using ZFN-mediated HDR at the albumin locus for expression of therapeutic proteins have been approved for MPSI and MPSII respectively (Trial numbers NCT02702115 and NCT03041324). This approach targeting the albumin locus as a "safe harbor" for integration and expression of therapeutic proteins from the liver has been applied to animal models of several other diseases [9, 57-59], and shows great promise as an alternative to conventional GT that could be used in pediatric patients. The present invention is aimed at converting the liver in a factory for the production and stable secretion of the enzyme ARSB, for treatment of MPSVI. The present inventors designed a gRNA specific for the 2nd exon of the mouse albumin gene (FIG. 12A). Then the present inventors generated two AAV2/8 vectors: the first vector encoded for SpCas9 under control of the liver-specific hybrid liver promoter (HLP) and with a short synthetic polyA (sh polyA) [60]. The second vector encoded for a gRNA expression cassette and the donor DNA. The Alb-specific or scramble gRNA was under control of the U6 promoter. The donor DNA was flanked by the inverted albumin gRNA target sites, comprising the PAM. The donor DNA contained STOP codons in all 3 frames, a kozak signal to drive the start of translation, the transgene DsRed and the bGH polyA (FIG. 12B). The present inventors expected that, after intravenous delivery, both vectors would reach the liver and, upon expression of Cas9, it would cleave both the Albumin locus and the donor DNA, causing NHEJ-mediated integration of the donor DNA in the albumin locus (FIG. 12C).

HITI is Feasible and Efficient in Mouse Hepatocytes

Figure 13:
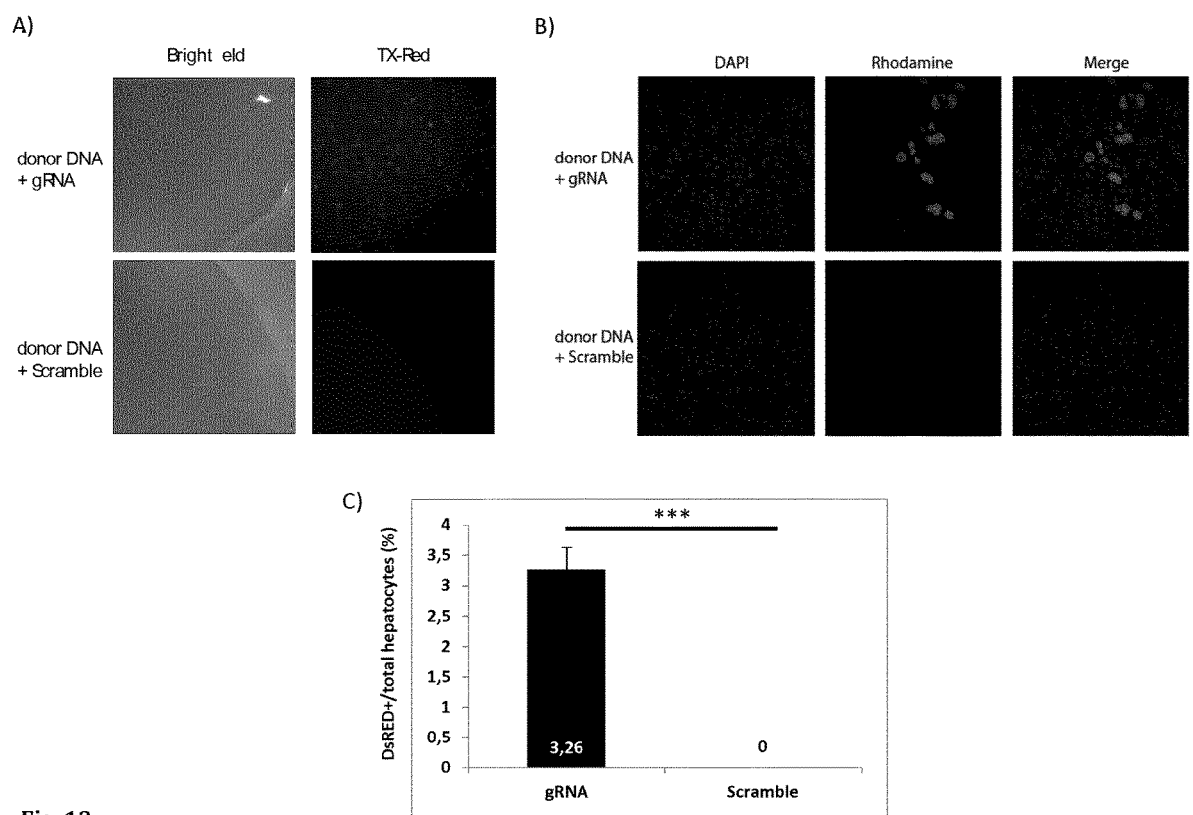
FIG. 13. Targeted integration of DsRed in the Alb locus in mouse hepatocytes. $4*10^{13}$GC/Kg of each vector were administered intravenously through the temporal vein at p2.

To assess whether HITI at the albumin locus in neonatal mice was feasible, 2-day old C57BL/6 mice received intravenous injection of AAV2/8 (dose of each vector: $4*10^{13}$ GC/Kg). Livers were harvested one month after injection and observed under a fluorescence stereomicroscope. gRNA-treated livers showed abundant presence of DsRed+ foci, which was consistent with the expected clonal expansion of hepatocytes after injection (FIG. 13A). Scramble-treated livers showed no DsRed+ foci. Fluorescence microscopy of liver cryosections showed 3,26% of DsRed+ hepatocytes in livers treated with gRNA, and their absence in scramble-treated livers (FIG. 13B, C). Interestingly, DsRed+ hepatocytes seemed to form clusters consistent with clonal expansion. (FIG. 13B). The present inventors also generated AAV2/8 vectors carrying an IRES-DsRed donor DNA, which were injected following the same conditions. In this case, both the gRNA-treated and scramble-treated livers showed presence of DsRed+ hepatocytes, possibly due to an hepatocyte-restricted promotorial activity of the IRES sequence that was confirmed in Hepa1.6 cells (data not shown). For this reason, the present inventors only used kozak as a START signal for the following experiments.

Cas9 INDEL Frequency in the Albumin Locus in Mouse Hepatocytes

In order to correlate the presence of DsRed+ hepatocytes to Cas9-mediated cleavage of the albumin locus, the present inventors extracted DNA from injected livers and performed PCR amplification of the region around the Cas9 target site. PCR fragments were subsequently used for Surveyor Assay, which showed presence of INDELs only in gRNA-treated livers and not in scramble-treated livers (FIG. 14A). The present inventors then used TIDE analysis to assess the frequency and types of INDELs generated. The present inventors observed 9,9% INDEL efficiency in gRNA-treated livers, and negligible INDELs in scramble-treated of PBS-injected livers (FIG. 14B). Interestingly, even if most deletions due to NHEJ repair are supposed to be between 1 and 6 bp, in all gRNA-treated livers the present inventors observed a very frequent 7 bp deletion (FIG. 20A, blue arrow). Sequence analysis based in the models used by Shen et al. for INDEL prediction allowed me to identify two small 4 bp microhomology regions at both sides of the DSB which cause efficient MMEJ repair via this 7 bp deletion (FIG. 14C).

Characterization of HITI Precision in the Alb Locus of Mouse Hepatocytes:

Next, the present inventors designed PCR primers in order to amplify the 5' and 3' junctions after targeted integration. For the 5' junction, the Fwd primer recognized the $1^{st}$ intron of albumin, while the Rev primer recognized the donor DNA. For the 3' junction, the Fwd primer recognized the donor DNA while the Rev primer recognized the 2nd exon of albumin (FIG. 15A). In both cases, the present inventors observed amplification of a PCR product of the expected size only in gRNA-treated livers, consistent with presence of both INDELs and DsRed+ hepatocytes. No PCR products were amplified from DNA extracted from scramble-treated livers (FIG. 15B, C). The amplified PCR products were then purified used for next-generation sequencing analysis. Between 80.000 and 350.000 reads were obtained for each junction. Consistently with data from bacterial clones sequencing, in the 5' junction the present inventors observed low frequency of insertions and 38% frequency of deletions (FIG. 16A). Most insertions were of 1 bp, while deletions mostly ranged from 1 to 47 bp, with 1 bp deletions being the most common (FIG. 16C). In the 3' junction, the present inventors observed a high frequency of 1 bp insertions at the cleavage site (FIG. 16B,C), as well as some 2 bp insertions. In total, deletions were more frequent (52%), but also more distributed around the cleavage site, ranging from 1 bp to 38 bp from the cleavage site. (FIG. 16B). Most common deletions were between 1 and 18 bp, and the present inventors also identified a common 42 bp deletion.

HITI is Efficient and Dose-Dependent in the Adult Mouse Liver

Next, the present inventors wanted to assess whether HITI could also be performed in the liver of adult mice at a similar efficiency as in neonatal mice. For this reason, 4-week old C57BL/6 mice were injected intravenously with the same $4*10^{13}$GC/Kg dose used in neonatal mice (High Dose, HD) or a lower dose of $1,3*10^{13}$GC/kg (Low Dose, LD) of each vector. One month after injection the present inventors used fluorescence microscopy to assess presence of DsRed+ hepatocytes. The present inventors observed 2,76% of DsRed+ hepatocytes in the HD group and 1,25% in the LD group. DsRed+ hepatocytes were absent in scramble-treated livers independently of the vector dose used (FIG. 17A, B). However, HITI efficiency was in both cases lower than achieved with neonatal injection. This could be explained by better transduction efficiency in the neonatal liver or by the clonal expansion of the modified hepatocytes, although theoretically HITI of DsRed in the albumin locus should confer no selective advantage.

ARSB Expression from the Albumin Locus Partially Rescues the MPSVI Phenotype

Next, the present inventors decided to use HITI to integrate the coding sequence or arylsulfatase B (ARSB) in the albumin locus of MPSVI mice. For that, the present inventors used the already mentioned AAV2/8-HLP-Cas9-shpolyA vector, and the present inventors generated another vector carrying the expression cassette for the Albumin-specific or scramble gRNA, as well as a target flanked donor DNA encoding for STOP signals in the 3 frames, a kozak signal to start translation, the coding sequence of ARSB and the bGH polyA (FIG. 18). Considering the deletions the present inventors had observed in the 3' junction using the DsRed donor DNA, the present inventors added a 200 bp Stuffer DNA between the bGH and the Cas9 target site in order to avoid unwanted deletions in the bGH sequence. Two-day-old MPSVI-/- mice were injected intravenously with $6*10^{13}$GC/Kg of each vector. Monthly measuring of blood levels or ARSB showed presence of ARSB only in the serum of gRNA-treated mice, while ARSB was completely absent in scramble-treated mice. All gRNA treated mice presented ARSB expression at 1 month after injection (FIG. 19). While 2 mice showed a relative decrease in ARSB levels between the first and second months, ARSB levels were stable after the second month. The levels obtained ranged between 1/6 and 1/3 of the levels obtained after injection of $2*10^{11}$GC/Kg of an AAV2/8-TBG-ARSB of the endogenous levels in unaffected mice, with the best performing mouse reaching 2572 pg/mL (FIG. 19). Since the levels obtained after injection of $2*10^{11}$GC/Kg of an AAV2/8-TBG-ARSB vector in adult MPSVI mice were higher than what was observed with the HITI approach, the inventors decided to test whether neonatal injection of this same vector at the same dose used for HITI could achieve higher levels of ARSB expression. For this, neonatal MPSVI-/- mice were injected with $6*10^{13}$GC/Kg of a AAV8-TBG-ARSB vector. As expected, ARSB levels at p30 were very high in the 3 analyzed mice but decreased at p60 and then remained stable at p90 (FIG. 19). Further analysis is being performed to assess whether this reduction continues at later timepoints and to compare the levels achieved with this strategy with the ones achieved with HITI. To determine whether the serum ARSB levels reached were enough to correct the MPSVI phenotype, the authors quantified the urinary GAG levels 3 months after injection and observed a 46% reduction in GAG levels in gRNA-treated mice compared to scramble-treated mice (FIG. 20), suggesting that the serum ARSB levels achieved are sufficient to restore GAG elimination in the tissues to levels comparable to the heterozygous MPSVI+/- mice. Similarly, mice injected with AAV8-TBG-ARSB showed 50% reduction in GAGs, and no statistically significant difference to gRNA-treated mice was observed. Further characterization of MPSVI phenotype correction at longer timepoints will be performed at sacrifice in order to quantify GAG accumulation in tissues like the cardiac valves.

HITI at the Albumin Locus Doesn't Affect Serum Albumin Levels

An important concern related to the strategy proposed to target Alb is the possible knock-out of Alb after genome editing. For this reason, I decided to assess whether treatment with Cas9 and the Alb-specific gRNA could reduce the serum albumin levels in treated MPSVI mice. For this, serum albumin levels were measured at p90. Although a relative decrease of albumin levels was observed in gRNA-treated mice when compared to scramble-treated or uninjected mice, this decrease was not significant and the levels observed were considered in the normal range for mice of this age (FIG. 21).

DISCUSSION

Dominantly inherited diseases have always been difficult to target by gene therapy. Genome editing could be the key tool to develop treatment strategies for GOF mutations.

HITI is a very flexible tool that could change the landscape of gene correction. HDR has severe limitations in non-dividing cells, and the size of the required homology arms can limit the size of the donor DNA that can be inserted by an AAV. Instead, HITI has been proven to work in both dividing and non-dividing cells, although more work needs to be done to understand whether increasing Cas9 cleavage or the presence of the donor DNA are necessary to improve its in vivo efficiency. The present inventors have shown that HITI can be used to insert a correct copy of the gene of interest to replace the mutant allele. Although IRES seems to be the best option, which would be consistent with the fact that the insertion the present inventors have performed is not before the ATG of the targeted gene, also kozak and T2A sequences could work depending on the particular approach. The present inventors are also working on developing a system for integrating the donor in an intron instead of an exon, avoiding potential toxicity derived from Cas9 cleaving both the GOF and wildtype alleles. Regardless, HITI can be used for gene correction in the retina for photoreceptor correction, although its efficiency can be further improved. HITI can also be used as a substitute of HDR for approaches aiming at converting the liver in a factory for the production of therapeutic proteins. Genome editing approaches are preferable over conventional gene delivery in cases where the treatment has to be delivered to a developing liver, since genome editing is persistent and the transgene expression will not be lost over time. Inserting the transgene at the very transcriptionally active albumin locus ensures high expression and secretion of the therapeutic protein even if the efficiency of HITI is low. The inventors have proven that this approach is sufficient to replace AAV-mediated ARSB expression in the liver as a neonatal therapeutic strategy for MPSVI that can potentially be used in pediatric patients to avoid defects in skeletal growth. Overall, genome editing and particularly the HITI platform are broadening the potential for treatment of genetic diseases to new heights, and the research conducted in the next years will define the landscape of its applicability for human use.

CONCLUSIONS

Taken together these results show that HITI at the rhodopsin locus is efficient in vivo in the retina of different species, being highly dependent on transduction by both AAV vectors as well as the efficiency of the gRNA. HITI can be used for allele-independent therapy of dominantly inherited diseases by knocking out both alleles and replacing them with the correct allele from the donor DNA.

REFERENCES

1. Cong, L., et al., *Multiplex genome engineering using CRISPR/Cas systems*. Science, 2013. 339 (6121): p. 819-23.
2. Jiang, W., et al., *RNA-guided editing of bacterial genomes using CRISPR-Cas systems*. Nat Biotechnol, 2013. 31 (3): p. 233-9.
3. Tu, Z., et al., *CRISPR/Cas9: a powerful genetic engineering tool for establishing large animal models of neurodegenerative diseases*. Mol Neurodegen, 2015. 10: p. 35.
4. Yanik, M., et al., *In vivo genome editing as a potential treatment strategy for inherited retinal dystrophies*. Prog Retin Eye Res, 2017. 56: p. 1-18.
5. Nishiyama, J., T. Mikuni, and R. Yasuda, *Virus-Mediated Genome Editing via Homology-Directed Repair in Mitotic and Postmitotic Cells in Mammalian Brain*. Neuron, 2017. 96 (4): p. 755-768 e5.
6. Anguela, X. M., et al., *Robust ZFN-mediated genome editing in adult hemophilic mice*. Blood, 2013. 122 (19): p. 3283-7.
7. Barzel, A., et al., *Promoterless gene targeting without nucleases ameliorates haemophilia B in mice*. Nature, 2015. 517 (7534): p. 360-4.
8. Li, H., et al., *In vivo genome editing restores haemostasis in a mouse model of haemophilia*. Nature, 2011. 475 (7355): p. 217-21.
9. Sharma, R., et al., *In vivo genome editing of the albumin locus as a platform for protein replacement therapy*. Blood, 2015. 126 (15): p. 1777-84.
10. Bakondi, B., *In vivo versus ex vivo CRISPR therapies for retinal dystrophy*. Expert Rev Ophthalmol, 2016. 11 (6): p. 397-400.
11. Lackner, D. H., et al., *A generic strategy for CRISPR-Cas9-mediated gene tagging*. Nat Commun, 2015. 6: p. 10237.
12. Suzuki, K., et al., *In vivo genome editing via CRISPR/Cas9 mediated homology-independent targeted integration*. Nature, 2016. 540 (7631): p. 144-149.
13. Brunetti-Pierri N, A. A., *Gene Therapy of Human Inherited Diseases*, in *The Metabolic and Molecular Bases of Inherited Diseases*, S. R, Editor. 2010, McGraw Hill: New York.
14. Ehrhardt, A., H. Xu, and M. A. Kay, *Episomal persistence of recombinant adenoviral vector genomes during the cell cycle in vivo*. J Virol, 2003. 77 (13): p. 7689-95.
15. Sakami, S., et al., *Probing mechanisms of photoreceptor degeneration in a new mouse model of the common form of autosomal dominant retinitis pigmentosa due to P23H opsin mutations*. J Biol Chem, 2011. 286 (12): p. 10551-67.
16. Olsson, J. E., et al., *Transgenic mice with a rhodopsin mutation (Pro23His): a mouse model of autosomal dominant retinitis pigmentosa*. Neuron, 1992. 9 (5): p. 815-30.
17. Fernandez-San Jose, P., et al., *Prevalence of Rhodopsin mutations in autosomal dominant Retinitis Pigmentosa in Spain: clinical and analytical review in 200 families*. Acta Ophthalmol, 2015. 93 (1): p. e38-44.
18. Ziviello, C., et al., *Molecular genetics of autosomal dominant retinitis pigmentosa (ADRP): a comprehensive study of 43 Italian families*. J Med Genet, 2005. 42 (7): p. e47.
19. Mendes, H. F., et al., *Mechanisms of cell death in rhodopsin retinitis pigmentosa: implications for therapy*. Trends Mol Med, 2005. 11 (4): p. 177-85.
20. Li, T., et al., *Transgenic mice carrying the dominant rhodopsin mutation P347S: evidence for defective vectorial transport of rhodopsin to the outer segments*. Proc Natl Acad Sci USA, 1996. 93 (24): p. 14176-81.
21. Botta, S., et al., *Rhodopsin targeted transcriptional silencing by DNA-binding*. Elife, 2016. 5: p. e12242.
22. Bakondi, B., et al., *In Vivo CRISPR/Cas9 Gene Editing Corrects Retinal Dystrophy in the S334ter-3 Rat Model of Autosomal Dominant Retinitis Pigmentosa*. Mol Ther, 2016. 24 (3): p. 556-63.
23. Latella, M. C., et al., *In vivo Editing of the Human Mutant Rhodopsin Gene by Electroporation of Plasmid-based CRISPR/Cas9 in the Mouse Retina*. Mol Ther Nucleic Acids, 2016. 5 (11): p. e389. 24. E Neufeld, J. M., The mucopolysaccharidoses, in The mucopolysaccharidoses, A. B. CR Scriver, WS Sly, DM Valle, Editor. 2001, McGraw-Hill: New York (2001). p. 3421-3452.
25. Cotugno, G., et al., *Impact of age at administration, lysosomal storage, and transgene regulatory elements on AAV2/8-mediated rat liver transduction*. PLOS One, 2012. 7 (3): p. e33286.
26. Ferla, R., et al., *Similar therapeutic efficacy between a single administration of gene therapy and multiple administrations of recombinant enzyme in a mouse model of lysosomal storage disease*. Hum Gene Ther, 2014. 25 (7): p. 609-18.
27. Ferla, R., et al., *Gene therapy for mucopolysaccharidosis type VI is effective in cats without pre-existing immunity to AAV8*. Hum Gene Ther, 2013. 24 (2): p. 163-9.
28. Tessitore, A., et al., *Biochemical, pathological, and skeletal improvement of mucopolysaccharidosis VI after gene transfer to liver but not to muscle*. Mol Ther, 2008. 16 (1): p. 30-7.

29. Alliegro, M., et al., *Low-dose Gene Therapy Reduces the Frequency of Enzyme Replacement Therapy in a Mouse Model of Lysosomal Storage Disease*. Mol Ther, 2016. 24 (12): p. 2054-2063.
30. Ferla, R., et al., *Non-clinical Safety and Efficacy of an AAV2/8 Vector Administered Intravenously for Treatment of Mucopolysaccharidosis Type VI*. Mol Ther Methods Clin Dev, 2017. 6: p. 143-158.
31. Cotugno, G., et al., *Long-term amelioration of feline Mucopolysaccharidosis VI after AAV-mediated liver gene transfer*. Mol Ther, 2011. 19 (3): p. 461-9.
32. Giugliani, R., et al., *Natural history and galsulfase treatment in mucopolysaccharidosis VI (MPS VI, Maroteaux-Lamy syndrome)—10-year follow-up of patients who previously participated in an MPS VI Survey Study*. Am J Med Genet A, 2014. 164A (8): p. 1953-64.
33. Desnick, R. J. and E. H. Schuchman, *Enzyme replacement therapy for lysosomal diseases: lessons from 20 years of experience and remaining challenges*. Annu Rev Genomics Hum Genet, 2012. 13: p. 307-35.
34. Neufeld, E. F., *Lysosomal storage diseases*. Annu Rev Biochem, 1991. 60: p. 257-80.
35. Ran, F. A., et al., *Genome engineering using the CRISPR-Cas9 system*. Nat Protoc, 2013. 8 (11): p. 2281-2308.
36. Auricchio, A., et al., *Isolation of highly infectious and pure adeno-associated virus type 2 vectors with a single-step gravity-flow column*. Hum Gene Ther, 2001. 12 (1): p. 71-6. 37. Maddalena, A., et al., *Triple Vectors Expand AAV Transfer Capacity in the Retina*. Mol Ther, 2018. 26 (2): p. 524-541.
38. Venkatesan, A. and A. Dasgupta, *Novel fluorescence-based screen to identify small synthetic internal ribosome entry site elements*. Mol Cell Biol, 2001. 21 (8): p. 2826-37.
39. Swiech, L., et al., *In vivo interrogation of gene function in the mammalian brain using CRISPR-Cas9*. Nat Biotechnol, 2015. 33 (1): p. 102-6.
40. Doria, M., A. Ferrara, and A. Auricchio, *AAV2/8 vectors purified from culture medium with a simple and rapid protocol transduce murine liver, muscle, and retina efficiently*. Hum Gene Ther Methods, 2013. 24 (6): p. 392-8.
41. Drittanti, L., et al., *High throughput production, screening and analysis of adeno-associated viral vectors*. Gene Ther, 2000. 7 (11): p. 924-9.
42. Liang, F. Q., et al., *Intraocular delivery of recombinant virus*. Methods Mol Med, 2001. 47: p. 125-39.
43. Mussolino, C., et al., *AAV-mediated photoreceptor transduction of the pig cone-enriched retina*. Gene Ther, 2011. 18 (7): p. 637-45.
44. Gombash Lampe, S. E., B. K. Kaspar, and K. D. Foust, *Intravenous injections in neonatal mice*. J Vis Exp, 2014 (93): p. e52037.
45. de Jong, J. G., et al., *Dimethylmethylene blue-based spectrophotometry of glycosaminoglycans in untreated urine: a rapid screening procedure for mucopolysaccharidoses*. Clin Chem, 1989. 35 (7): p. 1472-7.
46. Gerstung, M., E. Papaemmanuil, and P. J. Campbell, *Subclonal variant calling with multiple samples and prior knowledge*. Bioinformatics, 2014. 30 (9): p. 1198-204.
47. Dalkara, D. and J. A. Sahel, *Gene therapy for inherited retinal degenerations*. C R Biol, 2014. 337 (3): p. 185-92.
48. Trapani, I. and A. Auricchio, *Seeing the Light after 25 Years of Retinal Gene Therapy. Trends Mol Med*, 2018. 24 (8): p. 669-681.
49. O'Reilly, M., et al., *RNA interference-mediated suppression and replacement of human rhodopsin in vivo*. Am J Hum Genet, 2007. 81 (1): p. 127-35.
50. Chadderton, N., et al., *Improved retinal function in a mouse model of dominant retinitis pigmentosa following AAV-delivered gene therapy*. Mol Ther, 2009. 17 (4): p. 593-9.
51. Millington-Ward, S., et al., *Suppression and replacement gene therapy for autosomal dominant disease in a murine model of dominant retinitis pigmentosa*. Mol Ther, 2011. 19 (4): p. 642-9.
52. Suzuki, K. and J. C. Izpisua Belmonte, *In vivo genome editing via the HITI method as a tool for gene therapy*. J Hum Genet, 2018. 63 (2): p. 157-164.
53. Giannelli, S. G., et al., *Cas9/sgRNA selective targeting of the P23H Rhodopsin mutant allele for treating retinitis pigmentosa by intravitreal AAV9.PHP.B-based delivery*. Hum Mol Genet, 2018. 27 (5): p. 761-779.
54. Yu, W., et al., *Nrl knockdown by AAV-delivered CRISPR/Cas9 prevents retinal degeneration in mice*. Nat Commun, 2017. 8: p. 14716.
55. Burnight, E. R., et al., *Using CRISPR-Cas9 to Generate Gene-Corrected Autologous iPSCs for the Treatment of Inherited Retinal Degeneration*. Mol Ther, 2017. 25 (9): p. 1999-2013.
56. Bovolenta, P. and E. Cisneros, *Retinitis pigmentosa: conè photoreceptors starving to death*. Nat Neurosci, 2009. 12 (1): p. 5-6.
57. Porro, F., et al., *Promoterless gene targeting without nucleases rescues lethality of a Crigler-Najjar syndrome mouse model*. EMBO Mol Med, 2017. 9 (10): p. 1346-1355.
58. Ou, L., et al., *ZFN-Mediated In Vivo Genome Editing Corrects Murine Hurler Syndrome*. Mol Ther, 2019. 27 (1): p. 178-187.
59. Laoharawee, K., et al., *Dose-Dependent Prevention of Metabolic and Neurologic Disease in Murine MPS II by ZFN-Mediated In Vivo Genome Editing*. Mol Ther, 2018. 26 (4): p. 1127-1136.
60. McIntosh, J., et al., *Therapeutic levels of FVIII following a single peripheral vein administration of rAAV vector encoding a novel human factor VIII variant*. Blood, 2013. 121 (17): p. 3335-44.
61. Shen, M. W., et al., *Predictable and precise template-free CRISPR editing of pathogenic variants*. Nature, 2018. 563 (7733): p. 646-651.
62. Kim, E., et al., *In vivo genome editing with a small Cas9 orthologue derived from Campylobacter jejuni*. Nat Commun, 2017. 8: p. 14500.

The invention claimed is:

1. A system comprising
   a) a donor nucleic acid comprising
      a STOP codon upstream to translation initiation sequence (TIS), and
      an exogenous DNA sequence
   wherein said donor nucleic acid is flanked at 5' and 3' by inverted targeting sequences, and wherein the TIS is a kozak consensus sequence comprising the sequence of SEQ ID NO: 54 or SEQ ID NO: 55 wherein n is g or a, or the TIS is a an IRES sequence comprising the sequence SEQ ID NO: 24 or SEQ ID NO: 23;
   b) a complementary strand oligonucleotide homologous to the targeting sequence SEQ ID NO: 56-58 and
   c) a nuclease that recognizes the targeting sequence.

2. An expression vector that comprises the system according to claim 1.

3. The expression vector according to claim 2, wherein the vector is selected from the group consisting of: Adena associated vector (AAV), adenoviral vector, lentiviral vector, retroviral vector or naked plasmid DNA vector.

4. A host cell comprising the system according to claim 1.

5. A viral particle that comprises the system according to claim 1.

6. The viral particles according to claim 5, wherein the viral particle comprises capsid protein of an AAV.

7. The viral particle according to claim 6, wherein the viral particle comprises capsid proteins of an AAV of a serotype selected from one or more of the group consisting of AAV1, AAV2, AAV3, AAV4, AAV5, AAV6, AAV7, AAV8 AAV9 and AAV 10, preferably from the AAV2 or AAV8 serotype.

8. A pharmaceutical composition that comprises the system according to claim 1 and a pharmaceutical acceptable carrier.

9. A kit comprising: the system according to claim 1 in one or more containers.

10. The kit of claim 9 further comprising instructions or packaging materials that describe how to administer the system to a patient.

* * * * *

SEQUENCE LISTING

<160> NUMBER OF SEQ ID NOS: 62

<210> SEQ ID NO 1
<211> LENGTH: 20
<212> TYPE: DNA
<213> ORGANISM: Artificial Sequence

```
<220> FEATURE:
<223> OTHER INFORMATION: STOP codons

<400> SEQUENCE: 1
taataaataa taaataataa                                               20

<210> SEQ ID NO 2
<211> LENGTH: 675
<212> TYPE: DNA
<213> ORGANISM: Artificial Sequence
<220> FEATURE:
<223> OTHER INFORMATION: dicosoma red

<400> SEQUENCE: 2
atggatagca ctgagaacgt catcaagccc ttcatgcgct tcaaggtgca catggagggc    60
tccgtgaacg gccacgagtt cgagatcgag ggcgagggcg agggcaagcc ctacgagggc   120
acccagaccg ccaagctgca ggtgaccaag ggcggcccc tgcccttcgc ctgggacatc    180 ctgtccccc agttccagta cggctccaag gtgtacgtga agcacccgc cgacatcccc    240 gactacaaga agctgtcctt ccccgagggc ttcaagtggg agcgcgtgat gaacttcgag    300
gacggcggcg tggtgaccgt gacccaggac tcctccctgc aggacggcac cttcatctac   360
cacgtgaagt tcatcggcgt gaacttcccc tccgacggcc ccgtaatgca aagaagact    420 ctgggctggg agccctccac cgagcgcctg taccccgcg acggcgtgct gaagggcgag    480
atccacaagg cgctgaagct gaagggcggc ggccactacc tggtggagtt caagtcaatc    540
tacatggcca agaagcccgt gaagctgccc ggctactact acgtggactc caagctggac    600
atcacctccc acaacgagga ctacaccgtg gtggagcagt acgagcgcgc cgaggcccgc    660
caccacctgt tccag                                                    675

<210> SEQ ID NO 3
<211> LENGTH: 9292
<212> TYPE: DNA
<213> ORGANISM: Artificial Sequence
<220> FEATURE:
<223> OTHER INFORMATION: P939// pSpCas9(BB)-2A-GFP+gRNAScramble

<400> SEQUENCE: 3
atgtgagggc ctatttccca tgattccttc atatttgcat atacgataca aggctgttag    60
agagataatt ggaattaatt tgactgtaaa cacaaagata ttagtacaaa atacgtgacg   120
tagaaagtaa taatttcttg ggtagtttgc agttttaaaa ttatgtttta aaatggacta   180
tcatatgctt accgtaactt gaaagtattt cgatttcttg ctttatata tcttgtggaa    240 aggacgaaac accggactcg cgcgagtcga ggaggtttta gagctagaaa tagcaagtta   300
aaataaggct agtccgttat caacttgaaa aagtggcacc gagtcggtgc ttttttgttt   360
tagagctaga aatagcaagt taaataagg ctagtccgtt tttagcgcgt gcgccaattc    420
tgcagacaaa tggctctaga ggtacccgtt acataactta cggtaaatgg cccgcctggc   480
tgaccgccca acgaccccg cccattgacg tcaatagtaa cgccaatagg gactttccat    540
tgacgtcaat gggtggagta tttacggtaa actgcccact tggcagtaca tcaagtgtat   600
catatgccaa gtacgccccc tattgacgtc aatgacggta aatggcccgc ctggcattgt   660
gcccagtaca tgaccttatg gactttcct acttggcagt acatctacgt attagtcatc    720
gctattacca tggtcgaggt gagccccacg ttctgcttca ctctccccat ctccccccc   780 tccccacccc caatttgta tttatttat ttttaattat tttgtgcagc gatggggcg      840
```

```
ggggggggggg gggggcgcgc gccaggcggg gcggggcggg gcgaggggcg gggcggggcg    900
aggcggagag gtgcggcggc agccaatcag agcggcgcgc tccgaaagtt tccttttatg    960
gcgaggcggc ggcggcggcg gccctataaa aagcgaagcg cgcggcgggc gggagtcgct   1020
gcgacgctgc cttcgcccg tgccccgctc cgccgccgcc tcgcgccgcc cgccccggct   1080
ctgactgacc gcgttactcc cacaggtgag cgggcgggac ggcccttctc ctccgggctg   1140
taattagctg agcaagaggt aagggtttaa gggatggttg gttggtgggg tattaatgtt   1200
taattacctg gagcacctgc ctgaaatcac ttttttttcag gttggaccgg tgccaccatg   1260
gactataagg accacgacgg agactacaag gatcatgata ttgattacaa agacgatgac   1320
gataagatgg ccccaaagaa gaagcggaag gtcggtatcc acggagtccc agcagccgac   1380
aagaagtaca gcatcggcct ggacatcggc accaactctg tgggctgggc cgtgatcacc   1440
gacgagtaca aggtgcccag caagaaattc aaggtgctgg gcaacaccga ccggcacagc   1500
atcaagaaga acctgatcgg agccctgctg ttcgacagcg gcgaaacagc cgaggccacc   1560
cggctgaaga gaaccgccag aagaagatac accagacgga gaaccggat ctgctatctg   1620
caagagatct tcagcaacga gatggccaag gtggacgaca gcttcttcca cagactggaa   1680
gagtccttcc tggtggaaga ggataagaag cacgagcggc accccatctt cggcaacatc   1740
gtggacgagg tggcctacca cgagaagtac cccaccatct accacctgag aaagaaactg   1800
gtggacagca ccgacaaggc cgacctgcgg ctgatctatc tggcccctggc ccacatgatc   1860
aagttccggg gccacttcct gatcgagggc gacctgaacc ccgacaacag cgacgtggac   1920
aagctgttca tccagctggt gcagacctac aaccagctgt tcgaggaaaa ccccatcaac   1980
gccagcggcg tggacgccaa ggccatcctg tctgccagac tgagcaagag cagacggctg   2040
gaaaatctga tcgcccagct gcccggcgag aagaagaatg gcctgttcgg aaacctgatt   2100
gccctgagcc tgggcctgac ccccaacttc aagagcaact tcgacctggc cgaggatgcc   2160
aaactgcagc tgagcaagga cacctacgac gacgacctgg acaacctgct ggcccagatc   2220
ggcgaccagt acgccgacct gtttctggcc gccaagaacc tgtccgacgc catcctgctg   2280
agcgacatcc tgagagtgaa caccgagatc accaaggccc ccctgagcgc ctctatgatc   2340
aagagatacg acgagcacca ccaggacctg accctgctga aagctctcgt gcggcagcag   2400
ctgcctgaga gtacaaaga gattttcttc gaccagagca gaacggcta cgccggctac   2460
attgacggcg gagccagcca ggaagagttc tacaagttca tcaagcccat cctggaaaag   2520
atggacggca ccgaggaact gctcgtgaag ctgaacagag aggacctgct gcggaagcag   2580
cggaccttcg acaacggcag catcccccac cagatccacc tgggagagct gcacgccatt   2640
ctgcggcggc aggaagattt ttacccattc ctgaaggaca accgggaaaa gatcgagaag   2700
atcctgacct tccgcatccc ctactacgtg ggccctctgg ccaggggaaa cagcagattc   2760
gcctggatga ccagaaagag cgaggaaacc atcacccct ggaacttcga ggaagtggtg   2820
gacaagggcg cttccgccca gagcttcatc gagcggatga ccaacttcga taagaacctg   2880
cccaacgaga aggtgctgcc caagcacagc ctgctgtacg agtacttcac cgtgtataac   2940
gagctgacca aagtgaaata cgtgaccgag ggaatgagaa agcccgcctt cctgagcggc   3000
gagcagaaaa aggccatcgt ggacctgctg ttcaagacca ccggaaagt gaccgtgaag   3060
cagctgaaag aggactactt caagaaaatc gagtgcttcg actccgtgga aatctccggc   3120
gtggaagatc ggttcaacgc ctccctgggc acataccacg atctgctgaa aattatcaag   3180
gacaaggact tcctggacaa tgaggaaaac gaggacattc tggaagatat cgtgctgacc   3240
```

```
ctgacactgt tgaggacag agagatgatc gaggaacggc tgaaaaccta tgcccacctg    3300
ttcgacgaca aagtgatgaa gcagctgaag cggcggagat acaccggctg ggcaggctg    3360 agccggaagc tgatcaacgg catccggac aagcagtccg gcaagacaat cctggatttc    3420
ctgaagtccg acggcttcgc caacagaaac ttcatgcagc tgatccacga cgacagcctg    3480
acctttaaag aggacatcca gaaagcccag gtgtccggcc agggcgatag cctgcacgag    3540
cacattgcca atctggccgg cagccccgcc attaagaagg gcatcctgca gacagtgaag    3600
gtggtggacg agctcgtgaa agtgatgggc cggcacaagc ccgagaacat cgtgatcgaa    3660
atggccagag agaaccagac cacccagaag ggacagaaga cagccgcgca gagaatgaag    3720
cggatcgaag agggcatcaa agagctgggc agccagatcc tgaaagaaca ccccgtggaa    3780
aacacccagc tgcagaacga gaagctgtac ctgtactacc tgcagaatgg gcgggatatg    3840
tacgtggacc aggaactgga catcaaccgg ctgtccgact acgatgtgga ccatatcgtg    3900
cctcagagct ttctgaagga cgactccatc gacaacaagg tgctgaccag aagcgacaag    3960
aaccggggca gagcgacaa cgtgcccctcc gaagaggtcg tgaagaagat gaagaactac    4020
tggcggcagc tgctgaacgc caagctgatt acccagagaa agttcgacaa tctgaccaag    4080
gccgagagag gcggcctgag cgaactggat aaggccggct tcatcaagag acagctggtg    4140
gaaacccggc agatcacaaa gcacgtggca cagatcctgg actccgggat gaacactaag    4200
tacgacgaga atgacaagct gatccgggaa gtgaaagtga tcacccctgaa gtccaagctg    4260 gtgtccgatt ccggaagga tttccagtttt tacaaagtgc gcgagatcaa caactaccac    4320
cacgcccacg acgcctacct gaacgccgtc gtgggaaccg ccctgatcaa aaagtacccct    4380 aagctggaaa gcgagttcgt gtacggcgac tacaaggtgt acgacgtgcg gaagatgatc    4440
gccaagagcg agcaggaaat cggcaaggct accgccaagt acttcttcta cagcaacatc    4500
atgaactttt tcaagaccga gattaccctg gccaacggcg agatccggaa gcggcctctg    4560
atcgagacaa acggcgaaac cggggagatc gtgtgggata agggccggga ttttgccacc    4620
gtgcggaaag tgctgagcat gccccaagtg aatatcgtga aaaagaccga ggtgcagaca    4680
ggcggcttca gcaaagagtc tatcctgccc aagaggaaca gcgataagct gatcgccaga    4740
aagaaggact gggaccctaa gaagtacggc ggcttcgaca gccccaccgt ggcctattct    4800
gtgctggtgg tggccaaagt ggaaaagggc aagtccaaga aactgaagag tgtgaaagag    4860
ctgctgggga tcaccatcat ggaaagaagc agcttcgaga gaatcccat cgactttctg    4920 gaagccaagg gctacaaaga agtgaaaaag gacctgatca tcaagctgcc taagtactcc    4980
ctgttcgagc tggaaaacgg ccggaagaga atgctggcct ctgccggcga actgcagaag    5040
ggaaacgaac tggccctgcc ctccaaatat gtgaacttcc tgtacctggc cagccactat    5100
gagaagctga agggctcccc cgaggataat gagcagaaac agctgtttgt ggaacagcac    5160
aagcactacc tggacgagat catcgagcag atcagcgagt ctccaagag agtgatcctg    5220 gccgacgcta atctggacaa agtgctgtcc gcctacaaca agcaccggga taagcccatc    5280
agagagcagg ccgagaatat catccacctg tttaccctga ccaatctggg agccctgcc    5340 gccttcaagt actttgacac caccatcgac cggaagaggg acaccagcac caaagaggtg    5400
ctggacgcca ccctgatcca ccagagcatc accggcctgt acgagacacg gatcgacctg    5460
tctcagctgg gaggcgacaa aaggccggcg ccacgaaaaa aggccggcca ggcaaaaaag    5520
aaaaaggaat tcggcagtgg agagggcaga ggaagtctgc taacatgcgg tgacgtcgag    5580
```

```
gagaatcctg gcccagtgag caagggcgag gagctgttca ccggggtggt gcccatcctg    5640
gtcgagctgg acggcgacgt aaacggccac aagttcagcg tgtccggcga gggcgagggc    5700
gatgccacct acggcaagct gaccctgaag ttcatctgca ccaccggcaa gctgcccgtg    5760
ccctggccca ccctcgtgac caccctgacc tacggcgtgc agtgcttcag ccgctacccc    5820
gaccacatga agcagcacga cttcttcaag tccgccatgc ccgaaggcta cgtccaggag    5880
cgcaccatct tcttcaagga cgacggcaac tacaagaccc gcgccgaggt gaagttcgag    5940
ggcgacaccc tggtgaaccg catcgagctg aagggcatcg acttcaagga ggacggcaac    6000
atcctggggc acaagctgga gtacaactac aacagccaca acgtctatat catggccgac    6060
aagcagaaga acggcatcaa ggtgaacttc aagatccgcc acaacatcga ggacggcagc    6120
gtgcagctcg ccgaccacta ccagcagaac ccccccatcg gcgacggccc cgtgctgctg    6180
cccgacaacc actacctgag cacccagtcc gccctgagca agacccccaa cgagaagcgc    6240
gatcacatgg tcctgctgga gttcgtgacc gccgccggga tcactctcgg catggacgag    6300
ctgtacaagg aattctaact agagctcgct gatcagcctc gactgtgcct tctagttgcc    6360
agccatctgt tgtttgcccc tcccccgtgc cttccttgac cctggaaggt gccactccca    6420
ctgtcctttc ctaataaaat gaggaaattg catcgcattg tctgagtagg tgtcattcta    6480
ttctgggggg tggggtgggg caggacagca agggggagga ttgggaagag aatagcaggc    6540
atgctgggga gcggccgcag gaaccctag tgatggagtt ggccactccc tctctgcgcg    6600
ctcgctcgct cactgaggcc gggcgaccaa aggtcgcccg acgcccgggc tttgcccggg    6660
cggcctcagt gagcgagcga gcgcgcagct gcctgcaggg cgcctgatg cggtattttc    6720 tccttacgca tctgtgcggt atttcacacc gcatacgtca agcaaccat agtacgcgcc    6780 ctgtagcggc gcattaagcg cggcgggtgt ggtggttacg cgcagcgtga ccgctacact    6840
tgccagcgcc ctagcgcccg ctcctttcgc tttcttccct tcctttctcg ccacgttcgc    6900
cggctttccc cgtcaagctc taaatcgggg gctcccttta gggttccgat ttagtgcttt    6960
acggcacctc gaccccaaaa aacttgattt gggtgatggt tcacgtagtg gccatcgcc    7020 ctgatagacg gtttttcgcc ctttgacgtt ggagtccacg ttctttaata gtggactctt    7080
gttccaaact ggaacaacac tcaaccctat ctcgggctat tcttttgatt tataagggat    7140
tttgccgatt tcggcctatt ggttaaaaaa tgagctgatt taacaaaaat ttaacgcgaa    7200
ttttaacaaa atattaacgt ttacaatttt atggtgcact ctcagtacaa tctgctctga    7260
tgccgcatag ttaagccagc cccgacaccc gccaacaccc gctgacgcgc cctgacgggc    7320
ttgtctgctc ccggcatccg cttacagaca agctgtgacc gtctccggga gctgcatgtg    7380
tcagaggttt tcaccgtcat cacccgaaacg cgcgagacga aagggcctcg tgatacgcct    7440
atttttatag gttaatgtca tgataataat ggtttcttag acgtcaggtg gcacttttcg    7500
gggaaatgtg cgcggaaccc ctatttgttt atttttctaa atacattcaa atatgtatcc    7560
gctcatgaga caataaccct gataaatgct tcaataatat tgaaaaagga agagtatgag    7620
tattcaacat ttccgtgtcg cccttattcc cttttttgcg gcattttgcc ttcctgtttt    7680
tgctcaccca gaaacgctgg tgaaagtaaa agatgctgaa gatcagttgg gtgcacgagt    7740
gggttacatc gaactggatc tcaacagcgg taagatcctt gagagttttc gccccgaaga    7800
acgttttcca atgatgagca cttttaaagt tctgctatgt ggcgcggtat tatcccgtat    7860
tgacgccggg caagagcaac tcggtcgccg catacactat tctcagaatg acttggttga    7920
gtactcacca gtcacagaaa agcatcttac ggatggcatg acagtaagag aattatgcag    7980
```

```
tgctgccata accatgagtg ataacactgc ggccaactta cttctgacaa cgatcggagg    8040
accgaaggag ctaaccgctt ttttgcacaa catgggggat catgtaactc gccttgatcg    8100
ttgggaaccg gagctgaatg aagccatacc aaacgacgag cgtgacacca cgatgcctgt    8160
agcaatggca acaacgttgc gcaaactatt aactggcgaa ctacttactc tagcttcccg    8220
gcaacaatta atagactgga tggaggcgga taaagttgca ggaccacttc tgcgctcggc    8280
ccttccggct ggctggttta ttgctgataa atctggagcc ggtgagcgtg aagccgcgg     8340
tatcattgca gcactggggc cagatggtaa gccctcccgt atcgtagtta tctacacgac    8400
ggggagtcag gcaactatgg atgaacgaaa tagacagatc gctgagatag gtgcctcact    8460
gattaagcat tggtaactgt cagaccaagt ttactcatat atactttaga ttgatttaaa    8520
acttcatttt taatttaaaa ggatctaggt gaagatcctt tttgataatc tcatgaccaa    8580
aatcccttaa cgtgagtttt cgttccactg agcgtcagac cccgtagaaa agatcaaagg    8640
atcttcttga tccttttt ttctgcgcgt aatctgctgc ttgcaaacaa aaaaaccacc     8700
gctaccagcg gtggtttgtt tgccggatca agagctacca actctttttc cgaaggtaac    8760
tggcttcagc agagcgcaga taccaaatac tgtccttcta gtgtagccgt agttaggcca    8820
ccacttcaag aactctgtag caccgcctac atacctcgct ctgctaatcc tgttaccagt    8880
ggctgctgcc agtggcgata agtcgtgtct taccgggttg gactcaagac gatagttacc    8940
ggataaggcg cagcggtcgg gctgaacggg gggttcgtgc acacagccca gcttggagcg    9000
aacgacctac accgaactga gatacctaca gcgtgagcta tgagaaagcg ccacgcttcc    9060
cgaagggaga aaggcggaca ggtatccggt aagcggcagg gtcggaacag gagagcgcac    9120
gagggagctt ccagggggaa acgcctggta tctttatagt cctgtcgggt ttcgccacct    9180
ctgacttgag cgtcgatttt tgtgatgctc gtcaggggg cggagcctat ggaaaaacgc     9240
cagcaacgcg gccttttttac ggttcctggc cttttgctgg ccttttgctc ac           9292
```

<210> SEQ ID NO 4
<211> LENGTH: 9292
<212> TYPE: DNA
<213> ORGANISM: Artificial Sequence
<220> FEATURE:
<223> OTHER INFORMATION: p972// pSpCas9(BB)-2A-GFP+gRNA hRHO HITI

<400> SEQUENCE: 4

```
gtgagggcct atttcccatg attccttcat atttgcatat acgatacaag gctgttagag     60
agataattgg aattaatttg actgtaaaca caaagatatt agtacaaaat acgtgacgta    120
gaaagtaata atttcttggg tagtttgcag ttttaaaatt atgttttaaa atggactatc    180
atatgcttac cgtaacttga agtatttcg atttcttggc tttatatatc ttgtggaaag    240
gacgaaacac cgacaccagg agacttggaa cggttttaga gctagaaata gcaagttaaa    300
ataaggctag tccgttatca acttgaaaaa gtggcaccga tcggtgcttt tttgttttta    360
gagctagaaa tagcaagtta aaataaggct agtccgtttt tagcgcgtgc gccaattctg    420
cagacaaatg gctctagagg tacccgttac ataacttacg gtaaatggcc cgcctggctg    480
accgcccaac gacccccgcc cattgacgtc aatagtaacg ccaatagggga ctttccattg    540
acgtcaatgg gtggagtatt tacggtaaac tgcccacttg gcagtacatc aagtgtatca    600
tatgccaagt acgccccta ttgacgtcaa tgacggtaaa tggcccgcct ggcattgtgc     660
ccagtacatg accttatggg actttcctac ttggcagtac atctacgtat tagtcatcgc    720
```

```
tattaccatg gtcgaggtga gccccacgtt ctgcttcact ctccccatct cccccccctc    780
cccacccca attttgtatt tatttatttt ttaattattt tgtgcagcga tgggggcggg    840
ggggggggg gggcgcgcgc caggcggggc ggggcggggc gaggggcggg gcggggcgag    900
gcggagaggt gcggcggcag ccaatcagag cggcgcgctc cgaaagtttc cttttatggc    960
gaggcggcgg cggcggcggc cctataaaaa gcgaagcgcg cggcgggcgg gagtcgctgc   1020
gacgctgcct tcgccccgtg ccccgctccg ccgccgcctc gcgccgcccg ccccggctct   1080
gactgaccgc gttactccca caggtgagcg ggcgggacgg cccttctcct ccgggctgta   1140
attagctgag caagaggtaa gggtttaagg gatggttggt tggtggggta ttaatgttta   1200
attacctgga gcacctgcct gaaatcactt tttttcaggt tggaccggtg ccaccatgga   1260
ctataaggac cacgcacggag actacaagga tcatgatatt gattacaaag acgatgacga   1320
taagatggcc ccaaagaaga agcggaaggt cggtatccac ggagtcccag cagccgacaa   1380
gaagtacagc atcggcctgg acatcggcac caactctgtg ggctgggccg tgatcaccga   1440
cgagtacaag gtgcccagca gaaaattcaa ggtgctggga acaccgacc ggcacagcat   1500
caagaagaac ctgatcggag ccctgctgtt cgacagcggc gaaacagccg aggccacccg   1560
gctgaagaga accgccagaa gagatacac cagacgaag aaccggatct gctatctgca   1620
agagatcttc agcaacgaga tggccaaggt ggacgacagc ttcttccaca gactggaaga   1680
gtccttcctg gtgaagagg ataagaagca cgagcggcac cccatcttcg caacatcgt   1740
ggacgaggtg gcctaccacg agaagtaccc caccatctac cacctgagaa agaaactggt   1800
ggacagcacc gacaaggccg acctgcggct gatctatctg gccctggccc acatgatcaa   1860
gttccggggc cacttcctga tcgagggcga cctgaacccc gacaacagcg acgtggacaa   1920
gctgttcatc cagctggtgc agacctacaa ccagctgttc gaggaaaaacc ccatcaacgc   1980
cagcggcgtg gacgccaagg ccatcctgtc tgccagactg agcaagagca gcggctgga   2040
aaatctgatc gcccagctgc ccggcgagaa gaagaatggc ctgttcggaa acctgattgc   2100
cctgagcctg ggcctgaccc ccaacttcaa gagcaacttc gacctggccg aggatgccaa   2160
actgcagctg agcaaggaca cctacgacga cgacctggac aacctgctgg cccagatcgg   2220
cgaccagtac gccgacctgt ttctggccgc caagaacctg tccgacgcca tcctgctgag   2280
cgacatcctg agagtgaaca ccgagatcac caaggccccc ctgagcgcct ctatgatcaa   2340
gagatacgac gagcaccacc aggacctgac cctgctgaaa gctctcgtgc ggcagcagct   2400
gcctgagaag tacaaagaga ttttcttcga ccagagcaag aacggctacg ccggctacat   2460
tgacggcgga gccagccagg aagagttcta caagttcatc aagcccatcc tggaaaagat   2520
ggacggcacc gaggaactgc tcgtgaagct gaacagagag gacctgctgc ggaagcagcg   2580
gaccttcgac aacggcagca tcccccacca gatccacctg ggagagctgc acgccattct   2640
gcggcggcag gaagatttt acccattcct gaaggacaac cgggaaaaga tcgaagagat   2700
cctgaccttc cgcatcccct actacgtggg ccctctggcc aggggaaaca gcagattcgc   2760
ctggatgacc agaaagagcg aggaaaccat cacccctgg aacttcgagg aagtggtgga   2820
caagggcgct tccgcccaga gcttcatcga gcggatgacc aacttcgata agaacctgcc   2880
caacgagaag gtgctgccca gcacagcct gctgtacgag tacttcaccg tgtataacga   2940
gctgaccaaa gtgaaatacg tgaccgaggg aatgagaaag cccgccttcc tgagcggcga   3000
gcagaaaaag gccatcgtgg acctgctgtt caagaccaac cggaaagtga ccgtgaagca   3060
gctgaaagag gactacttca gaaaatcga gtgcttcgac tccgtggaaa tctccggcgt   3120
```

```
ggaagatcgg ttcaacgcct ccctgggcac ataccacgat ctgctgaaaa ttatcaagga      3180
caaggacttc ctggacaatg aggaaaacga ggacattctg aagatatcg tgctgaccct      3240 gacactgttt gaggacagag agatgatcga ggaacggctg aaaacctatg cccacctgtt     3300
cgacgacaaa gtgatgaagc agctgaagcg gcggagatac accggctggg gcaggctgag    3360
ccggaagctg atcaacggca tccgggacaa gcagtccggc aagacaatcc tggatttcct    3420
gaagtccgac ggcttcgcca acagaaactt catgcagctg atccacgacg acagcctgac    3480
ctttaaagag gacatccaga aagcccaggt gtccggccag ggcgatagcc tgcacgagca    3540
cattgccaat ctggccggca gccccgccat taagaagggc atcctgcaga cagtgaaggt    3600
ggtggacgag ctcgtgaaag tgatgggccg gcacaagccc gagaacatcg tgatcgaaat    3660
ggccagagag aaccagacca cccagaaggg acagaagaac agccgcgaga gaatgaagcg    3720
gatcgaagag ggcatcaaag agctgggcag ccagatcctg aaagaacacc ccgtggaaaa    3780
cacccagctg cagaacgaga gctgtacct gtactacctg cagaatgggc gggatatgta    3840
cgtggaccag gaactggaca tcaaccggct gtccgactac gatgtggacc atatcgtgcc    3900
tcagagcttt ctgaaggacg actccatcga caacaaggtg ctgaccagaa gcgacaagaa    3960
ccggggcaag agcgacaacg tgccctccga agaggtcgtg aagaagatga gaactactg    4020 gcggcagctg ctgaacgcca agctgattac ccagagaaag ttcgacaatc tgaccaaggc    4080
cgagagaggc ggcctgagcg aactggataa ggccggcttc atcaagagac agctggtgga    4140 aacccgcag atcacaaagc acgtggcaca gatcctggac tccggatga acactaagta     4200 cgacgagaat gacaagctga tccgggaagt gaaagtgatc accctgaagt ccaagctggt    4260
gtccgatttc cggaaggatt ccagtttta caagtgcgc gagatcaaca actaccacca    4320
cgcccacgac gcctacctga acgccgtcgt gggaaccgcc ctgatcaaaa gtaccctaa     4380 gctggaaagc gagttcgtgt acggcgacta caaggtgtac gacgtgcgga agatgatcgc    4440
caagagcgag caggaaatcg gcaaggctac cgccaagtac ttcttctaca gcaacatcat    4500 gaacttttc aagaccgaga ttaccctggc caacggcgag atccgaagc ggcctctgat     4560 cgagacaaac ggcgaaaccg gggagatcgt gtgggataag gccgggatt ttgccaccgt    4620 gcggaaagtg ctgagcatgc cccaagtgaa tatcgtgaaa aagaccgagg tgcagacagg    4680
cggcttcagc aaagagtcta tcctgcccaa gaggaacagc gataagctga tcgccagaaa    4740
gaaggactgg gaccctaaga gtacggcgg cttcgacagc cccaccgtgg cctattctgt    4800
gctggtggtg gccaaagtgg aaaagggcaa gtccaagaaa ctgaagagtg tgaaagagct    4860
gctggggatc accatcatgg aaagaagcag cttcgagaag aatcccatcg actttctgga    4920
agccaagggc tacaaagaag tgaaaaagga cctgatcatc aagctgccta agtactccct    4980
gttcgagctg gaaaacggcc ggaagagaat gctggcctct gccggcgaac tgcagaaggg    5040
aaacgaactg gccctgccct ccaaatatgt gaacttcctg tacctggcca gccactatga    5100
gaagctgaag ggctccccg aggataatga gcagaaacag ctgtttgtgg aacagcacaa    5160
gcactacctg gacgagatca tcgagcagat cagcgagttc tccaagagag tgatcctggc    5220
cgacgctaat ctggacaaag tgctgtccgc ctacaacaag caccgggata gcccatcag    5280 agagcaggcc gagaatatca tccacctgtt taccctgacc aatctgggag ccctgccgc    5340 cttcaagtac tttgacacca ccatcgaccg gaagaggtac accagcacca aagaggtgct    5400
ggacgccacc ctgatccacc agagcatcac cggcctgtac gagacacgga tcgacctgtc    5460
```

```
tcagctggga ggcgacaaaa ggccggcggc cacgaaaaag gccggccagg caaaaaagaa      5520
aaaggaattc ggcagtggag agggcagagg aagtctgcta acatgcggtg acgtcgagga      5580
gaatcctggc ccagtgagca agggcgagga gctgttcacc ggggtggtgc ccatcctggt      5640
cgagctggac ggcgacgtaa acggccacaa gttcagcgtg tccggcgagg gcgagggcga      5700
tgccacctac ggcaagctga ccctgaagtt catctgcacc accggcaagc tgcccgtgcc      5760
ctggcccacc ctcgtgacca ccctgaccta cggcgtgcag tgcttcagcc gctaccccga      5820
ccacatgaag cagcacgact tcttcaagtc cgccatgccc gaaggctacg tccaggagcg      5880
caccatcttc ttcaaggacg acggcaacta caagacccgc gccgaggtga agttcgaggg      5940
cgacaccctg gtgaaccgca tcgagctgaa gggcatcgac ttcaaggagg acggcaacat      6000
cctggggcac aagctggagt acaactacaa cagccacaac gtctatatca tggccgacaa      6060
gcagaagaac ggcatcaagg tgaacttcaa gatccgccac aacatcgagg acggcagcgt      6120
gcagctcgcc gaccactacc agcagaacac ccccatcggc gacggccccg tgctgctgcc      6180
cgacaaccac tacctgagca cccagtccgc cctgagcaaa gaccccaacg agaagcgcga      6240
tcacatggtc ctgctggagt tcgtgaccgc cgccgggatc actctcggca tggacgagct      6300
gtacaaggaa ttctaactag agctcgctga tcagcctcga ctgtgccttc tagttgccag      6360
ccatctgttg tttgccccte ccccgtgcct tccttgaccc tggaaggtgc cactcccact      6420
gtcctttcct aataaaatga ggaaattgca tcgcattgtc tgagtaggtg tcattctatt      6480
ctggggggtg gggtggggca ggacagcaag ggggaggatt gggaagagaa tagcaggcat      6540 gctgggagc ggccgcagga accctagtg atggagttgg ccactccctc tctgcgcgct      6600
cgctcgctca ctgaggccgg gcgaccaaag gtcgcccgac gcccgggctt tgcccgggcg      6660
gcctcagtga gcgagcgagc gcgcagctgc ctgcaggggc gcctgatgcg gtattttctc      6720
cttacgcatc tgtgcggtat ttcacaccgc atacgtcaaa gcaaccatag tacgcgccct      6780
gtagcggcgc attaagcgcg gcgggtgtgg tggttacgcg cagcgtgacc gctacacttg      6840
ccagcgccct agcgcccgct cctttcgctt tcttcccttc ctttctcgcc acgttcgccg      6900
gctttccccg tcaagctcta aatcgggggc tccctttagg gttccgattt agtgctttac      6960
ggcacctcga ccccaaaaaa cttgatttgg gtgatggttc acgtagtggg ccatcgccct      7020
gatagacggt ttttcgccct ttgacgttgg agtccacgtt ctttaatagt ggactcttgt      7080
tccaaactgg aacaacactc aaccctatct cgggctattc ttttgattta agggatttt      7140 tgccgatttc ggcctattgg ttaaaaaatg agctgattta acaaaaattt aacgcgaatt      7200
ttaacaaaat attaacgttt acaatttat ggtgcactct cagtacaatc tgctctgatg      7260
ccgcatagtt aagccagccc cgacacccgc caacacccgc tgacgcgccc tgacgggctt      7320
gtctgctccc ggcatccgct tacagacaag ctgtgaccgt ctccgggagc tgcatgtgtc      7380
agaggttttc accgtcatca ccgaaacgcg cgagacgaaa gggcctcgtg atacgcctat      7440
ttttataggt taatgtcatg ataataatgg tttcttagac gtcaggtggc acttttcggg      7500
gaaatgtgcg cggaacccct atttgtttat ttttctaaat acattcaaat atgtatccgc      7560
tcatgagaca ataaccctga taaatgcttc aataatattg aaaaggaag agtatgagta      7620 ttcaacattt ccgtgtcgcc cttattccct tttttgcggc attttgcctt cctgtttttg      7680
ctcacccaga aacgctggtg aaagtaaaag atgctgaaga tcagttgggt gcacgagtgg      7740
gttacatcga actggatctc aacagcggta agatccttga gttttcgc cccgaagaac      7800 gttttccaat gatgagcact tttaaagttc tgctatgtgg cgcggtatta tcccgtattg      7860
```

```
acgccgggca agagcaactc ggtcgccgca tacactattc tcagaatgac ttggttgagt    7920
actcaccagt cacagaaaag catcttacgg atggcatgac agtaagagaa ttatgcagtg    7980
ctgccataac catgagtgat aacactgcgg ccaacttact tctgacaacg atcggaggac    8040
cgaaggagct aaccgctttt tgcacaaca tgggggatca tgtaactcgc cttgatcgtt    8100
gggaaccgga gctgaatgaa gccataccaa cgacgagcg tgacaccacg atgcctgtag    8160
caatggcaac aacgttgcgc aaactattaa ctggcgaact acttactcta gcttcccggc    8220
aacaattaat agactggatg gaggcggata agttgcagg accacttctg cgctcggccc    8280
ttccggctgg ctggtttatt gctgataaat ctggagccgg tgagcgtgga agccgcggta    8340
tcattgcagc actggggcca gatggtaagc cctcccgtat cgtagttatc tacacgacgg    8400
ggagtcaggc aactatggat gaacgaaata gacagatcgc tgagataggt gcctcactga    8460
ttaagcattg gtaactgtca gaccaagttt actcatatat actttagatt gatttaaaac    8520
ttcatttta atttaaaagg atctaggtga agatcctttt tgataatctc atgaccaaaa    8580
tcccttaacg tgagttttcg ttccactgag cgtcagaccc cgtagaaaag atcaaaggat    8640
cttcttgaga tccttttttt ctgcgcgtaa tctgctgctt gcaaacaaaa aaaccaccgc    8700
taccagcggt ggtttgtttg ccggatcaag agctaccaac tcttttttccg aaggtaactg    8760
gcttcagcag agcgcagata ccaaatactg tccttctagt gtagccgtag ttaggccacc    8820
acttcaagaa ctctgtagca ccgcctacat acctcgctct gctaatcctg ttaccagtgg    8880
ctgctgccag tggcgataag tcgtgtctta ccgggttgga ctcaagacga tagttaccgg    8940
ataaggcgca gcggtcgggc tgaacggggg gttcgtgcac acagcccagc ttggagcgaa    9000
cgacctacac cgaactgaga tacctacagc gtgagctatg agaaagcgcc acgcttcccg    9060
aagggagaaa ggcggacagg tatccggtaa gcggcagggt cggaacagga gagcgcacga    9120
gggagcttcc agggggaaac gcctggtatc tttatagtcc tgtcgggttt cgccacctct    9180
gacttgagcg tcgatttttg tgatgctcgt caggggggcg gagccatatgg aaaaacgcca    9240
gcaacgcggc cttttttacgg ttcctggcct tttgctggcc ttttgctcac at           9292
```

<210> SEQ ID NO 5
<211> LENGTH: 9291
<212> TYPE: DNA
<213> ORGANISM: Artificial Sequence
<220> FEATURE:
<223> OTHER INFORMATION: p995/ SpCas9-2A-GFP-HITI mRHO

<400> SEQUENCE: 5

```
tcacatgtga gggcctattt cccatgattc cttcatattt gcatatacga tacaaggctg      60
ttagagagat aattggaatt aatttgactg taaacacaaa gatattagta caaaatacgt     120
gacgtagaaa gtaataattt cttgggtagt ttgcagtttt aaaattatgt tttaaaatgg     180
actatcatat gcttaccgta acttgaaagt atttcgattt cttggcttta tatatcttgt     240
ggaaaggacg aaacaccgca gccgcagtac tacctgggtt ttagagctag aaatagcaag    300
ttaaaataag gctagtccgt tatcaacttg aaaaagtggc accgagtcgg tgcttttttg    360
ttttagagct agaaatagca agttaaaata aggctagtcc gttttagcg cgtgcgccaa     420
ttctgcagac aaatggctct agaggtaccc gttacataac ttacggtaaa tggcccgcct    480
ggctgaccgc ccaacgaccc ccgcccattg acgtcaatag taacgccaat agggactttc    540
cattgacgtc aatgggtgga gtatttacgg taaactgccc acttggcagt acatcaagtg    600
```

| | |
|---|---|
| tatcatatgc caagtacgcc ccctattgac gtcaatgacg gtaaatggcc cgcctggcat | 660 |
| tgtgcccagt acatgacctt atgggacttt cctacttggc agtacatcta cgtattagtc | 720 |
| atcgctatta ccatggtcga ggtgagcccc acgttctgct tcactctccc catctccccc | 780 |
| ccctccccac ccccaatttt gtatttattt attttttaat tattttgtgc agcgatgggg | 840 |
| gcggggggg ggggggggcg cgcgccaggc ggggcggggc ggggcgaggg gcgggcggg | 900 |
| gcgaggcgga gaggtgcggc ggcagccaat cagagcggcg cgctccgaaa gtttccttt | 960 |
| atggcgaggc ggcggcggcg gcggccctat aaaaagcgaa gcgcgcggcg ggcgggagtc | 1020 |
| gctgcgacgt tgccttcgcc ccgtgccccg ctccgccgcc gctcgcgcc gcccgccccg | 1080 |
| gctctgactg accgcgttac tcccacaggt gagcgggcgg gacggcccctt ctcctccggg | 1140 |
| ctgtaattag ctgagcaaga ggtaagggtt taagggatgg ttggttggtg gggtattaat | 1200 |
| gtttaattac ctggagcacc tgcctgaaat cactttttt caggttggac cggtgccacc | 1260 |
| atggactata aggaccacga cggagactac aaggatcatg atattgatta caaagacgat | 1320 |
| gacgataaga tggcccccaaa gaagaagcgg aaggtcggta ccacggagt cccagcagcc | 1380 |
| gacaagaagt acagcatcgg cctggacatc ggcaccaact ctgtgggctg gccgtgatc | 1440 |
| accgacgagt acaaggtgcc cagcaagaaa ttcaaggtgc tgggcaacac cgaccggcac | 1500 |
| agcatcaaga gaacctgat cggagccctg ctgttcgaca gcggcgaaac agccgaggcc | 1560 |
| acccggctga agagaaccgc cagaagaaga taccagac ggaagaaccg gatctgctat | 1620 |
| ctgcaagaga tcttcagcaa cgagatggcc aaggtggacg acagcttctt ccacagactg | 1680 |
| gaagagtcct tcctggtgga agaggataag aagcacgagc ggcacccat cttcggcaac | 1740 |
| atcgtggacg aggtggccta ccacgagaag taccccacca tctaccacct gagaaagaaa | 1800 |
| ctggtggaca gcaccgacaa ggccgacctg cggctgatct atctggccct ggcccacatg | 1860 |
| atcaagttcc ggggccactt cctgatcgag ggcgacctga ccccgacaa cagcgacgtg | 1920 |
| gacaagctgt tcatccagct ggtgcagacc tacaaccagc tgttcgagga aaaccccatc | 1980 |
| aacgccagcg gcgtggacgc caaggccatc ctgtctgcca gactgagcaa gagcagacgg | 2040 |
| ctggaaaatc tgatcgccca gctgcccggc gagaagaaga tggcctgtt cggaaacctg | 2100 |
| attgccctga gcctgggcct gaccccaac ttcaagagca acttcgacct ggccgaggat | 2160 |
| gccaaactgc agctgagcaa ggacacctac gacgacgacc tggacaacct gctgcccag | 2220 |
| atcggcgacc agtacgccga cctgtttctg gccgccaaga acctgtccga cgccatcctg | 2280 |
| ctgagcgaca tcctgagagt gaacaccgag atcaccaagg ccccctgag cgcctctatg | 2340 |
| atcaagagat acgacgagca ccaccaggac ctgaccctgc tgaaagctct cgtgcggcag | 2400 |
| cagctgcctg agaagtacaa agagattttc ttcgaccaga gcaagaacgg ctacgccggc | 2460 |
| tacattgacg gcggagccag ccaggaagag ttctacaagt tcatcaagcc catcctggaa | 2520 |
| aagatggacg gcaccgagga actgctcgtg aagctgaaca gagaggacct gctgcggaag | 2580 |
| cagcggacct tcgacaacgg cagcatcccc caccagatcc acctgggaga gctgcacgcc | 2640 |
| attctgcggc ggcaggaaga ttttacccca ttcctgaagg acaaccggga aagatcgag | 2700 |
| aagatcctga ccttccgcat cccctactac gtgggccctc tggccagggg aaacagcaga | 2760 |
| ttcgcctgga tgaccagaaa gagcgaggaa accatcaccc cctggaactt cgaggaagtg | 2820 |
| gtggacaagg gcgcttccgc ccagagcttc atcgagcgga tgaccaactt cgataagaac | 2880 |
| ctgcccaacg agaaggtgct gcccaagcac agcctgctgt acgagtactt caccgtgtat | 2940 |
| aacgagctga ccaaagtgaa atacgtgacc gagggaatga gaaagcccgc cttcctgagc | 3000 |

```
ggcgagcaga aaaaggccat cgtggacctg ctgttcaaga ccaaccggaa agtgaccgtg    3060
aagcagctga agaggacta cttcaagaaa atcgagtgct tcgactccgt ggaaatctcc    3120
ggcgtggaag atcggttcaa cgcctccctg ggcacatacc acgatctgct gaaaattatc    3180
aaggacaagg acttcctgga caatgaggaa aacgaggaca ttctggaaga tatcgtgctg    3240
accctgacac tgtttgagga cagagagatg atcgaggaac ggctgaaaac ctatgcccac    3300
ctgttcgacg acaaagtgat gaagcagctg aagcggcgga gatacaccgg ctggggcagg    3360
ctgagccgga agctgatcaa cggcatccgg gacaagcagt ccggcaagac aatcctggat    3420
ttcctgaagt ccgacggctt cgccaacaga aacttcatgc agctgatcca cgacgacagc    3480 ctgacctta aagaggacat ccagaaagcc caggtgtccg gccagggcga tagcctgcac    3540
gagcacattg ccaatctggc cggcagcccc gccattaaga agggcatcct gcagacagtg    3600
aaggtggtgg acgagctcgt gaaagtgatg ggccggcaca gcccgagaa catcgtgatc    3660 gaaatggcca gagagaacca gaccacccag aagggacaga gaacagccg cgagagaatg    3720 aagcggatcg aagagggcat caaagagctg gcagccaga tcctgaaaga cacccccgtg    3780
gaaaacaccc agctgcagaa cgagaagctg tacctgtact acctgcagaa tgggcgggat    3840
atgtacgtgg accaggaact ggacatcaac cggctgtccg actacgatgt ggaccatatc    3900
gtgcctcaga gctttctgaa ggacgactcc atcgacaaca aggtgctgac cagaagcgac    3960
aagaaccggg gcaagagcga caacgtgccc tccgaagagg tcgtgaagaa gatgaagaac    4020
tactggcggc agctgctgaa cgccaagctg attacccaga gaagttcga caatctgacc    4080 aaggccgaga gaggcggcct gagcgaactg gataaggccg gcttcatcaa gagacagctg    4140
gtggaaaccc ggcagatcac aaagcacgtg gcacagatcc tggactcccg gatgaacact    4200
aagtacgacg agaatgacaa gctgatccgg gaagtgaaag tgatcaccct gaagtccaag    4260
ctggtgtccg atttccggaa ggatttccag ttttacaaag tgcgcgagat caacaactac    4320
caccacgccc acgacgccta cctgaacgcc gtcgtgggaa ccgccctgat caaaaagtac    4380
cctaagctgg aaagcgagtt cgtgtacggc gactacaagg tgtacgacgt gcggaagatg    4440
atcgccaaga gcgagcagga aatcggcaag gctaccgcca gtacttctt ctacagcaac    4500 atcatgaact tttcaagac cgagattacc ctggccaacg gcgagatccg gaagcggcct    4560
ctgatcgaga caaacggcga aaccggggag atcgtgtggg ataagggccg ggattttgcc    4620
accgtgcgga aagtgctgag catgccccaa gtgaatatcg tgaaaaagac cgaggtgcag    4680
acaggcggct tcagcaaaga gtctatcctg cccaagagga cagcgataa gctgatcgcc    4740 agaaagaagg actgggaccc taagaagtac ggcggcttcg acagccccac cgtggcctat    4800
tctgtgctgt tggtggccaa agtggaaaag ggcaagtcca agaaactgaa gagtgtgaaa    4860
gagctgctgg ggatcaccat catggaaaga agcagcttcg agaagaatcc catcgacttt    4920
ctggaagcca agggctacaa agaagtgaaa aaggacctga tcatcaagct gcctaagtac    4980
tccctgttcg agctggaaaa cggccggaag agaatgctgg cctctgccgg cgaactgcag    5040
aagggaaacg aactggccct gccctccaaa tatgtgaact tcctgtacct ggccagccac    5100
tatgagaagc tgaagggctc ccccgaggat aatgagcaga acagctgtt tgtggaacag    5160 cacaagcact acctggacga gatcatcgag cagatcagcg agttctccaa gagagtgatc    5220
ctggccgacg ctaatctgga caaagtgctg tccgcctaca acaagcaccg ggataagccc    5280
atcagagagc aggccgagaa tatcatccac ctgtttaccc tgaccaatct gggagcccct    5340
```

```
gccgccttca agtactttga caccaccatc gaccggaaga ggtacaccag caccaaagag    5400
gtgctggacg ccaccctgat ccaccagagc atcaccggcc tgtacgagac acggatcgac    5460
ctgtctcagc tgggaggcga caaaaggccg gcggccacga aaaaggccgg ccaggcaaaa    5520
aagaaaaagg aattcggcag tggagagggc agaggaagtc tgctaacatg cggtgacgtc    5580
gaggagaatc ctggcccagt gagcaagggc gaggagctgt tcaccggggt ggtgcccatc    5640
ctggtcgagc tggacggcga cgtaaacggc cacaagttca gcgtgtccgg cgagggcgag    5700
ggcgatgcca cctacggcaa gctgaccctg aagttcatct gcaccaccgg caagctgccc    5760
gtgccctggc ccaccctcgt gaccaccctg acctacggcg tgcagtgctt cagccgctac    5820
cccgaccaca tgaagcagca cgacttcttc aagtccgcca tgcccgaagg ctacgtccag    5880
gagcgcacca tcttcttcaa ggacgacggc aactacaaga cccgcgccga ggtgaagttc    5940
gagggcgaca ccctggtgaa ccgcatcgag ctgaagggca tcgacttcaa ggaggacggc    6000
aacatcctgg ggcacaagct ggagtacaac tacaacagcc acaacgtcta tatcatggcc    6060
gacaagcaga agaacggcat caaggtgaac ttcaagatcc gccacaacat cgaggacggc    6120
agcgtgcagc tcgccgacca ctaccagcag aacaccccca tcggcgacgg ccccgtgctg    6180
ctgcccgaca accactacct gagcacccag tccgccctga gcaaagaccc caacgagaag    6240
cgcgatcaca tggtcctgct ggagttcgtg accgccgccg ggatcactct cggcatggac    6300
gagctgtaca aggaattcta actagagctc gctgatcagc ctcgactgtg ccttctagtt    6360
gccagccatc tgttgtttgc ccctccccg tgccttcctt gaccctggaa ggtgccactc    6420
ccactgtcct ttcctaataa aatgaggaaa ttgcatcgca ttgtctgagt aggtgtcatt    6480
ctattctggg gggtggggtg gggcaggaca gcaaggggga ggattgggaa gagaatagca    6540
ggcatgctgg ggagcggccg caggaacccc tagtgatgga gttggccact ccctctctgc    6600
gcgctcgctc gctcactgag gccgggcgac caaaggtcgc ccgacgcccg ggctttgccc    6660
gggcggcctc agtgagcgag cgagcgcgca gctgcctgca ggggcgcctg atgcggtatt    6720
ttctccttac gcatctgtgc ggtatttcac accgcatacg tcaaagcaac catagtacgc    6780
gccctgtagc ggcgcattaa gcgcggcggg tgtggtggtt acgcgcagcg tgaccgctac    6840
acttgccagc gccctagcgc ccgctccttt cgctttcttc ccttcctttc tcgccacgtt    6900
cgccggcttt ccccgtcaag ctctaaatcg ggggctccct ttagggttcc gatttagtgc    6960
tttacggcac ctcgacccca aaaaacttga tttgggtgat ggttcacgta gtgggccatc    7020
gccctgatag acggtttttc gccctttgac gttggagtcc acgttcttta atagtggact    7080
cttgttccaa actggaacaa cactcaaccc tatctcgggc tattcttttg atttataagg    7140
gattttgccg atttcggcct attggttaaa aaatgagctg atttaacaaa aatttaacgc    7200
gaattttaac aaaatattaa cgtttacaat tttatggtgc actctcagta caatctgctc    7260
tgatgccgca tagttaagcc agccccgaca cccgccaaca cccgctgacg cgccctgacg    7320
ggcttgtctg ctcccggcat ccgcttacag acaagctgtg accgtctccg ggagctgcat    7380
gtgtcagagg ttttcaccgt catcaccgaa acgcgcgaga cgaaagggcc tcgtgatacg    7440
cctattttta taggttaatg tcatgataat aatggtttct tagacgtcag gtggcacttt    7500
tcggggaaat gtgcgcggaa cccctatttg tttatttttc taaatacatt caaatatgta    7560
tccgctcatg agacaataac cctgataaat gcttcaataa tattgaaaaa ggaagagtat    7620
gagtattcaa catttccgtg tcgcccttat tcccttttt gcggcatttt gccttcctgt    7680
ttttgctcac ccagaaacgc tggtgaaagt aaaagatgct gaagatcagt tgggtgcacg    7740
```

```
agtgggttac atcgaactgg atctcaacag cggtaagatc cttgagagtt ttcgccccga    7800
agaacgtttt ccaatgatga gcacttttaa agttctgcta tgtggcgcgg tattatcccg    7860
tattgacgcc gggcaagagc aactcggtcg ccgcatacac tattctcaga atgacttggt    7920
tgagtactca ccagtcacag aaaagcatct tacggatggc atgacagtaa gagaattatg    7980
cagtgctgcc ataaccatga gtgataacac tgcggccaac ttacttctga caacgatcgg    8040
aggaccgaag gagctaaccg cttttttgca acatggggg atcatgtaa ctcgccttga    8100 tcgttgggaa ccggagctga atgaagccat accaaacgac gagcgtgaca ccacgatgcc    8160
tgtagcaatg gcaacaacgt tgcgcaaact attaactggc gaactactta ctctagcttc    8220
ccggcaacaa ttaatagact ggatggaggc ggataaagtt gcaggaccac ttctgcgctc    8280
ggcccttccg gctggctggt ttattgctga taaatctgga gccggtgagc gtggaagccg    8340
cggtatcatt gcagcactgg ggccagatgg taagccctcc cgtatcgtag ttatctacac    8400
gacggggagt caggcaacta tggatgaacg aaatagacag atcgctgaga taggtgcctc    8460
actgattaag cattggtaac tgtcagacca agtttactca tatatacttt agattgattt    8520
aaaacttcat ttttaattta aaaggatcta ggtgaagatc ctttttgata atctcatgac    8580
caaaatccct aacgtgagt tttcgttcca ctgagcgtca ccccgtag aaaagatcaa    8640 aggatcttct tgagatcctt ttttctgcg cgtaatctgc tgcttgcaaa caaaaaaacc    8700
accgctacca gcggtggttt gtttgccgga tcaagagcta ccaactcttt ttccgaaggt    8760
aactggcttc agcagagcgc agataccaaa tactgtcctt ctagtgtagc cgtagttagg    8820
ccaccacttc aagaactctg tagcaccgcc tacatacctc gctctgctaa tcctgttacc    8880
agtggctgct gccagtggcg ataagtcgtg tcttaccggg ttggactcaa gacgatagtt    8940
accggataag gcgcagcggt cgggctgaac ggggggttcg tgcacacagc ccagcttgga    9000
gcgaacgacc tacaccgaac tgagatacct acagcgtgag ctatgagaaa gcgccacgct    9060
tcccgaaggg agaaaggcgg acaggtatcc ggtaagcggc agggtcggaa caggagagcg    9120
cacgagggag cttccagggg gaaacgcctg gtatctttat agtcctgtcg ggtttcgcca    9180
cctctgactt gagcgtcgat ttttgtgatg ctcgtcaggg gggcggagcc tatgaaaaaa    9240
cgccagcaac gcggcctttt tacggttcct ggccttttgc tggccttttg c    9291
```

<210> SEQ ID NO 6
<211> LENGTH: 9292
<212> TYPE: DNA
<213> ORGANISM: Artificial Sequence
<220> FEATURE:
<223> OTHER INFORMATION: p1070// pSpCas9(BB)-2A-GFP-gRNAalbumin

<400> SEQUENCE: 6

```
tgagggccta tttcccatga ttccttcata tttgcatata cgatacaagg ctgttagaga      60
gataattgga attaatttga ctgtaaacac aaagatatta gtacaaaata cgtgacgtag     120
aaagtaataa tttcttgggt agtttgcagt tttaaaatta tgttttaaaa tggactatca     180
tatgcttacc gtaacttgaa agtatttcga tttcttggct ttatatatct tgtggaaagg     240
acgaaacacc gacaagagtg agatcgccca tgttttagag ctagaaatag caagttaaaa     300
taaggctagt ccgttatcaa cttgaaaaag tggcaccgag tcggtgcttt tttgttttag     360
agctagaaat agcaagttaa aataaggcta gtccgttttt agcgcgtgcg ccaattctgc     420
agacaaatgg ctctagaggt acccgttaca taacttacgg taaatggccc gcctggctga     480
```

```
ccgcccaacg accccccgccc attgacgtca atagtaacgc caataggggac tttccattga    540
cgtcaatggg tggagtattt acggtaaact gcccacttgg cagtacatca agtgtatcat    600
atgccaagta cgccccctat tgacgtcaat gacggtaaat ggcccgcctg gcattgtgcc    660
cagtacatga ccttatggga cttttcctact tggcagtaca tctacgtatt agtcatcgct    720
attaccatgg tcgaggtgag ccccacgttc tgcttcactc tccccatctc ccccccctcc    780
ccaccccccaa ttttgtattt atttatttt taattatttt gtgcagcgat gggggcgggg    840
ggggggggggg ggcgcgcgcc aggcggggcg gggcggggcg aggggcgggg cggggcgagg    900
cggagaggtg cggcggcagc caatcagagc ggcgcgctcc gaaagtttcc ttttatggcg    960
aggcggcggc ggcggcggcc ctataaaaag cgaagcgcgc ggcgggcggg agtcgctgcg   1020
acgctgcctt cgccccgtgc cccgctccgc cgccgcctcg cgccgcccgc cccggctctg   1080
actgaccgcg ttactcccac aggtgagcgg gcgggacggc ccttctcctc cgggctgtaa   1140
ttagctgagc aagaggtaag ggtttaaggg atggttggtt ggtggggtat taatgtttaa   1200
ttacctggag caccttgcctg aaatcacttt ttttcaggtt ggaccggtgc caccatggac   1260
tataaggacc acgacggaga ctacaaggat catgatattg attacaaaga cgatgacgat   1320
aagatggccc caaagaagaa gcggaaggtc ggtatccacg gagtcccagc agccgacaag   1380
aagtacagca tcggcctgga catcggcacc aactctgtgg gctgggccgt gatcaccgac   1440
gagtacaagg tgcccagcaa gaaattcaag gtgctgggca acaccgaccg cacagcatc    1500
aagaagaacc tgatcggagc cctgctgttc gacagcggcg aaacagccga ggccacccgg   1560
ctgaagagaa ccgccagaag aagatacacc agacggaaga accggatctg ctatctgcaa   1620
gagatcttca gcaacgagat ggccaaggtg gacgacagct tcttccacag actggaagag   1680
tccttcctgg tggaagagga taagaagcac gagcggcacc ccatcttcgg caacatcgtg   1740
gacgaggtgg cctaccacga gaagtacccc accatctacc acctgagaaa gaaactggtg   1800
gacagcaccg acaaggccga cctgcggctg atctatctgg ccctggccca catgatcaag   1860
ttccggggcc acttcctgat cgagggcgac ctgaaccccg acaacagcga cgtggacaag   1920
ctgttcatcc agctggtgca gacctacaac cagctgttcg aggaaaaccc catcaacgcc   1980
agcggcgtgg acgccaaggc catcctgtct gccagactga gcaagagcag acggctggaa   2040
aatctgatcg cccagctgcc cggcgagaag aagaatggcc tgttcggaaa cctgattgcc   2100
ctgagcctgg gcctgacccc caacttcaag agcaacttcg acctggccga ggatgccaaa   2160
ctgcagctga gcaaggacac ctacgacgac gacctggaca acctgctggc ccagatcggc   2220
gaccagtacg ccgacctgtt tctggccgcc aagaacctgt ccgacgccat cctgctgagc   2280
gacatcctga gtgaacacac cgagatcacc aaggccccc tgagcgcctc tatgatcaag   2340
agatacgacg agcaccacca ggacctgacc ctgctgaaag ctctcgtgcg gcagcagctg   2400
cctgagaagt acaaagagat tttcttcgac cagagcaaga acggctacgc cggctacatt   2460
gacggcggag ccagccagga agagttctac aagttcatca agcccatcct ggaaaagatg   2520
gacggcaccg aggaactgct cgtgaagctg aacagagagg acctgctgcg aagcagcgg   2580
accttcgaca cggcagcat ccccaccag atccacctgg agagctgca cgccattctg    2640
cggcggcagg aagattttta cccattcctg aaggacaacc gggaaaagat cgagaagatc   2700
ctgaccttcc gcatccccta ctacgtgggc cctctggcca ggggaaacag cagattcgcc   2760
tggatgacca gaaagagcga ggaaaccatc acccccctgga acttcgagga agtggtggac   2820
aagggcgctt ccgcccagag cttcatcgag cggatgacca acttcgataa gaacctgccc   2880
```

```
aacgagaagg tgctgcccaa gcacagcctg ctgtacgagt acttcaccgt gtataacgag   2940
ctgaccaaag tgaaatacgt gaccgaggga atgagaaagc cgccttcct gagcggcgag    3000 cagaaaaagg ccatcgtgga cctgctgttc aagaccaacc ggaaagtgac cgtgaagcag   3060
ctgaaagagg actacttcaa gaaaatcgag tgcttcgact ccgtggaaat ctccggcgtg   3120
gaagatcggt tcaacgcctc cctgggcaca taccacgatc tgctgaaaat tatcaaggac   3180
aaggacttcc tggacaatga ggaaaacgag gacattctgg aagatatcgt gctgaccctg   3240
acactgtttg aggacagaga gatgatcgag gaacggctga aaacctatgc ccacctgttc   3300
gacgacaaag tgatgaagca gctgaagcgg cggagataca ccggctgggg caggctgagc   3360
cggaagctga tcaacggcat ccgggacaag cagtccggca agacaatcct ggatttcctg   3420
aagtccgacg gcttcgccaa cagaaacttc atgcagctga tccacgacga cagcctgacc   3480 tttaagagg acatccagaa agcccaggtg tccggccagg gcgatagcct gcacgagcac    3540
attgccaatc tggccggcag ccccgccatt aagaagggca tcctgcagac agtgaaggtg   3600
gtggacgagc tcgtgaaagt gatgggccgg cacaagcccg agaacatcgt gatcgaaatg   3660
gccagagaga accagaccac ccagaaggga cagaagaaca ccgcgagag aatgaagcgg    3720 atcgaagagg gcatcaaaga gctgggcagc cagatcctga agaacacccc cgtggaaaac   3780
acccagctgc agaacgagaa gctgtacctg tactacctgc agaatgggcg ggatatgtac   3840
gtggaccagg aactggacat caaccggctg tccgactacg atgtggacca tatcgtgcct   3900
cagagctttc tgaaggacga ctccatcgac aacaaggtgc tgaccagaag cgacaagaac   3960
cggggcaaga gcgacaacgt gcccctccgaa gaggtcgtga agaagatgaa gaactactgg   4020
cggcagctgc tgaacgccaa gctgattacc cagagaaagt tcgacaatct gaccaaggcc   4080
gagagaggcg gcctgagcga actggataag gccggcttca tcaagagaca gctggtggaa   4140
acccggcaga tcacaaagca cgtggcacag atcctggact cccggatgaa cactaagtac   4200
gacgagaatg acaagctgat ccgggaagtg aaagtgatca ccctgaagtc caagctggtg   4260
tccgatttcc ggaaggattt ccagttttac aaagtgcgcg agatcaacaa ctaccaccac   4320
gcccacgacg cctacctgaa cgccgtcgtg ggaaccgccc tgatcaaaaa gtaccctaag   4380
ctggaaagcg agttcgtgta cggcgactac aaggtgtacg acgtgcggaa gatgatcgcc   4440
aagagcgagc aggaaatcgg caaggctacc gccaagtact ccttctacag caacatcatg   4500 aacttttca agaccgagat tacccctggcc aacggcgaga tccggaagcg gcctctgatc   4560
gagacaaacg gcgaaaccgg ggagatcgtg tgggataagg ccgggatttt gccaccgtg    4620 cggaaagtgc tgagcatgcc ccaagtgaat atcgtgaaaa agaccgaggt gcagacaggc   4680
ggcttcagca aagagtctat cctgcccaag aggaacagcg ataagctgat cgccagaaag   4740
aaggactggg accctaagaa gtacggcggc ttcgacagcc ccaccgtggc ctattctgtg   4800
ctggtggtgg ccaaagtgga aaagggcaag tccaagaaac tgaagagtgt gaaagagctg   4860
ctggggatca ccatcatgga aagaagcagc ttcgagaaga tcccatcga ctttctggaa    4920 gccaagggct acaaagaagt gaaaaaggac ctgatcatca agctgcctaa gtactccctg   4980
ttcgagctga aaaacggccg gaagagaatg ctggcctctg ccggcgaact gcagaaggga   5040
aacgaactgg ccctgccctc caaatatgtg aacttcctgt acctggccag ccactatgag   5100
aagctgaagg gctcccccga ggataatgag cagaaacagc tgtttgtgga acagcacaag   5160
cactacctgg acgagatcat cgagcagatc agcgagttct ccaagagagt gatcctggcc   5220
```

```
gacgctaatc tggacaaagt gctgtccgcc tacaacaagc accgggataa gcccatcaga   5280
gagcaggccg agaatatcat ccacctgttt accctgacca atctgggagc ccctgccgcc   5340
ttcaagtact ttgacaccac catcgaccgg aagaggtaca ccagcaccaa agaggtgctg   5400
gacgccaccc tgatccacca gagcatcacc ggcctgtacg agacacggat cgacctgtct   5460
cagctgggag cgacaaaag gccggcggcc acgaaaaagg ccggccaggc aaaaaagaaa   5520
aaggaattcg gcagtggaga gggcagagga agtctgctaa catgcggtga cgtcgaggag   5580
aatcctggcc cagtgagcaa gggcgaggag ctgttcaccg gggtggtgcc catcctggtc   5640
gagctggacg gcgacgtaaa cggccacaag ttcagcgtgt ccggcgaggg cgagggcgat   5700
gccacctacg gcaagctgac cctgaagttc atctgcacca ccggcaagct gcccgtgccc   5760
tggcccaccc tcgtgaccac cctgacctac ggcgtgcagt gcttcagccg ctaccccgac   5820
cacatgaagc agcacgactt cttcaagtcc gccatgcccg aaggctacgt ccaggagcgc   5880
accatcttct tcaaggacga cggcaactac aagacccgcg ccgaggtgaa gttcgagggc   5940
gacaccctgg tgaaccgcat cgagctgaag ggcatcgact tcaaggagga cggcaacatc   6000
ctggggcaca agctggagta caactacaac agccacaacg tctatatcat ggccgacaag   6060
cagaagaacg gcatcaaggt gaacttcaag atccgccaca acatcgagga cggcagcgtg   6120
cagctcgccg accactacca gcagaacacc cccatcggcg acggccccgt gctgctgccc   6180
gacaaccact acctgagcac ccagtccgcc ctgagcaaag ccccaacga gaagcgcgat   6240 cacatggtcc tgctggagtt cgtgaccgcc gccgggatca ctctcggcat ggacgagctg   6300
tacaaggaat ctaactaga gctcgctgat cagcctcgac tgtgccttct agttgccagc   6360
catctgttgt ttgcccctcc cccgtgcctt ccttgaccct ggaaggtgcc actcccactg   6420
tcctttccta ataaaatgag gaaattgcat cgcattgtct gagtaggtgt cattctattc   6480
tggggggtgg ggtggggcag gacagcaagg gggaggattg ggaagagaat agcaggcatg   6540
ctggggagcg gccgcaggaa cccctagtga tggagttggc cactccctct ctgcgcgctc   6600
gctcgctcac tgaggccggg cgaccaaagg tcgcccgacg cccgggcttt gcccgggcgg   6660
cctcagtgag cgagcgagcg cgcagctgcc tgcaggggcg cctgatgcgg tattttctcc   6720
ttacgcatct gtgcggtatt tcacaccgca tacgtcaaag caaccatagt acgcgccctg   6780
tagcggcgca ttaagcgcgg cgggtgtggt ggttacgcgc agcgtgaccg ctacacttgc   6840
cagcgcccta gcgcccgctc ctttcgcttt cttcccttcc tttctcgcca cgttcgccgg   6900
ctttccccgt caagctctaa atcggggct ccctttaggg ttccgattta gtgctttacg   6960
gcacctcgac cccaaaaaac ttgatttggg tgatggttca cgtagtgggc catcgccctg   7020
atagacggtt tttcgccctt tgacgttgga gtccacgttc tttaatagtg gactcttgtt   7080
ccaaactgga acaacactca accctatctc gggctattct tttgatttat aagggatttt   7140
gccgatttcg gcctattggt taaaaaatga gctgatttaa caaaaattta acgcgaattt   7200
taacaaaata ttaacgttta caattttatg gtgcactctc agtacaatct gctctgatgc   7260
cgcatagtta agccagcccc gacacccgcc aacacccgct gacgcgccct gacgggcttg   7320
tctgctcccg gcatccgctt acagacaagc tgtgaccgtc tccgggagct gcatgtgtca   7380
gaggttttca ccgtcatcac cgaaacgcgc gagacgaaag gcctcgtga tacgcctatt   7440 tttataggtt aatgtcatga taataatggt ttcttagacg tcaggtggca cttttcgggg   7500
aaatgtgcgc ggaaccccta tttgtttatt tttctaaata cattcaaata tgtatccgct   7560
catgagacaa taaccctgat aaatgcttca ataatattga aaaggaaga gtatgagtat   7620
```

```
tcaacatttc cgtgtcgccc ttattcccct ttttgcggca ttttgccttc ctgttttgc    7680 tcacccagaa acgctggtga agtaaaaga tgctgaagat cagttgggtg cacgagtggg    7740
ttacatcgaa ctggatctca acagcggtaa gatccttgag agttttcgcc ccgaagaacg   7800
ttttccaatg atgagcactt taaagttct gctatgtggc gcggtattat cccgtattga    7860
cgccgggcaa gagcaactcg gtcgccgcat acactattct cagaatgact tggttgagta   7920
ctcaccagtc acagaaaagc atcttacgga tggcatgaca gtaagagaat tatgcagtgc   7980
tgccataacc atgagtgata acactgcggc caacttactt ctgacaacga tcggaggacc   8040
gaaggagcta accgcttttt tgcacaacat ggggatcat gtaactcgcc ttgatcgttg     8100
ggaaccggag ctgaatgaag ccataccaaa cgacgagcgt gacaccacga tgcctgtagc   8160
aatggcaaca acgttgcgca aactattaac tggcgaacta cttactctag cttcccggca   8220
acaattaata gactggatgg aggcggataa agttgcagga ccacttctgc gctcggccct   8280
tccggctggc tggtttattg ctgataaatc tggagccggt gagcgtggaa gccgcggtat   8340
cattgcagca ctggggccag atggtaagcc ctcccgtatc gtagttatct acacgacggg   8400
gagtcaggca actatggatg aacgaaatag acagatcgct gagataggtg cctcactgat   8460
taagcattgg taactgtcag accaagttta ctcatatata ctttagattg atttaaaact   8520 tcattttaa tttaaaagga tctaggtgaa gatcctttt gataatctca tgaccaaaat     8580
cccttaacgt gagttttcgt tccactgagc gtcagacccc gtagaaaaga tcaaaggatc   8640
ttcttgagat ccttttttc tgcgcgtaat ctgctgcttg caaacaaaaa aaccaccgct    8700
accagcggtg gtttgtttgc cggatcaaga gctaccaact ctttttccga aggtaactgg   8760
cttcagcaga gcgcagatac caaatactgt ccttctagtg tagccgtagt taggccacca   8820
cttcaagaac tctgtagcac cgcctacata cctcgctctg ctaatcctgt taccagtggc   8880
tgctgccagt ggcgataagt cgtgtcttac cgggttggac tcaagacgat agttaccgga   8940
taaggcgcag cggtcgggct gaacggggg ttcgtgcaca cagcccagct tggagcgaac    9000
gacctacacc gaactgagat acctacagcg tgagctatga aaagcgcca cgcttcccga    9060 agggagaaag gcggacaggt atccggtaag cggcagggtc ggaacaggag agcgcacgag   9120
ggagcttcca gggggaaacg cctggtatct ttatagtcct gtcgggtttc gccacctctg   9180
acttgagcgt cgatttttgt gatgctcgtc aggggggcgg agcctatgga aaaacgccag   9240
caacgcggcc ttttacggt tcctggcctt ttgctggcct tttgctcaca tg             9292
```

<210> SEQ ID NO 7
<211> LENGTH: 7887
<212> TYPE: DNA
<213> ORGANISM: Artificial Sequence
<220> FEATURE:
<223> OTHER INFORMATION: p946// pAAV-IRBP-SpCas9

<400> SEQUENCE: 7

```
tgcagctggc acgacaggtt tcccgactgg aaagcgggca gtgagcgcaa cgcaattaat    60
gtgagttagc tcactcatta ggcaccccag gctttacact ttatgcttcc ggctcgtatg   120
ttgtgtggaa ttgtgagcgg ataacaattt cacacaggaa acagctatga ccatgattac   180
gccagattta attaaggctg cgcgctcgct cgctcactga ggccgcccgg gcaaagcccg   240
ggcgtcgggc gacctttggt cgcccggcct cagtgagcga gcgagcgcgc agagagggag   300
tggccaactc catcactagg ggttccttgt agttaatgat taacccgcca tgctacttat   360
```

```
ctacgtagcc atgctctagg aagatcggaa ttcgccctta agctagtagc acagtgtctg    420
gcatgtagca ggaactaaaa taatggcagt gattaatgtt atgatatgca gacacaacac    480
agcaagataa gatgcaatgt accttctggg tcaaaccacc ctggccactc ctccccgata    540 cccaggttg atgtgcttga attagacagg attaaaggct tactgagct ggaagccttg      600 ccccaactca ggagtttagc cccagacctt ctgtccacca gcgcggccga ccggccaagg    660
gcgaattctg cagatatcca tcacactggc ggccgatccc cgggtaccgg tgccaccatg    720
tacccatacg atgttccaga ttacgcttcg ccgaagaaaa agcgcaaggt cgaagcgtcc    780
gacaagaagt acagcatcgg cctggacatc ggcaccaact ctgtgggctg gccgtgatc     840 accgacgagt acaaggtgcc cagcaagaaa ttcaaggtgc tgggcaacac cgaccggcac    900
agcatcaaga gaacctgat cggagccctg ctgttcgaca cgccgaaac agccgaggcc     960 acccggctga agagaaccgc cagaagaaga tacaccagac ggaagaaccg gatctgctat   1020
ctgcaagaga tcttcagcaa cgagatggcc aaggtggacg acagcttctt ccacagactg   1080
gaagagtcct tcctggtgga agaggataag aagcacgagc ggcaccccat cttcggcaac   1140
atcgtggacg aggtggccta ccacgagaag taccccacca tctaccacct gagaaagaaa   1200
ctggtggaca gcaccgacaa ggccgacctg cggctgatct atctggccct ggcccacatg   1260
atcaagttcc ggggccactt cctgatcgag ggcgacctga ccccgacaa cagcgacgtg    1320 gacaagctgt tcatccagct ggtgcagacc tacaaccagc tgttcgagga aaaccccatc   1380
aacgccagcg gcgtggacgc caaggccatc ctgtctgcca gactgagcaa gagcagacgg   1440
ctggaaaatc tgatcgccca gctgcccggc gagaagaaga tggcctgtt cggcaacctg    1500 attgccctga gcctgggcct gaccccaac ttcaagagca acttcgacct ggccgaggat    1560
gccaaactgc agctgagcaa ggacacctac gacgacgacc tggacaacct gctggcccag   1620
atcggcgacc agtacgccga cctgtttctg gccgccaaga acctgtccga cgccatcctg   1680
ctgagcgaca tcctgagagt gaacaccgag atcaccaagg ccccctgag cgcctctatg    1740 atcaagagat acgacgagca ccaccaggac ctgaccctgc tgaaagctct cgtgcggcag   1800
cagctgcctg agaagtacaa agagattttc ttcgaccaga gcaagaacgg ctacgccggc   1860
tacattgacg gcggagccag ccaggaagag ttctacaagt tcatcaagcc catcctggaa   1920
aagatggacg gcaccgagga actgctcgtg aagctgaaca gagaggacct gctgcggaag   1980
cagcggacct tcgacaacgg cagcatcccc caccagatcc acctgggaga gctgcacgcc   2040
attctgcggc ggcaggaaga ttttaccca ttcctgaagg acaaccggga aaagatcgag    2100
aagatcctga ccttccgcat cccctactac gtgggccctc tggccagggg aaacagcaga   2160
ttcgcctgga tgaccagaaa gagcgaggaa accatcaccc cctggaactt cgaggaagtg   2220
gtggacaagg gcgcttccgc ccagagcttc atcgagcgga tgaccaactt cgataagaac   2280
ctgcccaacg agaaggtgct gcccaagcac agcctgctgt acgagtactt caccgtgtat   2340
aacgagctga ccaaagtgaa atacgtgacc gagggaatga gaaagcccgc cttcctgagc   2400
ggcgagcaga aaaaggccat cgtggacctg ctgttcaaga ccaaccggaa agtgaccgtg   2460
aagcagctga aagaggacta cttcaagaaa atcgagtgct cgactccgt ggaaatctcc    2520 ggcgtggaag atcggttcaa cgcctccctg gcacatacc acgatctgct gaaaattatc    2580
aaggacaagg acttcctgga caatgaggaa aacgaggaca ttctggaaga tatcgtgctg   2640
accctgacac tgtttgagga cagagagatg atcgaggaac ggctgaaaac ctatgcccac   2700
ctgttcgacg acaaagtgat gaagcagctg aagcggcgga gatacaccgg ctggggcagg   2760
```

-continued

```
ctgagccgga agctgatcaa cggcatccgg acaagcagt ccggcaagac aatcctggat    2820
ttcctgaagt ccgacggctt cgccaacaga aacttcatgc agctgatcca cgacgacagc    2880
ctgacccttta agaggacat ccagaaagcc caggtgtccg gccagggcga tagcctgcac    2940
gagcacattg ccaatctggc cggcagcccc gccattaaga agggcatcct gcagacagtg    3000
aaggtggtgg acgagctcgt gaaagtgatg ggccggcaca gcccgagaa catcgtgatc    3060
gaaatggcca gagagaacca gaccacccag aagggacaga gaacagccg cgagagaatg    3120
aagcggatcg aagagggcat caaagagctg ggcagccaga tcctgaaaga cacccccgtg    3180
gaaaacaccc agctgcagaa cgagaagctg tacctgtact acctgcagaa tgggcgggat    3240
atgtacgtgg accaggaact ggacatcaac cggctgtccg actacgatgt ggaccatatc    3300
gtgcctcaga gctttctgaa ggacgactcc atcgacaaca aggtgctgac cagaagcgac    3360
aagaaccggg gcaagagcga caacgtgccc tccgaagagg tcgtgaagaa gatgaagaac    3420
tactggcggc agctgctgaa cgccaagctg attacccaga aaagttcga caatctgacc    3480
aaggccgaga gaggcggcct gagcgaactg gataaggccg gcttcatcaa gagacagctg    3540
gtggaaaccc ggcagatcac aaagcacgtg gcacagatcc tggactcccg gatgaacact    3600
aagtacgacg agaatgacaa gctgatccgg gaagtgaaag tgatcaccct gaagtccaag    3660
ctggtgtccg atttccggaa ggatttccag ttttacaaag tgcgcgagat caacaactac    3720
caccacgccc acgacgccta cctgaacgcc gtcgtgggaa ccgccctgat caaaaagtac    3780
cctaagctgg aaagcgagtt cgtgtacggc gactacaagg tgtacgacgt gcggaagatg    3840
atcgccaaga gcgagcagga aatcggcaag gctaccgcca agtacttctt ctacagcaac    3900
atcatgaact ttttcaagac cgagattacc ctggccaacg gcgagatccg gaagcggcct    3960
ctgatcgaga caaacggcga aaccggggag atcgtgtggg ataagggccg ggattttgcc    4020
accgtgcgga agtgctgag catgccccaa gtgaatatcg tgaaaaagac cgaggtgcag    4080
acaggcggct tcagcaaaga gtctatcctg cccaagagga cagcgataa gctgatcgcc    4140
agaaagaagg actgggaccc taagaagtac ggcggcttcg acagccccac cgtggcctat    4200
tctgtgctgg tggtggccaa agtggaaaag ggcaagtcca gaaactgaa gagtgtgaaa    4260
gagctgctgg ggatcaccat catggaaaga agcagcttcg agaagaatcc catcgacttt    4320
ctggaagcca agggctacaa agaagtgaaa aaggacctga tcatcaagct gcctaagtac    4380
tccctgttcg agctggaaaa cggccggaag agaatgctgg cctctgccgg cgaactgcag    4440
aagggaaacg aactggccct gccctccaaa tatgtgaact tcctgtacct ggccagccac    4500
tatgagaagc tgaagggctc ccccgaggat aatgagcaga acagctgtt tgtggaacag    4560
cacaagcact acctggacga gatcatcgag cagatcagcg agttctccaa gagagtgatc    4620
ctggccgacg ctaatctgga caaagtgctg tccgcctaca acaagcaccg ggataagccc    4680
atcagagagc aggccgagaa tatcatccac ctgtttaccc tgaccaatct gggagccct    4740
gccgccttca agtactttga caccaccatc gaccggaaga ggtacaccag caccaaagag    4800
gtgctggacg ccaccctgat ccaccagagc atcaccggcc tgtacgagac acggatcgac    4860
ctgtctcagc tgggaggcga cagccccaag aagaagagaa aggtggaggc cagctaagaa    4920
ttcaataaaa gatctttatt ttcattagat ctgtgtgttg gttttttgtg tgcggccgca    4980
ggaaccccta gtgatggagt tggccactcc ctctctgcgc gctcgctcgc tcactgaggc    5040
cgggcgacca aggtcgcccc gacgcccggg ctttgcccgg gcggcctcag tgagcgagcg    5100
```

-continued

```
agcgcgcagc tgcctgcagg ggcgcctgat gcggtatttt ctccttacgc atctgtgcgg   5160
tatttcacac cgcatacgtc aaagcaacca tagtacgcgc cctgtagcgg cgcattaagc   5220
gcggcgggtg tggtggttac gcgcagcgtg accgctacac ttgccagcgc cctagcgccc   5280
gctcctttcg ctttcttccc ttcctttctc gccacgttcg ccggctttcc ccgtcaagct   5340
ctaaatcggg ggctcccttt agggttccga tttagtgctt tacggcacct cgaccccaaa   5400
aaacttgatt tgggtgatgg ttcacgtagt gggccatcgc cctgatagac ggttttttcgc  5460 cctttgacgt tggagtccac gttctttaat agtggactct tgttccaaac tggaacaaca   5520
ctcaacccta tctcgggcta ttcttttgat ttataaggga ttttgccgat tcggcctat    5580 tggttaaaaa atgagctgat ttaacaaaaa tttaacgcga attttaacaa aatattaacg   5640
tttacaattt tatggtgcac tctcagtaca atctgctctg atgccgcata gttaagccag   5700
ccccgacacc cgccaacacc cgctgacgcg ccctgacggg cttgtctgct cccggcatcc   5760
gcttacagac aagctgtgac cgtctccggg agctgcatgt gtcagaggtt ttcaccgtca   5820
tcaccgaaac gcgcgagacg aaagggcctc gtgatacgcc tatttttata ggttaatgtc   5880
atgataataa tggtttctta gacgtcaggt ggcacttttc ggggaaatgt gcgcggaacc   5940
cctatttgtt tatttttcta aatacattca aatatgtatc cgctcatgag acaataaccc   6000
tgataaatgc ttcaataata ttgaaaaagg aagagtatga gtattcaaca tttccgtgtc   6060
gcccttattc ccttttttgc ggcatttttgc cttcctgttt ttgctcaccc agaaacgctg   6120
gtgaaagtaa aagatgctga agatcagttg ggtgcacgag tgggttacat cgaactggat   6180
ctcaacagcg gtaagatcct tgagagtttt cgccccgaag aacgttttcc aatgatgagc   6240
acttttaaag ttctgctatg tggcgcggta ttatcccgta ttgacgccgg gcaagagcaa   6300
ctcggtcgcc gcatacacta ttctcagaat gacttggttg agtactcacc agtcacagaa   6360
aagcatctta cggatggcat gacagtaaga gaattatgca gtgctgccat aaccatgagt   6420
gataacactg cggccaactt acttctgaca acgatcggag gaccgaagga gctaaccgct   6480 ttttttgcaca acatggggga tcatgtaact cgccttgatc gttgggaacc ggagctgaat   6540
gaagccatac caaacgacga gcgtgacacc acgatgcctg tagcaatggc aacaacgttg   6600
cgcaaactat taactggcga actacttact ctagcttccc ggcaacaatt aatagactgg   6660
atggaggcgg ataaagttgc aggaccactt ctgcgctcgg cccttccggc tggctggttt   6720
attgctgata atctggagc cggtgagcgt ggaagccgcg gtatcattgc agcactgggg   6780
ccagatggta agccctcccg tatcgtagtt atctacacga cggggagtca ggcaactatg   6840
gatgaacgaa atagacagat cgctgagata ggtgcctcac tgattaagca ttggtaactg   6900
tcagaccaag tttactcata tatactttag attgatttaa aacttcattt ttaatttaaa   6960
aggatctagg tgaagatcct ttttgataat ctcatgacca aaatccctta acgtgagttt   7020
tcgttccact gagcgtcaga ccccgtagaa aagatcaaag gatcttcttg agatcctttt   7080
tttctgcgcg taatctgctg cttgcaaaca aaaaaaccac cgctaccagc ggtggtttgt   7140
ttgccggatc aagagctacc aactcttttt ccgaaggtaa ctggcttcag cagagcgcag   7200
ataccaaata ctgtccttct agtgtagccg tagttaggcc accacttcaa gaactctgta   7260
gcaccgccta catacctcgc tctgctaatc ctgttaccag tggctgctgc cagtggcgat   7320
aagtcgtgtc ttaccgggtt ggactcaaga cgatagttac cggataaggc gcagcggtcg   7380
ggctgaacgg ggggttcgtg cacacagccc agcttggagc gaacgaccta caccgaactg   7440
agatacctac agcgtgagct atgagaaagc gccacgcttc ccgaagggag aaaggcggac   7500
```

```
aggtatccgg taagcggcag ggtcggaaca ggagagcgca cgaggagct  tccaggggga    7560 aacgcctggt atctttatag tcctgtcggg tttcgccacc tctgacttga gcgtcgattt    7620
ttgtgatgct cgtcaggggg gcggagccta tggaaaaacg ccagcaacgc ggcctttta     7680 cggttcctgg ccttttgctg ccttttgct  cacatgttct ttcctgcgtt atcccctgat    7740
tctgtggata accgtattac cgcctttgag tgagctgata ccgctcgccg cagccgaacg    7800
accgagcgca gcgagtcagt gagcgaggaa gcggaagagc gcccaatacg caaaccgcct    7860
ctccccgcgc gttggccgat tcattaa                                        7887
```

<210> SEQ ID NO 8
<211> LENGTH: 7908
<212> TYPE: DNA
<213> ORGANISM: Artificial Sequence
<220> FEATURE:
<223> OTHER INFORMATION: p1139_pAAV2.1._HLP_SpCas9(HA)_spA

<400> SEQUENCE: 8

```
ataacaattt cacacaggaa acagctatga ccatgattac gccagattta attaaggctg      60
cgcgctcgct cgctcactga ggccgcccgg gcaaagcccg ggcgtcgggc gacctttggt     120
cgcccggcct cagtgagcga gcgagcgcgc agagagggag tggccaactc catcactagg     180
ggttccttgt agttaatgat taacccgcca tgctacttat ctacgtagcc atgctctagg     240
aagatcggaa ttcgcccgga attcgccctt aagcggccgc aagcttaag  tgtttgctgc     300 ttgcaatgtt tgcccatttt agggtggaca caggacgctg tggtttctga gccaggggc     360 gactcagatc ccagccagtg gacttagccc ctgtttgctc ctccgataac tggggtgacc    420
ttggttaata ttcaccagca gcctccccg  ttgcccctct ggatccactg cttaaatacg    480
gacgaggaca gggccctgtc tcctcagctt caggcaccac cactgacctg gacagtgaa     540 tcaccggtac ctgcttttgc tcgcttggat ccccggtgcc accatgtccg gtgccaccat    600
gtacccatac gatgttccag attacgcttc gccgaagaaa aagcgcaagg tcgaagcgtc    660
cgacaagaag tacagcatcg gcctggacat cggcaccaac tctgtgggct gggccgtgat    720
caccgacgag tacaaggtgc ccagcaagaa attcaaggtg ctgggcaaca ccgaccggca    780
cagcatcaag aagaacctga tcggagccct gctgttcgac agcggcgaaa cagccgaggc    840
cacccggctg aagagaaccg ccagaagaag ataccaccga cggaagaacc ggatctgcta    900
tctgcaagag atcttcagca acgagatggc caaggtggac gacagcttct ccacagact     960 ggaagagtcc ttcctggtgg aagaggataa gaagcacgag cggcacccca tcttcggcaa   1020
catcgtggac gaggtggcct accacgagaa gtaccccacc atctaccacc tgagaaagaa   1080
actggtggac agcaccgaca aggccgacct gcggctgatc tatctggccc tggcccacat   1140
gatcaagttc cggggccact tcctgatcga gggcgacctg aaccccgaca cagcgacgt    1200 ggacaagctg ttcatccagc tggtgcagac ctacaaccag ctgttcgagg aaaacccat    1260 caacgccagc ggcgtggacg ccaaggccat cctgtctgcc agactgagca gagcagacg    1320 gctggaaaat ctgatcgccc agctgccgg  cgagaagaag aatggcctgt tcggcaacct   1380
gattgccctg agcctgggcc tgaccccaa  cttcaagagc aacttcgacc tggccgagga   1440
tgccaaactg cagctgagca aggacaccta cgacgacgac ctggacaacc tgctggccca   1500
gatcggcgac cagtacgccg acctgtttct ggccgccaag aacctgtccg acgccatcct   1560
gctgagcgac atcctgagag tgaacaccga gatcaccaag gcccccctga gcgcctctat   1620
```

```
gatcaagaga tacgacgagc accaccagga cctgaccctg ctgaaagctc tcgtgcggca    1680
gcagctgcct gagaagtaca aagagatttt cttcgaccag agcaagaacg gctacgccgg    1740
ctacattgac ggcggagcca gccaggaaga gttctacaag ttcatcaagc ccatcctgga    1800
aaagatggac ggcaccgagg aactgctcgt gaagctgaac agagaggacc tgctgcggaa    1860
gcagcggacc ttcgacaacg gcagcatccc ccaccagatc cacctgggag agctgcacgc    1920
cattctgcgg cggcaggaag attttttaccc attcctgaag gacaaccggg aaaagatcga    1980
gaagatcctg accttccgca tccctacta cgtgggccct ctggccaggg gaaacagcag    2040
attcgcctgg atgaccagaa agagcgagga accatcacc ccctggaact tcgaggaagt    2100
ggtggacaag ggcgcttccg cccagagctt catcgagcgg atgaccaact tcgataagaa    2160
cctgcccaac gagaaggtgc tgcccaagca gagcctgctg tacgagtact tcaccgtgta    2220
taacgagctg accaaagtga aatacgtgac cgagggaatg agaaagcccg ccttcctgag    2280
cggcgagcag aaaaaggcca tcgtggacct gctgttcaag accaaccgga aagtgaccgt    2340
gaagcagctg aaagaggact acttcaagaa aatcgagtgc ttcgactccg tggaaatctc    2400
cggcgtggaa gatcggttca acgcctccct gggcacatac cacgatctgc tgaaaattat    2460
caaggacaag gacttcctgg acaatgagga aaacgaggac attctggaag atatcgtgct    2520
gaccctgaca ctgtttgagg acagagagat gatcgaggaa cggctgaaaa cctatgccca    2580
cctgttcgac gacaaagtga tgaagcagct gaagcggcgg agatacaccg gctggggcag    2640
gctgagccgg aagctgatca acggcatccg ggacaagcag tccggcaaga caatcctgga    2700
tttcctgaag tccgacggct tcgccaacag aaacttcatg cagctgatcc acgacgacag    2760
cctgaccttt aaagaggaca tccagaaagc ccaggtgtcc ggccagggcg atagcctgca    2820
cgagcacatt gccaatctgg ccggcagccc cgccattaag aagggcatcc tgcagacagt    2880
gaaggtggtg gacgagctcg tgaaagtgat gggccggcac aagcccgaga catcgtgat    2940
cgaaatggcc agagagaacc agaccacca gaagggacaa gaacagcc gcgagagaat    3000
gaagcggatc gaagagggca tcaaagagct gggcagccag atcctgaaag aacaccccgt    3060
ggaaaacacc cagctgcaga cgagaagct gtacctgtac tacctgcaga tgggcgggaa    3120
tatgtacgtg gaccaggaac tggacatcaa ccggctgtcc gactacgatg tggaccatat    3180
cgtgcctcag agctttctga aggacgactc catcgacaac aaggtgctga ccagaagcga    3240
caagaaccgg ggcaagagcg acaacgtgcc ctccgaagag gtcgtgaaga agatgaagaa    3300
ctactggcgg cagctgctga acgccaagct gattacccag agaaagttcg acaatctgac    3360
caaggccgag agaggcggcc tgagcgaact ggataaggcc ggcttcatca agagacagct    3420
ggtgaaaacc cggcagatca caaagcacgt ggcacagatc ctggactccc ggatgaacac    3480
taagtacgac gagaatgaca agctgatccg ggaagtgaaa gtgatcaccc tgaagtccaa    3540
gctggtgtcc gatttccgga aggatttcca gttttacaaa gtgcgcgaga tcaacaacta    3600
ccaccacgcc cacgacgcct acctgaacgc cgtcgtggga accgccctga tcaaaaagta    3660
ccctaagctg gaaagcgagt tcgtgtacgg cgactacaag gtgtacgacg tgcggaagat    3720
gatcgccaag agcgagcagg aaatcggcaa ggctaccgcc aagtacttct tctacagcaa    3780
catcatgaac tttttcaaga ccgagattac cctggccaac ggcgagatcc ggaagcggcc    3840
tctgatcgag acaaacggcg aaaccgggga tcgtgtgtgg ataagggcc gggattttgc    3900
caccgtgcgg aaagtgctga gcatgcccca agtgaatatc gtgaaaaaga ccgaggtgca    3960
gacaggcggc ttcagcaaag agtctatcct gcccaagagg aacagcgata gctgatcgc    4020
```

```
cagaaagaag gactgggacc ctaagaagta cggcggcttc gacagcccca ccgtggccta    4080
ttctgtgctg gtggtggcca aagtggaaaa gggcaagtcc aagaaactga agagtgtgaa    4140
agagctgctg gggatcacca tcatggaaag aagcagcttc gagaagaatc ccatcgactt    4200
tctggaagcc aagggctaca agaagtgaa aaaggacctg atcatcaagc tgcctaagta     4260
ctccctgttc gagctggaaa acggccggaa gagaatgctg gcctctgccg gcgaactgca    4320
gaagggaaac gaactggccc tgcccctccaa atatgtgaac ttcctgtacc tggccagcca   4380
ctatgagaag ctgaagggct cccccgagga taatgagcag aaacagctgt tgtgtggaaca   4440 gcacaagcac tacctggacg agatcatcga gcagatcagc gagttctcca agagagtgat   4500
cctggccgac gctaatctgg acaaagtgct gtccgcctac aacaagcacc gggataagcc    4560
catcagagag caggccgaga atatcatcca cctgtttacc ctgaccaatc tgggagcccc    4620
tgccgccttc aagtactttg acaccaccat cgaccggaag aggtacacca gcaccaaaga   4680
ggtgctggac gccacccctga tccaccagag catcaccggc ctgtacgaga cacggatcga   4740
cctgtctcag ctgggaggcg acagccccaa gaagaagaga aaggtggagg ccagctaaga   4800
attcaataaa agatctttat tttcattaga tctgtgtgtt ggtttttgt gtgcggccgc     4860 aggaacccct agtgatggag ttggccactc cctctctgcg cgctcgctcg ctcactgagg    4920
ccgggcgacc aaaggtcgcc cgacgcccgg gctttgcccg gcggcctca gtgagcgagc     4980 gagcgcgcag ctgcctgcag gggcgcctga tgcggtattt tctccttacg catctgtgcg    5040
gtatttcaca ccgcatacgt caaagcaacc atagtacgcg ccctgtagcg gcgcattaag    5100
cgcggcgggt gtggtggtta cgcgcagcgt gaccgctaca cttgccagcg ccctagcgcc    5160
cgctcctttc gctttcttcc cttcctttct cgccacgttc gccggctttc cccgtcaagc    5220
tctaaatcgg gggctccctt tagggttccg atttagtgct ttacggcacc tcgaccccaa    5280
aaaacttgat ttgggtgatg gttcacgtag tgggccatcg ccctgataga cggttttttcg   5340 cccttttgacg ttggagtcca cgttctttaa tagtggactc ttgttccaaa ctggaacaac    5400
actcaaccct atctcgggct attcttttga tttataaggg attttgccga tttcggccta    5460
ttggttaaaa aatgagctga tttaacaaaa atttaacgcg aattttaaca aaatattaac    5520
gtttacaatt ttatggtgca ctctcagtac aatctgctct gatgccgcat agttaagcca    5580
gccccgacac ccgccaacac ccgctgacgc gccctgacgg gcttgtctgc tcccggcatc    5640
cgcttacaga caagctgtga ccgtctccgg gagctgcatg tgtcagaggt tttcaccgtc    5700
atcaccgaaa cgcgcgagac gaaagggcct cgtgatacgc ctatttttat aggttaatgt    5760
catgataata atggtttctt agacgtcagg tggcactttt cggggaaatg tgcgcggaac    5820
ccctatttgt ttatttttct aaatacattc aaatatgtat ccgctcatga acaataaccc    5880
ctgataaatg cttcaataat attgaaaaag gaagagtatg agtattcaac atttccgtgt    5940
cgcccttatt cccttttttg cggcattttg ccttcctgtt tttgctcacc cagaaacgct    6000
ggtgaaagta aaagatgctg aagatcagtt gggtgcacga gtgggttaca tcgaactgga    6060
tctcaacagc ggtaagatcc ttgagagttt tcgccccgaa gaacgttttc caatgatgag    6120
cacttttaaa gttctgctat gtggcgcggt attatcccgt attgacgccg ggcaagagca    6180
actcggtcgc cgcatacact attctcagaa tgacttggtt gagtactcac cagtcacaga    6240
aaagcatctt acgatggca tgacagtaag agaattatgc agtgctgcca taaccatgag    6300
tgataacact gcggccaact tacttctgac aacgatcgga ggaccgaagg agctaaccgc    6360
```

```
tttttttgcac aacatggggg atcatgtaac tcgccttgat cgttgggaac cggagctgaa    6420
tgaagccata ccaaacgacg agcgtgacac cacgatgcct gtagcaatgg caacaacgtt    6480
gcgcaaacta ttaactggcg aactacttac tctagcttcc cggcaacaat taatagactg    6540
gatggaggcg gataaagttg caggaccact tctgcgctcg gcccttccgg ctggctggtt    6600
tattgctgat aaatctggag ccggtgagcg tggaagccgc ggtatcattg cagcactggg    6660
gccagatggt aagccctccc gtatcgtagt tatctcacg acggggagtc aggcaactat    6720
ggatgaacga aatagacaga tcgctgagat aggtgcctca ctgattaagc attggtaact    6780
gtcagaccaa gtttactcat atatacttta gattgattta aaacttcatt tttaatttaa    6840
aaggatctag gtgaagatcc tttttgataa tctcatgacc aaaatccctt aacgtgagtt    6900
ttcgttccac tgagcgtcag accccgtaga aaagatcaaa ggatcttctt gagatccttt    6960
ttttctgcgc gtaatctgct gcttgcaaac aaaaaaacca ccgctaccag cggtggtttg    7020
tttgccggat caagagctac caactctttt tccgaaggta actggcttca gcagagcgca    7080
gataccaaat actgtccttc tagtgtagcc gtagttaggc caccacttca agaactctgt    7140
agcaccgcct acatacctcg ctctgctaat cctgttacca gtggctgctg ccagtggcga    7200
taagtcgtgt cttaccgggt tggactcaag acgatagtta ccggataagg cgcagcggtc    7260
gggctgaacg gggggttcgt gcacacagcc cagcttggag cgaacgacct acaccgaact    7320
gagataccta cagcgtgagc tatgagaaag cgccacgctt cccgaaggga gaaaggcgga    7380
caggtatccg gtaagcggca gggtcggaac aggagagcgc acgagggagc ttccaggggg    7440
aaacgcctgg tatctttata gtcctgtcgg gtttcgccac ctctgacttg agcgtcgatt    7500
tttgtgatgc tcgtcagggg ggcggagcct atggaaaaac gccagcaacg cggccttttt    7560
acggttcctg gccttttgct ggccttttgc tcacatgttc tttcctgcgt tatcccctga    7620
ttctgtggat aaccgtatta ccgcctttga gtgagctgat accgctcgcc gcagccgaac    7680
gaccgagcgc agcgagtcag tgagcgagga agcggaagag cgcccaatac gcaaaccgcc    7740
tctccccgcg cgttggccga ttcattaatg cagctggcac gacaggtttc ccgactggaa    7800
agcgggcagt gagcgcaacg caattaatgt gagttagctc actcattagg cacccccaggc    7860
tttacacttt atgcttccgg ctcgtatgtt gtgtggaatt gtgagcgg                 7908
```

<210> SEQ ID NO 9
<211> LENGTH: 6960
<212> TYPE: DNA
<213> ORGANISM: Artificial Sequence
<220> FEATURE:
<223> OTHER INFORMATION: p1135// pAAV2.1 mRHOgRNA-mRHO HITI (kozak-dsRED)_hVmd2-EGFP

<400> SEQUENCE: 9

```
ttaatgtgag ttagctcact cattaggcac cccaggcttt acactttatg cttccggctc     60
gtatgttgtg tggaattgtg agcggataac aatttcacac aggaaacagc tatgaccatg    120
attacgccag atttaattaa ggctgcgcgc tcgctcgctc actgaggccg cccgggcaaa    180
gcccgggcgt cgggcgacct ttggtcgccc ggcctcagtg agcgagcgag cgcgcagaga    240
gggagtggcc aactccatca ctaggggttc cttgtagtta atgattaacc cgccatgcta    300
cttatctacg tagccatgct ctaggaagat cggaattcgc ccttaaccac tagtaacggc    360
cgccagtgtg ctggaattcg ccctttcgag ggcctatttc ccatgattcc ttcatatttg    420
catatacgat acaaggctgt tagagagata attggaatta atttgactgt aaacacaaag    480
```

```
atattagtac aaaatacgtg acgtagaaag taataatttc ttgggtagtt tgcagtttta    540
aaattatgtt ttaaaatgga ctatcatatg cttaccgtaa cttgaaagta tttcgatttc    600
ttggctttat atatcttgtg gaaaggacga aacaccggca gccgcagtac tacctgggtt    660
ttagagctag aaatagcaag ttaaaataag gctagtccgt tatcaacttg aaaaagtggc    720
accgagtcgg tgcttttttg ttttagagct agaaatagca agctcgagca gcctgaattc    780
tgcagatatc catcacactg gcggccttaa ctcggatcca ctagtaacgg ccgccagtgt    840
gctggaattc aggccgccag gtagtactgc ggctgctaat aaataataag ccaccatgga    900
tagcactgag aacgtcatca agcccttcat gcgcttcaag gtgcacatgg agggctccgt    960
gaacggccac gagttcgaga tcgagggcga gggcgagggc aagccctacg agggcaccca   1020
gaccgccaag ctgcaggtga ccaagggcgg ccccctgccc ttcgcctggg acatcctgtc   1080
cccccagttc cagtacggct ccaaggtgta cgtgaagcac cccgccgaca tccccgacta   1140
caagaagctg tccttccccg agggcttcaa gtgggagcgc gtgatgaact tcgaggacgg   1200
cggcgtggtg accgtgaccc aggactcctc cctgcaggac ggcaccttca tctaccacgt   1260
gaagttcatc ggcgtgaact ccccctccga cggccccgta atgcagaaga agactctggg   1320
ctgggagccc tccaccgagc gcctgtaccc ccgcgacggc gtgctgaagg gcgagatcca   1380
caaggcgctg aagctgaagg gcggcggcca ctacctggtg gagttcaagt caatctacat   1440
ggccaagaag cccgtgaagc tgcccggcta ctactacgtg gactccaagc tggacatcac   1500
ctcccacaac gaggactaca ccgtggtgga gcagtacgag cgcgccgagg cccgccacca   1560
cctgttccag tagcggccgc gactctagaa ttcaactga gcgccggtcg ctaccattac   1620
caacttgtct ggtgtcaaaa ataataggcc tactagagtc gacctgcaga agcttggatc   1680
tgcctcgact gtgccttcta gttgccagcc atctgttgtt tgcccctccc ccgtgccttc   1740
cttgaccctg gaaggtgcca ctcccactgt cctttcctaa taaaatgagg aaattgcatc   1800
gcattgtctg agtaggtgtc attctattct ggggggtggg gtgggcagg acagcaaggg   1860 ggaggattgg gaagacaata gcaggcatgc tggggaccgc caggtagtac tgcggctgca   1920
agggcgaatt ctgcagatat ccatcacact ggcgttaagc gtcagcatat gcagaattct   1980
gtcattttac tagggtgatg aaattcccaa gcaacaccat cctttcaga taagggcact   2040 gaggctgaga gaggagctga aacctacccg gggtcaccac acacaggtgg caaggctggg   2100
accagaaacc aggactgttg actgcagccc ggtattcatt ctttccatag cccacagggc   2160
tgtcaaagac cccagggcct agtcagaggc tcctccttcc tggagagttc ctggcacaga   2220
agttgaagct cagcacagcc ccctaacccc caactctctc tgcaaggcct cagggtcag    2280 aacactggtg gagcagatcc tttagcctct ggattttagg gccatggtag aggggtgtt    2340 gccctaaatt ccagccctgg tctcagccca acaccctcca agaagaaatt agaggggcca   2400
tggccaggct gtgctagccg ttgcttctga gcagattaca agaagggact aagacaagga   2460
ctcctttgtg gaggtcctgg cttagggagt caagtgacgg cggctcagca ctcacgtggg   2520
cagtgccagc ctctaagagt gggcagggc actggccaca gagtcccagg gagtcccacc   2580
agcctagtcg ccagaccttc tgtgggcggc cgccatggtg agcaagggcg aggagctgtt   2640
caccggggtg gtgcccatcc tggtcgagct ggacggcgac gtaaacggcc acaagttcag   2700
cgtgtccggc gagggcgagg gcgatgccac ctacggcaag ctgaccctga agttcatctg   2760
caccaccggc aagctgcccg tgccctgcc caccctcgtg accaccctga cctacggcgt   2820
gcagtgcttc agccgctacc ccgaccacat gaagcagcac gacttcttca gtccgccat    2880
```

```
gcccgaaggc tacgtccagg agcgcaccat cttcttcaag gacgacggca actacaagac   2940
ccgcgccgag gtgaagttcg agggcgacac cctggtgaac cgcatcgagc tgaagggcat   3000
cgacttcaag gaggacggca acatcctggg gcacaagctg gagtacaact acaacagcca   3060
caacgtctat atcatggccg acaagcagaa gaacggcatc aaggtgaact tcaagatccg   3120
ccacaacatc gaggacggca gcgtgcagct cgccgaccac taccagcaga cacccccat    3180
cggcgacggc cccgtgctgc tgcccgacaa ccactacctg agcacccagt ccgccctgag   3240
caaagacccc aacgagaagc gcgatcacat ggtcctgctg gagttcgtga ccgccgccgg   3300
gatcactctc ggcatggacg agctgtacaa gtaataagct tggatccaat caacctctgg   3360
attacaaaat ttgtgaaaga ttgactggta ttcttaacta tgttgctcct tttacgctat   3420
gtggatacgc tgctttaatg cctttgtatc atgctattgc ttcccgtatg gctttcattt   3480
tctcctcctt gtataaatcc tggttgctgt ctctttatga ggagttgtgg cccgttgtca   3540
ggcaacgtgg cgtggtgtgc actgtgtttg ctgacgcaac ccccactggt tggggcattg   3600
ccaccacctg tcagctcctt ccgggacttt cgctttcccc cctccctatt gccacggcgg   3660
aactcatcgc cgcctgcctt gcccgctgct ggacaggggc tcggctgttg gcactgaca    3720
attccgtggt gttgtcgggg aagctgacgt cctttccatg gctgctcgcc tgtgttgcca   3780
cctggattct gcgcgggacg tccttctgct acgtcccttc ggccctcaat ccagcggacc   3840
ttccttcccg cggcctgctg ccggctctgc ggcctcttcc gcgtcttcga gatctgcctc   3900
gactgtgcct tctagttgcc agccatcgt  tgtttgcccc tccccgtgc cttccttgac    3960
cctggaaggt gccactccca ctgtcctttc ctaataaaat gaggaaattg catcgcattg   4020
tctgagtagg tgtcattcta ttctgggggg tggggtgggg caggacagca agggggagga   4080
ttgggaagac aatagcaggc atgctgggga ctcgagttaa gggcgaattc ccgattagga   4140
tcttcctaga gcatggctac gtagataagt agcatggcgg gttaatcatt aactacaagg   4200
aaccctagt  gatggagttg gccactccct ctctgcgcgc tcgctcgctc actgaggccg   4260
ggcgaccaaa ggtcgcccga cgcccgggct ttgcccgggc ggcctcagtg agcgagcgag   4320
cgcgcagcct taattaacct aattcactgg ccgtcgtttt acaacgtcgt gactgggaaa   4380
accctggcgt tacccaactt aatcgccttg cagcacatcc cctttcgcc  agctggcgta   4440
atagcgaaga ggcccgcacc gatcgccctt cccaacagtt gcgcagcctg aatggcgaat   4500
gggacgcgcc ctgtagcggc gcattaagcg cggcgggtgt ggtggttacg cgcagcgtga   4560
ccgctacact tgccagcgcc ctagcgcccg ctcctttcgc tttcttccct tcctttctcg   4620
ccacgttcgc cggctttccc cgtcaagctc taaatcgggg gctcccttta gggttccgat   4680
ttagtgcttt acggcacctc gaccccaaaa aacttgatta gggtgatggt tcacgtagtg   4740
ggccatcgcc ccgatagacg gttttttcgcc ctttgacgct ggagttcacg ttcctcaata  4800
gtggactctt gttccaaact ggaacaacac tcaaccctat ctcggtctat tcttttgatt   4860
tataagggat ttttccgatt tcggcctatt ggttaaaaaa tgagctgatt taacaaaaat   4920
ttaacgcgaa ttttaacaaa atattaacgt ttataatttc aggtggcatc tttcggggaa   4980
atgtgcgcgg aaccctatt  tgtttatttt tctaaataca ttcaaatatg tatccgctca   5040
tgagacaata accctgataa atgcttcaat aatattgaaa aaggaagagt atgagtattc   5100
aacatttccg tgtcgccctt attccctttt ttgcggcatt ttgccttcct gtttttgctc   5160
acccagaaac gctggtgaaa gtaaaagatg ctgaagatca gttgggtgca cgagtgggtt   5220
```

| | |
|---|---|
| acatcgaact ggatctcaat agtggtaaga tccttgagag ttttcgcccc gaagaacgtt | 5280 |
| ttccaatgat gagcactttt aaagttctgc tatgtggcgc ggtattatcc cgtattgacg | 5340 |
| ccgggcaaga gcaactcggt cgccgcatac actattctca gaatgacttg gttgagtact | 5400 |
| caccagtcac agaaaagcat cttacggatg gcatgacagt aagagaatta tgcagtgctg | 5460 |
| ccataaccat gagtgataac actgcggcca acttacttct gacaacgatc ggaggaccga | 5520 |
| aggagctaac cgcttttttg cacaacatgg gggatcatgt aactcgcctt gatcgttggg | 5580 |
| aaccggagct gaatgaagcc ataccaaacg acgagcgtga ccacgatg cctgtagtaa | 5640 |
| tggtaacaac gttgcgcaaa ctattaactg gcgaactact tactctagct tcccggcaac | 5700 |
| aattaataga ctggatggag gcggataaag ttgcaggacc acttctgcgc tcggcccttc | 5760 |
| cggctggctg gtttattgct gataaatctg gagccggtga gcgtgggtct cgcggtatca | 5820 |
| ttgcagcact ggggccagat ggtaagccct cccgtatcgt agttatctac acgacgggga | 5880 |
| gtcaggcaac tatggatgaa cgaaatagac agatcgctga gataggtgcc tcactgatta | 5940 |
| agcattggta actgtcagac caagtttact catatatact ttagattgat ttaaaacttc | 6000 |
| atttttaatt taaaaggatc taggtgaaga tcctttttga taatctcatg accaaaatcc | 6060 |
| cttaacgtga gttttcgttc cactgagcgt cagaccccgt agaaaagatc aaaggatctt | 6120 |
| cttgagatcc ttttttctg cgcgtaatct gctgcttgca acaaaaaaa ccaccgctac | 6180 |
| cagcggtggt ttgtttgccg gatcaagagc taccaactct ttttccgaag gtaactggct | 6240 |
| tcagcagagc gcagatacca atactgtcc ttctagtgta gccgtagtta ggccaccact | 6300 |
| tcaagaactc tgtagcaccg cctacatacc tcgctctgct aatcctgtta ccagtggctg | 6360 |
| ctgccagtgg cgataagtcg tgtcttaccg ggttggactc aagacgatag ttaccggata | 6420 |
| aggcgcagcg gtcgggctga acggggggtt cgtgcacaca gcccagcttg gagcgaacga | 6480 |
| cctacaccga actgagatac ctacagcgtg agctatgaga aagcgccacg cttcccgaag | 6540 |
| ggagaaaggc ggacaggtat ccggtaagcg gcagggtcgg aacaggagag cgcacgaggg | 6600 |
| agcttccagg gggaaacgcc tggtatcttt atagtcctgt cgggtttcgc cacctctgac | 6660 |
| ttgagcgtcg atttttgtga tgctcgtcag ggggcggag cctatggaaa aacgccagca | 6720 |
| acgcggcctt tttacggttc ctggcctttt gctgcggttt tgctcacatg ttctttcctg | 6780 |
| cgttatcccc tgattctgtg gataaccgta ttaccgcctt tgagtgagct gataccgctc | 6840 |
| gccgcagccg aacgaccgag cgcagcgagt cagtgagcga ggaagcggaa gggccgattc | 6900 |
| attaatgcag ctggcacgac aggtttcccg actggaaagc gggcagtgag cgcaacgcaa | 6960 |

<210> SEQ ID NO 10
<211> LENGTH: 6961
<212> TYPE: DNA
<213> ORGANISM: Artificial Sequence
<220> FEATURE:
<223> OTHER INFORMATION: p1116// pAAV_Scramble_mRHO HITI(kozak-
      dsRED)_hVmd2-EGFP

<400> SEQUENCE: 10

| | |
|---|---|
| ggaaacagct atgaccatga ttacgccaga tttaattaag gctgcgcgct cgctcgctca | 60 |
| ctgaggccgc ccgggcaaag cccgggcgtc gggcgacctt tggtcgcccg gcctcagtga | 120 |
| gcgagcgagc gcgcagagag ggagtggcca actccatcac tagggggttcc ttgtagttaa | 180 |
| tgattaaccc gccatgctac ttatctacgt agccatgctc taggaagatc ggaattcgcc | 240 |
| cttaaccact agtaacggcc gccagtgtgc tggaattcgc cctttcgagg gcctatttcc | 300 |

```
catgattcct tcatatttgc atatacgata caaggctgtt agagagataa ttggaattaa   360
tttgactgta aacacaaaga tattagtaca aaatacgtga cgtagaaagt aataatttct   420
tgggtagttt gcagttttaa aattatgttt taaaatggac tatcatatgc ttaccgtaac   480
ttgaaagtat ttcgatttct tggctttata tatcttgtgg aaaggacgaa acaccggact   540
cgcgcgagtc gaggaggttt tagagctaga aatagcaagt taaaataagg ctagtccgtt   600
atcaacttga aaaagtggca ccgagtcggt gcttttttgt tttagagcta gaaatagcaa   660
gctcgagcag cctgaattct gcagatatcc atcacactgg cggccttaac tcggatccac   720
tagtaacggc cgccagtgtg ctggaattcg aggccgccag gtagtactgc ggctgctaat   780
aaataataag ccaccatgga tagcactgag aacgtcatca agcccttcat gcgcttcaag   840
gtgcacatgg agggctccgt gaacggccac gagttcgaga tcgagggcga gggcgagggc   900
aagccctacg agggcaccca gaccgccaag ctgcaggtga ccaagggcgg cccctgccc    960
ttcgcctggg acatcctgtc ccccagttc cagtacggct ccaaggtgta cgtgaagcac   1020
cccgccgaca tccccgacta caagaagctg tccttccccg agggcttcaa gtgggagcgc   1080
gtgatgaact tcgaggacgg cggcgtggtg accgtgaccc aggactcctc cctgcaggac   1140
ggcaccttca tctaccacgt gaagttcatc ggcgtgaact cccctccga cggccccgta   1200
atgcagaaga agactctggg ctgggagccc tccaccgagc gcctgtaccc ccgcgacggc   1260
gtgctgaagg gcgagatcca aggcgctg aagctgaagg gcggcggcca ctacctggtg   1320
gagttcaagt caatctacat ggccaagaag cccgtgaagc tgcccggcta ctactacgtg   1380
gactccaagc tggacatcac ctcccacaac gaggactaca ccgtggtgga gcagtacgag   1440
cgcgccgagg cccgccacca cctgttccag tagcggccgc gactctagaa ttccaactga   1500
gcgccggtcg ctaccattac caacttgtct ggtgtcaaaa ataataggcc tactagagtc   1560
gacctgcaga agcttggatc tgcctcgact gtgccttcta gttgccagcc atctgttgtt   1620
tgcccctccc ccgtgccttc cttgaccctg gaaggtgcca ctcccactgt cctttcctaa   1680
taaaatgagg aaattgcatc gcattgtctg agtaggtgtc attctattct ggggggtggg   1740
gtggggcagg acagcaaggg ggaggattgg gaagacaata gcaggcatgc tggggaccgc   1800
caggtagtac tgcggctgca agggcgaatt ctgcagatat ccatcacact ggcgttaagc   1860
gtcagcatat gcagaattct gtcattttac tagggtgatg aaattcccaa gcaacaccat   1920
ccttttcaga taagggcact gaggctgaga gaggagctga aacctacccg gggtcaccac   1980
acacaggtgg caaggctggg accagaaacc aggactgttg actgcagccc ggtattcatt   2040
ctttccatag cccacagggc tgtcaaagac cccagggcct agtcagaggc tcctccttcc   2100
tggagagttc ctggcacaga agttgaagct cagcacagcc ccctaacccc caactctctc   2160
tgcaaggcct caggggtcag aacactggtg gagcagatcc tttagcctct ggattttagg   2220
gccatggtag aggggtgtt gccctaaatt ccagccctgg tctcagccca cacctccag    2280
agaagaaatt agagggccca tggccaggct gtgctagccg ttgcttctga gcagattaca   2340
agaagggact aagacaagga ctcctttgtg gaggtcctgg cttagggagt caagtgacgg   2400
cggctcagca ctcacgtggg cagtgccagc ctctaagagt gggcagggc actgccaca    2460
gagtcccagg gagtcccacc agcctagtcg ccagaccttc tgtgggcggc cgccatggtg   2520
agcaagggcg aggagctgtt caccggggtg gtgcccatcc tggtcgagct ggacggcgac   2580
gtaaacggcc acaagttcag cgtgtccggc gagggcgagg gcgatgccac ctacggcaag   2640
ctgaccctga agttcatctg caccaccggc aagctgcccg tgccctggcc caccctcgtg   2700
```

```
accaccctga cctacggcgt gcagtgcttc agccgctacc ccgaccacat gaagcagcac    2760
gacttcttca agtccgccat gcccgaaggc tacgtccagg agcgcaccat cttcttcaag    2820
gacgacggca actacaagac ccgcgccgag gtgaagttcg agggcgacac cctggtgaac    2880
cgcatcgagc tgaagggcat cgacttcaag gaggacggca acatcctggg gcacaagctg    2940
gagtacaact acaacagcca caacgtctat atcatggccg acaagcagaa gaacggcatc    3000
aaggtgaact tcaagatccg ccacaacatc gaggacggca gcgtgcagct cgccgaccac    3060
taccagcaga cacccccat cggcgacggc cccgtgctgc tgcccgacaa ccactacctg    3120
agcacccagt ccgccctgag caaagacccc aacgagaagc gcgatcacat ggtcctgctg    3180
gagttcgtga ccgccgccgg gatcactctc ggcatggacg agctgtacaa gtaataagct    3240
tggatccaat caacctctgg attacaaaat ttgtgaaaga ttgactggta ttcttaacta    3300
tgttgctcct tttacgctat gtggatacgc tgctttaatg cctttgtatc atgctattgc    3360
ttcccgtatg gctttcattt tctcctcctt gtataaatcc tggttgctgt ctctttatga    3420
ggagttgtgg cccgttgtca ggcaacgtgg cgtggtgtgc actgtgtttg ctgacgcaac    3480
ccccactggt tggggcattg ccaccacctg tcagctcctt tccggacttt cgctttcccc    3540
cctccctatt gccacggcgg aactcatcgc cgcctgcctt gcccgctgct ggacaggggc    3600
tcggctgttg ggcactgaca attccgtggt gttgtcgggg aagctgacgt cctttccatg    3660
gctgctcgcc tgtgttgcca cctggattct gcgcgggacg tccttctgct acgtcccttc    3720
ggccctcaat ccagcggacc ttccttcccg cggcctgctg ccggctctgc ggcctcttcc    3780
gcgtcttcga gatctgcctc gactgtgcct tctagttgcc agccatctgt tgtttgcccc    3840
tcccccgtgc cttccttgac cctggaaggt gccactccca ctgtcctttc ctaataaaat    3900
gaggaaattg catcgcattg tctgagtagg tgtcattcta ttctgggggg tggggtgggg    3960
caggacagca aggggagga ttgggaagac aatagcaggc atgctgggga ctcgagttaa    4020
gggcgaattc ccgattagga tcttcctaga gcatggctac gtagataagt agcatggcgg    4080
gttaatcatt aactcaaagg aaccctagt gatggagttg ccactccct ctctgcgcgc    4140 tcgctcgctc actgaggccg ggcgaccaaa ggtcgcccga cgcccgggct tgcccgggc    4200 ggcctcagtg agcgagcgag cgcgcagcct taattaacct aattcactgg ccgtcgtttt    4260
acaacgtcgt gactgggaaa accctggcgt tacccaactt aatcgccttg cagcacatcc    4320 cccttttcgcc agctggcgta atagcgaaga ggcccgcacc gatcgccctt cccaacagtt    4380
gcgcagcctg aatggcgaat gggacgcgcc ctgtagcggc gcattaagcg cggcgggtgt    4440
ggtggttacg cgcagcgtga ccgctacact gccagcgcc ctagcgcccg ctcctttcgc    4500
tttcttccct tcctttctcg ccacgttcgc cggctttccc cgtcaagctc taaatcgggg    4560 gctccctttta gggttccgat ttagtgcttt acggcacctc gaccccaaaa aacttgatta    4620
gggtgatggt tcacgtagtg ggccatcgcc ccgatagacg gttttcgcc ctttgacgct    4680 ggagttcacg ttcctcaata gtggactctt gttccaaact ggaacaacac tcaaccctat    4740
ctcggtctat tcttttgatt tataagggat ttttccgatt tcggcctatt ggttaaaaa    4800 tgagctgatt taacaaaaat ttaacgcgaa ttttaacaaa atattaacgt ttataattc     4860 aggtggcatc tttcggggaa atgtgcgcgg aaccctatt tgtttatttt tctaaataca    4920
ttcaaatatg tatccgctca tgagacaata accctgataa atgcttcaat aatattgaaa    4980
aaggaagagt atgagtattc aacatttccg tgtcgccctt attccctttt ttgcggcatt    5040
```
ttgccttcct gttttgctc acccagaaac gctggtgaaa gtaaagatg ctgaagatca    5100 gttgggtgca cgagtgggtt acatcgaact ggatctcaat agtggtaaga tccttgagag    5160
ttttcgcccc gaagaacgtt ttccaatgat gagcactttt aaagttctgc tatgtggcgc    5220
ggtattatcc cgtattgacg ccgggcaaga gcaactcggt cgccgcatac actattctca    5280
gaatgacttg gttgagtact caccagtcac agaaaagcat cttacggatg gcatgacagt    5340
aagagaatta tgcagtgctg ccataaccat gagtgataac actgcggcca acttacttct    5400
gacaacgatc ggaggaccga aggagctaac cgcttttttg cacaacatgg ggatcatgt    5460 aactcgcctt gatcgttggg aaccggagct gaatgaagcc ataccaaacg acgagcgtga    5520
caccacgatg cctgtagtaa tggtaacaac gttgcgcaaa ctattaactg gcgaactact    5580
tactctagct tcccggcaac aattaataga ctggatggag gcggataaag ttgcaggacc    5640
acttctgcgc tcggcccttc cggctggctg gtttattgct gataaatctg gagccggtga    5700
gcgtgggtct cgcggtatca ttgcagcact ggggccagat ggtaagccct cccgtatcgt    5760
agttatctac acgacgggga gtcaggcaac tatgatgaa cgaaatagac agatcgctga    5820
gataggtgcc tcactgatta agcattggta actgtcagac caagtttact catatatact    5880
ttagattgat ttaaaacttc atttttaatt taaaaggatc taggtgaaga tcctttttga    5940
taatctcatg accaaaatcc cttaacgtga gttttcgttc cactgagcgt cagaccccgt    6000
agaaaagatc aaaggatctt cttgagatcc ttttttctg cgcgtaatct gctgcttgca    6060
aacaaaaaaa ccaccgctac cagcggtggt ttgtttgccg gatcaagagc taccaactct    6120
ttttccgaag gtaactggct tcagcagagc gcagatacca aatactgtcc ttctagtgta    6180
gccgtagtta ggccaccact tcaagaactc tgtagcaccg cctacatacc tcgctctgct    6240
aatcctgtta ccagtggctg ctgccagtgg cgataagtcg tgtcttaccg ggttggactc    6300
aagacgatag ttaccggata aggcgcagcg gtcgggctga acggggggtt cgtgcacaca    6360
gcccagcttg gagcgaacga cctacaccga actgagatac ctacagcgtg agctatgaga    6420
aagcgccacg cttcccgaag ggagaaaggc ggacaggtat ccggtaagcg cagggtcgg    6480 aacaggagag cgcacgaggg agcttccagg gggaaacgcc tggtatcttt atagtcctgt    6540
cgggtttcgc cacctctgac ttgagcgtcg attttgtga tgctcgtcag ggggggcggag    6600 cctatggaaa aacgccagca acgcggcctt tttacggttc ctggccttt gctgcggttt    6660 tgctcacatg ttcttttcctg cgttatcccc tgattctgtg gataaccgta ttaccgcctt    6720
tgagtgagct gataccgctc gccgcagccg aacgaccgag cgcagcgagt cagtgagcga    6780
ggaagcggaa gggccgattc attaatgcag ctggcacgac aggtttcccg actggaaagc    6840
gggcagtgag cgcaacgcaa ttaatgtgag ttagctcact cattaggcac cccaggcttt    6900
acactttatg cttccggctc gtatgttgtg tggaattgtg agcggataac aatttcacac    6960
a                                                                     6961

<210> SEQ ID NO 11
<211> LENGTH: 7007
<212> TYPE: DNA
<213> ORGANISM: Artificial Sequence
<220> FEATURE:
<223> OTHER INFORMATION: p1048// pAAV2.1-Scramble-mRHO HITI(IRESdsRED)-
    Vmd2-EGFP

<400> SEQUENCE: 11
acacaggaaa cagctatgac catgattacg ccagatttaa ttaaggctgc gcgctcgctc    60

```
gctcactgag gccgcccggg caaagcccgg gcgtcgggcg acctttggtc gcccggcctc    120
agtgagcgag cgagcgcgca gagagggagt ggccaactcc atcactaggg gttccttgta    180
gttaatgatt aacccgccat gctacttatc tacgtagcca tgctctagga agatcggaat    240
tcgcccttaa ccactagtaa cggccgccag tgtgctggaa ttcgcccttt cgagggccta    300
tttcccatga ttccttcata tttgcatata cgatacaagg ctgttagaga gataattgga    360
attaatttga ctgtaaacac aaagatatta gtacaaaata cgtgacgtag aaagtaataa    420
tttcttgggt agtttgcagt tttaaaatta tgttttaaaa tggactatca tatgcttacc    480
gtaacttgaa agtatttcga tttcttggct ttatatatct tgtggaaagg acgaaacacc    540
ggactcgcgc gagtcgagga ggttttagag ctagaaatag caagttaaaa taaggctagt    600
ccgttatcaa cttgaaaaag tggcaccgag tcggtgcttt tttgttttag agctagaaat    660
agcaagctcg agcagcctga attctgcaga tatccatcac actggcggcc ttaactcgga    720
tccactagta acggccgcca gtgtgctgga attcgccctt ccgccaggta gtactgcggc    780
tgctaataaa taataatgac aaactgtaca tgccgttaac tgtaattttg cgtgattttt    840
ttgtagatgg atagcactga gaacgtcatc aagcccttca tgcgcttcaa ggtgcacatg    900
gagggctccg tgaacggcca cgagttcgag atcgagggcg agggcgaggg caagccctac    960
gagggcaccc agaccgccaa gctgcaggtg accaagggcg ccccctgcc cttcgcctgg   1020 gacatcctgt cccccagtt ccagtacggc tccaaggtgt acgtgaagca ccccgccgac   1080
atccccgact acaagaagct gtccttcccc gagggcttca gtgggagcg cgtgatgaac   1140 ttcgaggacg gcgcgtggt gaccgtgacc caggactcct ccctgcagga cggcaccttc   1200
atctaccacg tgaagttcat cggcgtgaac ttcccctccg acggccccgt aatgcagaag   1260
aagactctgg gctgggagcc ctccaccgag cgcctgtacc cccgcgacgg cgtgctgaag   1320
ggcgagatcc acaaggcgct gaagctgaag ggcggcggcc actacctggt ggagttcaag   1380
tcaatctaca tggccaagaa gcccgtgaag ctgcccggct actactacgt ggactccaag   1440
ctggacatca cctcccacaa cgaggactac accgtggtgg agcagtacga gcgcgccgag   1500
gcccgccacc acctgttcca gtagcggccg cgactctaga attccaactg agcgccggtc   1560
gctaccatta ccaacttgtc tggtgtcaaa aataataggc ctactagagt cgacctgcag   1620
aagcttggat ctgcctcgac tgtgccttct agttgccagc catctgttgt ttgcccctcc   1680
cccgtgcctt ccttgaccct ggaaggtgcc actcccactg tcctttccta ataaaatgag   1740
gaaattgcat cgcattgtct gagtaggtgt cattctattc tggggggtgg ggtggggcag   1800
gacagcaagg gggaggattg ggaagacaat agcaggcatg ctggggaccg ccaggtagta   1860
ctgcggctgc aagggcgaat tctgcagata tccatcacac tggcgttaag cgtcagcata   1920
tgcagaattc tgtcatttta ctagggtgat gaaattccca agcaacacca tccttttcag   1980
ataagggcac tgaggctgag agaggagctg aaacctaccc ggggtcacca cacacaggtg   2040
gcaaggctgg gaccagaaac caggactgtt gactgcagcc cggtattcat tctttccata   2100
gcccacaggg ctgtcaaaga ccccagggcc tagtcagagg ctcctccttc ctggagagtt   2160
cctggcacag aagttgaagc tcagcacagc cccctaaccc ccaactctct ctgcaaggcc   2220
tcaggggtca gaacactggt ggagcagatc ctttagcctc tggattttag ggccatggta   2280 gaggggggtgt tgccctaaat tccagccctg gtctcagccc aacaccctcc aagaagaaat   2340 tagagggggcc atggccaggc tgtgctagcc gttgcttctg agcagattac aagaagggac   2400
taagacaagg actcctttgt ggaggtcctg gcttaggag tcaagtgacg gcggctcagc   2460
```

```
actcacgtgg gcagtgccag cctctaagag tgggcagggg cactggccac agagtcccag    2520
ggagtcccac cagcctagtc gccagacctt ctgtgggcgg ccgccatggt gagcaagggc    2580
gaggagctgt tcaccggggt ggtgcccatc ctggtcgagc tggacggcga cgtaaacggc    2640
cacaagttca gcgtgtccgg cgagggcgag ggcgatgcca cctacggcaa gctgaccctg    2700
aagttcatct gcaccaccgg caagctgccc gtgccctggc ccaccctcgt gaccaccctg    2760
acctacggcg tgcagtgctt cagccgctac cccgaccaca tgaagcagca cgacttcttc    2820
aagtccgcca tgcccgaagg ctacgtccag gagcgcacca tcttcttcaa ggacgacggc    2880
aactacaaga cccgcgccga ggtgaagttc gagggcgaca ccctggtgaa ccgcatcgag    2940
ctgaagggca tcgacttcaa ggaggacggc aacatcctgg ggcacaagct ggagtacaac    3000
tacaacagcc acaacgtcta tatcatggcc gacaagcaga agaacggcat caaggtgaac    3060
ttcaagatcc gccacaacat cgaggacgga agcgtgcagc tcgccgacca ctaccagcag    3120
aacaccccca tcggcgacgg ccccgtgctg ctgcccgaca accactacct gagcacccag    3180
tccgccctga gcaaagaccc caacgagaag cgcgatcaca tggtcctgct ggagttcgtg    3240
accgccgccg ggatcactct cggcatggac gagctgtaca gtaataagc ttggatccaa    3300 tcaacctctg gattacaaaa tttgtgaaag attgactggt attcttaact atgttgctcc    3360
ttttacgcta tgtggatacg ctgctttaat gcctttgtat catgctattg cttcccgtat    3420
ggctttcatt ttctcctcct tgtataaatc ctggttgctg tctctttatg aggagttgtg    3480
gcccgttgtc aggcaacgtg gcgtggtgtg cactgtgttt gctgacgcaa ccccccactgg    3540 ttggggcatt gccaccacct gtcagctcct ttccgggact ttcgctttcc cctccctat     3600 tgccacggcg gaactcatcg ccgcctgcct tgcccgctgc tggacagggg ctcggctgtt    3660
gggcactgac aattccgtgg tgttgtcggg gaagctgacg tcctttccat ggctgctcgc    3720
ctgtgttgcc acctggattc tgcgcgggac gtccttctgc tacgtccctt cggccctcaa    3780
tccagcggac cttccttccc gcggcctgct gccggctctg cggcctcttc cgcgtcttcg    3840
agatctgcct cgactgtgcc ttctagttgc cagccatctg ttgtttgccc ctcccccgtg    3900
ccttccttga ccctggaagg tgccactccc actgtccttt cctaataaaa tgaggaaatt    3960
gcatcgcatt gtctgagtag gtgtcattct attctggggg gtggggtggg gcaggacagc    4020
aagggggagg attgggaaga caatagcagg catgctgggg actcgagtta agggcgaatt    4080
cccgattagg atcttcctag agcatggcta cgtagataag tagcatggcg ggttaatcat    4140
taactacaag gaacccctag tgatggagtt ggccactccc tctctgcgcg ctcgctcgct    4200
cactgaggcc gggcgaccaa aggtcgcccg acgcccgggc tttgcccggg cggcctcagt    4260
gagcgagcga gcgcgcagcc ttaattaacc taattcactg gccgtcgttt tacaacgtcg    4320
tgactgggaa aaccctggcg ttacccaact taatcgcctt gcagcacatc cccctttcgc    4380
cagctggcgt aatagcgaag aggcccgcac cgatcgccct tcccaacagt tgcgcagcct    4440
gaatggcgaa tgggacgcgc cctgtagcgg cgcattaagc gcggcgggtg tggtggttac    4500
gcgcagcgtg accgctacac ttgccagcgc cctagcgccc gctcctttcg ctttcttccc    4560
ttcctttctc gccacgttcg ccggctttcc ccgtcaagct ctaaatcggg gctccctttt    4620
agggttccga tttagtgctt tacggcacct cgaccccaaa aaacttgatt agggtgatgg    4680
ttcacgtagt gggccatcgc cccgatagac ggttttcgc cctttgacgc tggagttcac    4740
gttcctcaat agtggactct tgttccaaac tggaacaaca ctcaaccta tctcggtcta    4800
```

-continued

```
ttcttttgat ttataaggga tttttccgat ttcggcctat tggttaaaaa atgagctgat    4860
ttaacaaaaa tttaacgcga attttaacaa aatattaacg tttataattt caggtggcat    4920
ctttcgggga aatgtgcgcg gaacccctat ttgtttattt ttctaaatac attcaaatat    4980
gtatccgctc atgagacaat aaccctgata aatgcttcaa taatattgaa aaaggaagag    5040
tatgagtatt caacatttcc gtgtcgccct tattccctt tttgcggcat tttgccttcc    5100
tgttttgct cacccagaaa cgctggtgaa agtaaaagat gctgaagatc agttgggtgc    5160
acgagtgggt tacatcgaac tggatctcaa tagtggtaag atccttgaga gttttcgccc    5220
cgaagaacgt tttccaatga tgagcacttt taaagttctg ctatgtggcg cggtattatc    5280
ccgtattgac gccgggcaag agcaactcgg tcgccgcata cactattctc agaatgactt    5340
ggttgagtac tcaccagtca cagaaaagca tcttacggat ggcatgacag taagagaatt    5400
atgcagtgct gccataacca tgagtgataa cactgcggcc aacttacttc tgacaacgat    5460
cggaggaccg aaggagctaa ccgctttttt gcacaacatg ggggatcatg taactcgcct    5520
tgatcgttgg gaaccggagc tgaatgaagc cataccaaac gacgagcgtg acaccacgat    5580
gcctgtagta atggtaacaa cgttgcgcaa actattaact ggcgaactac ttactctagc    5640
ttcccggcaa caattaatag actggatgga ggcggataaa gttgcaggac cacttctgcg    5700
ctcggccctt ccggctggct ggtttattgc tgataaatct ggagccggtg agcgtgggtc    5760
tcgcggtatc attgcagcac tggggccaga tggtaagccc tcccgtatcg tagttatcta    5820
cacgacgggg agtcaggcaa ctatggatga acgaaataga cagatcgctg agataggtgc    5880
ctcactgatt aagcattggt aactgtcaga ccaagtttac tcatatatac tttagattga    5940
tttaaaactt catttttaat ttaaaaggat ctaggtgaag atcctttttg ataatctcat    6000
gaccaaaatc ccttaacgtg agttttcgtt ccactgagcg tcagaccccg tagaaaagat    6060
caaaggatct tcttgagatc cttttttct gcgcgtaatc tgctgcttgc aaacaaaaaa    6120
accaccgcta ccagcggtgg tttgtttgcc ggatcaagag ctaccaactc tttttccgaa    6180
ggtaactggc ttcagcagag cgcagatacc aaatactgtc cttctagtgt agccgtagtt    6240
aggccaccac ttcaagaact ctgtagcacc gcctacatac ctcgctctgc taatcctgtt    6300
accagtggct gctgccagtg gcgataagtc gtgtcttacc gggttggact caagacgata    6360
gttaccggat aaggcgcagc ggtcgggctg aacggggggt tcgtgcacac agcccagctt    6420
ggagcgaacg acctacaccg aactgagata cctacagcgt gagctatgag aaagcgccac    6480
gcttcccgaa gggagaaagg cggacaggta tccggtaagc ggcagggtcg gaacaggaga    6540
gcgcacgagg gagcttccag ggggaaacgc ctggtatctt tatagtcctg tcgggtttcg    6600
ccacctctga cttgagcgtc gatttttgtg atgctcgtca gggggcgga gcctatggaa    6660
aaacgccagc aacgcggcct ttttacggtt cctggccttt tgctgcggtt ttgctcacat    6720
gttctttcct gcgttatccc ctgattctgt ggataaccgt attaccgcct ttgagtgagc    6780
tgataccgct cgccgcagcc gaacgaccga gcgcagcgag tcagtgagcg aggaagcgga    6840
agggccgatt cattaatgca gctggcacga caggtttccc gactggaaag cgggcagtga    6900
gcgcaacgca attaatgtga gttagctcac tcattaggca ccccaggctt tacactttat    6960
gcttccggct cgtatgttgt gtggaattgt gagcggataa caatttc                 7007
```

<210> SEQ ID NO 12
<211> LENGTH: 7003
<212> TYPE: DNA
<213> ORGANISM: Artificial Sequence
<220> FEATURE:
<223> OTHER INFORMATION: p1047// pAAV2.1-mRHOgRNA-mRHOHITI(IRESdsRED)-hVDM2-EGFP

<400> SEQUENCE: 12

| | | | | | |
|---|---|---|---|---|---|
| cgtatgttgt | gtggaattgt | gagcggataa | caatttcaca | caggaaacag | ctatgaccat | 60 |
| gattacgcca | gatttaatta | aggctgcgcg | ctcgctcgct | cactgaggcc | gcccgggcaa | 120 |
| agcccgggcg | tcgggcgacc | tttggtcgcc | cggcctcagt | gagcgagcga | gcgcgcagag | 180 |
| agggagtggc | caactccatc | actaggggtt | ccttgtagtt | aatgattaac | ccgccatgct | 240 |
| acttatctac | gtagccatgc | tctaggaaga | tcggaattcg | cccttaacca | ctagtaacgg | 300 |
| ccgccagtgt | gctggaattc | gcccttcga | gggcctattt | cccatgattc | cttcatattt | 360 |
| gcatatacga | tacaaggctg | ttagagagat | aattggaatt | aatttgactg | taaacacaaa | 420 |
| gatattagta | caaaatacgt | gacgtagaaa | gtaataattt | cttgggtagt | ttgcagtttt | 480 |
| aaaattatgt | tttaaaatgg | actatcatat | gcttaccgta | acttgaaagt | atttcgattt | 540 |
| cttggcttta | tatatcttgt | ggaaaggacg | aaacaccgca | gccgcagtac | tacctgggtt | 600 |
| ttagagctag | aaatagcaag | ttaaaataag | gctagtccgt | tatcaacttg | aaaaagtggc | 660 |
| accgagtcgg | tgctttttg | ttttagagct | agaaatagca | agctcgagca | gcctgaattc | 720 |
| tgcagatatc | catcacactg | gcggccttaa | ctcggatcca | ctagtaacgg | ccgccagtgt | 780 |
| gctggaattc | aggccgccag | gtagtactgc | ggctgctaat | aaataataat | gacaaactgt | 840 |
| acatgccgtt | aactgtaatt | ttgcgtgatt | tttttgtaga | tggatagcac | tgagaacgtc | 900 |
| atcaagccct | tcatgcgctt | caaggtgcac | atggagggct | ccgtgaacgg | ccacgagttc | 960 |
| gagatcgagg | gcgagggcga | gggcaagccc | tacgagggca | cccagaccgc | caagctgcag | 1020 |
| gtgaccaagg | gcggccccct | gcccttcgcc | tgggacatcc | tgtcccccca | gttccagtac | 1080 |
| ggctccaagg | tgtacgtgaa | gcaccccgcc | gacatcccg | actacaagaa | gctgtccttc | 1140 |
| cccgagggct | tcaagtggga | gcgcgtgatg | aacttcgagg | acggcggcgt | ggtgaccgtg | 1200 |
| acccaggact | cctccctgca | ggacggcacc | ttcatctacc | acgtgaagtt | catcggcgtg | 1260 |
| aacttccccct | ccgacggccc | cgtaatgcag | aagaagactc | tgggctggga | gccctccacc | 1320 |
| gagcgcctgt | accccgcga | cggcgtgctg | aagggcgaga | tccacaaggc | gctgaagctg | 1380 |
| aagggcggcg | ccactacct | ggtggagttc | aagtcaatct | acatggccaa | gaagcccgtg | 1440 |
| aagctgcccg | gctactacta | cgtggactcc | aagctggaca | tcacctccca | caacgaggac | 1500 |
| tacaccgtgg | tggagcagta | cgagcgcgcc | gaggcccgcc | accacctgtt | ccagtagcgg | 1560 |
| ccgcgactct | agaattccaa | ctgagcgccg | gtcgctacca | ttaccaactt | gtctggtgtc | 1620 |
| aaaaataata | ggcctactag | agtcgacctg | cagaagcttg | gatctgcctc | gactgtgcct | 1680 |
| tctagttgcc | agccatctgt | tgtttgcccc | tcccccgtgc | cttccttgac | cctggaaggt | 1740 |
| gccactccca | ctgtcctttc | ctaataaaat | gaggaaattg | catcgcattg | tctgagtagg | 1800 |
| tgtcattcta | ttctgggggg | tggggtgggg | caggacagca | aggggagga | ttgggaagac | 1860 |
| aatagcaggc | atgctgggga | ccgccaggta | gtactgcggc | tgcaagggcg | aattctgcag | 1920 |
| atatccatca | cactggcgtt | aagcgtcagc | atatgcagaa | ttctgtcatt | ttactagggt | 1980 |
| gatgaaattc | ccaagcaaca | ccatccttt | cagataaggg | cactgaggct | gagagaggag | 2040 |
| ctgaaaccta | cccggggtca | ccacacacag | gtggcaaggc | tgggaccaga | aaccaggact | 2100 |
| gttgactgca | gccggtatt | cattctttcc | atagcccaca | gggctgtcaa | agaccccagg | 2160 |
| gcctagtcag | aggctcctcc | ttcctggaga | gttcctggca | cagaagttga | agctcagcac | 2220 |

```
agcccctaa ccccaactc tctctgcaag gcctcagggg tcagaacact ggtggagcag    2280
atcctttagc ctctggattt tagggccatg gtagaggggg tgttgccta aattccagcc    2340 ctggtctcag cccaacaccc tccaagaaga aattagaggg gccatggcca ggctgtgcta    2400
gccgttgctt ctgagcagat tacaagaagg gactaagaca aggactcctt tgtggaggtc    2460
ctggcttagg gagtcaagtg acggcggctc agcactcacg tgggcagtgc cagcctctaa    2520
gagtgggcag gggcactggc cacagagtcc cagggagtcc caccagccta gtcgccagac    2580
cttctgtggg cggccgccat ggtgagcaag ggcgaggagc tgttcaccgg ggtggtgccc    2640
atcctggtcg agctggacgg cgacgtaaac ggccacaagt tcagcgtgtc cggcgagggc    2700
gagggcgatg ccacctacgg caagctgacc ctgaagttca tctgcaccac cggcaagctg    2760
cccgtgccct ggcccaccct cgtgaccacc ctgacctacg gcgtgcagtg cttcagccgc    2820
taccccgacc acatgaagca gcacgacttc ttcaagtccg ccatgcccga aggctacgtc    2880
caggagcgca ccatcttctt caaggacgac ggcaactaca agacccgcgc cgaggtgaag    2940
ttcgagggcg acaccctggt gaaccgcatc gagctgaagg gcatcgactt caaggaggac    3000
ggcaacatcc tggggcacaa gctggagtac aactacaaca gccacaacgt ctatatcatg    3060
gccgacaagc agaagaacgg catcaaggtg aacttcaaga tccgccacaa catcgaggac    3120
ggcagcgtgc agctcgccga ccactaccag cagaacaccc ccatcggcga cggccccgtg    3180
ctgctgcccg acaaccacta cctgagcacc cagtccgccc tgagcaaaga ccccaacgag    3240
aagcgcgatc acatggtcct gctggagttc gtgaccgccg ccgggatcac tctcggcatg    3300
gacgagctgt acaagtaata agcttggatc caatcaacct ctggattaca aaatttgtga    3360
aagattgact ggtattctta actatgttgc tcctttacg ctatgtggat acgctgcttt    3420
aatgcctttg tatcatgcta ttgcttcccg tatggctttc attttctcct ccttgtataa    3480
atcctggttg ctgtctcttt atgaggagtt gtggcccgtt gtcaggcaac gtggcgtggt    3540
gtgcactgtg tttgctgacg caacccccac tggttgggggc attgccacca cctgtcagct    3600
cctttccggg actttcgctt tccccctccc tattgccacg gcggaactca tcgccgcctg    3660
ccttgcccgc tgctggacag gggctcggct gttgggcact gacaattccg tggtgttgtc    3720
ggggaagctg acgtcctttc catggctgct cgcctgtgtt gccacctgga ttctgcgcgg    3780
gacgtccttc tgctacgtcc cttcggccct caatccagcg gaccttcctt cccgcggcct    3840
gctgccggct ctgcggcctc ttccgcgtct tcgagatctg cctcgactgt gccttctagt    3900
tgccagccat ctgttgtttg ccctcccccc gtgccttcct tgaccctgga aggtgccact    3960
cccactgtcc tttcctaata aaatgaggaa attgcatcgc attgtctgag taggtgtcat    4020
tctattctgg ggggtggggt ggggcaggac agcaagggggg aggattggga agacaatagc    4080
aggcatgctg gggactcgag ttaagggcga attcccgatt aggatcttcc tagagcatgg    4140
ctacgtagat aagtagcatg gcgggttaat cattaactac aaggaacccc tagtgatgga    4200
gttggccact ccctctctgc gcgctcgctc gctcactgag gccgggcgac caaaggtcgc    4260
ccgacgcccg ggctttgccc gggcggcctc agtgagcgag cgagcgcgca gccttaatta    4320
acctaattca ctggccgtcg ttttacaacg tcgtgactgg gaaaaccctg gcgttaccca    4380
acttaatcgc cttgcagcac atccccctt cgccagctgg cgtaatagcg aagaggcccg    4440
caccgatcgc ccttcccaac agttgcgcag cctgaatggc gaatgggacg cgccctgtag    4500
cggcgcatta agcgcggcgg gtgtggtggt tacgcgcagc gtgaccgcta cacttgccag    4560
```

```
cgccctagcg cccgctcctt tcgctttctt cccttccttt ctcgccacgt tcgccggctt    4620
tccccgtcaa gctctaaatc gggggctccc tttagggttc cgatttagtg ctttacggca    4680
cctcgacccc aaaaaacttg attagggtga tggttcacgt agtgggccat cgccccgata    4740
gacggttttt cgcccttga cgctggagtt cacgttcctc aatagtggac tcttgttcca    4800
aactggaaca acactcaacc ctatctcggt ctattctttt gatttataag ggattttcc    4860
gatttcggcc tattggttaa aaatgagct gatttaacaa aaatttaacg cgaattttaa    4920
caaaatatta acgtttataa tttcaggtgg catctttcgg ggaaatgtgc gcggaacccc    4980
tatttgttta ttttctaaa tacattcaaa tatgtatccg ctcatgagac aataaccctg    5040
ataaatgctt caataatatt gaaaaggaa gagtatgagt attcaacatt tccgtgtcgc    5100
ccttattccc ttttttgcgg cattttgcct tcctgttttt gctcacccag aaacgctggt    5160
gaaagtaaaa gatgctgaag atcagttggg tgcacgagtg ggttacatcg aactggatct    5220
caatagtggt aagatccttg agagttttcg ccccgaagaa cgttttccaa tgatgagcac    5280
ttttaaagtt ctgctatgtg gcgcggtatt atcccgtatt gacgccgggc aagagcaact    5340
cggtcgccgc atacactatt ctcagaatga cttggttgag tactcaccag tcacagaaaa    5400
gcatcttacg gatggcatga cagtaagaga attatgcagt gctgccataa ccatgagtga    5460
taacactgcg gccaacttac ttctgacaac gatcggagga ccgaaggagc taaccgcttt    5520
tttgcacaac atgggggatc atgtaactcg ccttgatcgt tgggaaccgg agctgaatga    5580
agccatacca aacgacgagc gtgacaccac gatgcctgta gtaatggtaa caacgttgcg    5640
caaactatta actggcgaac tacttactct agcttcccgg caacaattaa tagactggat    5700
ggaggcggat aaagttgcag gaccacttct gcgctcggcc cttccggctg gctggtttat    5760
tgctgataaa tctggagccg gtgagcgtgg gtctcgcggt atcattgcag cactggggcc    5820
agatggtaag ccctcccgta tcgtagttat ctacacgacg gggagtcagg caactatgga    5880
tgaacgaaat agacagatcg ctgagatagg tgcctcactg attaagcatt ggtaactgtc    5940
agaccaagtt tactcatata ctttagat tgatttaaaa cttcattttt aatttaaaag    6000
gatctaggtg aagatccttt ttgataatct catgaccaaa atcccttaac gtgagttttc    6060
gttccactga gcgtcagacc ccgtagaaaa gatcaaagga tcttcttgag atcctttttt    6120
tctgcgcgta atctgctgct tgcaaacaaa aaaaccaccg ctaccagcgg tggtttgttt    6180
gccggatcaa gagctaccaa ctctttttcc gaaggtaact ggcttcagca gagcgcagat    6240
accaaatact gtccttctag tgtagccgta gttaggccac cacttcaaga actctgtagc    6300
accgcctaca tacctcgctc tgctaatcct gttaccagtg gctgctgcca gtggcgataa    6360
gtcgtgtctt accgggttgg actcaagacg atagttaccg gataaggcgc agcggtcggg    6420
ctgaacgggg ggttcgtgca cacagcccag cttggagcga acgacctaca ccgaactgag    6480
atacctacag cgtgagctat gagaaagcgc cacgcttccc gaaggagaa aggcggacag    6540
gtatccggta agcggcaggg tcggaacagg agagcgcacg agggagcttc caggggggaaa    6600
cgcctggtat ctttatagtc ctgtcgggtt tcgccacctc tgacttgagc gtcgattttt    6660
gtgatgctcg tcaggggggc ggagcctatg gaaaaacgcc agcaacgcgg cctttttacg    6720
gttcctggcc ttttgctgcg gtttgctca catgttcttt cctgcgttat cccctgattc    6780
tgtggataac cgtattaccg cctttgagtg agctgatacc gctcgccgca gccgaacgac    6840
cgagcgcagc gagtcagtga gcgaggaagc ggaagggccg attcattaat gcagctggca    6900
cgacaggttt cccgactgga aagcgggcag tgagcgcaac gcaattaatg tgagttagct    6960
```
cactcattag gcaccccagg ctttacactt tatgcttccg gct           7003

<210> SEQ ID NO 13
<211> LENGTH: 6356
<212> TYPE: DNA
<213> ORGANISM: Artificial Sequence
<220> FEATURE:
<223> OTHER INFORMATION: p1138// pAAV-mRHO HITI (kozak-hRHO-T2A-dsRED) +
      mRHO gRNA

<400> SEQUENCE: 13

| | |
|---|---|
| cggataacaa tttcacacag gaaacagcta tgaccatgat tacgccagat ttaattaagg | 60 |
| ctgcgcgctc gctcgctcac tgaggccgcc cgggcaaagc ccgggcgtcg ggcgaccttt | 120 |
| ggtcgcccgg cctcagtgag cgagcgagcg cgcagagagg gagtggccaa ctccatcact | 180 |
| aggggttcct tgtagttaat gattaacccg ccatgctact tatctacgta gcccgccgcc | 240 |
| agtgtgatgg atgccgccag tgtgatggat atctgcagaa ttcaggctgc tcgagcttgc | 300 |
| tatttctagc tctaaaacaa aaaagcaccg actcggtgcc acttttttcaa gttgataacg | 360 |
| gactagcctt attttaactt gctatttcta gctctaaaac ccaggtagta ctgcggctgc | 420 |
| cggtgtttcg tcctttccac aagatatata agccaagaa atcgaaatac ttcaagtta | 480 |
| cggtaagcat atgatagtcc attttaaaac ataattttaa aactgcaaac tacccaagaa | 540 |
| attattactt tctacgtcac gtattttgta ctaatatctt tgtgtttaca gtccaaatta | 600 |
| attccaatta tctctctaac agccttgtat cgtatatgca aatatgaagg aatcatggga | 660 |
| aactcgaggt cagcctgaat tccagcacac tggcggccgt tactagtatc tgcagaattc | 720 |
| gcccttgcag ccgcagtact acctggcggt ccccagcatg cctgctattg tcttcccaat | 780 |
| cctccccctt gctgtcctgc ccacccccac ccccagaat agaatgacac ctactcagac | 840 |
| aatgcgatgc aatttcctca ttttattagg aaaggacagt gggagtggca ccttccaggg | 900 |
| tcaaggaagg cacgggggag gggcaaacaa cagatggctg caactagaa ggcacagtcg | 960 |
| aggcagatct cgaagacgcg gaagaggccg cagagccggc agcaggccgc gggaaggaag | 1020 |
| gtccgctgga ttgagggccg aagggacgta gcagaaggac gtcccgcgca gaatccaggt | 1080 |
| ggcaacacag gcgagcagcc atggaaagga cgtcagcttc cccgacaaca ccacggaatt | 1140 |
| gtcagtgccc aacagccgag cccctgtcca gcagcgggca aggcaggcgg cgatgagttc | 1200 |
| cgccgtggca atagggaggg ggaaagcgaa agtcccggaa aggagctgac aggtggtggc | 1260 |
| aatgccccaa ccagtggggg ttgcgtcagc aaacacagtg cacaccacgc cacgttgcct | 1320 |
| gacaacgggc cacaactcct cataaagaga cagcaaccag gatttataca aggaggagaa | 1380 |
| aatgaaagcc atacgggaag caatagcatg atacaaaggc attaaagcag cgtatccaca | 1440 |
| tagcgtaaaa ggagcaacat agttaagaat accagtcaat ctttcacaaa ttttgtaatc | 1500 |
| cagaggttga ttggatccta ctggaacagg tggtggcggg cctcggcgcg ctcgtactgc | 1560 |
| tccaccacgg tgtagtcctc gttgtgggag gtgatgtcca gcttggagtc cacgtagtag | 1620 |
| tagccgggca gcttcacggg cttcttggcc atgtagattg acttgaactc caccaggtag | 1680 |
| tggccgccgc ccttcagctt cagcgccttg tggatctcgc cctcagcac gccgtcgcgg | 1740 |
| gggtacaggc gctcggtgga gggctcccag cccagagtct tcttctgcat tacggggccg | 1800 |
| tcggagggga agttcacgcc gatgaacttc acgtggtaga tgaaggtgcc gtcctgcagg | 1860 |
| gaggagtcct gggtcacggt caccacgccg ccgtcctcga agttcatcac gcgctcccac | 1920 |
| ttgaagccct cggggaagga cagcttcttg tagtcgggga tgtcggcggg gtgcttcacg | 1980 |

-continued

```
tacaccttgg agccgtactg gaactggggg gacaggatgt cccaggcgaa gggcagggg    2040 ccgcccttgg tcacctgcag cttggcggtc tgggtgccct cgtagggctt gccctcgccc    2100
tcgccctcga tctcgaactc gtggccgttc acggagccct ccatgtgcac cttgaagcgc    2160
atgaagggct tgatgacgtt ctcagtgcta tccataggtc caggattctc ctcgacgtca    2220
ccgcatgtta gcagacttcc tctgccctct ccgcttccgg ccggggccac ctggctcgtc    2280
tccgtcttgg acacggtagc agaggcctca tcgtcaccca gtgggttctt gccgcagcag    2340
atggtggtga gcatgcagtt ccggaactgc ttgttcatca tgatatagat gacagggttg    2400
tagatggcgg cgctcttggc aaagaacgct gggatggtca tgaagatggg accgaagttg    2460
gagccctggt gggtgaagat gtagaatgcc acgctggcgt agggcaccca gcagatcagg    2520
aaagcgatga ccatgatgat gaccatgcgg gtgacctcct tctctgcctt ctgtgtggtg    2580
gctgactcct gctgctgggc agcggcctcc ttgacggtga agacgagctg cccatagcag    2640
aaaaagatga taatcatggg gatggtgaag tggaccacga acatgtagat gacaaaagac    2700
tcgttgttga cctccggctt gagcgtgtag tagtcgattc cacacgagca ctgcaggccc    2760
tcggggatgt acctggacca gccggcgagt ggggtgcgg cgcaggccag cgccatgacc    2820
caggtgaagg caacgcccat gatggcatgg ttctccccga agcggaagtt gctcatgggc    2880
ttacacacca ccacgtaccg ctcgatggcc aggaccacca aggaccacag ggcaatttca    2940
ccgcccaggg tggcaaagaa gccctccaaa ttgcatcctg tgggcccgaa gacgaagtat    3000
ccatgcagag aggtgtagag ggtgctggtg aagccaccta ggaccatgaa gaggtcagcc    3060
acggctaggt tgagcaggat gtagttgaga ggcgtgcgca gcttcttgtg ctggacggtg    3120
acgtagagcg tgaggaagtt gatggggaag cccagcacga tcagcagaaa catgtaggcg    3180
gccagcatgg agaactgcca tggctcagcc aggtagtact gtgggtactc gaagggctg    3240 cgtaccacac ccgtcgcatt ggagaagggc acgtagaagt tagggccttc tgtgccattc    3300
atggtggctt attatttatt agcagccgca gtactacctg gcggaagggc gaattccagc    3360
acactggcgg ccgttactag gaattccgat cttcctagag cataattccc gattaggatc    3420
ttcctagagc atggctacgt agataagtag catggcgggt taatcattaa ctacaaggaa    3480 ccctagtga tggagttggc cactccctct ctgcgcgctc gctcgctcac tgaggccggg    3540
cgaccaaagg tcgcccgacg cccgggcttt gcccgggcgg cctcagtgag cgagcgagcg    3600
cgcagcctta attaacctaa ttcactggcc gtcgttttac aacgtcgtga ctgggaaaac    3660
cctggcgtta cccaacttaa tcgccttgca gcacatcccc ctttcgccag ctggcgtaat    3720
agcgaagagg cccgcaccga tcgcccttcc caacagttgc gcagcctgaa tggcgaatgg    3780
gacgcgccct gtagcggcgc attaagcgcg gcgggtgtgg tggttacgcg cagcgtgacc    3840
gctacacttg ccagcgccct agcgcccgct cctttcgctt tcttcccttc ctttctcgcc    3900
acgttcgccg gctttccccg tcaagctcta aatcgggggc tccctttagg gttccgattt    3960
agtgctttac ggcacctcga ccccaaaaaa cttgattagg gtgatggttc acgtagtggg    4020
ccatcgcccc gatagacggt ttttcgccct ttgacgctgg agttcacgtt cctcaatagt    4080
ggactcttgt tccaaactgg aacaacactc aaccctatct cggtctattc ttttgattta    4140
taagggattt ttccgatttc ggcctattgg ttaaaaaatg agctgattta acaaaaattt    4200
aacgcgaatt ttaacaaaat attaacgttt ataatttcag gtggcatctt tcggggaaat    4260
gtgcgcggaa cccctatttg tttatttttc taaatacatt caaatatgta tccgctcatg    4320
```

```
agacaataac cctgataaat gcttcaataa tattgaaaaa ggaagagtat gagtattcaa    4380
catttccgtg tcgcccttat tccctttttt gcggcatttt gccttcctgt ttttgctcac    4440
ccagaaacgc tggtgaaagt aaaagatgct gaagatcagt tgggtgcacg agtgggttac    4500
atcgaactgg atctcaatag tggtaagatc cttgagagtt ttcgccccga gaacgttttt    4560
ccaatgatga gcacttttaa agttctgcta tgtggcgcgg tattatcccg tattgacgcc    4620
gggcaagagc aactcggtcg ccgcatacac tattctcaga atgacttggt tgagtactca    4680
ccagtcacag aaaagcatct tacggatggc atgacagtaa gagaattatg cagtgctgcc    4740
ataaccatga gtgataacac tgcggccaac ttacttctga caacgatcgg aggaccgaag    4800
gagctaaccg cttttttgca caacatgggg gatcatgtaa ctcgccttga tcgttgggaa    4860
ccggagctga atgaagccat accaaacgac gagcgtgaca ccacgatgcc tgtagtaatg    4920
gtaacaacgt tgcgcaaact attaactggc gaactactta ctctagcttc ccggcaacaa    4980
ttaatagact ggatggaggc ggataaagtt gcaggaccac ttctgcgctc ggcccttccg    5040
gctggctggt ttattgctga taaatctgga gccggtgagc gtgggtctcg cggtatcatt    5100
gcagcactgg ggccagatgg taagccctcc cgtatcgtag ttatctacac gacggggagt    5160
caggcaacta tggatgaacg aaatagacag atcgctgaga taggtgcctc actgattaag    5220
cattggtaac tgtcagacca agtttactca tatatacttt agattgattt aaaacttcat    5280
ttttaattta aaaggatcta ggtgaagatc ctttttgata atctcatgac caaaatccct    5340
taacgtgagt tttcgttcca ctgagcgtca gaccccgtag aaaagatcaa aggatcttct    5400
tgagatcctt ttttttctgcg cgtaatctgc tgcttgcaaa caaaaaaacc accgctacca    5460
gcggtggttt gtttgccgga tcaagagcta ccaactcttt ttccgaaggt aactggcttc    5520
agcagagcgc agataccaaa tactgtcctt ctagtgtagc cgtagttagg ccaccacttc    5580
aagaactctg tagcaccgcc tacatacctc gctctgctaa tcctgttacc agtggctgct    5640
gccagtggcg ataagtcgtg tcttaccggg ttggactcaa gacgatagtt accggataag    5700
gcgcagcggt cgggctgaac ggggggttcg tgcacacagc ccagcttgga gcgaacgacc    5760
tacaccgaac tgagatacct acagcgtgag ctatgagaaa gcgccacgct tcccgaaggg    5820
agaaaggcgg acaggtatcc ggtaagcggc agggtcggaa caggagagcg cacgagggag    5880
cttccagggg gaaacgcctg gtatctttat agtcctgtcg ggtttcgcca cctctgactt    5940
gagcgtcgat ttttgtgatg ctcgtcaggg gggcggagcc tatggaaaaa cgccagcaac    6000
gcggcctttt tacggttcct ggccttttgc tgcggttttg ctcacatgtt ctttcctgcg    6060
ttatcccctg attctgtgga taaccgtatt accgcctttg agtgagctga taccgctcgc    6120
cgcagccgaa cgaccgagcg cagcgagtca gtgagcgagg aagcggaaga gcgcccaata    6180
cgcaaaccgc ctctccccgc gcgttggccg attcattaat gcagctggca cgacaggttt    6240
cccgactgga aagcgggcag tgagcgcaac gcaattaatg tgagttagct cactcattag    6300
gcaccccagg ctttacactt tatgcttccg gctcgtatgt tgtgtggaat tgtgag        6356
```

<210> SEQ ID NO 14
<211> LENGTH: 6960
<212> TYPE: DNA
<213> ORGANISM: Artificial Sequence
<220> FEATURE:
<223> OTHER INFORMATION: p1118// pAAV_Scramble_sRHO HITI(kozak-
     dsRED)_hVmd2-EGFP

<400> SEQUENCE: 14

-continued

```
tatgaccatg attacgccag atttaattaa ggctgcgcgc tcgctcgctc actgaggccg      60
cccgggcaaa gcccgggcgt cgggcgacct ttggtcgccc ggcctcagtg agcgagcgag     120
cgcgcagaga gggagtggcc aactccatca ctaggggttc cttgtagtta atgattaacc     180
cgccatgcta cttatctacg tagccatgct ctaggaagat cggaattcgc ccttaaccac     240
tagtaacggc cgccagtgtg ctggaattcg cccttttcgag ggcctatttc ccatgattcc    300
ttcatatttg catatacgat acaaggctgt tagagagata attggaatta atttgactgt     360
aaacacaaag atattagtac aaaatacgtg acgtagaaag taataatttc ttgggtagtt     420
tgcagtttta aaattatgtt ttaaaatgga ctatcatatg cttaccgtaa cttgaaagta     480
tttcgatttc ttggctttat atatcttgtg gaaaggacga aacaccggac tcgcgcgagt     540
cgaggaggtt ttagagctag aaatagcaag ttaaaataag gctagtccgt tatcaacttg     600
aaaaagtggc accgagtcgg tgcttttttg ttttagagct agaaatagca agctcgagca     660
gcctgaattc tgcagatatc catcacactg gcggccttaa ctcggatcca ctagtaacgg     720
ccgccagtgt gctggaattc aggcccctttt gagtatccgc agtacttccc cagcatgcct    780
gctattgtct tcccaatcct ccccccttgct gtcctgcccc accccacccc cagaatagaa    840
atgcacccta ctcagacaat gcgatgcaat ttcctcattt tattaggaaa ggacagtggg    900
agtggcacct tccagggtca aggaaggcac ggggaggggg caaacaacag atggctggca     960
actagaaggc acagtcgagg cagatccaag cttctgcagg tcgactctag taggcctatt    1020
atttttgaca ccagacaagt tggtaatggt agcgaccggc gctcagttgg aattctagag    1080
tcgcggccgc tactgaaaca ggtggtggcg ggcctcggcg cgtcgtact gctccaccac     1140 ggtgtagtcc tcgttgtggg aggtgatgtc cagcttggag tccacgtagt agtagccggg    1200
cagcttcacg ggcttcttgg ccatgtagat tgacttgaac tccaccaggt agtggccgcc    1260
gcccttcagc ttcagcgcct tgtggatctc gcccttcagc acgccgtcgc ggggtacag     1320 gcgctcggtg gagggctccc agcccagagt cttcttctgc attacggggc cgtcggaggg    1380
gaagttcacg ccgatgaact tcacgtggta gatgaaggtg ccgtcctgca gggaggagtc    1440
ctgggtcacg gtcaccacgc cgccgtcctc gaagttcatc acgcgctccc acttgaagcc    1500
ctcggggaag acagcttct tgtagtcggg gatgtcggcg gggtgcttca cgtacacctt    1560
ggagccgtac tggaactggg gggacaggat gtcccaggcg aagggcaggg ggccgccctt    1620
ggtcacctgc agcttggcgg tctgggtgcc ctcgtagggc ttgccctcgc cctcgccctc    1680
gatctcgaac tcgtggccgt tcacggagcc ctccatgtgc accttgaagc gcatgaaggg    1740
cttgatgacg ttctcagtgc tatccatggt ggcttattat ttattacccc tttgagtatc    1800
cgcagtacta agggcgaatt ctgcagatat ccatcacact ggcgttaagc gtcagcatat    1860
gcagaattct gtcattttac tagggtgatg aaattcccaa gcaacaccat ccttttcaga    1920
taagggcact gaggctgaga gaggagctga acctacccg gggtcaccac acacaggtgg     1980
caaggctggg accagaaacc aggactgttg actgcagccc ggtattcatt ctttccatag    2040
cccacagggc tgtcaaagac cccagggcct agtcagaggc tcctccttcc tggagagttc    2100
ctggcacaga agttgaagct cagcacagcc cctaacccc caactctctc tgcaaggcct    2160 cagggtcag aacactggtg gagcagatcc tttagcctct ggattttagg gccatggtag     2220 aggggggtgtt gccctaaatt ccagcccctgg tctcagccca cacccctcca agaagaaatt    2280
agaggggcca tggccaggct gtgctagccg ttgcttctga gcagattaca agaagggact    2340
aagacaagga ctcctttgtg gaggtcctgg cttagggagt caagtgacgg cggctcagca    2400
```

```
ctcacgtggg cagtgccagc ctctaagagt gggcaggggc actggccaca gagtcccagg    2460
gagtcccacc agcctagtcg ccagaccttc tgtgggcggc cgccatggtg agcaagggcg    2520
aggagctgtt caccggggtg gtgcccatcc tggtcgagct ggacggcgac gtaaacggcc    2580
acaagttcag cgtgtccggc gagggcgagg gcgatgccac ctacggcaag ctgaccctga    2640
agttcatctg caccaccggc aagctgcccg tgccctggcc caccctcgtg accaccctga    2700
cctacggcgt gcagtgcttc agccgctacc ccgaccacat gaagcagcac gacttcttca    2760
agtccgccat gcccgaaggc tacgtccagg agcgcaccat cttcttcaag gacgacggca    2820
actacaagac ccgcgccgag gtgaagttcg agggcgacac cctggtgaac cgcatcgagc    2880
tgaagggcat cgacttcaag gaggacggca acatcctggg gcacaagctg gagtacaact    2940
acaacagcca caacgtctat atcatggccg acaagcagaa gaacggcatc aaggtgaact    3000
tcaagatccg ccacaacatc gaggacggca gcgtgcagct cgccgaccac taccagcaga    3060
acacccccat cggcgacggc cccgtgctgc tgcccgacaa ccactacctg agcacccagt    3120
ccgccctgag caaagacccc aacgagaagc gcgatcacat ggtcctgctg gagttcgtga    3180
ccgccgccgg gatcactctc ggcatggacg agctgtacaa gtaataagct tggatccaat    3240
caacctctgg attacaaaat ttgtgaaaga ttgactggta ttcttaacta tgttgctcct    3300
tttacgctat gtggatacgc tgctttaatg cctttgtatc atgctattgc ttcccgtatg    3360
gctttcattt tctcctcctt gtataaatcc tggttgctgt ctctttatga ggagttgtgg    3420
cccgttgtca ggcaacgtgg cgtggtgtgc actgtgtttg ctgacgcaac ccccactggt    3480
tggggcattg ccaccacctg tcagctcctt ccgggactt tcgctttccc cctccctatt    3540 gccacgcgg aactcatcgc cgcctgcctt gcccgctgct ggacaggggc tcggctgttg    3600
ggcactgaca attccgtggt gttgtcgggg aagctgacgt cctttccatg gctgctcgcc    3660
tgtgttgcca cctggattct gcgcgggacg tccttctgct acgtcccttc ggccctcaat    3720
ccagcggacc ttccttcccg cggcctgctg ccggctctgc ggcctcttcc gcgtcttcga    3780
gatctgcctc gactgtgcct tctagttgcc agccatctgt tgtttgcccc tcccccgtgc    3840
cttccttgac cctggaaggt gccactccca ctgtcctttc ctaataaaat gaggaaattg    3900
catcgcattg tctgagtagg tgtcattcta ttctgggggg tggggtgggg caggacagca    3960
agggggagga ttgggaagac aatagcaggc atgctgggga ctcgagttaa gggcgaattc    4020
ccgattagga tcttcctaga gcatggctac gtagataagt agcatggcgg gttaatcatt    4080
aactacaagg aaccctagt gatggagttg gccactccct ctctgcgcgc tcgctcgctc    4140
actgaggccg ggcgaccaaa ggtcgcccga cgcccgggct ttgcccgggc ggcctcagtg    4200
agcgagcgag cgcgcagcct taattaacct aattcactgg ccgtcgtttt acaacgtcgt    4260
gactgggaaa accctggcgt tacccaactt aatcgccttg cagcacatcc ccctttcgcc    4320
agctggcgta atagcgaaga ggcccgcacc gatcgccctt cccaacagtt gcgcagcctg    4380
aatggcgaat gggacgcgcc ctgtagcggc gcattaagcg cggcgggtgt ggtggttacg    4440
cgcagcgtga ccgctacact tgccagcgcc ctagcgcccg ctcctttcgc tttcttccct    4500
tcctttctcg ccacgttcgc cggctttccc cgtcaagctc taaatcgggg gctcccttta    4560
gggttccgat ttagtgcttt acggcacctc gaccccaaaa aacttgatta gggtgatggt    4620
tcacgtagtg gccatcgcc ccgatagacg gttttcgcc ctttgacgct ggagttcacg    4680
ttcctcaata gtggactctt gttccaaact ggaacaacac tcaaccctat ctcggtctat    4740
```

```
tcttttgatt tataagggat ttttccgatt tcggcctatt ggttaaaaaa tgagctgatt    4800
taacaaaaat ttaacgcgaa ttttaacaaa atattaacgt ttataatttc aggtggcatc    4860
tttcggggaa atgtgcgcgg aacccctatt tgtttatttt tctaaataca ttcaaatatg    4920
tatccgctca tgagacaata accctgataa atgcttcaat aatattgaaa aggaagagt    4980 atgagtattc aacatttccg tgtcgccctt attccctttt ttgcggcatt ttgccttcct    5040
gtttttgctc acccagaaac gctggtgaaa gtaaaagatg ctgaagatca gttgggtgca    5100
cgagtgggtt acatcgaact ggatctcaat agtggtaaga tccttgagag ttttcgcccc    5160
gaagaacgtt ttccaatgat gagcactttt aaagttctgc tatgtggcgc ggtattatcc    5220
cgtattgacg ccgggcaaga gcaactcggt cgccgcatac actattctca gaatgacttg    5280
gttgagtact caccagtcac agaaaagcat cttacggatg gcatgacagt aagagaatta    5340
tgcagtgctg ccataaccat gagtgataac actgcggcca acttacttct gacaacgatc    5400
ggaggaccga aggagctaac cgcttttttg cacaacatgg gggatcatgt aactcgcctt    5460
gatcgttggg aaccggagct gaatgaagcc ataccaaacg acgagcgtga ccacgatg    5520 cctgtagtaa tggtaacaac gttgcgcaaa ctattaactg gcgaactact tactctagct    5580
tcccggcaac aattaataga ctggatggag gcggataaag ttgcaggacc acttctgcgc    5640
tcggcccttc cggctggctg gtttattgct gataaatctg gagccggtga gcgtgggtct    5700
cgcggtatca ttgcagcact ggggccagat ggtaagccct cccgtatcgt agttatctac    5760
acgacgggga gtcaggcaac tatggatgaa cgaaatagac agatcgctga gataggtgcc    5820
tcactgatta gcattggta actgtcagac caagtttact catatatact ttagattgat    5880
ttaaaacttc attttttaatt taaaaggatc taggtgaaga tccttttga taatctcatg    5940 accaaaatcc cttaacgtga gttttcgttc cactgagcgt cagacccgt agaaaagatc    6000 aaaggatctt cttgagatcc ttttttttctg cgcgtaatct gctgcttgca acaaaaaaa    6060 ccaccgctac cagcggtggt ttgtttgccg gatcaagagc taccaactct ttttccgaag    6120
gtaactggct tcagcagagc gcagatacca atactgtcc ttctagtgta gccgtagtta    6180
ggccaccact tcaagaactc tgtagcaccg cctacatacc tcgctctgct aatcctgtta    6240
ccagtggctg ctgccagtgg cgataagtcg tgtcttaccg ggttggactc aagacgatag    6300
ttaccggata aggcgcagcg gtcgggctga acgggggggtt cgtgcacaca gcccagcttg    6360
gagcgaacga cctacaccga actgagatac ctacagcgtg agctatgaga aagcgccacg    6420
cttcccgaag ggagaaaggc ggacaggtat ccggtaagcg gcagggtcgg aacaggagag    6480
cgcacgaggg agcttccagg gggaaacgcc tggtatcttt atagtcctgt cgggtttcgc    6540
cacctctgac ttgagcgtcg attttttgtga tgctcgtcag ggggggcggag cctatggaaa    6600 aacgccagca acgcggcctt tttacggttc ctggcctttt gctgcggttt tgctcacatg    6660
ttctttcctg cgttatcccc tgattctgtg ataaccgta ttaccgcctt tgagtgagct    6720
gataccgctc gccgcagccg aacgaccgag cgcagcgagt cagtgagcga ggaagcggaa    6780
gggccgattc attaatgcag ctggcacgac aggtttcccg actggaaagc gggcagtgag    6840
cgcaacgcaa ttaatgtgag ttagctcact cattaggcac cccaggcttt acactttatg    6900
cttccggctc gtatgttgtg tggaattgtg agcggataac aatttcacac aggaaacagc    6960
```

<210> SEQ ID NO 15
<211> LENGTH: 6963
<212> TYPE: DNA
<213> ORGANISM: Artificial Sequence

```
<220> FEATURE:
<223> OTHER INFORMATION: p1126// pAAV_sRHOgRNA_sRHO HITI(kozak-
      dsRED)_hVmd2-EGFP

<400> SEQUENCE: 15
tcgtatgttg tgtggaattg tgagcggata caatttcac acaggaaaca gctatgacca      60
tgattacgcc agatttaatt aaggctgcgc gctcgctcgc tcactgaggc cgcccgggca     120
aagcccgggc gtcgggcgac ctttggtcgc ccggcctcag tgagcgagcg agcgcgcaga    180
gagggagtgg ccaactccat cactagggg tccttgtagt taatgattaa cccgccatgc    240
tacttatcta cgtagccatg ctctaggaag atcggaattc gcccttaacc actagtaacg    300
gccgccagtg tgctggaatt cgcccttttcg agggcctatt tcccatgatt ccttcatatt    360
tgcatatacg atacaaggct gttagagaga taattggaat taatttgact gtaaacacaa    420
agatattagt acaaaatacg tgacgtagaa agtaataatt tcttgggtag tttgcagttt    480
taaaattatg ttttaaaatg gactatcata tgcttaccgt aacttgaaag tatttcgatt    540
tcttggcttt atatatcttg tggaaaggac gaaacaccga gtactgcgga tactcaaagg    600
ttttagagct agaaatagca agttaaaata aggctagtcc gttatcaact tgaaaaagtg    660
gcaccgagtc ggtgcttttt tgttttagag ctagaaatag caagctcgag cagcctgaat    720
tctgcagata tccatcacac tggcggcctt aactcggatc cactagtaac ggccgccagt    780
gtgctggaat tcgcccttag tactgcggat actcaaaggg gtaataaata ataagccacc    840
atggatagca ctgagaacgt catcaagccc ttcatgcgct tcaaggtgca catggagggc    900
tccgtgaacg gccacgagtt cgagatcgag ggcgagggcg agggcaagcc ctacgagggc    960
acccagaccg ccaagctgca ggtgaccaag ggcggccccc tgcccttcgc ctgggacatc   1020
ctgtcccccc agttccagta cggctccaag gtgtacgtga agcaccccgc cgacatcccc   1080
gactacaaga agctgtcctt ccccgagggc ttcaagtggg agcgcgtgat gaacttcgag   1140
gacggcggcg tggtgaccgt gacccaggac tcctccctgc aggacggcac cttcatctac   1200
cacgtgaagt tcatcggcgt gaacttcccc tccgacggcc ccgtaatgca agaagagact   1260
ctgggctggg agccctccac cgagcgcctg taccccgcg acggcgtgct gaagggcgag   1320
atccacaagg cgctgaagct gaagggcggc ggccactacc tggtggagtt caagtcaatc   1380
tacatggcca agaagcccgt gaagctgccc ggctactact acgtggactc caagctggac   1440
atcacctccc acaacgagga ctacaccgtg gtggagcagt acgagcgcgc cgaggcccgc   1500
caccacctgt tccagtagcg gccgcgactc tagaattcca actgagcgcc ggtcgctacc   1560
attaccaact tgtctggtgt caaaaataat aggcctacta gagtcgacct gcagaagctt   1620
ggatctgcct cgactgtgcc ttctagttgc cagccatctg ttgtttgccc ctcccccgtg   1680
ccttccttga ccctggaagg tgccactccc actgtccttt cctaataaaa tgaggaaatt   1740
gcatcgcatt gtctgagtag gtgtcattct attctggggg gtggggtggg caggacagc   1800 aaggggagg attgggaaga caatagcagg catgctgggg aagtactgcg gatactcaaa    1860
ggggaagggc gaattctgca gatatccatc acactggcgt taagcgtcag catatgcaga    1920
attctgtcat tttactaggg tgatgaaatt cccaagcaac accatccttt tcagataagg    1980
gcactgaggc tgagagagga gctgaaacct acccgggtc accacacaca ggtggcaagg    2040
ctgggaccag aaaccaggac tgttgactgc agcccggtat tcattctttc catagcccac    2100
agggctgtca aagaccccag ggcctagtca gaggctcctc cttcctggag agttcctggc    2160
acagaagttg aagctcagca cagccccta acccccaact ctctctgcaa ggcctcaggg    2220
```

```
gtcagaacac tggtggagca gatcctttag cctctggatt ttagggccat ggtagagggg    2280
gtgttgccct aaattccagc cctggtctca gcccaacacc ctccaagaag aaattagagg    2340
ggccatggcc aggctgtgct agccgttgct tctgagcaga ttacaagaag ggactaagac    2400
aaggactcct ttgtggaggt cctggcttag ggagtcaagt gacggcggct cagcactcac    2460
gtgggcagtg ccagcctcta agagtgggca ggggcactgg ccacagagtc ccagggagtc    2520
ccaccagcct agtcgccaga ccttctgtgg gcggccgcca tggtgagcaa gggcgaggag    2580
ctgttcaccg gggtggtgcc catcctggtc gagctggacg gcgacgtaaa cggccacaag    2640
ttcagcgtgt ccggcgaggg cgagggcgat gccacctacg gcaagctgac cctgaagttc    2700
atctgcacca ccggcaagct gcccgtgccc tggcccaccc tcgtgaccac cctgacctac    2760
ggcgtgcagt gcttcagccg ctaccccgac cacatgaagc agcacgactt cttcaagtcc    2820
gccatgcccg aaggctacgt ccaggagcgc accatcttct tcaaggacga cggcaactac    2880
aagacccgcg ccgaggtgaa gttcgagggc gacaccctgg tgaaccgcat cgagctgaag    2940
ggcatcgact tcaaggagga cggcaacatc ctggggcaca gctggagta caactacaac    3000 agccacaacg tctatatcat ggccgacaag cagaagaacg gcatcaaggt gaacttcaag    3060
atccgccaca acatcgagga cggcagcgtg cagctcgccg accactacca gcagaacacc    3120
cccatcggcg acggccccgt gctgctgccc gacaaccact acctgagcac ccagtccgcc    3180
ctgagcaaag accccaacga aaagcgcgat cacatggtcc tgctggagtt cgtgaccgcc    3240
gccgggatca ctctcggcat ggacgagctg tacaagtaat aagcttggat ccaatcaacc    3300
tctggattac aaaatttgtg aaagattgac tggtattctt aactatgttg ctccttttac    3360
gctatgtgga tacgctgctt taatgccttt gtatcatgct attgcttccc gtatggcttt    3420
cattttctcc tccttgtata atcctggtt gctgtctctt tatgaggagt tgtggcccgt    3480
tgtcaggcaa cgtggcgtgg tgtgcactgt gtttgctgac gcaacccccca ctggttgggg    3540 cattgccacc acctgtcagc tcctttccgg gactttcgct ttccccctcc ctattgccac    3600
ggcggaactc atcgccgcct gccttgcccg ctgctggaca ggggctcggc tgttgggcac    3660
tgacaattcc gtggtgttgt cggggaagct gacgtccttt ccatggctgc tcgcctgtgt    3720
tgccacctgg attctgcgcg gacgtcctt ctgctacgtc ccttcggccc tcaatccagc    3780
ggaccttcct tcccgcggcc tgctgccggc tctgcggcct cttccgcgtc ttcgagatct    3840
gcctcgactg tgccttctag ttgccagcca tctgttgttt gcccctcccc cgtgccttcc    3900
ttgaccctgg aaggtgccac tcccactgtc ctttcctaat aaaatgagga aattgcatcg    3960
cattgtctga gtaggtgtca ttctattctg ggggtgggg tgggcagga cagcaagggg    4020 gaggattggg aagacaatag caggcatgct ggggactcga gttaagggcg aattcccgat    4080
taggatcttc ctagagcatg gctacgtaga taagtagcat ggcgggttaa tcattaacta    4140
caaggaaccc ctagtgatgg agttggccac tccctctctg cgcgctcgct cgctcactga    4200
ggccgggcga ccaaaggtcg cccgacgccc gggctttgcc cggcggcct cagtgagcga    4260 gcgagcgcgc agccttaatt aacctaattc actggccgtc gttttacaac gtcgtgactg    4320
ggaaaaccct ggcgttaccc aacttaatcg ccttgcagca catcccccctt cgccagctg    4380 gcgtaatagc gaagaggccc gcaccgatcg cccttcccaa cagttgcgca gcctgaatgg    4440
cgaatgggac gcgccctgta gcggcgcatt aagcgcggcg ggtgtggtgg ttacgcgcag    4500
cgtgaccgct acacttgcca gcgccctagc gcccgctcct ttcgctttct tcccttcctt    4560
```

```
tctcgccacg ttcgccggct ttccccgtca agctctaaat cgggggctcc ctttagggtt    4620
ccgatttagt gctttacggc acctcgaccc caaaaaactt gattagggtg atggttcacg    4680
tagtgggcca tcgcccgat agacggtttt tcgcccttg acgctggagt tcacgttcct     4740
caatagtgga ctcttgttcc aaactggaac aacactcaac cctatctcgg tctattcttt    4800
tgatttataa gggattttc cgatttcggc ctattggtta aaaatgagc tgatttaaca      4860
aaaatttaac gcgaatttta acaaaatatt aacgtttata atttcaggtg gcatctttcg    4920
gggaaatgtg cgcggaaccc ctatttgttt atttttctaa atacattcaa atatgtatcc    4980
gctcatgaga caataaccct gataaatgct tcaataatat tgaaaaagga agagtatgag    5040
tattcaacat ttccgtgtcg cccttattcc cttttttgcg gcattttgcc ttcctgtttt    5100
tgctcaccca gaaacgctgg tgaaagtaaa agatgctgaa gatcagttgg gtgcacgagt    5160
gggttacatc gaactggatc tcaatagtgg taagatcctt gagagttttc gccccgaaga    5220
acgttttcca atgatgagca cttttaaagt tctgctatgt ggcgcggtat tatcccgtat    5280
tgacgccggg caagagcaac tcggtcgccg catacactat tctcagaatg acttggttga    5340
gtactcacca gtcacagaaa agcatcttac ggatggcatg acagtaagag aattatgcag    5400
tgctgccata accatgagtg ataacactgc ggccaactta cttctgacaa cgatcggagg    5460
accgaaggag ctaaccgctt ttttgcacaa catgggggat catgtaactc gccttgatcg    5520
ttgggaaccg gagctgaatg aagccatacc aaacgacgag cgtgacacca cgatgcctgt    5580
agtaatggta acaacgttgc gcaaactatt aactggcgaa ctacttactc tagcttcccg    5640
gcaacaatta atagactgga tggaggcgga taaagttgca ggaccacttc tgcgctcggc    5700
ccttccggct ggctggttta ttgctgataa atctggagcc ggtgagcgtg gtctcgcgg    5760
tatcattgca gcactggggc cagatggtaa gccctcccgt atcgtagtta tctacacgac    5820
ggggagtcag gcaactatgg atgaacgaaa tagacagatc gctgagatag gtgcctcact    5880
gattaagcat tggtaactgt cagaccaagt ttactcatat atactttaga ttgatttaaa    5940
acttcatttt taatttaaaa ggatctaggt gaagatcctt tttgataatc tcatgaccaa    6000
aatcccttaa cgtgagtttt cgttccactg agcgtcagac cccgtagaaa agatcaaagg    6060
atcttcttga tccttttt ttctgcgcgt aatctgctgc ttgcaaacaa aaaaaccacc      6120
gctaccagcg gtggtttgtt tgccggatca agagctacca actctttttc cgaaggtaac    6180
tggcttcagc agagcgcaga taccaaatac tgtccttcta gtgtagccgt agttaggcca    6240
ccacttcaag aactctgtag caccgcctac atacctcgct ctgctaatcc tgttaccagt    6300
ggctgctgcc agtggcgata agtcgtgtct taccgggttg gactcaagac gatagttacc    6360
ggataaggcg cagcggtcgg gctgaacggg gggttcgtgc acacagccca gcttggagcg    6420
aacgacctac accgaactga gatacctaca gcgtgagcta tgagaaagcg ccacgcttcc    6480
cgaagggaga aaggcggaca ggtatccggt aagcggcagg gtcggaacag gagagcgcac    6540
gagggagctt ccagggggaa acgcctggta tctttatagt cctgtcgggt ttcgccacct    6600
ctgacttgag cgtcgatttt tgtgatgctc gtcaggggg cggagcctat ggaaaaacgc     6660
cagcaacgcg gcctttttac ggttcctggc cttttgctgc ggtttgctc acatgttctt    6720
tcctgcgtta tccctgatt ctgtggataa ccgtattacc gcctttgagt gagctgatac     6780
cgctcgccgc agccgaacga ccgagcgcag cgagtcagtg agcgaggaag cggaagggcc    6840
gattcattaa tgcagctggc acgacaggtt tcccgactgg aaagcgggca gtgagcgcaa    6900
cgcaattaat gtgagttagc tcactcatta ggcaccccag gctttacact ttatgcttcc    6960
```

<210> SEQ ID NO 16
<211> LENGTH: 7004
<212> TYPE: DNA
<213> ORGANISM: Artificial Sequence
<220> FEATURE:
<223> OTHER INFORMATION: p1222// pAAV2.1_sRHOgRNA+sRHO HITI (IRES-dsRED)_Vmd2_GFP

<400> SEQUENCE: 16

```
caggaaacag ctatgaccat gattacgcca gatttaatta aggctgcgcg ctcgctcgct      60
cactgaggcc gcccgggcaa agcccgggcg tcgggcgacc tttggtcgcc cggcctcagt     120
gagcgagcga gcgcgcagag agggagtggc caactccatc actaggggtt ccttgtagtt     180
aatgattaac cgccatgct  acttatctac gtagccatgc tctaggaaga tcggaattcg     240
cccttaacca ctagtaacgg ccgccagtgt gctggaattc gcccttcga  gggcctattt     300
cccatgattc cttcatattt gcatatacga tacaaggctg ttagagagat aattggaatt     360
aatttgactg taaacacaaa gatattagta caaaatacgt gacgtagaaa gtaataattt     420
cttgggtagt ttgcagtttt aaaattatgt tttaaaatgg actatcatat gcttaccgta     480
acttgaaagt atttcgattt cttggcttta tatcttgt   ggaaaggacg aaacaccgga     540
ctcgcgcgag tcgaggaggt tttagagcta gaaatagcaa gttaaaataa ggctagtccg     600
ttatcaactt gaaaaagtgg caccgagtcg gtgctttttt gttttagagc tagaaatagc     660
aagctcgagc agcctgaatt ctgcagatat ccatcacact ggcggcctta actcggatcc     720
actagtaacg gccgccagtg tgctggaatt caggccccct tgagtatccg cagtacttcc     780
ccagcatgcc tgctattgtc ttcccaatcc tcccccttgc tgtcctgccc caccccaccc     840
cccagaatag aatgacacct actcagacaa tgcgatgcaa tttcctcatt ttattaggaa     900
aggacagtgg gagtggcacc ttccagggtc aaggaaggca gggggagggg caaacaaca     960
gatggctggc aactagaagg cacagtcgag gcagatccaa gcttctgcag gtcgactcta    1020
gtaggcctat tattttgac  accagacaag ttggtaatgg tagcgaccgg cgctcagttg    1080
gaattctaga gtcgcggccg ctactggaac aggtggtggc gggcctcggc gcgctcgtac    1140
tgctccacca cggtgtagtc ctcgttgtgg gaggtgatgt ccagcttgga gtccacgtag    1200
tagtagccgg gcagcttcac gggcttcttg gccatgtaga ttgacttgaa ctccaccagg    1260
tagtggccgc cgcccttcag cttcagcgcc ttgtggatct cgcccttcag cacgccgtcg    1320
cggggtaca  ggcgctcggt ggagggctcc cagcccagag tcttcttctg cattacgggg    1380
ccgtcggagg ggaagttcac gccgatgaac ttcacgtggt agatgaaggt gccgtcctgc    1440
agggaggagt cctgggtcac ggtcaccacg ccgccgtcct cgaagttcat cacgcgctcc    1500
cacttgaagc cctcggggaa ggacagcttc ttgtagtcgg ggatgtcggc ggggtgcttc    1560
acgtacacct tggagccgta ctggaactgg ggggacagga tgtcccaggc gaagggcagg    1620
gggccgccct tggtcacctg cagcttggcg gtctgggtgc cctcgtaggg cttgccctcg    1680
ccctcgccct cgatctcgaa ctcgtggccg ttcacggagc cctccatgtg caccttgaag    1740
cgcatgaagg gcttgatgac gttctcagtg ctatccatct acaaaaaaat cacgcaaaat    1800
tacagttaac ggcatgtaca gtttgtcatt attatttatt accccttga gtatccgcag    1860
tactaagggc gaattctgca gatatccatc acactggcgt taagcgtcag catatgcaga    1920
attctgtcat tttactaggg tgatgaaatt cccaagcaac accatccttt tcagataagg    1980
```

```
gcactgaggc tgagagagga gctgaaacct acccggggtc accacacaca ggtggcaagg    2040
ctgggaccag aaaccaggac tgttgactgc agcccggtat tcattctttc catagcccac    2100
agggctgtca aagacccag  ggcctagtca gaggctcctc cttcctggag agttcctggc    2160
acagaagttg aagctcagca cagcccccta acccccaact ctctctgcaa ggcctcaggg    2220
gtcagaacac tggtggagca gatcctttag cctctggatt ttagggccat ggtagagggg    2280
gtgttgccct aaattccagc cctggtctca gcccaacacc ctccaagaag aaattagagg    2340
ggccatggcc aggctgtgct agccgttgct tctgagcaga ttacaagaag ggactaagac    2400
aaggactcct ttgtggaggt cctggcttag ggagtcaagt gacggcggct cagcactcac    2460
gtgggcagtg ccagcctcta agagtgggca ggggcactgg ccacagagtc ccagggagtc    2520
ccaccagcct agtcgccaga ccttctgtgg gcggccgcca tggtgagcaa gggcgaggag    2580
ctgttcaccg ggtggtgccc catcctggtc gagctggacg gcgacgtaaa cggccacaag    2640
ttcagcgtgt ccggcgaggg cgagggcgat gccacctacg gcaagctgac cctgaagttc    2700
atctgcacca ccggcaagct gcccgtgccc tggcccaccc tcgtgaccac cctgacctac    2760
ggcgtgcagt gcttcagccg ctaccccgac cacatgaagc agcacgactt cttcaagtcc    2820
gccatgcccg aaggctacgt ccaggagcgc accatcttct tcaaggacga cggcaactac    2880
aagacccgcg ccgaggtgaa gttcgagggc gacaccctgg tgaaccgcat cgagctgaag    2940
ggcatcgact tcaaggagga cggcaacatc ctggggcaca agctggagta caactacaac    3000
agccacaacg tctatatcat ggccgacaag cagaagaacg gcatcaaggt gaacttcaag    3060
atccgccaca acatcgagga cggcagcgtg cagctcgccg accactacca gcagaacacc    3120
cccatcggcg acggccccgt gctgctgccc gacaaccact acctgagcac ccagtccgcc    3180
ctgagcaaag accccaacga aagcgcgat  cacatggtcc tgctggagtt cgtgaccgcc    3240
gccgggatca ctctcggcat ggacgagctg tacaagtaat aagcttggat ccaatcaacc    3300
tctggattac aaaatttgtg aaagattgac tggtattctt aactatgttg ctccttttac    3360
gctatgtgga tacgctgctt taatgccttt gtatcatgct attgcttccc gtatggcttt    3420
cattttctcc tccttgtata atcctggtt  gctgtctctt tatgaggagt tgtggcccgt    3480
tgtcaggcaa cgtggcgtgg tgtgcactgt gtttgctgac gcaacccccca ctggttgggg    3540 cattgccacc acctgtcagc tcctttccgg gactttcgct ttcccctcc ctattgccac    3600 ggcggaactc atcgccgcct gccttgcccg ctgctggaca ggggctcggc tgttgggcac    3660
tgacaattcc gtggtgttgt cggggaagct gacgtccttt ccatggctgc tcgcctgtgt    3720
tgccacctgg attctgcgcg gacgtccttt ctgctacgtc ccttcggccc tcaatccagc    3780
ggaccttcct tcccgcggcc tgctgccggc tctgcggcct cttccgcgtc ttcgagatct    3840
gcctcgactg tgccttctag ttgccagcca tctgttgttt gcccctcccc cgtgccttcc    3900
ttgaccctgg aaggtgccac tcccactgtc ctttcctaat aaaatgagga aattgcatcg    3960
cattgtctga gtaggtgtca ttctattctg ggggtgggg  tggggcagga cagcaagggg    4020
gaggattggg aagacaatag caggcatgct ggggactcga gttaagggcg aattcccgat    4080
taggatcttc ctagagcatg gctacgtaga taagtagcat ggcgggttaa tcattaacta    4140
caaggaaccc ctagtgatgg agttggccac tccctctctg cgcgctcgct cgctcactga    4200
ggccgggcga ccaaaggtcg cccgacgccc gggctttgcc cggcgggcct cagtgagcga    4260
gcgagcgcgc agccttaatt aacctaattc actggccgtc gttttacaac gtcgtgactg    4320
```

```
ggaaaaccct ggcgttaccc aacttaatcg ccttgcagca catccccctt tcgccagctg   4380
gcgtaatagc gaagaggccc gcaccgatcg cccttcccaa cagttgcgca gcctgaatgg   4440
cgaatgggac gcgccctgta gcggcgcatt aagcgcggcg ggtgtggtgg ttacgcgcag   4500
cgtgaccgct acacttgcca gcgccctagc gcccgctcct ttcgctttct tcccttcctt   4560
tctcgccacg ttcgccggct ttccccgtca agctctaaat cggggggctcc ctttagggtt   4620 ccgatttagt gctttacggc acctcgaccc caaaaaactt gattagggtg atggttcacg   4680
tagtgggcca tcgcccgat agacggtttt tcgccctttg acgctggagt tcacgttcct   4740
caatagtgga ctcttgttcc aaactggaac aacactcaac cctatctcgg tctattcttt   4800
tgatttataa gggatttttc cgatttcggc ctattggtta aaaaatgagc tgatttaaca   4860
aaaatttaac gcgaatttta acaaaatatt aacgtttata atttcaggtg gcatctttcg   4920
gggaaatgtg cgcggaaccc ctatttgttt atttttctaa atacattcaa atatgtatcc   4980
gctcatgaga caataacccct gataaatgct tcaataatat tgaaaaagga agagtatgag   5040
tattcaacat ttccgtgtcg cccttattcc cttttttgcg gcattttgcc ttcctgtttt   5100
tgctcaccca gaaacgctgg tgaaagtaaa agatgctgaa gatcagttgg gtgcacgagt   5160
gggttacatc gaactggatc tcaatagtgg taagatcctt gagagttttc gccccgaaga   5220
acgttttcca atgatgagca cttttaaagt tctgctatgt ggcgcggtat tatcccgtat   5280
tgacgccggg caagagcaac tcggtcgccg catacactat tctcagaatg acttggttga   5340
gtactcacca gtcacagaaa agcatcttac ggatggcatg acagtaagag aattatgcag   5400
tgctgccata accatgagtg ataacactgc ggccaactta cttctgacaa cgatcggagg   5460
accgaaggag ctaaccgctt ttttgcacaa catgggggat catgtaactc gccttgatcg   5520
ttgggaaccg gagctgaatg aagccatacc aaacgacgag cgtgacacca cgatgcctgt   5580
agtaatggta acaacgttgc gcaaactatt aactggcgaa ctacttactc tagcttcccg   5640
gcaacaatta atagactgga tggaggcgga taaagttgca ggaccacttc tgcgctcggc   5700
ccttccggct ggctggttta ttgctgataa atctggagcc ggtgagcgtg gtctcgcgg   5760 tatcattgca gcactggggc cagatggtaa gccctcccgt atcgtagtta tctacacgac   5820
ggggagtcag gcaactatgg atgaacgaaa tagacagatc gctgagatag gtgcctcact   5880
gattaagcat tggtaactgt cagaccaagt ttactcatat atactttaga ttgatttaaa   5940
acttcatttt taatttaaaa ggatctaggt gaagatcctt tttgataatc tcatgaccaa   6000
aatcccttaa cgtgagtttt cgttccactg agcgtcagac cccgtagaaa agatcaaagg   6060
atcttcttga tccttttttt tctgcgcgt aatctgctgc ttgcaaacaa aaaaaccacc   6120
gctaccagcg gtggtttgtt tgccggatca agagctacca actctttttc cgaaggtaac   6180
tggcttcagc agagcgcaga taccaaatac tgtccttcta gtgtagccgt agttaggcca   6240
ccacttcaag aactctgtag caccgcctac atacctcgct ctgctaatcc tgttaccagt   6300
ggctgctgcc agtggcgata agtcgtgtct taccgggttg gactcaagac gatagttacc   6360
ggataaggcg cagcggtcgg gctgaacggg gggttcgtgc acacagccca gcttggagcg   6420
aacgacctac accgaactga gatacctaca gcgtgagcta tgagaaagcg ccacgcttcc   6480
cgaagggaga aaggcggaca ggtatccggt aagcggcagg gtcggaacag gagagcgcac   6540
gagggagctt ccagggggaa acgcctggta tctttatagt cctgtcgggt ttcgccacct   6600
ctgacttgag cgtcgatttt tgtgatgctc gtcaggggg cggagcctat ggaaaaacgc   6660
cagcaacgcg gcctttttac ggttcctggc cttttgctgc ggttttgctc acatgttctt   6720
```

```
tcctgcgtta tccccctgatt ctgtggataa ccgtattacc gcctttgagt gagctgatac    6780
cgctcgccgc agccgaacga ccgagcgcag cgagtcagtg agcgaggaag cggaagggcc    6840
gattcattaa tgcagctggc acgacaggtt cccgactgg aaagcgggca gtgagcgcaa    6900
cgcaattaat gtgagttagc tcactcatta ggcaccccag gctttacact ttatgcttcc    6960
ggctcgtatg ttgtgtggaa ttgtgagcgg ataacaattt caca                     7004
```

<210> SEQ ID NO 17
<211> LENGTH: 6874
<212> TYPE: DNA
<213> ORGANISM: Artificial Sequence
<220> FEATURE:
<223> OTHER INFORMATION: p1227// pAAV2.1_sRHOgRNA+sRHO HITI (IRES-dsRED)_Vmd2_GFP

<400> SEQUENCE: 17

```
attacgccag atttaattaa ggctgcgcgc tcgctcgctc actgaggccg cccgggcaaa      60
gcccgggcgt cgggcgacct ttggtcgccc ggcctcagtg agcgagcgag cgcgcagaga    120
gggagtggcc aactccatca ctaggggttc cttgtagtta atgattaacc cgccatgcta    180
cttatctacg tagccatgct ctaggaagat cggaattcgc ccttaaccac tagtaacggc    240
cgccagtgtg ctggaattcg ccctttcgag ggcctatttc ccatgattcc ttcatatttg    300
catatacgat acaaggctgt tagagagata attggaatta atttgactgt aaacacaaag    360
atattagtac aaaatacgtg acgtagaaag taataatttc ttgggtagtt tgcagtttta    420
aaattatgtt ttaaaatgga ctatcatatg cttaccgtaa cttgaaagta tttcgatttc    480
ttggctttat atatcttgtg gaaaggacga aacaccgagt actgcggata ctcaaaggtt    540
ttagagctag aaatagcaag ttaaaataag gctagtccgt tatcaacttg aaaaagtggc    600
accgagtcgg tgcttttttg ttttagagct agaaatagca agctcgagca gcctgaattc    660
tgcagatatc catcacactg gcggccttaa ctcggatcca ctagtaacgg ccgccagtgt    720
gctggaattc aggccccttt gagtatccgc agtacttccc cagcatgcct gctattgtct    780
tcccaatcct ccccccttgct gtcctgcccc accccacccc ccagaataga atgcaccta    840 ctcagacaat gcgatgcaat ttcctcattt tattaggaaa ggacagtggg agtggcacct    900
tccagggtca aggaaggcac ggggagggg caaacaacag atggctggca actagaaggc    960
acagtcgagg cagatccaag cttctgcagg tcgactctag taggcctatt attttgaca   1020 ccagacaagt tggtaatggt agcgaccggc gctcagttgg aattctagag tcgcggccgc  1080
tactggaaca ggtggtggcg gcctcggcg cgctcgtact gctccaccac ggtgtagtcc   1140
tcgttgtggg aggtgatgtc cagcttggag tccacgtagt agtagccggg cagcttcacg  1200
ggcttcttgg ccatgtagat tgacttgaac tccaccaggt agtggccgcc gcccttcagc  1260
ttcagcgcct tgtggatctc gcccttcagc acgccgtcgc ggggtacag gcgctcggtg   1320 gagggctccc agcccagagt cttcttctgc attacgggc cgtcgaggg gaagttcacg   1380 ccgatgaact tcacgtggta gatgaaggtg ccgtcctgca gggaggagtc ctgggtcacg  1440
gtcaccacgc cgccgtcctc gaagttcatc acgcgctccc acttgaagcc ctcggggaag  1500
gacagcttct tgtagtcggg gatgtcggcg gggtgcttca cgtacacctt ggagccgtac  1560
tggaactggg gggacaggat gtcccaggcg aagggcaggg ggccgccctt ggtcacctgc  1620 agcttggcg tctgggtgcc ctcgtagggc ttgcccctcgc cctcgccctc gatctcgaac   1680
tcgtggccgt tcacggagcc ctccatgtgc accttgaagc gcatgaaggg cttgatgacg  1740
```

```
ttctcagtgc tatccatcta caaaaaaatc acgcaaaatt acagttaacg gcatgtacag    1800
tttgtcatta ttatttatta cccctttgag tatccgcagt actaagggcg aattctgcag    1860
atatccatca cactggcgtt aagcgtcagc atatgcagaa ttctgtcatt ttactagggt    1920
gatgaaattc ccaagcaaca ccatcctttt cagataaggg cactgaggct gagagaggag    1980
ctgaaaccta cccggggtca ccacacacag gtggcaaggc tgggaccaga aaccaggact    2040
gttgactgca gcccggtatt cattctttcc atagcccaca gggctgtcaa agaccccagg    2100
gcctagtcag aggctcctcc ttcctggaga gttcctggca cagaagttga agctcagcac    2160 agcccccta ac ccccaactc tctctgcaag gcctcagggg tcagaacact ggtggagcag    2220
atcctttagc ctctggattt tagggccatg gtagaggggg tgttgcccta aattccagcc    2280
ctggtctcag cccaacaccc tccaagaaga aattagaggg gccatggcca ggctgtgcta    2340
gccgttgctt ctgagcagat tacaagaagg gactaagaca aggactcctt tgtggaggtc    2400
ctggcttagg gagtcaagtg acggcggctc agcactcacg tgggcagtgc cagcctctaa    2460
gagtgggcag gggcactggc cacagagtcc cagggagtcc caccagccta gtcgccagac    2520
cttctgtggg cggccgccat ggtgagcaag ggcgaggagc tgttcaccgg ggtggtgccc    2580
atcctggtcg agctggacgg cgacgtaaac ggccacaagt tcagcgtgtc cggcgagggc    2640
gagggcgatg ccacctacgg caagctgacc ctgaagttca tctgcaccac cggcaagctg    2700
cccgtgccct ggcccaccct cgtgaccacc ctgacctacg gcgtgcagtg cttcagccgc    2760
taccccgacc acatgaagca gcacgacttc ttcaagtccg ccatgcccga aggctacgtc    2820
caggagcgca ccatcttctt caaggacgac ggcaactaca agacccgcgc cgaggtgaag    2880
ttcgagggcg acaccctggt gaaccgcatc gagctgaagg gcatcgactt caaggaggac    2940
ggcaacatcc tggggcacaa gctggagtac aactacaaca gccacaacgt ctatatcatg    3000
gccgacaagc agaagaacgg catcaaggtg aacttcaaga tccgccacaa catcgaggac    3060
ggcagcgtgc agctcgccga ccactaccag cagaacaccc ccatcggcga cggccccgtg    3120
ctgctgcccg acaaccacta cctgagcacc cagtccgccc tgagcaaaga ccccaacgag    3180
aagcgcgatc acatggtcct gctggagttc gtgaccgccg ccgggatcac tctcggcatg    3240
gacgagctgt acaagtaata agcttggatc caatcaacct ctggattaca aaatttgtga    3300
aagattgact ggtattctta actatgttgc tccttttacg ctatgtggat acgctgcttt    3360
aatgcctttg tatcatgcta ttgcttcccg tatggctttc attttctcct ccttgtataa    3420
atcctggttg ctgtctcttt atgaggagtt gtggcccgtt gtcaggcaac gtggcgtggt    3480
gtgcactgtg tttgctgacg caaccccac tggttgggc attgccacca cctgtcagct    3540
cctttccggg actttcgctt tccccctccc tattgccacg gcggaactca tcgccgcctg    3600
ccttgcccgc tgctggacag gggctcggct gttgggcact gacaattccg tggtgttgtc    3660
ggggaagctg acgtcctttc catggctgct cgcctgtgtt gccacctgga ttctgcgcgg    3720
gacgtccttc tgctacgtcc cttcggccct caatccagcg gaccttcctt cccgcggcct    3780
gctgccggct ctgcggcctc ttccgcgtct tcgagatctg cctcgactgt gccttctagt    3840
tgccagccat ctgttgtttg cccctcccc gtgccttcct tgaccctgga aggtgccact    3900
cccactgtcc tttcctaata aaatgaggaa attgcatcgc attgtctgag taggtgtcat    3960
tctattctgg ggggtggggt ggggcaggac agcaagggg aggattggga agacaatagc    4020
aggcatgctg gggactcgag ttaagggcga attcccgatt aggatcttcc tagagcatgg    4080
```

```
ctacgtagat aagtagcatg gcgggttaat cattaactac accttaatta acctaattca    4140
ctggccgtcg ttttacaacg tcgtgactgg gaaaaccctg gcgttaccca acttaatcgc    4200
cttgcagcac atcccccttt cgccagctgg cgtaatagcg aagaggcccg caccgatcgc    4260
ccttcccaac agttgcgcag cctgaatggc gaatgggacg cgccctgtag cggcgcatta    4320
agcgcggcgg gtgtggtggt tacgcgcagc gtgaccgcta cacttgccag cgccctagcg    4380
cccgctcctt tcgctttctt cccttccttt ctcgccacgt tcgccggctt tccccgtcaa    4440
gctctaaatc gggggctccc tttagggttc cgatttagtg ctttacggca cctcgacccc    4500
aaaaaacttg attagggtga tggttcacgt agtgggccat cgccccgata gacggttttt    4560
cgccctttga cgctggagtt cacgttcctc aatagtggac tcttgttcca aactggaaca    4620
acactcaacc ctatctcggt ctattctttt gatttataag ggattttccc gatttcggcc    4680
tattggttaa aaaatgagct gatttaacaa aaatttaacg cgaattttaa caaaatatta    4740
acgtttataa tttcaggtgg catctttcgg ggaaatgtgc gcggaacccc tatttgttta    4800
tttttctaaa tacattcaaa tatgtatccg ctcatgagac aataaccctg ataaatgctt    4860
caataatatt gaaaaaggaa gagtatgagt attcaacatt tccgtgtcgc ccttattccc    4920
ttttttgcgg cattttgcct tcctgttttt gctcacccag aaacgctggt gaaagtaaaa    4980
gatgctgaag atcagttggg tgcacgagtg ggttacatcg aactggatct caatagtggt    5040
aagatccttg agagttttcg ccccgaagaa cgttttccaa tgatgagcac ttttaaagtt    5100
ctgctatgtg gcgcggtatt atcccgtatt gacgccgggc aagagcaact cggtcgccgc    5160
atacactatt ctcagaatga cttggttgag tactcaccag tcacagaaaa gcatcttacg    5220
gatggcatga cagtaagaga attatgcagt gctgccataa ccatgagtga taacactgcg    5280
gccaacttac ttctgacaac gatcggagga ccgaaggagc taaccgcttt tttgcacaac    5340
atgggggatc atgtaactcg ccttgatcgt tgggaaccgg agctgaatga agccatacca    5400
aacgacgagc gtgacaccac gatgcctgta gtaatggtaa caacgttgcg caaactatta    5460
actggcgaac tacttactct agcttcccgg caacaattaa tagactggat ggaggcggat    5520
aaagttgcag gaccacttct gcgctcggcc cttccggctg gctggtttat tgctgataaa    5580
tctggagccg gtgagcgtgg gtctcgcggt atcattgcag cactggggcc agatggtaag    5640
ccctcccgta tcgtagttat ctacacgacg gggagtcagg caactatgga tgaacgaaat    5700
agacagatcg ctgagatagg tgcctcactg attaagcatt ggtaactgtc agaccaagtt    5760
tactcatata tactttagat tgatttaaaa cttcattttt aatttaaaag gatctaggtg    5820
aagatccttt ttgataatct catgaccaaa atcccttaac gtgagttttc gttccactga    5880
gcgtcagacc ccgtagaaaa gatcaaagga tcttcttgag atcctttttt tctgcgcgta    5940
atctgctgct tgcaaacaaa aaaaccaccg ctaccagcgg tggtttgttt gccggatcaa    6000
gagctaccaa ctcttttttcc gaaggtaact ggcttcagca gagcgcagat accaaatact    6060
gtccttctag tgtagccgta gttaggccac cacttcaaga actctgtagc accgcctaca    6120
tacctcgctc tgctaatcct gttaccagtg gctgctgcca gtggcgataa gtcgtgtctt    6180
accgggttgg actcaagacg atagttaccg gataaggcgc agcggtcggg ctgaacgggg    6240
ggttcgtgca cacagcccag cttggagcga acgacctaca ccgaactgag atacctacag    6300
cgtgagctat gagaaagcgc cacgcttccc gaagggagaa aggcggacag gtatccggta    6360
agcggcaggg tcggaacagg agagcgcacg agggagcttc caggggggaaa cgcctggtat    6420
ctttatagtc ctgtcgggtt tcgccacctc tgacttgagc gtcgattttt gtgatgctcg    6480
```

```
tcagggggc ggagcctatg gaaaaacgcc agcaacgcgg ccttttacg gttcctggcc      6540 ttttgctgcg gttttgctca catgttcttt cctgcgttat cccctgattc tgtggataac      6600
cgtattaccg cctttgagtg agctgatacc gctcgccgca gccgaacgac cgagcgcagc      6660
gagtcagtga gcgaggaagc ggaagggccg attcattaat gcagctggca cgacaggttt      6720
cccgactgga aagcgggcag tgagcgcaac gcaattaatg tgagttagct cactcattag      6780 gcacccagg ctttacactt tatgcttccg gctcgtatgt tgtgtggaat tgtgagcgga      6840
taacaatttc acacaggaaa cagctatgac catg                                 6874
```

<210> SEQ ID NO 18
<211> LENGTH: 4742
<212> TYPE: DNA
<213> ORGANISM: Artificial Sequence
<220> FEATURE:
<223> OTHER INFORMATION: p1160//pAAV_Alb5'HITI(kozak-dsRED) + gRNA mAlb 5'

<400> SEQUENCE: 18

```
ttacgccaga tttaattaag gctgcgcgct cgctcgctca ctgaggccgc ccgggcaaag        60
cccgggcgtc gggcgacctt tggtcgcccg gcctcagtga gcgagcgagc gcgcagagag       120
ggagtggcca actccatcac taggggttcc ttgtagttaa tgattaaccc gccatgctac       180
ttatctacgt agccatgctc taggaagatc ggaattacta gtaacggccg ccagtgtgct       240
ggcacaagag tgagatcgcc catcggtccc cagcatgcct gctattgtct tcccaatcct       300
cccccttgct gtcctgcccc accccacccc ccagaataga atgacaccta ctcagacaat       360
gcgatgcaat ttcctcattt tattaggaaa ggacagtggg agtggcacct tccagggtca       420
aggaaggcac gggggagggg caaacaacag atggctggca actagaaggc acagtcgagg       480
cagatccaag cttctgcagg tcgactctag taggcctatt attttttgaca ccagacaagt       540 tggtaatggt agcgaccggc gctcagttgg aattctagag tcgcggccgc tactggaaca       600
ggtggtggcg ggcctcggcg cgctcgtact gctccaccac ggtgtagtcc tcgttgtggg       660
aggtgatgtc cagcttggag tccacgtagt agtagccggg cagcttcacg ggcttcttgg       720
ccatgtagat tgacttgaac tccaccaggt agtggccgcc gcccttcagc ttcagcgcct       780
tgtggatctc gcccttcagc acgccgtcgc ggggtacag cgctcggtg gagggctccc       840 agcccagagt cttcttctgc attacggggc cgtcggaggg gaagttcacg ccgatgaact       900
tcacgtggta gatgaaggtg ccgtcctgca gggaggagtc ctgggtcacg gtcaccacgc       960
cgccgtcctc gaagttcatc acgcgctccc acttgaagcc ctcggggaag acagcttct      1020 tgtagtcggg gatgtcggcg gggtgcttca cgtacaccctt ggagccgtac tggaactggg      1080
gggacaggat gtcccaggcg aagggcaggg ggccgccctt ggtcacctgc agcttggcgg      1140
tctgggtgcc ctcgtagggc ttgccctcgc cctcgccctc gatctcgaac tcgtggccgt      1200
tcacggagcc ctccatgtgc accttgaagc gcatgaaggg cttgatgacg ttctcagtgc      1260
tatccatggt ggcttattat ttattattta ttaacaagag tgagatcgcc catcgggaat      1320
tgccgccagt gtgatggata tctgcagaat tcaggctgct cgagcttgct atttctagct      1380
ctaaaacaaa aaagcaccga ctcggtgcca cttttcaag ttgataacgg actagcctta      1440
ttttaacttg ctatttctag ctctaaaacc tcctcgactc gcgcgagtcc ggtgtttcgt      1500
cctttccaca agatatataa agccaagaaa tcgaaatact ttcaagttac ggtaagcata      1560
tgatagtcca ttttaaaaca taattttaaa actgcaaact acccaagaaa ttattacttt      1620
```

-continued

```
ctacgtcacg tattttgtac taatatcttt gtgtttacag tccaaattaa ttccaattat    1680
ctctctaaca gccttgtatc gtatatgcaa atatgaagga atcatgggaa actcgaggtc    1740
agcctgaatt aattcccgat taggatcttc ctagagcatg gctacgtaga taagtagcat    1800
ggcgggttaa tcattaacta caaggaaccc ctagtgatgg agttggccac tccctctctg    1860
cgcgctcgct cgctcactga ggccgggcga ccaaaggtcg cccgacgccc gggctttgcc    1920
cgggcggcct cagtgagcga gcgagcgcgc agccttaatt aacctaattc actgccgtc     1980 gttttacaac gtcgtgactg ggaaaaccct ggcgttaccc aacttaatcg ccttgcagca    2040 catcccctt  tcgccagctg gcgtaatagc gaagaggccc gcaccgatcg cccttcccaa    2100
cagttgcgca gcctgaatgg cgaatgggac gcgccctgta gcggcgcatt aagcgcggcg    2160
ggtgtggtgg ttacgcgcag cgtgaccgct acacttgcca gcgccctagc gcccgctcct    2220
ttcgctttct tcccttcctt tctcgccacg ttcgccggct ttccccgtca gctctaaat     2280 cggggggctcc ctttagggtt ccgatttagt gctttacggc acctcgaccc caaaaaactt   2340
gattagggtg atggttcacg tagtgggcca tcgccccgat agacggtttt tcgccctttg    2400
acgctggagt tcacgttcct caatagtgga ctcttgttcc aaactggaac aacactcaac    2460
cctatctcgg tctattcttt tgatttataa gggattttc  cgatttcggc ctattggtta    2520
aaaaatgagc tgatttaaca aaaatttaac gcgaatttta acaaaatatt aacgtttata    2580
atttcaggtg gcatctttcg gggaaatgtg cgcggaaccc ctatttgttt attttttctaa   2640 atacattcaa atatgtatcc gctcatgaga caataaccct gataaatgct tcaataatat    2700
tgaaaaagga agagtatgag tattcaacat ttccgtgtcg cccttattcc cttttttgcg    2760 gcatttgcc  ttcctgttttt tgctcaccca gaaacgctgg tgaaagtaaa agatgctgaa    2820
gatcagttgg gtgcacgagt gggttacatc gaactggatc tcaatagtgg taagatcctt    2880
gagagttttc gccccgaaga acgttttcca atgatgagca ctttaaagt  tctgctatgt    2940 ggcgcggtat tatcccgtat tgacgccggg caagagcaac tcggtcgccg catacactat    3000
tctcagaatg acttggttga gtactcacca gtcacagaaa agcatcttac ggatggcatg    3060
acagtaagag aattatgcag tgctgccata accatgagtg ataacactgc ggccaactta    3120
cttctgacaa cgatcggagg accgaaggag ctaaccgctt ttttgcacaa catgggggat    3180
catgtaactc gccttgatcg ttgggaaccg gagctgaatg aagccatacc aaacgacgag    3240
cgtgacacca cgatgcctgt agtaatggta acaacgttgc gcaaactatt aactggcgaa    3300
ctacttactc tagcttcccg gcaacaatta atagactgga tggaggcgga taaagttgca    3360
ggaccacttc tgcgctcggc ccttccggct ggctggttta ttgctgataa atctggagcc    3420
ggtgagcgtg gtctcgcgg  tatcattgca gcactgggc  cagatggtaa gccctcccgt    3480
atcgtagtta tctacacgac ggggagtcag gcaactatgg atgaacgaaa tagacagatc    3540
gctgagatag gtgcctcact gattaagcat tggtaactgt cagaccaagt ttactcatat    3600
atactttaga ttgatttaaa acttcatttt taatttaaaa ggatctaggt gaagatcctt    3660
tttgataatc tcatgaccaa aatcccttaa cgtgagtttt cgttccactg agcgtcagac    3720
cccgtagaaa agatcaaagg atcttcttga gatccttttt tctgcgcgt  aatctgctgc    3780 ttgcaaacaa aaaaccacc  gctaccagcg gtggtttgtt tgccggatca agagctacca    3840 actcttttc  cgaaggtaac tggcttcagc agagcgcaga taccaaatac tgtccttcta    3900
gtgtagccgt agttaggcca ccacttcaag aactctgtag caccgcctac atacctcgct    3960
```

```
ctgctaatcc tgttaccagt ggctgctgcc agtggcgata agtcgtgtct taccgggttg   4020
gactcaagac gatagttacc ggataaggcg cagcggtcgg gctgaacggg gggttcgtgc   4080
acacagccca gcttggagcg aacgacctac accgaactga gatacctaca gcgtgagcta   4140
tgagaaagcg ccacgcttcc cgaagggaga aggcggaca ggtatccggt aagcggcagg    4200
gtcggaacag gagagcgcac gagggagctt ccaggggaa acgcctggta tctttatagt    4260
cctgtcgggt ttcgccacct ctgacttgag cgtcgatttt tgtgatgctc gtcaggggg    4320
cggagcctat ggaaaaacgc cagcaacgcg ccttttttac ggttcctggc cttttgctgc   4380
ggttttgctc acatgttctt tcctgcgtta tcccctgatt ctgtggataa ccgtattacc   4440
gcctttgagt gagctgatac cgctcgccgc agccgaacga ccgagcgcag cgagtcagtg   4500
agcgaggaag cggaagagcg cccaatacgc aaaccgcctc tccccgcgcg ttggccgatt   4560
cattaatgca gctggcacga caggtttccc gactggaaag cgggcagtga gcgcaacgca   4620
attaatgtga gttagctcac tcattaggca ccccaggctt tacactttat gcttccggct   4680
cgtatgttgt gtggaattgt gagcggataa caatttcaca caggaaacag ctatgaccat   4740
ga                                                                  4742
```

<210> SEQ ID NO 19
<211> LENGTH: 4742
<212> TYPE: DNA
<213> ORGANISM: Artificial Sequence
<220> FEATURE:
<223> OTHER INFORMATION: p1161//pAAV_Alb5'HITI(kozak-dsRED) + scramble

<400> SEQUENCE: 19

```
cacaggaaac agctatgacc atgattacgc cagatttaat taaggctgcg cgctcgctcg     60
ctcactgagg ccgcccgggc aaagcccggg cgtcgggcga cctttggtcg cccggcctca    120
gtgagcgagc gagcgcgcag agagggagtg gccaactcca tcactagggg ttccttgtag    180
ttaatgatta acccgccatg ctacttatct acgtagccat gctctaggaa gatcggaatt    240
actagtaacg gccgccagtg tgctggcaca agagtgagat cgcccatcgg tccccagcat    300
gcctgctatt gtcttcccaa tcctcccct tgctgtcctg ccccacccca cccccagaa     360
tagaatgaca cctactcaga caatgcgatg caatttcctc atttttattag gaaaggacag   420
tgggagtggc accttccagg gtcaaggaag gcacggggga ggggcaaaca acagatggct   480
ggcaactaga aggcacagtc gaggcagatc caagcttctg caggtcgact ctagtaggcc   540
tattatttt gacaccagac aagttggtaa tggtagcgac cggcgctcag ttggaattct    600
agagtcgcgg ccgctactgg aacaggtggt ggcgggcctc ggcgcgctcg tactgctcca    660
ccacggtgta gtcctcgttg tgggaggtga tgtccagctt ggagtccacg tagtagtagc    720
cgggcagctt cacgggcttc ttggccatgt agattgactt gaactccacc aggtagtggc    780
cgccgccctt cagcttcagc gccttgtgga tctcgccctt cagcacgccg tcgcgggggt    840
acaggcgctc ggtggagggc tcccagccca gagtcttctt ctgcattacg ggccgtcgg    900
aggggaagtt cacgccgatg aacttcacgt ggtagatgaa ggtgccgtcc tgcagggagg    960
agtcctgggt cacggtcacc acgccgccgt cctcgaagtt catcacgcgc tcccacttga   1020
agccctcggg gaaggacagc ttcttgtagt cggggatgtc ggcggggtgc ttcacgtaca   1080
ccttggagcc gtactggaac tgggggaca ggatgtccca ggcgaagggc agggggccgc    1140
ccttggtcac ctgcagcttg gcggtctggg tgccctcgta gggcttgccc tcgccctcgc   1200
cctcgatctc gaactcgtgg ccgttcacgg agccctccat gtgcaccttg aagcgcatga   1260
```

```
agggcttgat gacgttctca gtgctatcca tggtggctta ttatttatta tttattaaca   1320
agagtgagat cgcccatcgg gaattgccgc cagtgtgatg gatatctgca gaattcaggc   1380
tgctcgagct tgctatttct agctctaaaa caaaaaagca ccgactcggt gccacttttt   1440
caagttgata acgactagc cttatttaa cttgctattt ctagctctaa acatgggcg     1500
atctcactct tgtcggtgtt tcgtcctttc cacaagatat ataaagccaa gaaatcgaaa   1560
tactttcaag ttacggtaag catatgatag tccattttaa aacataattt taaaactgca   1620
aactacccaa gaaattatta ctttctacgt cacgtatttt gtactaatat ctttgtgttt   1680
acagtccaaa ttaattccaa ttatctctct aacagccttg tatcgtatat gcaaatatga   1740
aggaatcatg ggaaactcga ggtcagcctg aattaattcc cgattaggat cttcctagag   1800
catggctacg tagataagta gcatggcggg ttaatcatta actacaagga acccctagtg   1860
atggagttgg ccactccctc tctgcgcgct cgctcgctca ctgaggccgg gcgaccaaag   1920
gtcgcccgac gcccgggctt tgcccggcg gcctcagtga gcgagcgagc gcgcagcctt   1980
aattaaccta attcactggc cgtcgtttta caacgtcgtg actgggaaaa ccctggcgtt   2040
acccaactta atcgccttgc agcacatccc cctttcgcca gctggcgtaa tagcgaagag   2100
gcccgcaccg atcgcccttc ccaacagttg cgcagcctga atggcgaatg gacgcgccc   2160
tgtagcggcg cattaagcgc ggcgggtgtg gtggttacgc gcagcgtgac cgctacactt   2220
gccagcgccc tagcgcccgc tcctttcgct ttcttccctt cctttctcgc cacgttcgcc   2280
ggctttcccc gtcaagctct aaatcggggg ctcccttag ggttccgatt tagtgcttta    2340
cggcacctcg accccaaaaa acttgattag ggtgatggtt cacgtagtgg gccatcgccc   2400
cgatagacgg ttttcgccc tttgacgctg gagttcacgt tcctcaatag tggactcttg    2460
ttccaaactg gaacaacact caaccctatc tcggtctatt cttttgattt ataagggatt   2520
tttccgattt cggcctattg gttaaaaat gagctgattt aacaaaaatt taacgcgaat    2580
tttaacaaaa tattaacgtt tataatttca ggtggcatct ttcggggaaa tgtgcgcgga   2640
acccctattt gtttattttt ctaaatacat tcaaatatgt atccgctcat gagacaataa   2700
ccctgataaa tgcttcaata atattgaaaa aggaagagta tgagtattca acatttccgt   2760
gtcgccctta ttccctttt tgcggcattt tgccttcctg ttttgctca cccagaaacg    2820
ctggtgaaag taaaagatgc tgaagatcag ttgggtgcac gagtgggtta catcgaactg   2880
gatctcaata gtggtaagat ccttgagagt tttcgccccg aagaacgttt tccaatgatg   2940
agcacttta aagttctgct atgtggcgcg gtattatccc gtattgacgc cgggcaagag    3000
caactcggtc gccgcataca ctattctcag aatgacttgg ttgagtactc accagtcaca   3060
gaaaagcatc ttacgatgg catgacagta agagaattat gcagtgctgc cataaccatg    3120
agtgataaca ctgcggccaa cttacttctg acaacgatcg gaggaccgaa ggagctaacc   3180
gcttttttgc acaacatggg gatcatgta actcgccttg atcgttggga accggagctg    3240
aatgaagcca taccaaacga cgagcgtgac accacgatgc ctgtagtaat ggtaacaacg   3300
ttgcgcaaac tattaactgg cgaactactt actctagctt cccggcaaca attaatagac   3360
tggatggagg cggataaagt tgcaggacca cttctgcgct cggcccttcc ggctggctgg   3420
tttattgctg ataaatctgg agccggtgag cgtgggtctc gcggtatcat tgcagcactg   3480
gggccagatg gtaagccctc ccgtatcgta gttatctaca cgacggggag tcaggcaact   3540
atggatgaac gaaatagaca gatcgctgag ataggtgcct cactgattaa gcattggtaa   3600
```

| | | | | |
|---|---|---|---|---|
| ctgtcagacc | aagtttactc | atatatactt | tagattgatt | taaaacttca | ttttttaattt | 3660 |
| aaaaggatct | aggtgaagat | cctttttgat | aatctcatga | ccaaaatccc | ttaacgtgag | 3720 |
| ttttcgttcc | actgagcgtc | agaccccgta | gaaaagatca | aaggatcttc | ttgagatcct | 3780 |
| tttttttctgc | gcgtaatctg | ctgcttgcaa | acaaaaaaac | caccgctacc | agcggtggtt | 3840 |
| tgtttgccgg | atcaagagct | accaactctt | tttccgaagg | taactggctt | cagcagagcg | 3900 |
| cagataccaa | atactgtcct | tctagtgtag | ccgtagttag | gccaccactt | caagaactct | 3960 |
| gtagcaccgc | ctacatacct | cgctctgcta | atcctgttac | cagtggctgc | tgccagtggc | 4020 |
| gataagtcgt | gtcttaccgg | gttggactca | agacgatagt | taccggataa | ggcgcagcgg | 4080 |
| tcgggctgaa | cggggggttc | gtgcacacag | cccagcttgg | agcgaacgac | ctacaccgaa | 4140 |
| ctgagatacc | tacagcgtga | gctatgagaa | agcgccacgc | ttcccgaagg | gagaaaggcg | 4200 |
| gacaggtatc | cggtaagcgg | cagggtcgga | acaggagagc | gcacgaggga | gcttccaggg | 4260 |
| ggaaacgcct | ggtatcttta | tagtcctgtc | gggtttcgcc | acctctgact | tgagcgtcga | 4320 |
| tttttgtgat | gctcgtcagg | ggggcggagc | ctatggaaaa | acgccagcaa | cgcggccttt | 4380 |
| ttacggttcc | tggccttttg | ctggccttttg | ctcacatgt | tctttcctgc | gttatcccct | 4440 |
| gattctgtgg | ataaccgtat | taccgccttt | gagtgagctg | ataccgctcg | ccgcagccga | 4500 |
| acgaccgagc | gcagcgagtc | agtgagcgag | gaagcggaag | agcgcccaat | acgcaaaccg | 4560 |
| cctctccccg | cgcgttggcc | gattcattaa | tgcagctggc | acgacaggtt | cccgactgg | 4620 |
| aaagcgggca | gtgagcgcaa | cgcaattaat | gtgagttagc | tcactcatta | ggcaccccag | 4680 |
| gctttacact | ttatgcttcc | ggctcgtatg | ttgtgtggaa | ttgtgagcgg | ataacaattt | 4740 |
| ca | | | | | | 4742 |

<210> SEQ ID NO 20
<211> LENGTH: 5743
<212> TYPE: DNA
<213> ORGANISM: Artificial Sequence
<220> FEATURE:
<223> OTHER INFORMATION: p1336// pAAV_mAlb5' HITI(kozak-ARSB) + Stuffer DNA + gRNA

<400> SEQUENCE: 20

| | | | | |
|---|---|---|---|---|
| cacaggaaac | agctatgacc | atgattacgc | cagatttaat | taaggctgcg | cgctcgctcg | 60 |
| ctcactgagg | ccgcccgggc | aaagcccggg | cgtcgggcga | cctttggtcg | cccggcctca | 120 |
| gtgagcgagc | gagcgcgcag | agagggagtg | gccaactcca | tcactagggg | ttccttgtag | 180 |
| ttaatgatta | acccgccatg | ctacttatct | acgtagccat | gctctaggaa | gatcggaatt | 240 |
| cgcccttaaa | ctagtaacgg | ccgccagtgt | gctggaattc | aggctgacct | cgagtttccc | 300 |
| atgattcctt | catatttgca | tatacgatac | aaggctgtta | gagagataat | tggaattaat | 360 |
| ttggactgta | aacacaaaga | tattagtaca | aaatacgtga | cgtagaaagt | aataatttct | 420 |
| tgggtagttt | gcagttttaa | aattatgttt | taaaatggac | tatcatatgc | ttaccgtaac | 480 |
| ttgaaagtat | ttcgatttct | tggctttata | tatcttgtgg | aaaggacgaa | acaccgacaa | 540 |
| gagtgagatc | gcccattgtt | ttagagctag | aaatagcaag | ttaaaataag | gctagtccgt | 600 |
| tatcaacttg | aaaaagtggc | accgagtcgg | tgcttttttg | ttttagagct | agaaatagca | 660 |
| agctcgagca | gcctgaattc | tgcagatatc | catcacactg | gcggcttaag | ctagcactag | 720 |
| taacggccgc | cagtgtgctg | gaattcgccc | ttcaagagt | gagatcgccc | atcgggacta | 780 |
| caagaagctg | tccttccccg | agggcttcaa | gtgggagcgc | gtgattcccc | agcatgcctg | 840 |

```
ctattgtctt cccaatcctc ccccttgctg tcctgcccca ccccaccccc cagaatagaa    900
tgacacctac tcagacaatg cgatgcaatt tcctcatttt attaggaaag gacagtggga    960
gtggcacctt ccagggtcaa ggaaggcacg ggggaggggc aaacaacaga tggctggcaa   1020
ctagaaggca cagtcgaggc agatctacta gaatcgataa gcttgattcg agctacatcc   1080
aagggcccca caccccagtg gccttgggat cacagcgggg gtcctgtgca gggaagtaca   1140
cggggactga gtgtttatgg tagaactgta ggcgggacag gagctttgtg acgatgtgag   1200
gatattctct ggacaggtca tgtctttctt cagggtcccg atcaatatca aagagccaga   1260
gggtcttggt tggtgggtct gatgagggta tctcagaaac attgtattga dacggtggag   1320
ggaaccagta accacagcct gggtagcccg tgaggagttt ccaatttcca tgtctaattg   1380
cagcatggac agatgtgtta aaggctgaat attctggaag agaagagtca tcctttgctg   1440
gagccatgct gttcctggga cacggtgaag agtccacgaa gttcgggtca atattatgca   1500
gcagctcaat tctgggggat gggcttcctt cactgatggt tttccacacg tcgaagccat   1560
ccagaggctt tgtgccattg gtgtgtcccc tggccagctt cacgagtgtt ggcagccagt   1620
cagagatgtg gatgagctcc cggttcttca cgcccttctg cttcagcaag gggcttgcca   1680
caaagcccac ccctcggacg cctccttccc acaggctcca ttttcttcct cgaaggggcc   1740
agttattacc ccctgccaaa gtctgccctc cgttatctgt agaaaagatg aacaccgtgt   1800
tgttccagag cccactgctt tttaaagctg cagtgacatt tcctactgct tcatccataa   1860
gggacaccat tcctgcatag tgatgcctgt tcttgtcttg ataaagtca tatggcttca    1920
agtattcctc agggacctga aggggctcat gcacagactg gagagcaagg tagagaaaca   1980
gaggcttctc tggtggatgg ttagttatga gggctatagc cctttggtg aatatgtttg    2040
ttgaatacat attttatat cctgttgcaa cttcttcgcc atctcgaaaa tcaagagcac    2100
atcgtgtgac attcagagcg tcaattaatg tacagcgttc atgggaataa taatcttcac   2160
tacccaggag atatccaaag taggtatcaa atcctcggcg ggttggaagg cattcttttcc   2220
ggtacattcc caggtgccat tttccgacca tatgggtagt ataacctgct tcttttagga   2280
gctggggcag gagttttttca tccagaggaa cacagctggg ctgacagggc cagattattt   2340
ggtgctgtaa acctgtacgg atctggtagc ggccagtgag cagctggctc cgcgacggcg   2400
tgcacagcgc ctgcgtgtag tagttgtcca ggagcacccc gccggccgcc agcgcgtcca   2460
ggtgcggcgt gcggatgcgg gagccgtgga agccgacgtc gttccagcct aggtcgtctg   2520
ccagcaagaa gaccaggtgg ggcggccggc tggccccggc gcccgagccc ggcggcgcca   2580
acaacagcag cagcagcagc gggaggacga cggggaggag cagccgccga ggtccgggc    2640
ctcggggcaa gctcgccgcg ccgcgcggac ccatggtggc ttattattta ttatttatta   2700
acaagagtga gatcgcccat cggaagggcg aattctgcag atatccatca cactggcggc   2760
ctcgagttaa gggcgaattc ccgattagga tcttcctaga gcatggctac gtagataagt   2820
agcatggcgg gttaatcatt aactacaagg aacccctagt gatggagttg gccactccct   2880
ctctgcgcgc tcgctcgctc actgaggccg ggcgaccaaa ggtcgcccga cgcccgggct   2940
ttgcccgggc ggcctcagtg agcgagcgag cgcgcagcct taattaacct aattcactgg   3000
ccgtcgtttt acaacgtcgt gactgggaaa accctggcgt tacccaactt aatcgccttg   3060
cagcacatcc ccctttcgcc agctggcgta atagcgaaga ggcccgcacc gatcgccctt   3120
cccaacagtt gcgcagcctg aatggcgaat gggacgcgcc ctgtagcggc gcattaagcg   3180
cggcgggtgt ggtggttacg cgcagcgtga ccgctacact tgccagcgcc ctagcgcccg   3240
```

```
ctcctttcgc tttcttccct tcctttctcg ccacgttcgc cggctttccc cgtcaagctc    3300
taaatcgggg gctcccttta gggttccgat ttagtgcttt acggcacctc gaccccaaaa    3360
aacttgatta gggtgatggt tcacgtagtg ggccatcgcc ccgatagacg gttttcgcc     3420 ctttgacgct ggagttcacg ttcctcaata gtggactctt gttccaaact ggaacaacac    3480
tcaaccctat ctcggtctat tcttttgatt tataagggat ttttccgatt tcggcctatt    3540
ggttaaaaaa tgagctgatt taacaaaaat ttaacgcgaa ttttaacaaa atattaacgt    3600
ttataatttc aggtggcatc tttcggggaa atgtgcgcgg aacccctatt tgtttatttt    3660
tctaaataca ttcaaatatg tatccgctca tgagacaata accctgataa atgcttcaat    3720
aatattgaaa aaggaagagt atgagtattc aacatttccg tgtcgccctt attccctttt    3780
ttgcggcatt ttgccttcct gttttgctc acccagaaac gctggtgaaa gtaaaagatg     3840
ctgaagatca gttgggtgca cgagtgggtt acatcgaact ggatctcaat agtggtaaga    3900
tccttgagag ttttcgcccc gaagaacgtt ttccaatgat gagcactttt aaagttctgc    3960
tatgtggcgc ggtattatcc cgtattgacg ccgggcaaga gcaactcggt cgccgcatac    4020
actattctca gaatgacttg gttgagtact caccagtcac agaaaagcat cttacggatg    4080
gcatgacagt aagagaatta tgcagtgctg ccataaccat gagtgataac actgcggcca    4140
acttacttct gacaacgatc ggaggaccga aggagctaac cgcttttttg cacaacatgg    4200
gggatcatgt aactcgcctt gatcgttggg aaccggagct gaatgaagcc ataccaaacg    4260
acgagcgtga caccacgatg cctgtagtaa tggtaacaac gttgcgcaaa ctattaactg    4320
gcgaactact tactctagct tcccggcaac aattaataga ctggatggag gcggataaag    4380
ttgcaggacc acttctgcgc tcggcccttc cggctggctg gtttattgct gataaatctg    4440
gagccggtga gcgtgggtct cgcggtatca ttgcagcact ggggccagat ggtaagccct    4500
cccgtatcgt agttatctac acgacgggga gtcaggcaac tatggatgaa cgaaatagac    4560
agatcgctga gataggtgcc tcactgatta agcattggta actgtcagac caagtttact    4620
catatatact ttagattgat ttaaaacttc atttttaatt taaaaggatc taggtgaaga    4680
tcctttttga taatctcatg accaaaatcc cttaacgtga gttttcgttc cactgagcgt    4740
cagaccccgt agaaaagatc aaaggatctt cttgagatcc ttttttctg cgcgtaatct    4800 gctgcttgca acaaaaaaa ccaccgctac cagcggtggt ttgtttgccg gatcaagagc    4860
taccaactct ttttccgaag gtaactggct tcagcagagc gcagatacca aatactgtcc    4920
ttctagtgta gccgtagtta ggccaccact tcaagaactc tgtagcaccg cctacatacc    4980
tcgctctgct aatcctgtta ccagtggctg ctgccagtgg cgataagtcg tgtcttaccg    5040
ggttggactc aagacgatag ttaccggata aggcgcagcg tcgggctga acggggggtt     5100 cgtgcacaca gcccagcttg gagcgaacga cctacaccga actgagatac ctacagcgtg    5160
agctatgaga aagcgccacg cttcccgaag ggagaaaggc ggacaggtat ccggtaagcg    5220
gcagggtcgg aacaggagag cgcacgaggg agcttccagg gggaaacgcc tggtatcttt    5280
atagtcctgt cgggtttcgc cacctctgac ttgagcgtcg attttttgtga tgctcgtcag    5340 gggggcggag cctatggaaa aacgccagca acgcggcctt tttacggttc ctggccttt     5400 gctgcggttt tgctcacatg ttctttcctg cgttatcccc tgattctgtg ataaccgta     5460 ttaccgcctt tgagtgagct gataccgctc gccgcagccg aacgaccgag cgcagcgagt    5520
cagtgagcga ggaagcggaa gagcgcccaa tacgcaaacc gcctctcccc gcgcgttggc    5580
```

| | |
|---|---|
| cgattcatta atgcagctgg cacgacaggt ttcccgactg gaaagcgggc agtgagcgca | 5640 |
| acgcaattaa tgtgagttag ctcactcatt aggcacccca ggctttacac tttatgcttc | 5700 |
| cggctcgtat gttgtgtgga attgtgagcg gataacaatt tca | 5743 |

<210> SEQ ID NO 21
<211> LENGTH: 5693
<212> TYPE: DNA
<213> ORGANISM: Artificial Sequence
<220> FEATURE:
<223> OTHER INFORMATION: p1240// pAAV2.1_mAlb5' HITI (kozak-ARSB) NEW + Scramble

<400> SEQUENCE: 21

| | |
|---|---|
| atgaccatga ttacgccaga tttaattaag gctgcgcgct cgctcgctca ctgaggccgc | 60 |
| ccgggcaaag cccgggcgtc gggcgacctt tggtcgcccg gcctcagtga gcgagcgagc | 120 |
| gcgcagagag ggagtggcca actccatcac tagggggttcc ttgtagttaa tgattaaccc | 180 |
| gccatgctac ttatctacgt agccatgctc taggaagatc ggaattcgcc cttaaactag | 240 |
| taacggccgc cagtgtgctg gaattcaggc tgacctcgag tttcccatga ttccttcata | 300 |
| tttgcatata cgatacaagg ctgttagaga gataattgga attaatttgg actgtaaaca | 360 |
| caaagatatt agtacaaaat acgtgacgta gaaagtaata atttcttggg tagtttgcag | 420 |
| ttttaaaatt atgttttaaa atggactatc atatgcttac cgtaacttga agtatttcg | 480 |
| atttcttggc tttatatatc ttgtggaaag gacgaaacac cggactcgcg cgagtcgagg | 540 |
| agtgttttag agctagaaat agcaagttaa aataaggcta gtccgttatc aacttgaaaa | 600 |
| agtggcaccg agtcggtgct tttttgtttt agagctagaa atagcaagct cgagcagcct | 660 |
| gaattctgca gatatccatc acactggcgg cttaagctag cactagtaac ggccgccagt | 720 |
| gtgctggaat tcgcccttac aagagtgaga tcgcccatcg gtccccagca tgcctgctat | 780 |
| tgtcttccca atcctccccc ttgctgtcct gccccacccc accccccaga atagaatgac | 840 |
| acctactcag acaatgcgat gcaatttcct cattttatta ggaaaggaca gtgggagtgg | 900 |
| caccttccag ggtcaaggaa ggcacggggg aggggcaaac aacagatggc tggcaactag | 960 |
| aaggcacagt cgaggcagat ctactagaat cgataagctt gattcgagct acatccaagg | 1020 |
| gccccacacc ccagtggcct tgggatcaca gcggggtcc tgtgcaggga agtacacggg | 1080 |
| gactgagtgt ttatggtaga actgtaggcg ggacaggagc tttgtgacga tgtgaggata | 1140 |
| ttctctggac aggtcatgtc tttcttcagg gtcccgatca atatcaaaga gccagagggt | 1200 |
| cttggttggt gggtctgatg agggtatctc agaaacattg tattgagacg gtggagggaa | 1260 |
| ccagtaacca cagcctgggt agcccgtgag gagtttccaa tttccatgtc taattgcagc | 1320 |
| atggacagat gtgttaaagg ctgaatattc tggaagagaa gagtcatcct ttgctggagc | 1380 |
| catgctgttc ctgggacacg gtgaagagtc cacgaagttc gggtcaatat tatgcagcag | 1440 |
| ctcaattctg ggggatgggc ttccttcact gatggttttc cacacgtcga agccatccag | 1500 |
| aggctttgtg ccattggtgt gtcccctggc cagcttcacg agtgttggca gccagtcaga | 1560 |
| gatgtggatg agctcccggt tcttcacgcc cttctgcttc agcaagggggc ttgccacaaa | 1620 |
| gcccacccct cggacgcctc cttcccacag gctccatttt cttcctcgaa ggggccagtt | 1680 |
| attacccccct gccaaagtct gccctccgtt atctgtagaa aagatgaaca ccgtgttgtt | 1740 |
| ccagagccca ctgcttttta aagctgcagt gacatttcct actgcttcat ccataaggga | 1800 |
| caccattcct gcatagtgat gcctgttctt gtcttggata aagtcatatg gcttcaagta | 1860 |

```
ttcctcaggg acctgaaggg gctcatgcac agactggaga gcaaggtaga gaaacagagg    1920
cttctctggt ggatggttag ttatgagggc tatagcccct ttggtgaata tgtttgttga    1980
atacatattt ttatatcctg ttgcaacttc ttcgccatct cgaaaatcaa gagcacatcg    2040
tgtgacattc agagcgtcaa ttaatgtaca gcgttcatgg gaataataat cttcactacc    2100
caggagatat ccaaagtagg tatcaaatcc tcggcgggtt ggaaggcatt ctttccggta    2160
cattcccagg tgccattttc cgaccatatg ggtagtataa cctgcttctt ttaggagctg    2220
gggcaggagt ttttcatcca gaggaacaca gctgggctga cagggccaga ttatttggtg    2280
ctgtaaacct gtacggatct ggtagcggcc agtgagcagc tggctccgcg acggcgtgca    2340
cagcggctgc gtgtagtagt tgtccaggag caccccgccg gccgccagcg cgtccaggtg    2400
cggcgtgcgg atgcgggagc cgtggaagcc gacgtcgttc cagcctaggt cgtctgccag    2460
caagaagacc aggtggggcg gccggctggc cccgcgccc gagcccggcg gcgccaacaa    2520
cagcagcagc agcagcggga ggacgacggg gaggagcagc cgccgaggtc cggggcctcg    2580
gggcaagctc gccgcgccgc gcggacccat ggtggcttat tatttattat ttattaacaa    2640
gagtgagatc gcccatcgga agggcgaatt ctgcagatat ccatcacact ggcggcctcg    2700
agttaagggc gaattcccga ttaggatctt cctagagcat ggctacgtag ataagtagca    2760
tggcgggtta atcattaact acaaggaacc cctagtgatg gagttggcca ctccctctct    2820
gcgcgctcgc tcgctcactg aggccgggcg accaaaggtc gcccgacgcc cgggctttgc    2880
ccgggcggcc tcagtgagcg agcgagcgcg cagccttaat taacctaatt cactggccgt    2940
cgttttacaa cgtcgtgact gggaaaaccc tggcgttacc caacttaatc gccttgcagc    3000
acatccccct ttcgccagct ggcgtaatag cgaagaggcc cgcaccgatc gcccttccca    3060
acagttgcgc agcctgaatg gcgaatggga cgcgccctgt agcggcgcat taagcgcggc    3120
gggtgtggtg gttacgcgca gcgtgaccgc tacacttgcc agcgccctag cgcccgctcc    3180
tttcgctttc ttcccttcct ttctcgccac gttcgccggc tttccccgtc aagctctaaa    3240
tcgggggctc cctttagggt tccgatttag tgctttacgg cacctcgacc ccaaaaaact    3300
tgattagggt gatggttcac gtagtgggcc atcgccccga tagacggttt ttcgcccttt    3360
gacgctggag ttcacgttcc tcaatagtgg actcttgttc caaactggaa caacactcaa    3420
ccctatctcg gtctattctt ttgatttata agggattttt ccgatttcgg cctattggtt    3480
aaaaaatgag ctgatttaac aaaaatttaa cgcgaatttt aacaaaatat taacgtttat    3540
aatttcaggt ggcatctttc ggggaaatgt gcgcggaacc cctatttgtt tatttttcta    3600
aatacattca aatatgtatc cgctcatgag acaataaccc tgataaatgc ttcaataata    3660
ttgaaaaagg aagagtatga gtattcaaca tttccgtgtc gcccttattc ccttttttgc    3720
ggcattttgc cttcctgttt ttgctcaccc agaaacgctg gtgaaagtaa aagatgctga    3780
agatcagttg ggtgcacgag tgggttacat cgaactggat ctcaatagtg gtaagatcct    3840
tgagagtttt cgccccgaag aacgttttcc aatgatgagc acttttaaag ttctgctatg    3900
tggcgcggta ttatcccgta ttgacgccgg gcaagagcaa ctcggtcgcc gcatacacta    3960
ttctcagaat gacttggttg agtactcacc agtcacagaa aagcatctta cggatggcat    4020
gacagtaaga gaattatgca gtgctgccat aaccatgagt gataacactg cggccaactt    4080
acttctgaca acgatcggag gaccgaagga gctaaccgct tttttgcaca acatggggga    4140
tcatgtaact cgccttgatc gttgggaacc ggagctgaat gaagccatac caaacgacga    4200
gcgtgacacc acgatgcctg tagtaatggt aacaacgttg cgcaaactat taactggcga    4260
```

```
actacttact ctagcttccc ggcaacaatt aatagactgg atggaggcgg ataaagttgc    4320
aggaccactt ctgcgctcgg cccttccggc tggctggttt attgctgata aatctggagc    4380
cggtgagcgt gggtctcgcg gtatcattgc agcactgggg ccagatggta agccctcccg    4440
tatcgtagtt atctacacga cggggagtca ggcaactatg gatgaacgaa atagacagat    4500
cgctgagata ggtgcctcac tgattaagca ttggtaactg tcagaccaag tttactcata    4560
tatactttag attgatttaa aacttcattt ttaatttaaa aggatctagg tgaagatcct    4620
ttttgataat ctcatgacca aaatccctta acgtgagttt tcgttccact gagcgtcaga    4680
ccccgtagaa aagatcaaag gatcttcttg agatcctttt tttctgcgcg taatctgctg    4740
cttgcaaaca aaaaaaccac cgctaccagc ggtggtttgt ttgccggatc aagagctacc    4800
aactcttttt ccgaaggtaa ctggcttcag cagagcgcag ataccaaata ctgtccttct    4860
agtgtagccg tagttaggcc accacttcaa gaactctgta gcaccgccta catacctcgc    4920
tctgctaatc ctgttaccag tggctgctgc cagtggcgat aagtcgtgtc ttaccgggtt    4980
ggactcaaga cgatagttac cggataaggc gcagcggtcg ggctgaacgg ggggttcgtg    5040
cacacagccc agcttggagc gaacgaccta caccgaactg agatacctac agcgtgagct    5100
atgagaaagc gccacgcttc ccgaagggag aaaggcggac aggtatccgg taagcggcag    5160
ggtcggaaca ggagagcgca cgagggagct tccaggggga aacgcctggt atctttatag    5220
tcctgtcggg tttcgccacc tctgacttga gcgtcgattt ttgtgatgct cgtcaggggg    5280
gcggagccta tggaaaaacg ccagcaacgc ggccttttta cggttcctgg ccttttgctg    5340
gccttttgct cacatgttct ttcctgcgtt atcccctgat tctgtggata accgtattac    5400
cgcctttgag tgagctgata ccgctcgccg cagccgaacg accgagcgca gcgagtcagt    5460
gagcgaggaa gcggaagagc gcccaatacg caaaccgcct ctccccgcgc gttggccgat    5520
tcattaatgc agctggcacg acaggtttcc cgactggaaa gcgggcagtg agcgcaacgc    5580
aattaatgtg agttagctca ctcattaggc accccaggct ttacacttta tgcttccggc    5640
tcgtatgttg tgtggaattg tgagcggata acaatttcac acaggaaaca gct           5693
```

<210> SEQ ID NO 22
<211> LENGTH: 5693
<212> TYPE: DNA
<213> ORGANISM: Artificial Sequence
<220> FEATURE:
<223> OTHER INFORMATION: p1239//pAAV2.1_mAlb5' HITI (kozak-ARSB) NEW +
     gRNA

<400> SEQUENCE: 22

```
gatttaatta aggctgcgcg ctcgctcgct cactgaggcc gcccgggcaa agcccgggcg      60
tcgggcgacc tttggtcgcc cggcctcagt gagcgagcga gcgcgcagag agggagtggc     120
caactccatc actaggggtt ccttgtagtt aatgattaac cgccatgct acttatctac     180 gtagccatgc tctaggaaga tcggaattcg cccttaaact agtaacggcc gccagtgtgc     240
tggaattcag gctgacctcg agtttcccat gattccttca tatttgcata tacgatacaa     300
ggctgttaga gagataattg gaattaattt ggactgtaaa cacaaagata ttagtacaaa     360
atacgtgacg tagaaagtaa taatttcttg ggtagtttgc agttttaaaa ttatgttta     420 aaatggacta tcatatgctt accgtaactt gaaagtattt cgatttcttg gctttatata     480
tcttgtggaa aggacgaaac accgacaaga gtggatcgc ccattgtttt agagctagaa     540
atagcaagtt aaaataaggc tagtccgtta tcaacttgaa aaagtggcac cgagtcggtg     600
```

```
cttttttgtt ttagagctag aaatagcaag ctcgagcagc ctgaattctg cagatatcca    660
tcacactggc ggcttaagct agcactagta acggccgcca gtgtgctgga attcgccctt    720
acaagagtga gatcgcccat cggtccccag catgcctgct attgtcttcc caatcctccc    780
ccttgctgtc ctgccccacc ccacccccca gaatagaatg acacctactc agacaatgcg    840
atgcaatttc ctcattttat taggaaagga cagtgggagt ggcaccttcc agggtcaagg    900
aaggcacggg ggaggggcaa acaacagatg gctggcaact agaaggcaca gtcgaggcag    960
atctactaga atcgataagc ttgattcgag ctacatccaa gggccccaca ccccagtggc   1020
cttgggatca cagcggggt cctgtgcagg aagtacacg gggactgagt gtttatggta   1080
gaactgtagg cgggacagga gctttgtgac gatgtgagga tattctctgg acaggtcatg   1140
tctttcttca gggtcccgat caatatcaaa gagccagagg gtcttggttg gtgggtctga   1200
tgagggtatc tcagaaacat tgtattgaga cggtggaggg aaccagtaac cacagcctgg   1260
gtagcccgtg aggagtttcc aatttccatg tctaattgca gcatggacag atgtgttaaa   1320
ggctgaatat tctggaagag aagagtcatc ctttgctgga gccatgctgt tcctgggaca   1380
cggtgaagag tccacgaagt tcgggtcaat attatgcagc agctcaattc tggggatgg   1440 gcttccttca ctgatggttt tccacacgtc gaagccatcc agaggctttg tgccattggt   1500
gtgtcccctg ccagcttca cgagtgttgg cagccagtca gagatgtgga tgagctcccg   1560
gttcttcacg cccttctgct tcagcaaggg gcttgccaca aagcccaccc ctcggacgcc   1620
tccttcccac aggctccatt ttcttcctcg aagggccag ttattacccc ctgccaaagt   1680
ctgccctccg ttatctgtag aaaagatgaa caccgtgttg ttccagagcc cactgctttt   1740
taaagctgca gtgacatttc ctactgcttc atccataagg acaccattc ctgcatagtg   1800 atgcctgttc ttgtcttga taaagtcata tggcttcaag tattcctcag ggacctgaag   1860
gggctcatgc acagactgga gagcaaggta gagaaacaga ggcttctctg gtggatggtt   1920
agttatgagg gctatagccc ttttggtgaa tatgtttgtt gaatacatat ttttatatcc   1980
tgttgcaact tcttcgccat ctcgaaaatc aagagcacat cgtgtgacat tcagagcgtc   2040
aattaatgta cagcgttcat gggaataata atcttcacta cccaggagat atccaaagta   2100
ggtatcaaat cctcggcggg ttggaaggca ttctttccgg tacattccca ggtgccatt   2160 tccgaccata tgggtagtat aacctgcttc ttttaggagc tggggcagga ttttcatc   2220 cagaggaaca cagctgggct gacagggcca gattatttgg tgctgtaaac ctgtacggat   2280
ctggtagcgg ccagtgagca gctggctccg cgacggcgtg cacagcggct gcgtgtagta   2340
gttgtccagg agcaccccgc cggccgccag cgcgtccagg tgcggcgtgc ggatgcggga   2400
gccgtggaag ccgacgtcgt tccagcctag gtcgtctgcc agcaagaaga ccaggtgggg   2460
cggccggctg gccccggcgc ccgagcccgg cggcgccaac aacagcagca gcagcagcgg   2520
gaggacgacg gggaggagca gccgccgagg tccgggccct cggggcaagc tcgccgcgcc   2580
gcgcggaccc atggtggctt attatttatt atttattaac aagagtgaga tcgcccatcg   2640
gaagggcgaa ttctgcagat atccatcaca ctggcggcct cgagttaagg gcgaattccc   2700
gattaggatc ttcctagagc atggctacgt agataagtag catggcgggt taatcattaa   2760
ctacaaggaa ccctagtga tggagttggc cactccctct ctgcgcgctc gctcgctcac   2820
tgaggccggg cgaccaaagg tcgcccgacg cccgggcttt gcccgggcgg cctcagtgag   2880
cgagcgagcg cgcagcctta attaacctaa ttcactgggc gtcgttttac aacgtcgtga   2940
```

```
ctgggaaaac cctggcgtta cccaacttaa tcgccttgca gcacatcccc ctttcgccag   3000
ctggcgtaat agcgaagagg cccgcaccga tcgcccttcc caacagttgc gcagcctgaa   3060
tggcgaatgg gacgcgccct gtagcggcgc attaagcgcg gcgggtgtgg tggttacgcg   3120
cagcgtgacc gctacacttg ccagcgccct agcgcccgct cctttcgctt tcttcccttc   3180
ctttctcgcc acgttcgccg gctttccccg tcaagctcta atcgggggc tccctttagg    3240
gttccgattt agtgctttac ggcacctcga ccccaaaaaa cttgattagg gtgatggttc   3300
acgtagtggg ccatcgcccc gatagacggt ttttcgccct ttgacgctgg agttcacgtt   3360
cctcaatagt ggactcttgt tccaaactgg aacaacactc aaccctatct cggtctattc   3420
ttttgattta aagggatttt tccgatttc ggcctattgg ttaaaaatg agctgattta     3480
acaaaatttt aacgcgaatt ttaacaaaat attaacgttt ataatttcag gtggcatctt   3540
tcggggaaat gtgcgcggaa cccctatttg tttattttc taaatacatt caaatatgta    3600
tccgctcatg agacaataac cctgataaat gcttcaataa tattgaaaaa ggaagagtat   3660
gagtattcaa catttccgtg tcgcccttat tccctttttt gcggcatttt gccttcctgt   3720
ttttgctcac ccagaaacgc tggtgaaagt aaaagatgct gaagatcagt tgggtgcacg   3780
agtgggttac atcgaactgg atctcaatag tggtaagatc cttgagagtt ttcgccccga   3840
agaacgtttt ccaatgatga gcacttttaa agttctgcta tgtggcgcgg tattatcccg   3900
tattgacgcc gggcaagagc aactcggtcg ccgcatacac tattctcaga atgacttggt   3960
tgagtactca ccagtcacag aaaagcatct tacggatggc atgacagtaa gagaattatg   4020
cagtgctgcc ataaccatga gtgataacac tgcggccaac ttacttctga caacgatcgg   4080
aggaccgaag gagctaaccg cttttttgca acatggggg gatcatgtaa ctcgccttga    4140
tcgttgggaa ccgagctga atgaagccat accaaacgac gagcgtgaca ccacgatgcc    4200
tgtagtaatg gtaacaacgt tgcgcaaact attaactggc gaactactta ctctagcttc   4260
ccggcaacaa ttaatagact ggatggaggc ggataaagtt gcaggaccac ttctgcgctc   4320
ggcccttccg gctggctggt ttattgctga taaatctgga gccggtgagc gtgggtctcg   4380
cggtatcatt gcagcactgg ggccagatgg taagccctcc cgtatcgtag ttatctacac   4440
gacggggagt caggcaacta tggatgaacg aaatagacag atcgctgaga taggtgcctc   4500
actgattaag cattggtaac tgtcagacca agtttactca tatatacttt agattgattt   4560
aaaacttcat ttttaattta aaaggatcta ggtgaagatc ctttttgata atctcatgac   4620
caaaatccct taacgtgagt tttcgttcca ctgagcgtca gacccgtag aaaagatcaa    4680
aggatcttct tgagatcctt ttttttctgcg cgtaatctgc tgcttgcaaa caaaaaaacc   4740
accgctacca gcggtggttt gtttgccgga tcaagagcta ccaactcttt ttccgaaggt   4800
aactggcttc agcagagcgc agataccaaa tactgtcctt ctagtgtagc cgtagttagg   4860
ccaccacttc aagaactctg tagcaccgcc tacatacctc gctctgctaa tcctgttacc   4920
agtggctgct gccagtggcg ataagtcgtg tcttaccggg ttggactcaa gacgatagtt   4980
accggataag gcgcagcggt cgggctgaac ggggggttcg tgcacacagc ccagcttgga   5040
gcgaacgacc tacaccgaac tgagatacct acagcgtgag ctatgagaaa gcgccacgct   5100
tcccgaaggg agaaaggcgg acaggtatcc ggtaagcggc agggtcggaa caggagagcg   5160
cacgagggag cttccagggg gaaacgcctg gtatctttat agtcctgtcg ggtttcgcca   5220
cctctgactt gagcgtcgat ttttgtgatg ctcgtcaggg gggcggagcc tatgaaaaaa   5280
cgccagcaac gcggcctttt tacggttcct ggccttttgc tgcggttttg ctcacatgtt   5340
```

-continued

```
ctttcctgcg ttatccctg attctgtgga taaccgtatt accgcctttg agtgagctga      5400
taccgctcgc cgcagccgaa cgaccgagcg cagcgagtca gtgagcgagg aagcggaaga      5460
gcgcccaata cgcaaaccgc ctctccccgc gcgttggccg attcattaat gcagctggca      5520
cgacaggttt cccgactgga aagcgggcag tgagcgcaac gcaattaatg tgagttagct      5580
cactcattag gcaccccagg ctttacactt tatgcttccg gctcgtatgt tgtgtggaat      5640
tgtgagcgga taacaatttc acacaggaaa cagctatgac catgattacg cca            5693
```

<210> SEQ ID NO 23
<211> LENGTH: 48
<212> TYPE: DNA
<213> ORGANISM: Artificial Sequence
<220> FEATURE:
<223> OTHER INFORMATION: ires

<400> SEQUENCE: 23

```
aggtggtagc cgcaaacata gttcaataca aacttgctgt ctcggcgg                   48
```

<210> SEQ ID NO 24
<211> LENGTH: 50
<212> TYPE: DNA
<213> ORGANISM: Artificial Sequence
<220> FEATURE:
<223> OTHER INFORMATION: ires

<400> SEQUENCE: 24

```
tgacaaactg tacatgccgt taactgtaat tttgcgtgat ttttttgtag                 50
```

<210> SEQ ID NO 25
<211> LENGTH: 21
<212> TYPE: PRT
<213> ORGANISM: Artificial Sequence
<220> FEATURE:
<223> OTHER INFORMATION: T2A

<400> SEQUENCE: 25

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 26
<211> LENGTH: 22
<212> TYPE: PRT
<213> ORGANISM: Artificial Sequence
<220> FEATURE:
<223> OTHER INFORMATION: P2A

<400> SEQUENCE: 26

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 27
<211> LENGTH: 23
<212> TYPE: PRT
<213> ORGANISM: Artificial Sequence
<220> FEATURE:
<223> OTHER INFORMATION: E2A

<400> SEQUENCE: 27

```
Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 28
<211> LENGTH: 25
<212> TYPE: PRT
<213> ORGANISM: Artificial Sequence
<220> FEATURE:
<223> OTHER INFORMATION: F2A

<400> SEQUENCE: 28

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 29
<211> LENGTH: 20
<212> TYPE: DNA
<213> ORGANISM: Artificial Sequence
<220> FEATURE:
<223> OTHER INFORMATION: gRNA

<400> SEQUENCE: 29
gcagccgcag tactacctgg                                           20

<210> SEQ ID NO 30
<211> LENGTH: 20
<212> TYPE: DNA
<213> ORGANISM: Artificial Sequence
<220> FEATURE:
<223> OTHER INFORMATION: gRNA

<400> SEQUENCE: 30
agtactgcgg atactcaaag                                           20

<210> SEQ ID NO 31
<211> LENGTH: 20
<212> TYPE: DNA
<213> ORGANISM: Artificial Sequence
<220> FEATURE:
<223> OTHER INFORMATION: gRNA

<400> SEQUENCE: 31
acaagagtga gatcgcccat                                           20

<210> SEQ ID NO 32
<211> LENGTH: 63
<212> TYPE: DNA
<213> ORGANISM: Artificial Sequence
<220> FEATURE:
<223> OTHER INFORMATION: T2A

<400> SEQUENCE: 32
ggaagcggag agggcagagg aagtctgcta acatgcggtg acgtcgagga gaatcctgga   60
cct                                                             63

<210> SEQ ID NO 33
<211> LENGTH: 20
<212> TYPE: DNA
<213> ORGANISM: Artificial Sequence
<220> FEATURE:
<223> OTHER INFORMATION: gRNA
```

```
<400> SEQUENCE: 33
gactcgcgcg agtcgaggag                                                  20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tggaaggtca atgaggctct                                                  20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
gaccccacag agacaagctc                                                  20

<210> SEQ ID NO 36
<211> LENGTH: 18
<212> TYPE: DNA
<213> ORGANISM: Artificial Sequence
<220> FEATURE:
<223> OTHER INFORMATION: primer

<400> SEQUENCE: 36
tgggcagact aggtctgg                                                    18

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
tgtcttccac atgttgaagc                                                  20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
ccatggtgat gcggttttgg                                                  20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
atgtagttga ggggtgtgcg                                                  20

<210> SEQ ID NO 40
```

```
<211> LENGTH: 20
<212> TYPE: DNA
<213> ORGANISM: Artificial Sequence
<220> FEATURE:
<223> OTHER INFORMATION: primer

<400> SEQUENCE: 40
cagtgcctgg agttgcgctg                                              20

<210> SEQ ID NO 41
<211> LENGTH: 21
<212> TYPE: DNA
<213> ORGANISM: Artificial Sequence
<220> FEATURE:
<223> OTHER INFORMATION: primer

<400> SEQUENCE: 41
gggcccaaag acgaagtagc c                                            21

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
aggcctcagc agcatccttg                                              20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
gtggtggtga agcctccgaa                                              20

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
attacggtct catagggcct gc                                           22

<210> SEQ ID NO 45
<211> LENGTH: 23
<212> TYPE: DNA
<213> ORGANISM: Artificial Sequence
<220> FEATURE:
<223> OTHER INFORMATION: primer

<400> SEQUENCE: 45
gcacacattt ctactggaca gca                                          23

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
```

```
cagtgcctgg agttgcgctg                                               20

<210> SEQ ID NO 47
<211> LENGTH: 22
<212> TYPE: DNA
<213> ORGANISM: Artificial Sequence
<220> FEATURE:
<223> OTHER INFORMATION: primer

<400> SEQUENCE: 47
ggcttgatga cgttctcagt gc                                            22

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
cgacctgcag aagcttggat ct                                            22

<210> SEQ ID NO 49
<211> LENGTH: 21
<212> TYPE: DNA
<213> ORGANISM: Artificial Sequence
<220> FEATURE:
<223> OTHER INFORMATION: primer

<400> SEQUENCE: 49
gggcccaaag acgaagtagc c                                             21

<210> SEQ ID NO 50
<211> LENGTH: 22
<212> TYPE: DNA
<213> ORGANISM: Artificial Sequence
<220> FEATURE:
<223> OTHER INFORMATION: primer

<400> SEQUENCE: 50
gcctgctcga ccatgctata ct                                            22

<210> SEQ ID NO 51
<211> LENGTH: 22
<212> TYPE: DNA
<213> ORGANISM: Artificial Sequence
<220> FEATURE:
<223> OTHER INFORMATION: primer

<400> SEQUENCE: 51
ccttggagcc gtactggaac tg                                            22

<210> SEQ ID NO 52
<211> LENGTH: 22
<212> TYPE: DNA
<213> ORGANISM: Artificial Sequence
<220> FEATURE:
<223> OTHER INFORMATION: primer

<400> SEQUENCE: 52
cgacctgcag aagcttggat ct                                            22

<210> SEQ ID NO 53
<211> LENGTH: 20
<212> TYPE: DNA
```

```
<213> ORGANISM: Artificial Sequence
<220> FEATURE:
<223> OTHER INFORMATION: primer

<400> SEQUENCE: 53
tctctggctg ccacattgct                                               20

<210> SEQ ID NO 54
<211> LENGTH: 6
<212> TYPE: DNA
<213> ORGANISM: Artificial Sequence
<220> FEATURE:
<223> OTHER INFORMATION: kozak

<400> SEQUENCE: 54 gccacc                                                               6

<210> SEQ ID NO 55
<211> LENGTH: 6
<212> TYPE: DNA
<213> ORGANISM: Artificial Sequence
<220> FEATURE:
<223> OTHER INFORMATION: kozak
<220> FEATURE:
<221> NAME/KEY: misc_feature
<222> LOCATION: (4)..(4)
<223> OTHER INFORMATION: n is g or a

<400> SEQUENCE: 55 gccncc                                                               6

<210> SEQ ID NO 56
<211> LENGTH: 20
<212> TYPE: DNA
<213> ORGANISM: Artificial Sequence
<220> FEATURE:
<223> OTHER INFORMATION: oligonucleotide

<400> SEQUENCE: 56
ccaggtagta ctgcggctgc                                               20

<210> SEQ ID NO 57
<211> LENGTH: 20
<212> TYPE: DNA
<213> ORGANISM: Artificial Sequence
<220> FEATURE:
<223> OTHER INFORMATION: oligonucleotide

<400> SEQUENCE: 57
ctttgagtat ccgcagtact                                               20

<210> SEQ ID NO 58
<211> LENGTH: 20
<212> TYPE: DNA
<213> ORGANISM: Artificial Sequence
<220> FEATURE:
<223> OTHER INFORMATION: oligonucleotide

<400> SEQUENCE: 58
atgggcgatc tcactcttgt                                               20

<210> SEQ ID NO 59
<211> LENGTH: 38
<212> TYPE: DNA
<213> ORGANISM: Mus musculus

<400> SEQUENCE: 59
```

```
ccccttcgag cagccgcagt actacctggc ggaaccat                        38

<210> SEQ ID NO 60
<211> LENGTH: 38
<212> TYPE: DNA
<213> ORGANISM: Mus musculus

<400> SEQUENCE: 60
ggggaagctc gtcggcgtca tgatggaccg ccttggta                        38

<210> SEQ ID NO 61
<211> LENGTH: 58
<212> TYPE: DNA
<213> ORGANISM: Mus musculus

<400> SEQUENCE: 61
tctctccctg tttccacaga caagagtgag atcgcccatc ggtataatga atttggga  58

<210> SEQ ID NO 62
<211> LENGTH: 57
<212> TYPE: DNA
<213> ORGANISM: Mus musculus

<400> SEQUENCE: 62
agagagggac aaaggtgtct gttctcactc tagcgggtag ccatattact aaaccct   57
```